US011426412B2

(12) United States Patent
Hallur et al.

(10) Patent No.: US 11,426,412 B2
(45) Date of Patent: Aug. 30, 2022

(54) IMIDAZO-PYRIDINE COMPOUNDS AS PAD INHIBITORS

(71) Applicant: JUBILANT EPIPAD LLC, Yardley, PA (US)

(72) Inventors: Gurulingappa Hallur, Bangalore (IN); Athisayamani Jeyaraj Duraiswamy, Bangalore (IN); Buchi Reddy Purra, Bangalore (IN); N.V.S.K. Rao, Bangalore (IN); Sridharan Rajagopal, Bangalore (IN); Rajendra Kristam, Bangalore (IN)

(73) Assignee: JUBILANT EPIPAD LLC, Yardley, PA (US)

( * ) Notice: Subject to any disclaimer, the term of this patent is extended or adjusted under 35 U.S.C. 154(b) by 0 days.

(21) Appl. No.: 16/757,120

(22) PCT Filed: Oct. 16, 2018

(86) PCT No.: PCT/IN2018/050671

§ 371 (c)(1),
(2) Date: Apr. 17, 2020

(87) PCT Pub. No.: WO2019/077631

PCT Pub. Date: Apr. 25, 2019

(65) Prior Publication Data

US 2020/0237771 A1 Jul. 30, 2020

(30) Foreign Application Priority Data

Oct. 18, 2017 (IN) ............................ 201741037110

(51) Int. Cl.
*C07D 471/04* (2006.01)
*C07D 498/04* (2006.01)
(Continued)

(52) U.S. Cl.
CPC ........ *A61K 31/5383* (2013.01); *A61K 31/437* (2013.01); *C07D 471/04* (2013.01); *C07D 498/04* (2013.01)

(58) Field of Classification Search
CPC .. C07D 471/04; C07D 498/04; A61K 31/437; A61K 31/5383
(Continued)

(56) References Cited

U.S. PATENT DOCUMENTS 3,565,896 A 2/1971 Ghielmetti et al.
3,970,753 A 7/1976 Durant
(Continued)

FOREIGN PATENT DOCUMENTS

CN 101838264 9/2010
CN 105461693 A 4/2016
(Continued)

OTHER PUBLICATIONS

International Search Report & Written Opinion, dated Feb. 14, 2019, in International Application No. PCT/IN2018/050671.

Lewis, H.D., et al., Inhibition of PAD4 Activity Is Sufficient to Disrupt Mouse and Human NET Formation, Nature Chemical Biology, vol. 11., No. 3, pp. 189-191, 2015.

Candi, et al., The Cornified Envelope: A Model of Cell Death in the Skin, Nat. Rev. Mol. Cell Biol., vol. 6, pp. 328-340, 2005.

Cedervall, et al., NETosis in cancer, Oncoscience, vol. 2, No. 11, pp. 900-901, 2015.

(Continued)

*Primary Examiner* — Niloofar Rahmani
(74) *Attorney, Agent, or Firm* — Knobbe, Martens, Olson & Bear, LLP

(57) ABSTRACT

Heterocyclic compounds of Formula (I), (II), and (III) are described herein along with their polymorphs, stereoisomers, prodrugs, solvates, co-crystals, intermediates, pharmaceutically acceptable salts, and metabolites thereof. The compounds described herein, their polymorphs, stereoisomers, prodrugs, solvates, co-crystals, intermediates, pharmaceutically acceptable salts, and metabolites thereof are PAD4 inhibitors and may be useful in the treatment of various disorders, for example rheumatoid arthritis, vasculitis, systemic lupus erythematosis, cutaneous lupus erythematosis, ulcerative colitis, cancer, cystic fibrosis, asthma, multiple sclerosis and psoriasis. The process of preparation of the compounds of Formula (I), (II), and (III), their polymorphs, stereoisomers, prodrugs, solvates, co-crystals, intermediates, pharmaceutically acceptable salts, and metabolites thereof, along with a pharmaceutical composition comprising a compound of Formula (I), Formula (II), Formula (III), or a pharmaceutically acceptable salt thereof have also been described.

Formula (I)

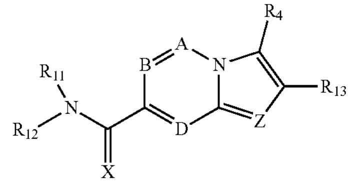

Formula (II)

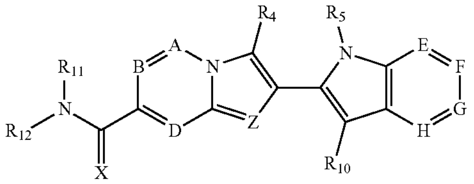

Formula (III)

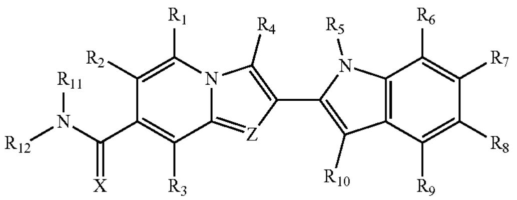

12 Claims, No Drawings

(51) Int. Cl.
*A61K 31/5383* (2006.01)
*A61K 31/437* (2006.01)

(58) Field of Classification Search
USPC .......................................................... 514/230.5
See application file for complete search history.

(56) References Cited

U.S. PATENT DOCUMENTS

| | | | |
|---|---|---|---|
| 3,985,881 A | 10/1976 | Mehrhof et al. | |
| 4,246,274 A | 1/1981 | Regel et al. | |
| 4,315,855 A | 2/1982 | Schefczik | |
| 4,495,191 A | 1/1985 | Ehrhardt et al. | |
| 4,703,056 A | 10/1987 | Hideg et al. | |
| 4,757,081 A | 7/1988 | Yonekura et al. | |
| 4,871,735 A | 10/1989 | Heider et al. | |
| 4,871,751 A | 10/1989 | Yonekura et al. | |
| 4,962,113 A | 10/1990 | Tsushima et al. | |
| 5,001,132 A | 3/1991 | Manoury et al. | |
| 5,010,094 A | 4/1991 | Schade et al. | |
| 5,047,411 A * | 9/1991 | Takasugi .............. | C07D 471/04 514/300 |
| 5,100,890 A | 3/1992 | Siegel et al. | |
| 5,179,125 A | 1/1993 | Mimura et al. | |
| 5,210,266 A | 5/1993 | Mimura et al. | |
| 5,229,516 A | 7/1993 | Messer et al. | |
| 5,244,908 A | 9/1993 | Takatani et al. | |
| 5,273,980 A | 12/1993 | Frenette et al. | |
| 5,330,989 A | 7/1994 | Soll et al. | |
| 5,420,289 A | 5/1995 | Musser et al. | |
| 5,541,033 A | 7/1996 | Blakeney et al. | |
| 5,547,814 A | 8/1996 | Blakeney et al. | |
| 5,550,162 A | 8/1996 | Frost et al. | |
| 5,554,621 A | 9/1996 | Poindexter et al. | |
| 5,663,183 A | 9/1997 | Frost et al. | |
| 6,844,445 B2 | 1/2005 | Wierzbicki et al. | |
| 6,887,868 B2 | 5/2005 | Fu | |
| 8,148,408 B2 | 4/2012 | Bunnelle et al. | |
| 8,642,660 B2 | 2/2014 | Goldfarb | |
| 9,067,898 B1 | 6/2015 | Illig | |
| 2002/0094989 A1 | 7/2002 | Hale et al. | |
| 2002/0173531 A1 | 11/2002 | Wierzbicki et al. | |
| 2003/0018025 A1 | 1/2003 | Thurkauf et al. | |
| 2004/0229160 A1 | 11/2004 | Naiini et al. | |
| 2005/0159334 A1 | 7/2005 | Gluck et al. | |
| 2005/0228014 A1 | 10/2005 | Marquess et al. | |
| 2006/0270686 A1 | 11/2006 | Kelly et al. | |
| 2007/0191371 A1 | 8/2007 | Bennett et al. | |
| 2007/0219218 A1 | 9/2007 | Yu et al. | |
| 2008/0280891 A1 | 11/2008 | Kelly et al. | |
| 2010/0249127 A1 | 9/2010 | Namdev et al. | |
| 2017/0105971 A1 | 4/2017 | Catrina et al. | |
| 2017/0174672 A1 | 6/2017 | Amberg et al. | |
| 2021/0015810 A1 | 1/2021 | Venkateshappa et al. | |
| 2021/0371431 A1 | 12/2021 | Vadivelu et al. | |

FOREIGN PATENT DOCUMENTS

| | | | |
|---|---|---|---|
| CN | 10756630 | A | 8/2017 |
| CN | 107163044 | A | 9/2017 |
| CN | 108358917 | A | 8/2018 |
| CN | 110105299 | A | 8/2019 |
| CN | 110963997 | A | 9/2019 |
| CN | 107056630 | B | 1/2020 |
| CN | 111606904 | A | 9/2020 |
| DE | 1961595 | A | 6/1970 |
| DE | 19717371 | A1 | 6/1970 |
| DE | 2832677 | A1 | 2/1980 |
| DE | 3210570 | A1 | 10/1983 |
| DE | 3628545 | A1 | 4/1987 |
| DE | 3901723 | A1 | 7/1990 |
| DE | 4227522 | A1 | 2/1994 |
| DE | 19834751 | | 2/2000 |
| EP | 0090269 | A1 | 10/1983 |
| EP | 0218118 | A1 | 4/1987 |
| EP | 0239391 | A2 | 9/1987 |
| EP | 0259793 | A1 | 3/1988 |
| EP | 0301751 | A1 | 2/1989 |
| EP | 0370852 | A1 | 5/1990 |
| EP | 0218118 | B1 | 9/1991 |
| EP | 0471236 | A1 | 2/1992 |
| EP | 0259793 | B1 | 7/1992 |
| EP | 0301751 | B1 | 3/1993 |
| EP | 0533056 | A2 | 3/1993 |
| EP | 0535924 | A1 | 4/1993 |
| EP | 0533056 | A3 | 6/1993 |
| EP | 0666250 | A1 | 8/1995 |
| EP | 0747378 | A1 | 12/1996 |
| EP | 07646440 | A1 | 3/1997 |
| EP | 0819977 | A1 | 1/1998 |
| EP | 0666250 | B1 | 2/1998 |
| EP | 1245565 | A1 | 10/2002 |
| EP | 1245565 | B1 | 9/2003 |
| EP | 1388342 | A1 | 2/2004 |
| EP | 2194035 | A2 | 6/2010 |
| EP | 2194035 | A3 | 6/2010 |
| EP | 20194035 | B1 | 11/2011 |
| EP | 3 112 362 | A1 | 1/2017 |
| FR | 2102082 | A2 | 4/1972 |
| FR | 2102082 | B2 | 10/1974 |
| FR | 2706895 | A1 | 12/1994 |
| FR | 2706895 | B1 | 8/1995 |
| GB | 1230663 | A | 5/1971 |
| GB | 1356789 | A | 6/1974 |
| JP | 62187452 | A | 8/1987 |
| JP | H 02215809 | A | 8/1990 |
| JP | 06184076 | | 12/1992 |
| JP | 07304770 | | 5/1994 |
| JP | 11119379 | A1 | 4/1999 |
| JP | 2001233712 | A | 8/2001 |
| JP | 200506247 | A | 3/2005 |
| JP | 20080280344 | A | 11/2008 |
| JP | 2009209090 | A | 9/2009 |
| JP | 2009274984 | | 11/2009 |
| JP | 2011063589 | A | 3/2011 |
| JP | 2011207765 | | 10/2011 |
| JP | 2019156770 | A | 9/2019 |
| JP | 2021054909 | | 4/2021 |
| RU | 2371444 | C1 | 10/2009 |
| WO | WO 86/05519 | | 9/1986 |
| WO | WO 9106537 | A2 | 5/1991 |
| WO | WO 910537 | A3 | 10/1991 |
| WO | WO 9301157 | A1 | 1/1993 |
| WO | WO 9312094 | A1 | 6/1993 |
| WO | WO 9320099 | A2 | 10/1993 |
| WO | WO 9320099 | A3 | 11/1993 |
| WO | WO 9401407 | A2 | 1/1994 |
| WO | WO 9401407 | A3 | 3/1994 |
| WO | WO 9422829 | A2 | 10/1994 |
| WO | WO 9422834 | A1 | 10/1994 |
| WO | WO 9427971 | A1 | 12/1994 |
| WO | WO 9422829 | A3 | 1/1995 |
| WO | WO 9509843 | A1 | 4/1995 |
| WO | WO 9511226 | A1 | 4/1995 |
| WO | WO 9521164 | A1 | 8/1995 |
| WO | WO 9521832 | A1 | 8/1995 |
| WO | WO 9610012 | A1 | 4/1996 |
| WO | WO 9616040 | A1 | 5/1996 |
| WO | WO 9709066 | A1 | 3/1997 |
| WO | WO 9724119 | A1 | 7/1997 |
| WO | WO 9740051 | A1 | 10/1997 |
| WO | WO 9817648 | A1 | 4/1998 |
| WO | WO 9824766 | A1 | 6/1998 |
| WO | WO 9834609 | A1 | 8/1998 |
| WO | WO 9836749 | A1 | 8/1998 |
| WO | WO 9838156 | A1 | 9/1998 |
| WO | WO 9906387 | A2 | 2/1999 |
| WO | WO 9906387 | A3 | 4/1999 |
| WO | WO 9932447 | A2 | 7/1999 |
| WO | WO 9932447 | A3 | 10/1999 |
| WO | WO 2000007978 | A1 | 2/2000 |
| WO | WO 2000023420 | A1 | 4/2000 |
| WO | WO 2000026203 | A1 | 5/2000 |
| WO | WO 2001070731 | A1 | 9/2001 |

(56) References Cited

FOREIGN PATENT DOCUMENTS

| | | | |
|---|---|---|---|
| WO | WO 2001077075 | A2 | 10/2001 |
| WO | WO 2001087293 | A1 | 11/2001 |
| WO | WO 2002002518 | A2 | 1/2002 |
| WO | WO 2002002520 | A2 | 1/2002 |
| WO | WO 20020283673 | A1 | 1/2002 |
| WO | WO 2001077075 | A3 | 3/2002 |
| WO | WO 2002002518 | A3 | 8/2002 |
| WO | WO 2002002520 | A3 | 8/2002 |
| WO | WO 2002066478 | A1 | 8/2002 |
| WO | WO 20020234716 | A3 | 8/2002 |
| WO | WO 2002070510 | A2 | 9/2002 |
| WO | WO 2002076964 | A1 | 10/2002 |
| WO | WO 2002076979 | A1 | 10/2002 |
| WO | WO 2002088089 | A1 | 11/2002 |
| WO | WO 2002098869 | A2 | 12/2002 |
| WO | WO 2002100813 | A2 | 12/2002 |
| WO | WO 2002070510 | A3 | 1/2003 |
| WO | WO 2008000408 | A1 | 1/2003 |
| WO | WO 2003037887 | A1 | 5/2003 |
| WO | WO 2003044016 | A1 | 5/2003 |
| WO | WO 2003044017 | A1 | 5/2003 |
| WO | WO 2003066613 | A1 | 8/2003 |
| WO | WO 2003084916 | A2 | 10/2003 |
| WO | WO 2002100813 | A3 | 11/2003 |
| WO | WO 2003035076 | A3 | 11/2003 |
| WO | WO 2003084916 | A3 | 12/2003 |
| WO | WO 2002098869 | A3 | 2/2004 |
| WO | WO 2004011430 | A1 | 2/2004 |
| WO | WO 2004014372 | A1 | 2/2004 |
| WO | WO 2004022558 | A2 | 3/2004 |
| WO | WO 2004035579 | A1 | 4/2004 |
| WO | WO 2004022558 | A3 | 5/2004 |
| WO | WO 2004/052846 | A1 | 6/2004 |
| WO | WO 2004048363 | A1 | 6/2004 |
| WO | WO 2004058679 | A2 | 7/2004 |
| WO | WO 2004058679 | A3 | 8/2004 |
| WO | WO 20004078731 | A1 | 9/2004 |
| WO | WO 2004109400 | A2 | 12/2004 |
| WO | WO 2005058823 | A1 | 6/2005 |
| WO | WO 200100350 | A1 | 10/2005 |
| WO | WO 2005092899 | A1 | 10/2005 |
| WO | WO 2005105805 | A1 | 11/2005 |
| WO | WO 2005105805 | A9 | 1/2006 |
| WO | WO 2006048330 | A1 | 5/2006 |
| WO | WO 2006062224 | A1 | 6/2006 |
| WO | WO 2006069125 | A1 | 6/2006 |
| WO | WO 2006102588 | A1 | 9/2006 |
| WO | WO 2006105971 | A1 | 10/2006 |
| WO | WO 2004109400 | A3 | 11/2006 |
| WO | WO 2006126119 | A1 | 11/2006 |
| WO | WO 2006126939 | A1 | 11/2006 |
| WO | WO 2006130707 | A2 | 12/2006 |
| WO | WO 2006133104 | A2 | 12/2006 |
| WO | WO 2006130707 | A3 | 1/2007 |
| WO | WO 2006133104 | A3 | 4/2007 |
| WO | WO 2007087548 | A2 | 8/2007 |
| WO | WO 2007106469 | A2 | 9/2007 |
| WO | WO 2007106989 | A2 | 9/2007 |
| WO | WO 2007073503 | A2 | 11/2007 |
| WO | WO 2007073505 | A3 | 11/2007 |
| WO | WO 2007105989 | A3 | 11/2007 |
| WO | WO 2007133108 | A1 | 11/2007 |
| WO | WO 2007106469 | A3 | 12/2007 |
| WO | WO 2008008059 | A1 | 1/2008 |
| WO | WO 20082022945 | A1 | 2/2008 |
| WO | WO 2008051757 | A1 | 5/2008 |
| WO | WO 2008064320 | A2 | 5/2008 |
| WO | WO 2008065500 | A2 | 6/2008 |
| WO | WO 2008065500 | A3 | 6/2008 |
| WO | WO 2008066789 | A2 | 6/2008 |
| WO | WO 2008079988 | A2 | 7/2008 |
| WO | WO 2008104077 | A1 | 9/2008 |
| WO | WO 2008112715 | A2 | 9/2008 |
| WO | WO 2008064320 | A3 | 10/2008 |
| WO | WO 2008121687 | A2 | 10/2008 |
| WO | WO 2008123582 | A1 | 10/2008 |
| WO | WO 2007112715 | A3 | 11/2008 |
| WO | WO 2008135526 | A1 | 11/2008 |
| WO | WO 2008156142 | A1 | 12/2008 |
| WO | WO 2009010925 | A2 | 1/2009 |
| WO | WO 2009023179 | A2 | 2/2009 |
| WO | WO 2009038842 | A2 | 3/2009 |
| WO | WO 2009048152 | A2 | 4/2009 |
| WO | WO 2009054914 | A1 | 4/2009 |
| WO | WO 2009010925 | A3 | 7/2009 |
| WO | WO 2009080351 | A1 | 7/2009 |
| WO | WO 2009104819 | A1 | 8/2009 |
| WO | WO 2009048152 | A3 | 9/2009 |
| WO | WO 2009112651 | A1 | 9/2009 |
| WO | WO 2009137309 | A2 | 11/2009 |
| WO | WO 2009140101 | A2 | 11/2009 |
| WO | WO 2005123703 | A2 | 12/2009 |
| WO | WO 2009038842 | A3 | 12/2009 |
| WO | WO 2009153313 | A1 | 12/2009 |
| WO | WO 2010048207 | A2 | 4/2010 |
| WO | WO 2010075973 | A1 | 7/2010 |
| WO | WO 2010077680 | A2 | 7/2010 |
| WO | WO 2010091409 | A1 | 8/2010 |
| WO | WO 2010098495 | A1 | 9/2010 |
| WO | WO 2010151799 | A2 | 12/2010 |
| WO | WO 2011023989 | A1 | 3/2011 |
| WO | WO 2011086178 | A1 | 7/2011 |
| WO | WO 2011100380 | A1 | 8/2011 |
| WO | WO 2011123751 | A2 | 10/2011 |
| WO | WO 2012006202 | A1 | 1/2012 |
| WO | WO 2012006203 | A1 | 1/2012 |
| WO | WO 2012/022045 | A1 | 2/2012 |
| WO | WO 2012022265 | A1 | 2/2012 |
| WO | WO 2021028810 | A1 | 2/2012 |
| WO | WO 2012058133 | A1 | 5/2012 |
| WO | WO 2012087833 | A1 | 6/2012 |
| WO | WO 2013000994 | A1 | 1/2013 |
| WO | WO 2013002879 | A1 | 1/2013 |
| WO | WO 2013002880 | A1 | 1/2013 |
| WO | WO 2013018371 | A1 | 2/2013 |
| WO | WO 2013025733 | A1 | 2/2013 |
| WO | WO 2013068470 | A1 | 5/2013 |
| WO | WO 2013096049 | A1 | 6/2013 |
| WO | WO 2013096055 | A1 | 6/2013 |
| WO | WO 2013096059 | A1 | 6/2013 |
| WO | WO 2013096060 | A1 | 6/2013 |
| WO | WO 2013096681 | A1 | 6/2013 |
| WO | WO 2013120464 | A1 | 8/2013 |
| WO | WO 2013127729 | A1 | 9/2013 |
| WO | WO 2010077680 | A3 | 10/2013 |
| WO | WO 2013174895 | A1 | 11/2013 |
| WO | WO 2013178810 | A1 | 12/2013 |
| WO | WO 2013192430 | A2 | 12/2013 |
| WO | WO 2014/015905 | A1 | 1/2014 |
| WO | WO 2014013182 | A1 | 1/2014 |
| WO | WO 2014031872 | A2 | 2/2014 |
| WO | WO 2014031986 | A1 | 2/2014 |
| WO | WO 2014031872 | A3 | 4/2014 |
| WO | WO 2014077321 | A1 | 5/2014 |
| WO | WO 2014/100719 | A2 | 6/2014 |
| WO | WO 2014100764 | A2 | 6/2014 |
| WO | WO 2014100764 | A3 | 9/2014 |
| WO | WO 2014152018 | A1 | 9/2014 |
| WO | WO 2015011397 | A1 | 1/2015 |
| WO | WO 2015031295 | A1 | 3/2015 |
| WO | WO 2015034820 | A1 | 3/2015 |
| WO | WO 2015086512 | A1 | 6/2015 |
| WO | WO 2015086527 | A1 | 6/2015 |
| WO | WO 2015108038 | A1 | 7/2015 |
| WO | WO 2015140051 | A1 | 9/2015 |
| WO | WO 2015197028 | A1 | 12/2015 |
| WO | WO 2016008433 | A1 | 1/2016 |
| WO | WO 2016031815 | A1 | 3/2016 |
| WO | WO 2016034675 | A1 | 3/2016 |
| WO | WO 2016036636 | A1 | 3/2016 |
| WO | WO 2016051306 | A2 | 4/2016 |
| WO | WO 2016102727 | A1 | 6/2016 |
| WO | WO 2016/185279 | A1 | 11/2016 |
| WO | WO 2017024180 | A1 | 2/2017 |

(56) References Cited

FOREIGN PATENT DOCUMENTS

| | | | |
|---|---|---|---|
| WO | WO 2017025510 | A1 | 2/2017 |
| WO | WO 2017/042182 | | 3/2017 |
| WO | WO 2017068412 | A1 | 4/2017 |
| WO | WO 2017106634 | A1 | 6/2017 |
| WO | WO 2017109095 | A1 | 6/2017 |
| WO | WO 2017/118762 | | 7/2017 |
| WO | WO 2017/147102 | | 8/2017 |
| WO | WO 2017216281 | A1 | 12/2017 |
| WO | WO 2018002848 | A1 | 1/2018 |
| WO | WO 2018019204 | A1 | 2/2018 |
| WO | WO 2018026971 | A1 | 2/2018 |
| WO | WO 2018112843 | A1 | 6/2018 |
| WO | WO 2018119036 | A1 | 6/2018 |
| WO | WO 2018121610 | A1 | 7/2018 |
| WO | WO 2018183411 | A1 | 10/2018 |
| WO | WO 2018208985 | A2 | 11/2018 |
| WO | WO 2018234342 | A1 | 12/2018 |
| WO | WO 2019007696 | A1 | 1/2019 |
| WO | WO 2019/058393 | A1 | 3/2019 |
| WO | WO 2019/077631 | A1 | 4/2019 |
| WO | WO 2019079783 | A1 | 4/2019 |
| WO | WO 2019/087214 | A1 | 5/2019 |
| WO | WO 2019/102494 | A1 | 5/2019 |
| WO | WO 2019126081 | A1 | 6/2019 |
| WO | WO 2019154047 | A1 | 8/2019 |
| WO | WO 2019160014 | A1 | 8/2019 |
| WO | WO 2019175897 | A1 | 9/2019 |
| WO | WO 2019205147 | A1 | 10/2019 |
| WO | WO 2019213234 | A1 | 11/2019 |
| WO | WO 2020028723 | A1 | 2/2020 |
| WO | WO 2020029980 | A1 | 2/2020 |
| WO | WO 2020045216 | A1 | 3/2020 |
| WO | WO 2020083971 | A2 | 4/2020 |
| WO | WO 2020092394 | A1 | 5/2020 |
| WO | WO 2020201773 | A1 | 10/2020 |
| WO | WO 2020246910 | A1 | 12/2020 |
| WO | WO 2021014949 | A1 | 1/2021 |
| WO | WO 2021018858 | A1 | 2/2021 |
| WO | WO 2021060432 | A1 | 4/2021 |
| WO | WO 2021095241 | A1 | 5/2021 |
| WO | WO 2021096238 | A1 | 5/2021 |

OTHER PUBLICATIONS

Christophorou et al., Citrullination regulates pluripotency and histone H1 binding to chromatin, Nature, vol. 507, pp. 104-108, 2014.

Chumanevich et al., Suppression of colitis in mice by CI-amidine: a novel peptidylarginine deiminase inhibitor, Am. J. Physiol. Gastrointest. Liver Physiol., vol. 300, No. 6, pp. G929-G938, 2011.

Gyorgy, et al., Citrullination: A posttranslational modification in health and death, Int. J. Biochem. Cell Biol., vol. 38, pp. 1662-1677, 2006.

Ireland, et al., Autophagy in antigen-presenting cells results in presentation of citrullinated peptides to CD4 T Cells, J. Exp. Med., vol. 208, pp. 2625-2632, 2011.

Jones, et al., Protein arginine deiminase 4 (PAD4): current understanding and future therapeutic potential, Curr. Opin. Drug Disc. Devel., vol. 12, pp. 616-627, 2009.

Knight, et al., Peptidylarginine Deiminase Inhibition Reduces Vascular Damage and Modulates Innate Immune Responses in Murine Models of Atherosclerosis, Circ. Res., vol. 114, No. 6, pp. 947-956, 2014.

Kochi, et al., PADI4 polymorphism predisposes male smokers to rheumatoid arthritis, Ann. Rheum. Dis., vol. 70, pp. 512-515, 2011.

Lange, et al., Protein deiminases: New players in the developmentally regulated loss of neural regenerative ability, Dev. Biol., vol. 355, No. 2, pp. 205-214, 2011.

Li, et al., Regulation of p53 Target Gene Expression by Peptidylarginine Deiminase 4, Molecular & Cell Biology, vol. 28, No. 15, pp. 4745-4758, 2008.

Liu, et al. Overexpression of peptidylarginine deiminase IV features in apoptosis of haematopoietic cells, Apoptosis, vol. 11, pp. 183-196, 2006.

Loos, et al., Citrullination of CXCL10 and CXCL11 by peptidylarginine deiminase: a naturally occurring posttranslational modification of chemokines and new dimension of immunoregulation, Blood, vol. 112, pp. 2648-2656, 2008.

Makrygiannakis, et al., Citrullination is an Inflammation-Dependent Process, Ann. Rheum. Dis., vol. 65, pp. 1219-1222, 2006.

Mastronardi, et al., Increased Citrullination of Histone H3 in Multiple Sclerosis Brain and Animal Models of Demyelination: A Role for Tumor Necrosis Factor-Induced Peptidylarginine Deiminase 4 Translocation, J. NeuroSci., vol. 26, pp. 11387-11396, 2006.

Nakashima, et al., Molecular Characterization of Peptidylarginine Deiminase in HL-60 Cells Induced by Retinoic Acid and 1a,25-Dihydroxyvitamin D3, J. Biol. Chem., vol. 274, pp. 27786-27792, 1999.

Slack, et al., Protein arginine deiminase 4: a target for an epigenetic cancer therapy. Cellular and Molecular Life Sciences, vol. 68, No. 4, pp. 709-720, 2011.

Wang, et al., Histone hypercitrullination mediates chromatin decondensation and neutrophil extracellular trap formation, J. Cell Biol., vol. 184, pp. 205-213, 2009.

Willis, et al., N-a-Benzoyl-N5-(2-Chloro-1-Iminoethyl)-1-Ornithine Amide, a Protein Arginine Deiminase Inhibitor, Reduces the Severity of Murine Collagen-Induced, Arthritis J. Immunol., vol. 186, No. 7, pp. 4396-4404, 2011.

Acharya et al., "Neuronal PAD4 expression and protein citrullination: Possible role in production of autoantibodies associated with neurodegenerative disease", J. Autoimmun., vol. 38, pp. 369-380, 2012.

Arisan, et al., "Putative Roles for Peptidylarginine Deiminases in COVID-19", International Journal of Molecular Sciences, vol. 21, No. 13, in 29 pages, 2020.

Barber, et al., "Restoring function in exhausted CD8 T cells during chronic viral infection", Nature, vol. 439, No. 7077, pp. 682-687, 2005.

Barbhan, et al., "The PD1:PD-L1/2 Pathway from Discovery to Clinical Implementation", Frontiers In Immunology, vol. 7, No. 550, pp. 1-17, 2016.

Barnes, et al., "Targeting potential drivers of COVID-19: Neutrophil extracellular traps", Journal of Experimental Medicine, vol. 217, No. 6, in 7 pages, 2020.

Bertini, et al., "Carbazole-containing arylcarboxamides as BACE1 inhibitors," Bioorganic & Medicinal Chemistry Letters (2011), 21 (22), 6657-6661.

Borregaard, "Neutrophils, from Marrow to Microbes", Immunity, vol. 33, No. 5, pp. 657-670, 2010.

Brinkmann, et al., "Neutrophil Extracellular Traps Kill Bacteria", Science, vol. 303, No. 5663, pp. 1532-1535, 2004.

Chen, et al., "Anti-PD-1/PD-L1 therapy of human cancer: past, present, and future", Journal of Clinical Investigation, vol. 125, No. 9, pp. 3384-3391, 2015.

Chang et al., "Increased PADI4 expression in blood and tissues of patients with malignant tumors", BMC Cancer, vol. 9, pages 40, 2009.

Chiummiento, et a;., "New indolic non-peptidic HIB protease inhibitors from (S)-glycidol: synthesis and preliminary biological activity," Tetrahedron (2009), 65(31), 5984-5989.

Curiel, et al., "Blockade of B7-H1 improves myeloid dendritic cell mediated antiturmor or immunity", Nature Medicine, vol. 9, No. 5, pp. 562-567, 2003.

Dimauro et al., Discovery of Aminoquinaolines as Potent, Orally Bioavailable Inhibitor of Lck: Synthesis, SAR, and in Vivo Anti-inflammatory Activity, Journal of Medical Chemistry, vol. 49, No. 19, pp. 5671-5686, 2006.

Dong, et al., "Tumor-associated B7-H1 promotes T-cell apoptosis: A potential mechanism of immune evasion", Nature Medicine, vol. 8, No. 8, pp. 793-800, 2002.

Dong, et al., "PD-1 and its ligands are important immune checkpoints in cancer", Oncotarget, vol. 8, No. 2, pp. 2171-2186, 2017.

First Examination Report dated Sep. 8, 2021 received in Indian Patent Application No. 201741033768.

Flies, et al., "The New B7S: Playing a Pivotal Rose in Tumor Immunity", Immunotherapy, vol. 30, No. 3, PP. 251-260, 2007.

(56) References Cited

OTHER PUBLICATIONS

Flies, et al., "Blockade of the B7-H1/PD-1 Pathway for Cancer Immunotherapy", Yale J. Biology Medicine, vol. 84, No. 4, pp. 409-421, 2011.
Fuhrmann, Jakob, et al., "Chemical Biology of Protein Arginine Modifications in Epigenetic Regular," Chemical Reviews, 2015, 115, 5413-5461.
Francisco, et al., "PD-L1 regulates the development, maintenance, and function of induced regulatory T cells", Journal of Experimental Medicine, vol. 206, No. 13, pp. 3015-3029, 2009.
Guo, et al., "Development of Benzophenone-Alkyne Bifunctional Sigma Receptor Ligands," ChemBioChem (2012), 13(15), 2277-2289.
Hamanishi, et al., "PD-1/PD-L1 blockade in cancer treatment: perspectives and issues", Int. J. Clin. Oncol., vol. 21, pp. 462-473, 2016.
Hankovsky, et al., "New antiarrhythmic agents. 2,2,5,5-Tetramethyl-3-pyrroline-3-carboxamides and 2,2,5,5 tetramethylpyrrolidine-3-carboxamides," Journal of Medicinal Chemistry (1986), 29(7), 1138-52.
He, et al., "Development of PD-1/PD-L1 Pathway in Tumor Immune Microenvironment and Treatment for Non-Small Cell Lung Cancer", Scientific Reports, vol. 5, pp. 1-9, 2015.
International Search Report and WritTen Opinion dated Nov. 12, 2018 for PCT/IN2018/050614.
International Search Report & Written Opinion, dated Feb. 20, 2019, in International Application No. PCT/IN2018/05671.
International Search Report & Written Opinion, dated May 20, 2019 in International Application No. PCT/IN2019/050203.
Labrie, et all., "In vitro activity of novel dual action MDR anthranilamide modulators with inhibitory activity at CYP450," Bioorganic & Medicinal Chemistry (2006), 14(23), 7972-7987.
Lakshmann, et al., "Synthesis and evaluation of novel N-substituted-6 methoxynapthalene-2-carboxamides as potential chemosensitizing agents for cancer," Chemical & Pharmaceutical Bulletin (2008), 56(7), 894-896.
Lai, et al., "A Novel PD-L1-targeting Antagonistic DNA Aptamer With Antitumor Effects", Mol. Therapy—Nucl. Acids, vol. 5, pp. e397, 2016.
Lee, et al., Interferon regulatory factor-1 is prerequisite to the constitutive expression and IFN-y-induced upregulation of B7-H1 (CD274), FEBS Letters, vol. 580, pp. 755-762.
"Letter to the Editors-in-Chief", Thrombosis Research 191, pp. 26-27, 2020.
Leung, et al., "The CD28-B7 Family in Anti-Tumor Immunity: Emerging Concepts in Cancer Immunotherapy", Immune Network, vol. 14, No. 6, pp. 265-276, 2014.
Mohanan, Sunish, et al., "Potential of Peptidylarginine Deiminase Enzymes and Protein Citrullination in Cancer Pathogenesis," Biochemistry Research International, vol. 2012, article ID 895343.
Muenst, et al., "Expression of programmed death ligand 1 (PD-L1) is associated with poor prognosis in human breast cancer", Breast Cancer Res. Treat., vol. 146, No. 1, pp. 15-24, 2014.
Nathan, "Neutrophils and COVID-19: Nots, NETs, and knots", The Journal of Experimental Medicine, vol. 217, No. 9, in 3 pages, 2020.
Neeli et al., "Histone Deimination As a Response to Inflammatory Stimuli in Neutrophils", J. Immunol., vol. 180, pp. 1895-1902, 2008.
Omran, et al., "Synthesis and biological evaluation of a new Donepezil-like Thiaindanones as AChE inhibitors," Journal of Enyzme Inhibition and Medicinal Chemistry (2008), 23(5), 696-703.
Patsoukis, et al., "PD-1 inhibits T cell proliferation by upregulating p27 and p15 and suppressing Cdc25A", Cell Cycle, vol. 11, No. 23, pp. 4305-4309, 2012.
Schönrich, et al., "Neutrophil Extracellular Traps Go Viral", Frontiers in Immunology, vol. 7, No. 366 in 7 pages, 2016.
Sheppard, et al., "PD-1 inhibts T-cell receptor induced phosphorylation of the ZAP70/CD3 signalosome and downstream signaling to PKC0", FEBS Letters, vol. 574, pp. 37-41, 2004.
Smahel, Michal, "PD-1/PD-L1 Blockade Therapy for Tumors with Downregulated MHC Class I Expresssion", Int. J. Mol. Sci., vol. 18, No. 6, pp. 1331, 2017.
Topalian, et al., "Targeting the PD-1/B7-H1 (PD-L1) pathway to activate anti-tumor immunity", Curr. Opin. Immunol., vol. 24, No. 2, pp. 207-212, 2012.
Vinay, et al., "Immune evasion in cancer: Mechanistic basis and therapeutic strategies", Seminars In Cancer Biology, vol. 35, pp. S185-S198, 2015.
Wang, Shu, et al., "Peptidylarginine deiminases in citrullination, gene regulation, health and pathogenesis," Biochim Biophys Acta, Oct. 2013; 1829 (10): 1126-1135.
Wang, et al., "Prognostic sigificance of PD-L1 in solid tumor", Medicine Baltimore, vol. 96, No. 18, pp. e6369, 2017.
Wang, et al., "PD-LI expression in human cancers and its association with clinical outcomes", Oncotargets and Therapy, vol. 9, pp. 5023-5039, 2016.
Wei, Lianhu, et al., "Novel Inhibitors of Protein Arginine Deiminase with Potential Activity in Multiple Sclerosis Animal Model," Journal of Medicinal Chemistry, 2013, 56, 1715-1722.
Zamarron, et al., "Dual Roles of Immune Cells and Their Factors in Cancer Development and Progression", Intl. J. Biol. Sciences, vol. 7, No. 5, pp. 651-658, 2011.
Zawrotniak, et al., "Neutrophil extracellular traps (NETs)—formation and implications", ACTA Biochimica Polonica, vol. 60, No. 3, pp. 277-284, 2013.
Zhuravel, et al, "Solution-phase synthesis of a combinatorial library of 3-[4-(Coumarin-3-yl)1,3thiazol-2-ylcarbamoyl]propanoic acid amides," Molecules (2005), 10(2), 444-456.
Zou, et al., "Neutrophil extracellular traps in COVID-19", JCI Insight, vol. 5, No. 11, pp. 1-11, 2020.
Zou, et al., "PD-L1 (B7-H1) and PD-1 pathway blockade for cancer therapy: Mechanisms, response biomarkers, and combinations", Sci. Transl. Med., vol. 8, No. 328, pp. 328rv4, 2016.
Chemical Abstracts, STN Registry Database, Record for RN 1648388-87-7, Entered into STN Feb. 16, 2015.
Cromwell, et al., "Amino ketones. III. B-Tetrahydroisoquinlino ketones and derivatives. Reaction with Grignard reagents," Journal of the American Chemical Society (1944), 66, 872-3.
Evans, et al. "Phenoxyacetic acids as PPAR partial agonists: Synthesis, optimization, and in vivo efficacy," Bioorganic & Medicinal Chemistry Letters (2011), 21(8), 2345-2350.
Fukagawa, Tomokichi, "The biuret reaction. VII. Primary-Quarternary bases which give the biuret reaction," Z. physiol. Chem. (1931), 201, 40-6.
Goi, et al., "Synthesis and pharmacological properties of pyridinecarbonyl derivatives of 7-substituted theophyllines," Chimica Therapeutica (1973), 8(6), 634-7.
Hwang, et al., "Synthesis and Evaluation of methylsufonylnitrobenzamides (MSNBAs) as inhibtors of the thyroid hormone receptr-coactivator interaction," Bioorganic & Medicinal Chemistry Letters (2013), 23(6), 1891-1895.
Ivaschenko, et al., "Synthesis, biological evaluation and in silico modeling of novel integrase strand transfer inhibtors (INSTIs)," European Journal of Medicinal Chemistry (2020), 190, 112064.
Nicolaou, et al., "Synthesis of imides, N-acyl vinylogous carbamates and ureas, and nitriles by oxidation of amides and amines with Dess-Martin periodinane," Angewandte Chemie, International Edition (2005), 44(37), 5992-5997.
Piper, et al., "Synthesis of potential inhibtors of hypoxanthine-guanine phosphoribosyltransferase for testing as antiprotozoal agents. 1. 7-Substituted 6oxopurines," Journal of Medicinal Chemistry (1980), 23(4), 357-64.
Spassova, et al., "Synthesis of N-(3-azido-2 hydroxpropyl), N(3-phthalimido-2-hydroxpropyl) and N(-3-amino-2 hydroxpropyl) derivatives of heterocyclic bases," Collection of Czechoslovak Chemical Communications (1994), 59(5), 1153-74.
Uenishi, et al, "Structural effects of diazonaphthoquinone-photoactivecompound backbone on resist lithographic properties," Proceedings of SPIE-The International Society for Optical Engineering (1991), 1466(Adv. Resist Technol. Process. 8), 102-16.

(56) References Cited

OTHER PUBLICATIONS

Vooturi, et al., "Solution-phase parallel synthesis of novel membrane-targeted antibiotics," Journal of Combinatorial Chemistry (2010), 12(1), 151-160.
Zajdel, et al, "Solid-phase synthesis of aryl-alkylamine derivatives using protected aminoalchohol building blocks on SynPhase lanterns," QSAR & Combinatorial Science (2007), 26(2), 215-219.

* cited by examiner

IMIDAZO-PYRIDINE COMPOUNDS AS PAD INHIBITORS

PRIORITY AND CROSS REFERENCE TO RELATED APPLICATIONS

This application is the U.S. National Stage Application under 35 U.S.C. § 371 of International Application No. PCT/IN2018/050671, filed Oct. 16, 2018, designating the U.S. and published in English as WO 2019/077631 A1 on Apr. 25, 2019, which claims the benefit of Indian Patent Application No. IN 201741037110, filed Oct. 18, 2017.

TECHNICAL FIELD OF THE INVENTION

The present disclosure relates to imidazo-pyridine compounds of Formula (I), (II), and (III) along with their polymorphs, stereoisomers, prodrugs, solvates, co-crystals, intermediates, pharmaceutically acceptable salts, and metabolites thereof which inhibit PAD4 enzyme.

Formula (I)

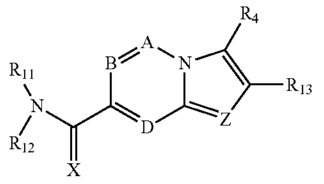

Formula (II)

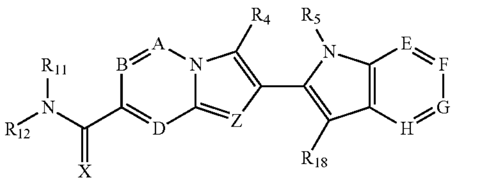

Formula (III)

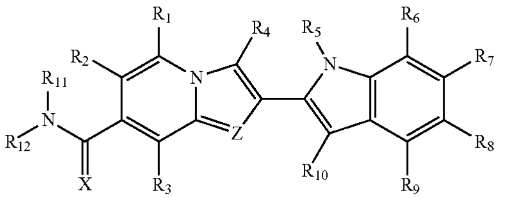

The process for the preparation of the above said heterocyclic compounds of the Formula (I), (II), and (III), their polymorphs, stereoisomers, prodrugs, solvates, co-crystals, intermediates, pharmaceutically acceptable salts, pharmaceutical compositions, and metabolites useful in the preparation of such compounds, are also described herein which are useful in the preparation of such compounds.

The compounds described herein inhibit PAD4 enzyme of the PAD family and may be used in the treatment of various disorders associated with cell division or inflammation.

BACKGROUND OF THE INVENTION

The PAD (protein arginine deiminase) consists of a family of enzymes that afford the process of citrullination in living tissues (J. E. Jones, et al. Curr. Opin. Drug Discov. Devel., 2009, 12, 616-627). The PAD family consists of PAD1, PAD2, PAD3, PAD4, and PAD6 individual enzymes. The enzymes of PAD family affect and regulate various physiological and pathological processes in human body and thus are important.

The elevation in the levels of these enzymes has been implicated in various ailments, for example, cell differentiation (K. Nakashima et al., J. Biol. Chem., 1999, 274, 27786-27792), stem cell pluripotency (M. A. Christophorou et al., Nature, 2014, 507, 104-108), apoptosis (G. Y. Liu, Apoptosis, 2006, 11, 183-196), neutrophil extracellular trap (NET) formation (Y. Wang et al., J. Cell Biol., 2009, 184, 205-213), transcriptional regulation (P. Li et al., Mol. Cell Biol., 2008, 28, 4745-4758), antigen processing in autophagy (J. M. Ireland el al., J. Exp. Med., 2011, 208, 2625-2632), inflammation (D. Makrygiannakis et al., Ann. Rheum. Dis., 2006, 65, 1219-1222), the cornification of skin (E. Candi et al., Nat. Rev. Mol. Cell Biol., 2005, 6, 328-340), demyelination in multiple sclerosis (F. G. Mastronardi et al., J. Neurosci., 2006, 26, 11387-11396), chemokine regulation (T. Loos et al., Blood, 2008, 112, 2648-2656), spinal cord injury repair (S. Lange et al., Dev. Biol., 2011, 355, 205-214), and various normal cellular processes. The elevation in the PAD enzyme levels become a direct cause of the above-mentioned ailments by enchancing the rate of citrullination process.

The enzymes not only catalyze citrullination but also produce autoantibodies that recognize the citrullinated proteins. The introduction of citrulline, resultant of PAD activity, changes both the structure and function of proteins. At physiological activity levels, PADs regulate many cell signaling pathways like cell differentiation, apoptosis, and gene transcription (György et al. Int. J. Biochem. Cell Biol., 2006, 38, 1662-1677). Thus, these enzymes play a crucial role on the pathogenesis of the above-mentioned diseases.

PAD4 has also been known for their involvement in the formation of neutrophil extracellular traps (NETs) and more specifically in the histone citrullination that occurs during NETosis (J. Cedervall, A.-K. Olsson, Oncoscience, 2015, 2(11), 900-901). Thus, PAD4 enzyme is linked to diseases characterized by abnormal levels of neutrophil extracellular traps (NETs). The proposed role of PAD4 in NETosis is pertinent for rheumatoid arthritis (RA) as NETs are deficient in the absence of PAD4 and PAD4 is released extracellulary in RA joints, probably due to the pathological status of RA neutrophils. Therefore, PAD inhibitor drugs would provide significant therapeutic potential because of the fact that NETs are implicated in many diseases.

Examples of some PAD inhibitor compounds are chloro-amidine, fluoro-chloridine and their related analogs that are known and act as mechanism-based inhibitors that irreversibly inactivate PAD4 and other PAD isozymes (H. D. Lewis et al., Nature Chemical Biology, 2015, 11, 189-191). These compounds have utility against rheumatoid arthritis (RA). PAD4, detected in synovial tissue, has been found to be responsible for citrullination of a variety of joint proteins. These citrullinated protein substrates produce anti-citrullinated antibodies which are responsible for disease pathogenesis (Y. Kochi et al., Ann. Rheum. Dis., 2011, 70, 512-515).

Since the compounds that inhibit PAD4 enzyme activity have also been known for reducing pathological activity in numerous ailments, therefore such compounds can be utilized in injuries and disease pathologies. In this way PAD4 inhibitors have wider applicability in the treatment of ailments, specially those related with NETs.

US20050159334 discloses the treatment of RA with the administration of suitable PAD inhibitor, thus the PAD inhibitor compounds have a direct implication in treating RA.

The PAD inhibitor compounds like chloro-amidine has been widely studied to demonstrate their efficacy in a number of animal disease models like, collagen-induced arthritis (V. C. Willis et al., J. Immunol., 2011, 186(7), 4396-4404), dextran sulfate sodium (DSS)-induced experimental colitis (A. A. Chumanevich et al., Am. J. Physiol. Gastrointest. Liver Physiol., 2011, 300(6), G929-G938), lupus-prone MRL/lpr mice atherosclerosis and arterial thrombosis (J. S. Knight et al., Circ. Res., 2014, 114(6), 947-956), spinal cord injury repair (S. Lange et al., Dev. Biol., 2011, 355(2), 205-214), and experimental autoimmune encephalomyelitis (EAE).

Similar to RA, the use of PAD4 inhibitors in the treatment of cancers (J. L. Slack et al., Cellular and Molecular Life Sciences, 2011, 68(4), 709-720) has also been studied earlier. It is suggested that PAD4 inhibitors have an anti-proliferative role as well. PAD4 deiminases arginine residues in histones at the promoters of p53-target genes such as p21, which are involved in cell cycle arrest and induction of apoptosis (P. Li et al., Molecular & Cell Biology, 2008, 28(15), 4745-4758).

The PAD4 inhibitory compounds, as described above, have vast utility. Therefore, the identification of a chemical moiety that facilitates PAD inhibition is necessary. However, the use of PAD inhibitors in various other ailments where dysregulated PAD activity is implicated still needs to be explored. Identification and development of new PAD4 inhibitor compounds treating PAD4 mediated disorders are direly required to treat diseases like example rheumatoid arthritis, vasculitis, systemic lupus erythematosis, cutaneous lupus erythematosis, ulcerative colitis, cancer, cystic fibrosis, asthma, multiple sclerosis and psoriasis efficiently.

SUMMARY OF INVENTION

The present disclosure discloses a compound of Formula I

Formula (I)

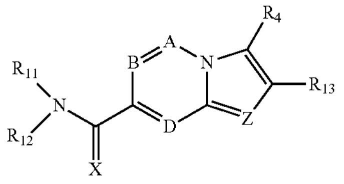

X is selected from O or S; Z is N; A is selected from N or $CR_1$;

B is selected from N or $CR_2$; D is selected from N or $CR_3$; $R_1$, $R_2$, $R_3$, and $R_4$ are independently selected from hydrogen, hydroxyl, cyano, amino, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-6}$ heterocyclyl, $C_{1-6}$ heteroaryl, $C(O)NR_{15}$, $C(O)C_{1-6}$ alkylamino, $C(O)C_{5-6}$ aryl, $C(O)C_{1-6}$ heteroaryl, $C(O)C_{1-6}$ alkyl, $C(O)C_{1-6}$ haloalkyl, $SO_2C_{1-6}$ alkyl, $SO_2C_{1-6}$ haloalkyl, $SO_2C_{3-6}$ cycloalkyl, $SO_2NR_{15}$, $SO_2NC_{1-6}$ alkylamino, $SO_2C_{5-6}$ aryl, or $SO_2C_{1-6}$ heteroaryl, wherein $C_{1-6}$ alkyl, $C_{1-6}$ alkoxy, $C_{1-6}$ heteroaryl, and $C_{1-6}$ haloalkoxy, is optionally substituted with one or more of the groups selected from hydrogen, oxo, $C_{1-6}$ alkyl, $C_{1-6}$ alkoxy, $C_{1-6}$ haloalkyl, $C_{3-6}$ cycloalkyl, $C_{5-10}$ aryl, $C_{1-6}$ heterocyclyl, $C_{1-6}$ heteroaryl, cyano, and hydroxyl; $R_{11}$ is hydrogen; $R_{12}$ is selected from $C_{1-6}$ alkylamino, and 5-10 membered monocyclic or bicyclic saturated heterocyclic ring with 1-3 heteroatoms selected from N, S or O, or $R_{11}$ and $R_{12}$ can be taken together to form a 5-10 membered monocyclic or bicyclic saturated or unsaturated heterocyclic ring with 1-5 heteroatoms selected from N, S or O, wherein the 5-10 membered monocyclic or bicyclic saturated or unsaturated heterocyclic ring is optionally substituted with the substituents selected from amino, $C_{1-6}$ alkylamino, $C_{1-6}$ acylamino, $—NHC(NH)CH_2Cl$, $—NH(CO)CH{=}CH—CH_2—N(CH_3)_2$, $C_{1-6}$ alkyl, halogen, $C_{1-6}$ alkoxy, or hydroxyl; $R_{13}$ is selected from hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-10}$ heterocyclyl, $C_{1-10}$ heteroaryl, $C(O)C_{1-6}$ alkyl, $C(O)C_{1-6}$ haloalkyl, $C(O)NR_{15}$, $C(O)C_{1-6}$ alkylamino, $C(O)C_{5-6}$ aryl, $C(O)C_{1-6}$ heteroaryl, $SO_2C_{1-6}$ alkyl, $SO_2C_{1-6}$ haloalkyl, $SO_2C_{3-6}$ cycloalkyl, $SO_2NR_{15}$, $SO_2NC_{1-6}$ alkylamino, $SO_2C_{5-6}$ aryl, or $SO_2C_{1-6}$ heteroaryl, wherein $C_{1-6}$ alkyl, $C_{1-6}$ alkoxy, $C_{3-6}$ cycloalkyl, $C_{5-10}$ aryl, $C_{1-10}$ heterocyclyl, and $C_{1-10}$ heteroaryl, is optionally substituted with one or more of the groups selected from hydrogen, $C_{1-6}$ alkyl, $C_{1-6}$ haloalkyl, $C_{1-6}$ alkoxy, $C_{3-6}$ cycloalkyl, $C_{5-6}$ aryl, $C_{1-6}$ heteroaryl, $C_{1-6}$ heterocyclyl, oxo, halogen, hydroxyl, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, $—CH_2OH$, and cyano; and $R_{15}$ is selected from the group consisting of hydrogen, $C_{1-6}$ alkyl, and combinations thereof.

The present disclosure also describes compound of Formula II

Formula (II)

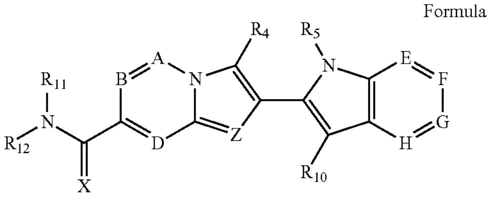

X is selected from O or S; Z is N; A is selected from N or $CR_1$; B is selected from N or $CR_2$; D is selected from N or $CR_3$; E is selected from N or $CR_6$; F is absent or is selected from N, and $CR_7$; G is absent or is selected from N, and $CR_8$; H is absent or is selected from N, and $CR_9$; $R_1$, $R_2$, $R_3$, $R_4$, $R_5$, $R_6$, $R_7$, $R_8$, $R_9$ and $R_{10}$ are independently selected from hydrogen, hydroxyl, cyano, amino, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-10}$ heterocyclyl, $C_{1-10}$ heteroaryl, $C(O)C_{1-6}$ alkyl, $C(O)C_{1-6}$ haloalkyl, $C(O)NR_{15}$, $C(O)C_{1-6}$ alkylamino, $C(O)C_{5-6}$ aryl, $C(O)C_{1-6}$ heteroaryl, $SO_2C_{1-6}$ alkyl, $SO_2C_{1-6}$ haloalkyl, $SO_2C_{3-6}$ cycloalkyl, $SO_2NR_{15}$, $SO_2NC_{1-6}$ alkylamino, $SO_2C_{5-6}$ aryl, or $SO_2C_{1-6}$ heteroaryl, wherein $C_{1-6}$ alkyl, $C_{1-6}$ alkoxy, $C_{1-10}$ heteroaryl, and $C_{1-6}$ haloalkoxy, is optionally substituted with one or more of the groups selected from hydrogen, oxo, $C_{1-6}$ alkyl, $C_{1-6}$ alkoxy, $C_{1-6}$ haloalkyl, $C_{1-6}$ alkylhydroxy, $C_{3-6}$ cycloalkyl, $C_{5-9}$ aryl, $C_{1-6}$ heterocyclyl, $C_{1-6}$ heteroaryl, cyano, halogen, and hydroxyl, wherein $C_{5-9}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano;

$R_{11}$ and $R_{12}$ are taken together to form a 5-10 membered monocyclic or bicyclic saturated or unsaturated heterocyclic ring with 1-5 heteroatoms selected from N, S or O, wherein the 5-10 membered monocyclic or bicyclic saturated or unsaturated heterocyclic ring is optionally substituted with the substituents selected from amino, $C_{1-6}$ alkylamino, $C_{1-6}$ acylamino, —NHC(NH)$CH_2Cl$, NH(CO)CH═CH—$CH_2$—N$(CH_3)_2$, $C_{1-6}$ alkyl, halogen, $C_{1-6}$ alkoxy, or hydroxyl; and $R_{15}$ is selected from the group consisting of hydrogen, $C_{1-6}$ alkyl, and combinations thereof.

The present disclosure further describes compound of Formula III

Formula (III)

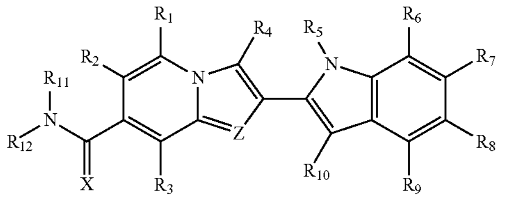

X is selected from O or S; Z is N; $R_1$, $R_2$, $R_3$, $R_4$, $R_5$, $R_6$, $R_7$, $R_8$, $R_9$ and $R_{10}$ are independently selected from hydrogen, hydroxyl, cyano, amino, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-10}$ heterocyclyl, $C_{1-10}$ heteroaryl, C(O)$C_{1-6}$ alkyl, C(O)$C_{1-6}$ haloalkyl, C(O)$NR_{15}$, C(O)$C_{1-6}$ alkylamino, C(O)$C_{5-6}$ aryl, C(O)$C_{1-6}$ heteroaryl, $SO_2C_{1-6}$ alkyl, $SO_2C_{1-6}$ haloalkyl, $SO_2C_{3-6}$ cycloalkyl, $SO_2NR_{15}$, $SO_2NC_{1-6}$ alkylamino, $SO_2C_{5-6}$ aryl, or $SO_2C_{1-6}$ heteroaryl, wherein $C_{1-6}$ alkyl, $C_{1-6}$ alkoxy, $C_{1-10}$ heteroaryl, and $C_{1-6}$ haloalkoxy, is optionally substituted with one or more of the groups selected from hydrogen, oxo, $C_{1-6}$ alkyl, $C_{1-6}$ alkoxy, $C_{1-6}$ haloalkyl, $C_{1-6}$ alkylhydroxy, $C_{3-6}$ cycloalkyl, $C_{5-9}$ aryl, $C_{1-6}$ heterocyclyl, $C_{1-6}$ heteroaryl, cyano, halogen, and hydroxyl, wherein $C_{5-9}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano;

$R_{11}$ and $R_{12}$ are taken together to form a 5-10 membered monocyclic or bicyclic saturated or unsaturated heterocyclic ring with 1-5 heteroatoms selected from N, S or O, wherein the 5-10 membered monocyclic or bicyclic saturated or unsaturated heterocyclic ring is optionally substituted with the substituents selected from amino, $C_{1-6}$ alkylamino, $C_{1-6}$ acylamino, —NHC(NH)$CH_2Cl$, NH(CO)CH═CH—$CH_2$—N$(CH_3)_2$, $C_{1-6}$ alkyl, halogen, $C_{1-6}$ alkoxy, or hydroxyl; and $R_{15}$ is selected from the group consisting of hydrogen, $C_{1-6}$ alkyl, and combinations thereof.

The present disclosure further describes the process of preparation of compounds of Formula (I), Formula (II), and Formula (III) or its polymorphs, stereoisomers, prodrugs, solvates, co-crystals, intermediates, pharmaceutically acceptable salts, and metabolites thereof.

The present disclosure further discloses a pharmaceutical composition comprising a compound of Formula (I), Formula (II), and Formula (III) or a pharmaceutically acceptable salt thereof, together with a pharmaceutically acceptable carrier, optionally in combination with one or more other pharmaceutical compositions.

The present disclosure further discloses a method for inhibiting one or more PAD family in a cell with an effective amount of the compound of the present disclosure.

The present disclosure further discloses a method of treating a condition mediated by one or more PAD's, the method comprising administering to a subject suffering from a condition mediated by one or more PAD family, a therapeutically effective amount of the compound of Formula (I), Formula (II), and Formula (III) or the pharmaceutical composition of the present disclosure with other clinically relevant agents or biological agents to a subject in need thereof.

The present disclosure further discloses a compound of Formula (I), Formula (II) and Formula (III) used for the treatment of rheumatoid arthritis, vasculitis, systemic lupus erythematosus, ulcerative colitis, cancer, cystic fibrosis, asthma, cutaneous lupus erythematosis, and psoriasis.

These and other features, aspects, and advantages of the present subject matter will become better understood with reference to the following description. This summary is provided to introduce a selection of concepts in a simplified form. This summary is not intended to identify key features or essential features of the disclosure, nor is it intended to be used to limit the scope of the subject matter.

DETAILED DESCRIPTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

Throughout the description and the claims which follow, unless the context requires otherwise, the word "comprise", and variations such as "comprises" and "comprising", will be understood to imply the inclusion of a stated integer or step or group of integers but not to the exclusion of any other integer or step or group of integers or steps.

The term "including" is used to mean "including but not limited to". "Including" and "including but not limited to" are used interchangeably.

In the structural formulae given herein and throughout the present disclosure, the following terms have been indicated meaning, unless specifically stated otherwise.

Furthermore, the compound of Formula (I), Formula (II), and Formula (III) can be its derivatives, analogs, stereoisomer's, diastereomers, geometrical isomers, polymorphs, solvates, co-crystals, intermediates, metabolites, prodrugs or pharmaceutically acceptable salts and compositions.

The compounds of Formula (I), Formula (II), and Formula (III) and their polymorphs, stereoisomers, prodrugs, solvates, co-crystals, intermediates, pharmaceutically acceptable salts, and metabolites thereof can also be referred as "compounds of the present disclosure".

The compounds according to Formula (I), Formula (II), and Formula (III) contain one or more asymmetric centres (also referred to as a chiral centres) and may, therefore, exist as individual enantiomers, diastereoisomers, or other stereoisomeric forms, or as mixtures thereof. Chiral centres, such as chiral carbon atoms, may also be present in a substituent such as an alkyl group. Where the stereochemistry of a chiral centre present in Formula (I), Formula (II), and Formula (III), or in any chemical structure illustrated herein, is not specified, the structure is intended to encompass any stereoisomer and all mixtures thereof. Thus, compounds according to Formula (I), Formula (II), and Formula (III) containing one or more chiral centres may be used as racemic modifications including racemic mixtures and racemates, enantiomerically-enriched mixtures, or as enantiomerically-pure individual stereoisomers.

Individual stereoisomers of a compound according to Formula (I), Formula (II), and Formula (III) which contain one or more asymmetric centres may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. It will be appreciated that where the desired stereoisomer is converted into another chemical entity by one of the separation procedures described above, a further step is required to liberate the desired form.

Alternatively, specific stereoisomers may be synthesised by asymmetric synthesis using optically active reagents, substrates, catalysts or solvents, or by converting one enantiomer to the other by asymmetric transformation.

It is to be understood that the references herein to compounds of Formula (I), Formula (II), and Formula (III) nd salts thereof covers the compounds of Formula (I), Formula (II), and Formula (III) as free bases, or as salts thereof, for example as pharmaceutically acceptable salts thereof. Thus, in one embodiment, the invention is directed to compounds of Formula (I), Formula (II), and Formula (III) as the free base. In another embodiment, the invention is directed to compounds of Formula (I), Formula (II), and Formula (III) and salts thereof. In a further embodiment, the invention is directed to compounds of Formula (I), Formula (II), and Formula (III) and pharmaceutically acceptable salts thereof.

It will be appreciated that pharmaceutically acceptable salts of the compounds according to Formula (I, II, and III) may be prepared. Indeed, in certain embodiments of the invention, pharmaceutically acceptable salts of the compounds according to Formula (I), Formula (II), and Formula (III) may be preferred over the respective free base because such salts impart greater stability or solubility to the molecule thereby facilitating formulation into a dosage form. Accordingly, the invention is further directed to compounds of Formula (I), Formula (II), and Formula (III) and pharmaceutically acceptable salts thereof.

"Enantiomeric excess" (ee) is the excess of one enantiomer over the other expressed as a percentage. In a racemic modification, since both enantiomers are present in equal amounts, the enantiomeric excess is zero (0% ee). However, if one enantiomer were enriched such that it constitutes 95% of the product, then the enantiomeric excess would be 90% ee (the amount of the enriched enantiomer, 95%, minus the amount of the other enantiomer, 5%).

"Enantiomerically enriched" refers to products whose enantiomeric excess (ee) is greater than zero. For example, 'enantiomerically enriched' refers to products whose enantiomeric excess is greater than 50% ee, greater than 75% ee, and greater than 90% ee. 'Enantiomerically pure' refers to products whose enantiomeric excess is 99% or greater.

Included within the scope of the 'compounds of the invention' are all solvates (including hydrates), complexes, polymorphs, prodrugs, radiolabelled derivatives, and stereoisomers of the compounds of Formula (I), Formula (II), and Formula (III) and salts thereof.

The compounds of the invention may exist in solid or liquid form. In the solid state, the compounds of the invention may exist in crystalline or non-crystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. Solvates may involve non-aqueous solvents such as ethanol, iso-propyl alcohol, N,N-dimethylsulfoxide (DMSO), acetic acid, ethanolamine, and ethyl acetate, or they may involve water as the solvent that is incorporated into the crystalline lattice. Solvates wherein water is the solvent that is incorporated into the crystalline lattice are typically referred to as 'hydrates'. Hydrates include stoichiometric hydrates as well as compositions containing variable amounts of water. The invention includes all such solvates.

It will be further appreciated that certain compounds of the invention that exist in crystalline form, including the various solvates thereof, may exhibit polymorphism (i.e. the capacity to occur in different crystalline structures). These different crystalline forms are typically known as 'polymorphs'. The invention includes such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. It will be appreciated that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The invention also includes isotopically-labelled compounds, which are identical to the compounds of Formula (I, II, and III) and salts thereof, but for the fact that one or more atoms are replaced by an atom having an atomic mass or mass number different from the atomic mass or mass number most commonly found in nature. Examples of isotopes that can be incorporated into the compounds of the invention include isotopes of hydrogen, carbon, nitrogen, oxygen and fluorine, such as $^{3}H$, $^{11}C$, $^{14}C$ and $^{18}F$.

The term "co-crystals" refers to solids that are crystalline single phase materials composed of two or more different molecular and/or ionic compounds generally in a stoichiometric ratio which are neither solvates nor simple salts.

The term "substituted" in reference to a group indicates that a hydrogen atom attached to a member atom within a group is replaced. It should be understood that the term 'substituted' includes the implicit provision that such substitution be in accordance with the permitted valence of the substituted atom and the substituent and that the substitution results in a stable compound (i.e. one that does not spontaneously undergo transformation such as rearrangement, cyclisation, or elimination). In certain embodiments, a single atom may be substituted with more than one substituent as long as such substitution is in accordance with the permitted valence of the atom. Suitable substituents are defined herein for each substituted or optionally substituted group.

The term "polymorphs" refers to crystal forms of the same molecule, and different polymorphs may have different physical properties such as, for example, melting temperatures, heats of fusion, solubilities, dissolution rates and/or vibrational spectra as a result of the arrangement or conformation of the molecules in the crystal lattice.

The term "prodrugs" refers to the precursor of the compound of Formula (I, II, and III) which on administration undergoes chemical conversion by metabolic processes before becoming active pharmacological substances. In general, such prodrugs will be functional derivatives of a compound of the invention, which are readily convertible in vivo into a compound of the invention.

The term "alkyl" refers to a saturated hydrocarbon chain having the specified number of carbon atoms. For example, which are not limited, $C_{1-6}$ alkyl refers to an alkyl group having from 1-6 carbon atoms, or 1-3 carbon atoms. Alkyl groups may be straight or branched chained groups. Representative branched alkyl groups have one, two, or three branches. Preferred alkyl groups include, without limitation, methyl, ethyl, n-propyl, isopropyl, butyl, and isobutyl.

The term "C(O) alkyl" refers to an alkyl group as defined above attached via carbonyl linkage to the rest of the molecule. For example, $C(O)C_{1-6}$ alkyl refers to an alkyl group having from 1-6 carbon atoms, or 1-3 carbon atoms attached via carbonyl linkage to the rest of the molecule. Preferred C(O) alkyl groups include, without limitation, —$C(O)CH_3$, —$C(O)CH_2CH_3$, and the like.

The term "$SO_2$ alkyl" refers to an alkyl group as defined above attached via sulfonyl linkage to the rest of the molecule. For example, $SO_2C_{1-6}$ alkyl refers to an alkyl group having from 1-6 carbon atoms, or 1-3 carbon atoms attached via sulfonyl linkage to the rest of the molecule. Preferred $SO_2$ alkyl groups include, without limitation, —$SO_2CH_3$, —$SO_2CH_2CH_3$, and the like.

The term "alkoxy" refers to an alkyl group attached via an oxygen linkage to the rest of the molecule. For example, $C_{1-6}$ alkoxy refers to an alkyl group having from 1-6 carbon atoms, or 1-3 carbon atoms attached via an oxygen linkage to the rest of the molecule. Preferred alkoxy groups include, without limitation, —$OCH_3$ (methoxy), —$OC_2H_5$(ethoxy) and the like.

The term "alkylamino" refers to an alkyl group as defined above attached via amino or alkyl linkage to the rest of the molecule. For example, $C_{1-6}$ alkylamino refers to an alkyl group having from 1-6 carbon atoms, or 1-3 carbon atoms attached via amino linkage to the rest of the molecule. Preferred alkylamino groups include, without limitation, —$NHCH_3$, —$N(CH_3)_2$, and the like.

The term "C(O)NR" refers to an alkylamino group as defined above attached via a carbonyl linkage to the rest of the molecule. Preferred C(O)NR groups include, $C(O)NCH_3$, $C(O)NCH_2CH_3$, and the like.

The term "$SO_2NR$" refers to an alkylamino group as defined above attached via a sulfonyl linkage to the rest of the molecule. Preferred $SO_2NR$ groups include, $SO_2NCH_3$, $SO_2NCH_2CH_3$, and the like.

The term "C(O) alkylamino" refers to an alkylamino group as defined above attached via carbonyl linkage to the rest of the molecule. For example, $C(O)C_{1-6}$ alkylamino refers to an alkylamino group having from 1-6 carbon atoms, or 1-3 carbon atoms attached via carbonyl linkage to the rest of the molecule. Preferred C(O) alkylamino groups include, without limitation, —$C(O)NHCH_3$, —$C(O)N(CH_3)_2$, and the like.

The term "$SO_2$ alkylamino" refers to an alkylamino group as defined above attached via sulfonyl linkage to the rest of the molecule. For example, $SO_2C_{1-6}$ alkylamino refers to an alkylamino group having from 1-6 carbon atoms, or 1-3 carbon atoms attached via sulfonyl linkage to the rest of the molecule. Preferred $SO_2$ alkylamino groups include, without limitation, —$SO_2NHCH_3$, —$SO_2N(CH_3)_2$, and the like.

The term "acylamino" refers to an acyl group attached via carbonyl linkage to the rest of the molecule. For example, $C_{1-6}$ acylamino refers to an acyl group having from 1-6 carbon atoms, or 1-3 carbon atoms attached via amino linkage to the rest of the molecule. Preferred acylamino groups include, without limitation, —$(CO)NHCH_3$, —$(CO)N(CH_3)_2$, and the like.

The term "haloalkyl" refers to an alkyl group as defined above containing halogen and attached via alkyl linkage to the rest of the molecule. For example, $C_{1-6}$ haloalkyl refers to an alkyl group having from 1-6 carbon atoms, or 1-3 carbon atoms attached via halo linkage to the rest of the molecule. Preferred haloalkyl groups include, without limitation, —$CH_2Cl$, —$CHCl_2$, and the like.

The term "C(O) haloalkyl" refers to an haloalkyl group as defined above attached via carbonyl linkage to the rest of the molecule. For example, $C(O)C_{1-6}$ haloalkyl refers to an haloalkyl group having from 1-6 carbon atoms, or 1-3 carbon atoms attached via carbonyl linkage to the rest of the molecule. Preferred C(O) haloalkyl groups include, without limitation, —$(CO)CH_2Cl$, —$C(O)CHCl_2$, and the like.

The term "$SO_2$ haloalkyl" refers to an haloalkyl group as defined above attached via sulfonyl linkage to the rest of the molecule. For example, $SO_2C_{1-6}$ haloalkyl refers to an haloalkyl group having from 1-6 carbon atoms, or 1-3 carbon atoms attached via sulfonyl linkage to the rest of the molecule. Preferred $SO_2$ haloalkyl groups include, without limitation, —$SO_2CH_2Cl$, —$SO_2CHCl_2$, and the like.

The term "haloalkoxy" refers to an alkoxy group as defined above attached via oxygen linkage to the rest of the molecule. For example, $C_{1-6}$ haloalkoxy refers to an alkoxy group having from 1-6 carbon atoms, or 1-3 carbon atoms attached via halo linkage to the rest of the molecule. Preferred haloalkoxy groups include, without limitation, —$OCH_2Cl$, —$OCHCl_2$, and the like.

The term "halogen" refers to a halogen radical, for example, fluoro, chloro, bromo, or iodo. "Haloalkyl" refers to an alkyl group, as herein before defined, in which at least one of the hydrogen atoms has been replaced with a halogen radical. "$C_{1-6}$ haloalkyl" refers to a $C_{1-6}$ alkyl group in which at least one of the hydrogen atoms has been replaced with a halogen radical. An example of 'haloalkyl' is trifluoromethyl or 2,2,2-trifluoroethyl.

The term "cycloalkyl" refers to a saturated hydrocarbon ring having a specified number of carbon atoms. For example, which are not limited, $C_{3-6}$ cycloalkyl refers to a cycloalkyl group having from 3 to 6 member atoms, or 3 member atoms. Preferred cycloalkyl groups include, without limitation, cyclopropyl, cyclobutyl, cyclopentyl, cyclohexyl, groups and the like.

The term "$SO_2C_{3-6}$ cycloalkyl" refers to an cycloalkyl group as defined above attached via sulfonyl linkage to the rest of the molecule. For example, $SO_2C_{3-6}$ cycloalkyl refers to a cycloalkyl group having from 3-6 carbon atoms attached via sulfonyl linkage to the rest of the molecule. Preferred $SO_2$ cycloalkyl groups include, without limitation, —$SO_2C_3$ cycloalkyl, and the like.

The term "aryl" refers to aromatic ring having a specified number of carbon atoms. For example, $C_{5-6}$ aryl refers to an aryl group having 5 or 6 member atoms, or 6 member atoms. Preferred aryl groups include, without limitation, phenyl, and the like.

The term "C(O) aryl" refers to an aryl group as defined above attached via carbonyl linkage to the rest of the molecule. For example, $C(O)C_{5-6}$ aryl refers to an alkyl group having from 5-6 carbon atoms attached via carbonyl linkage to the rest of the molecule. Preferred C(O) aryl groups include, without limitation, —$C(O)C_6H_5$, —C(O) $C_5H_5$, and the like.

The term "$SO_2$ aryl" refers to an aryl group as defined above attached via sulfonyl linkage to the rest of the molecule. For example, $SO_2C_{5-6}$ aryl refers to an aryl group having from 5-6 carbon atoms attached via sulfonyl linkage to the rest of the molecule. Preferred $SO_2$ aryl groups include, without limitation, —$SO_2C_6H_5$, —$SO_2C_5H_5$, and the like.

The term "heteroaryl" refers to aromatic rings containing from 1 to 3 heteroatoms in the ring. "Heteroaryl" groups may be substituted with one or one or more substituents if so defined herein. The "$C_{1-6}$ heteroaryl" rings having 1 or 6 carbon as member atoms. The "heteroaryl" includes pyridinyl, tetrazolyl and pyrazolyl. "Heteroatom" refers to a nitrogen, sulfur, or oxygen atom, for example a nitrogen atom or an oxygen atom.

The term "C(O) heteroaryl" refers to an heteroaryl group as defined above attached via carbonyl linkage to the rest of the molecule. For example, $C(O)C_{1-6}$ heteroaryl refers to an alkyl group having from 1-6 carbon atoms attached via carbonyl linkage to the rest of the molecule. Preferred C(O) heteroaryl groups include, without limitation, —C(O) pyridinyl, —C(O) pyrazolyl, and the like.

The term "$SO_2$ heteroaryl" refers to an aryl group as defined above attached via sulfonyl linkage to the rest of the molecule. For example, $SO_2C_{1-6}$ heteroaryl refers to an aryl group having from 1-6 carbon atoms attached via sulfonyl linkage to the rest of the molecule. Preferred $SO_2$ heteroaryl groups include, without limitation, —$SO_2$ pyridinyl, —$SO_2$ pyrazolyl, and the like.

The term "heterocyclic" and "heterocyclyl" refer to saturated or unsaturated monocyclic aliphatic rings containing 5, 6, or 7 ring members including 1 or 2 heteroatoms or to saturated or unsaturated bicyclic aliphatic rings containing 5, 6 or 7 ring members including 1 or 2 heteroatoms. In certain embodiments, 'heterocyclyl' groups are saturated. In other embodiments, 'heterocyclyl' groups are unsaturated. 'Heterocyclyl' groups containing more than one heteroatom may contain different heteroatoms. 'Heterocyclyl' groups may be substituted with one or more substituents as defined herein. 'Heterocyclyl' includes piperidinyl, tetrahydropyranyl, azepinyl, oxazepinyl, azabicyclo[3.1.0]hexanyl.

The phrase "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free base form with a suitable acid.

Salts and solvates having non-pharmaceutically acceptable counter-ions or associated solvents are within the scope of the present invention, for example, for use as intermediates in the preparation of other compounds of Formula (I), Formula (II), and Formula (III) and their pharmaceutically acceptable salts. Thus one embodiment of the invention embraces compounds of Formula (I), Formula (II), and Formula (III) and salts thereof. Compounds according to Formula (I), Formula (II), and Formula (III) contain a basic functional group and are therefore capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenyl acetate, propionate, butyrate, iso-butyrate, valerate, maleate, hydroxymaleate, acrylate, fumarate, malate, tartrate, citrate, salicylate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, naphthoate, hydroxynaphthoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), aminobenzenesulfonate, p-toluenesulfonate (tosylate), and naphthalene-2-sulfonate.

The term "PAD inhibitor" or "inhibitor of PAD" is used to identify a compound, which is capable of interacting with neutrophil extracellular traps (NETs) and more specifically in the histone citrullination that occurs during NETosis. Inhibiting PAD4 enzymatic activity means reducing the ability of PAD4 enzyme so as to inhibit the formation of citrulline through citrullination process. Preferably, such inhibition is specific to PAD4 enzyme.

A term once described, the same meaning applies for it, throughout the patent.

Despite of the vast utility of the PAD4 inhibitory compounds, as described above, the identification of a chemical moiety that facilitates PAD inhibition still remains a problem. Identification and development of new PAD4 inhibitor compounds treating PAD4 mediated disorders are direly required to treat diseases like example rheumatoid arthritis, vasculitis, systemic lupus erythematosis, cutaneous lupus erythematosis, ulcerative colitis, cancer, cystic fibrosis, asthma, multiple sclerosis and psoriasis.

In an embodiment of the present disclosure, there is provided a compound of Formula I their polymorphs, stereoisomers, prodrugs, solvates, co-crystals, intermediates, pharmaceutically acceptable salts, and metabolites thereof, wherein Formula (I)

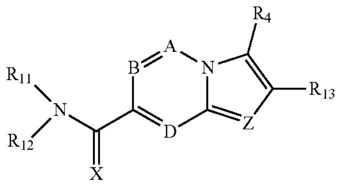

X is selected from O or S; Z is N; A is selected from N or $CR_1$;

B is selected from N or $CR_2$; D is selected from N or $CR_3$; $R_1$, $R_2$, $R_3$, and $R_4$ are independently selected from hydrogen, hydroxyl, cyano, amino, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-6}$ heterocyclyl, $C_{1-6}$ heteroaryl, $C(O)NR_{15}$, $C(O)C_{1-6}$ alkylamino, $C(O)C_{5-6}$ aryl, $C(O)C_{1-6}$ heteroaryl, $C(O)C_{1-6}$ alkyl, $C(O)C_{1-6}$ haloalkyl, $SO_2C_{1-6}$ alkyl, $SO_2C_{1-6}$ haloalkyl, $SO_2C_{3-6}$ cycloalkyl, $SO_2NR_{15}$, $SO_2NC_{1-6}$ alkylamino, $SO_2C_{5-6}$ aryl, or $SO_2C_{1-6}$ heteroaryl, wherein $C_{1-6}$ alkyl, $C_{1-6}$ alkoxy, $C_{1-6}$ heteroaryl, and $C_{1-6}$ haloalkoxy, is optionally substituted with one or more of the groups selected from hydrogen, oxo, $C_{1-6}$ alkyl, $C_{1-6}$ alkoxy, $C_{1-6}$ haloalkyl, $C_{3-6}$ cycloalkyl, $C_{5-10}$ aryl, $C_{1-6}$ heterocyclyl, $C_{1-6}$ heteroaryl, cyano, and hydroxyl; $R_{11}$ is hydrogen; $R_{12}$ is selected from $C_{1-6}$ alkylamino, and 5-10 membered monocyclic or bicyclic saturated heterocyclic ring with 1-3 heteroatoms selected from N, S or O, or $R_{11}$ and $R_{12}$ can be taken together to form a 5-10 membered monocyclic or bicyclic saturated or unsaturated heterocyclic ring with 1-5 heteroatoms selected from N, S or O, wherein the 5-10 membered monocyclic or bicyclic saturated or unsaturated heterocyclic ring is optionally substituted with the substituents selected from amino, $C_{1-6}$ alkylamino, $C_{1-6}$ acylamino, —NHC(NH)$CH_2Cl$, —NH(CO)CH═CH—$CH_2$—$N(CH_3)_2$, $C_{1-6}$ alkyl, halogen, $C_{1-6}$ alkoxy, or hydroxyl; $R_{13}$ is selected from hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-10}$ heterocyclyl, $C_{1-10}$ heteroaryl, $C(O)C_{1-6}$ alkyl, $C(O)C_{1-6}$ haloalkyl, $C(O)NR_{15}$, $C(O)C_{1-6}$ alkylamino, $C(O)C_{5-6}$ aryl, $C(O)C_{1-6}$ heteroaryl, $SO_2C_{1-6}$ alkyl, $SO_2C_{1-6}$ haloalkyl, $SO_2C_{3-6}$ cycloalkyl, $SO_2NR_{15}$, $SO_2NC_{1-6}$ alkylamino, $SO_2C_{5-6}$ aryl, or $SO_2C_{1-6}$ heteroaryl, wherein $C_{1-6}$ alkyl, $C_{1-6}$ alkoxy, $C_{3-6}$ cycloalkyl, $C_{5-10}$ aryl, $C_{1-10}$ heterocyclyl, and $C_{1-10}$ heteroaryl, is optionally substituted with one or more of the groups selected from hydrogen, $C_{1-6}$ alkyl, $C_{1-6}$ haloalkyl, $C_{1-6}$ alkoxy, $C_{3-6}$ cycloalkyl, $C_{5-6}$ aryl, $C_{1-6}$ heteroaryl, $C_{1-6}$ heterocyclyl, oxo, halogen, hydroxyl, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano; and $R_{15}$ is selected from the group consisting of hydrogen, $C_{1-6}$ alkyl, and combinations thereof.

In an embodiment of the present disclosure, there is provided a compound of Formula I as described herein, wherein X is selected from O or S; Z is N; A is selected from N or $CR_1$; B is selected from N or $CR_2$; D is selected from N or $CR_3$; $R_1$, $R_2$, $R_3$, and $R_4$ are independently selected from hydrogen, hydroxyl, cyano, amino, halogen, $C_{1-4}$ alkyl, $C_{1-4}$ alkoxy, $C_{3-6}$ cycloalkyl, $C_{1-4}$ haloalkyl, $C_{1-4}$ haloalkoxy, $C_{1-4}$ acylamino, $C_{1-4}$ alkylamino, $C_{5-6}$ aryl, $C_{1-6}$ heterocyclyl, $C_{1-6}$ heteroaryl, $C(O)NR_{15}$, $C(O)C_{1-4}$ alkylamino, C(O) $C_{5-6}$ aryl, $C(O)C_{1-6}$ heteroaryl, $C(O)C_{1-4}$ alkyl, $C(O)C_{1-4}$ haloalkyl, $SO_2C_{1-4}$ alkyl, $SO_2C_{1-4}$ haloalkyl, $SO_2C_{3-6}$ cycloalkyl, $SO_2NR_{15}$, $SO_2NC_{1-4}$ alkylamino, $SO_2C_{5-6}$ aryl, or $SO_2C_{1-6}$ heteroaryl, wherein $C_{1-4}$ alkyl, $C_{1-4}$ alkoxy, $C_{1-6}$ heteroaryl, and $C_{1-4}$ haloalkoxy, is optionally substituted with one or more of the groups selected from hydrogen, oxo, $C_{1-4}$ alkyl, $C_{1-4}$ alkoxy, $C_{1-4}$ haloalkyl, $C_{3-6}$ cycloalkyl, $C_{5-6}$ aryl, $C_{1-6}$ heterocyclyl, $C_{1-6}$ heteroaryl, cyano, and hydroxyl; $R_{11}$ is hydrogen; $R_{12}$ is selected from $C_{1-6}$ alkylamino, and 5-10 membered monocyclic or bicyclic saturated heterocyclic ring with 1-3 heteroatoms selected from N, S or O, or $R_{11}$ and $R_{12}$ can be taken together to form a 5-10 membered monocyclic or bicyclic saturated or unsaturated heterocyclic ring with 1-5 heteroatoms selected from N, S or O, wherein the 5-10 membered monocyclic or bicyclic saturated or unsaturated heterocyclic ring is optionally substituted with the substituents selected from amino, $C_{1-6}$ alkylamino, $C_{1-6}$ acylamino, —NHC(NH)$CH_2Cl$, NH(CO)CH═CH—$CH_2$—$N(CH_3)_2$, $C_{1-6}$ alkyl, halogen, $C_{1-6}$ alkoxy, and hydroxyl; $R_{13}$ is selected from hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-10}$ heterocyclyl, $C_{1-10}$ heteroaryl, $C(O)C_{1-6}$ alkyl, $C(O)C_{1-6}$ haloalkyl, $C(O)NR_{15}$, $C(O)C_{1-6}$ alkylamino, $C(O)C_{5-6}$ aryl, $C(O)C_{1-6}$ heteroaryl, $SO_2C_{1-6}$ alkyl, $SO_2C_{1-6}$ haloalkyl, $SO_2C_{3-6}$ cycloalkyl, $SO_2NR_{15}$, $SO_2NC_{1-6}$ alkylamino, $SO_2C_{5-6}$ aryl, and $SO_2C_{1-6}$ heteroaryl, wherein $C_{1-6}$ alkyl, $C_{1-6}$ alkoxy, $C_{3-6}$ cycloalkyl, $C_{5-10}$ aryl, $C_{1-10}$ heterocyclyl, and $C_{1-10}$ heteroaryl, is optionally substituted with one or more of the groups selected from hydrogen, $C_{1-6}$ alkyl, $C_{1-6}$ haloalkyl, $C_{1-6}$ alkoxy, $C_{3-6}$ cycloalkyl, $C_{5-6}$ aryl, $C_{1-6}$ heteroaryl, $C_{1-6}$ heterocyclyl, oxo, halogen, hydroxyl, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano; and $R_{15}$ is selected from the group consisting of hydrogen, $C_{1-6}$ alkyl, and combinations thereof.

In an embodiment of the present disclosure, there is provided a compound of Formula I as described herein, wherein X is selected from O or S; Z is N; A is selected from N or $CR_1$; B is selected from N or $CR_2$; D is selected from N or $CR_3$; $R_1$, $R_2$ and $R_3$, are independently selected from hydrogen, hydroxyl, cyano, amino, halogen, $C_{1-4}$ alkyl, $C_{1-4}$ alkoxy, $C_{3-5}$ cycloalkyl, $C_{1-4}$ haloalkyl, $C_{1-4}$ haloalkoxy, $C_{5-6}$ aryl, $C_{1-6}$ heterocyclyl, or $C_{1-6}$ heteroaryl; $R_4$ is selected from hydrogen, hydroxyl, cyano, amino, halogen, $C_{1-4}$ alkyl, $C_{1-4}$ alkoxy, $C_{3-6}$ cycloalkyl, $C_{1-4}$ haloalkyl, $C_{1-4}$ haloalkoxy, $C_{1-4}$ acylamino, $C_{1-4}$ alkylamino, $C_{5-6}$ aryl, $C_{1-6}$ heterocyclyl, $C_{1-6}$ heteroaryl, C(O)$NR_{15}$, C(O)$C_{1-4}$ alkylamino, C(O) $C_{5-6}$ aryl, C(O)$C_{1-6}$ heteroaryl, C(O)$C_{1-4}$ alkyl, C(O)$C_{1-4}$ haloalkyl, $SO_2C_{1-4}$ alkyl, $SO_2C_{1-4}$ haloalkyl, $SO_2C_{3-6}$ cycloalkyl, $SO_2NR_{15}$, $SO_2NC_{1-4}$ alkylamino, $SO_2C_{5-6}$ aryl, or $SO_2C_{1-6}$ heteroaryl, wherein $C_{1-4}$ alkyl, $C_{1-4}$ alkoxy, $C_{1-6}$ heteroaryl, and $C_{1-4}$ haloalkoxy, is optionally substituted with one or more of the groups selected from hydrogen, oxo, $C_{1-4}$ alkyl, $C_{1-4}$ alkoxy, $C_{1-4}$ haloalkyl, $C_{3-6}$ cycloalkyl, $C_{5-6}$ aryl, $C_{1-6}$ heterocyclyl, $C_{1-6}$ heteroaryl, cyano, and hydroxyl; $R_{11}$ is hydrogen; $R_{12}$ is selected from $C_{1-6}$ alkylamino, and 5-10 membered monocyclic or bicyclic saturated heterocyclic ring with 1-3 heteroatoms selected from N, S or O, or $R_{11}$ and $R_{12}$ can be taken together to form a 5-10 membered monocyclic or bicyclic saturated or unsaturated heterocyclic ring with 1-5 heteroatoms selected from N, S or O, wherein the 5-10 membered monocyclic or bicyclic saturated or unsaturated heterocyclic ring is optionally substituted with the substituents selected from amino, $C_{1-6}$ alkylamino, $C_{1-6}$ acylamino, —NHC(NH)$CH_2$Cl, NH(CO)CH═CH—$CH_2$—N$(CH_3)_2$, $C_{1-6}$ alkyl, halogen, $C_{1-6}$ alkoxy, or hydroxyl; $R_{13}$ is selected from hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-10}$ heterocyclyl, $C_{1-10}$ heteroaryl, C(O)$C_{1-6}$ alkyl, C(O)$C_{1-6}$ haloalkyl, C(O) $NR_{15}$, C(O)$C_{1-6}$ alkylamino, C(O)$C_{5-6}$ aryl, C(O)$C_{1-6}$ heteroaryl, $SO_2C_{1-6}$ alkyl, $SO_2C_{1-6}$ haloalkyl, $SO_2C_{3-6}$ cycloalkyl, $SO_2NR_{15}$, $SO_2NC_{1-6}$ alkylamino, $SO_2C_{5-6}$ aryl, or $SO_2C_{1-6}$ heteroaryl, wherein $C_{1-6}$ alkyl, $C_{1-6}$ alkoxy, $C_{3-6}$ cycloalkyl, $C_{5-10}$ aryl, $C_{1-10}$ heterocyclyl, and $C_{1-10}$ heteroaryl, is optionally substituted with one or more of the groups selected from hydrogen, $C_{1-6}$ alkyl, $C_{1-6}$ haloalkyl, $C_{1-6}$ alkoxy, $C_{3-6}$ cycloalkyl, $C_{5-6}$ aryl, $C_{1-6}$ heteroaryl, $C_{1-6}$ heterocyclyl, oxo, halogen, hydroxyl, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2$OH, and cyano; and $R_{15}$ is selected from the group consisting of hydrogen, $C_{1-6}$ alkyl, and combinations thereof.

In an embodiment of the present disclosure, there is provided a compound of Formula I as described herein, wherein X is selected from O or S; Z is N; A is selected from N or $CR_1$; B is selected from N or $CR_2$; D is selected from N or $CR_3$; $R_1$, $R_2$, $R_3$, and $R_4$ are independently selected from hydrogen, hydroxyl, cyano, amino, halogen, $C_{1-4}$ alkyl, $C_{1-4}$ alkoxy, $C_{3-6}$ cycloalkyl, $C_{1-4}$ haloalkyl, $C_{1-4}$ haloalkoxy, $C_{1-4}$ acylamino, $C_{1-4}$ alkylamino, $C_{5-6}$ aryl, $C_{1-6}$ heterocyclyl, $C_{1-6}$ heteroaryl, C(O)$NR_{15}$, C(O)$C_{1-4}$ alkylamino, C(O) $C_{5-6}$ aryl, C(O)$C_{1-6}$ heteroaryl, C(O)$C_{1-4}$ alkyl, C(O)$C_{1-4}$ haloalkyl, $SO_2C_{1-4}$ alkyl, $SO_2C_{1-4}$ haloalkyl, $SO_2C_{3-6}$ cycloalkyl, $SO_2NR_{15}$, $SO_2NC_{1-4}$ alkylamino, $SO_2C_{5-6}$ aryl, or $SO_2C_{1-6}$ heteroaryl, wherein $C_{1-4}$ alkyl, $C_{1-4}$ alkoxy, $C_{1-6}$ heteroaryl, and $C_{1-4}$ haloalkoxy, is optionally substituted with one or more of the groups selected from hydrogen, oxo, $C_{1-4}$ alkyl, $C_{1-4}$ alkoxy, $C_{1-4}$ haloalkyl, $C_{3-6}$ cycloalkyl, $C_{5-6}$ aryl, $C_{1-6}$ heterocyclyl, $C_{1-6}$ heteroaryl, cyano, and hydroxyl; $R_{11}$ is hydrogen; $R_{12}$ is selected from $C_{1-6}$ alkylamino, and 5-10 membered monocyclic or bicyclic saturated heterocyclic ring with 1-3 heteroatoms selected from N, S or O, or $R_{11}$ and $R_{12}$ can be taken together to form a 5-10 membered monocyclic or bicyclic saturated or unsaturated heterocyclic ring with 1-5 heteroatoms selected from N, S or O, wherein the 5-10 membered monocyclic or bicyclic saturated or unsaturated heterocyclic ring is optionally substituted with the substituents selected from amino, $C_{1-6}$ alkylamino, $C_{1-6}$ acylamino, —NHC(NH)$CH_2$Cl, NH(CO)CH═CH—$CH_2$—N$(CH_3)_2$, $C_{1-6}$ alkyl, halogen, $C_{1-6}$ alkoxy, and hydroxyl; $R_{13}$ is selected from hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from cyano, halogen, $C_{1-6}$ alkyl, $C_{1-6}$ alkoxy, $C_{3-6}$ cycloalkyl, $C_{1-6}$ haloalkyl, $C_{5-10}$ aryl, $C_{1-10}$ heterocyclyl, or $C_{1-10}$ heteroaryl, wherein $C_{1-6}$ alkyl, $C_{1-6}$ alkoxy, $C_{3-6}$ cycloalkyl, $C_{5-10}$ aryl, $C_{1-10}$ heterocyclyl, and $C_{1-10}$ heteroaryl, is optionally substituted with one or more of the groups selected from hydrogen, $C_{1-6}$ alkyl, $C_{1-6}$ haloalkyl, $C_{1-6}$ alkoxy, $C_{3-6}$ cycloalkyl, $C_{5-6}$ aryl, $C_{1-6}$ heteroaryl, $C_{1-6}$ heterocyclyl, oxo, halogen, hydroxyl, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2$OH, and cyano; and $R_{15}$ is selected from the group consisting of hydrogen, $C_{1-6}$ alkyl, and combinations thereof.

In an embodiment of the present disclosure, there is provided a compound of Formula I as described herein, wherein X is selected from O or S; Z is N; A is selected from N or $CR_1$; B is selected from N or $CR_2$; $R_1$, $R_2$, and $R_3$ are independently selected from hydrogen, hydroxyl, cyano, amino, halogen, $C_{1-4}$ alkyl, $C_{1-4}$ alkoxy, $C_{3-5}$ cycloalkyl, $C_{1-4}$ haloalkyl, $C_{1-4}$ haloalkoxy, $C_{5-6}$ aryl, $C_{1-6}$ heterocyclyl, or $C_{1-6}$ heteroaryl; $R_4$ is selected from hydrogen, hydroxyl, cyano, amino, halogen, $C_{1-4}$ alkyl, $C_{1-4}$ alkoxy, $C_{3-5}$ cycloalkyl, $C_{1-4}$ haloalkyl, $C_{1-4}$ haloalkoxy, $C_{5-6}$ aryl, $C_{1-4}$ heterocyclyl, $C_{1-4}$ heteroaryl, C(O)$C_{1-4}$ alkyl, C(O)$C_{1-4}$ haloalkyl, C(O)$NR_{15}$, C(O)$C_{1-4}$ alkylamino, C(O)$C_{5-6}$ aryl, C(O)$C_{1-4}$ heteroaryl, $SO_2C_{1-4}$ alkyl, $SO_2C_{1-4}$ haloalkyl, $SO_2C_{3-6}$ cycloalkyl, $SO_2NR_{15}$, $SO_2NC_{1-4}$ alkylamino, $SO_2C_{5-6}$ aryl, $SO_2C_{1-4}$ heteroaryl, $C_{1-4}$ acylamino, or $C_{1-4}$ alkylamino, wherein $C_{1-4}$ alkyl, $C_{1-4}$ alkoxy, $C_{1-4}$ heteroaryl, and $C_{1-4}$ haloalkoxy, is optionally substituted with one or more of the groups selected from hydrogen, oxo, $C_{1-4}$ alkyl, $C_{1-4}$ alkoxy, $C_{1-4}$ haloalkyl, $C_{3-5}$ cycloalkyl, $C_{5-6}$ aryl, $C_{1-4}$ heterocyclyl, $C_{1-4}$ heteroaryl, cyano, and hydroxyl; $R_{11}$ is hydrogen; $R_{12}$ is selected from $C_{1-4}$ alkylamino, and 5-10 membered monocyclic or bicyclic saturated heterocyclic ring with 1-3 heteroatoms selected from N, S or O, or $R_{11}$ and $R_{12}$ can be taken together to form a 5-10 membered monocyclic or bicyclic saturated or unsaturated heterocyclic ring with 1-5 heteroatoms selected from N, S or O, wherein the 5-10 membered monocyclic or bicyclic saturated or unsaturated heterocyclic ring is optionally substituted with the substituents selected from amino, $C_{1-6}$ alkylamino, $C_{1-6}$ acylamino, —NHC(NH)$CH_2$Cl, NH(CO)CH═CH—$CH_2$—N$(CH_3)_2$, $C_{1-6}$ alkyl, halogen, $C_{1-6}$ alkoxy, or hydroxyl; $R_{13}$ is selected from hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-10}$ heterocyclyl, $C_{1-10}$ heteroaryl, C(O)$C_{1-6}$ alkyl, C(O)$C_{1-6}$ haloalkyl, C(O)$NR_{15}$, C(O)$C_{1-6}$ alkylamino, C(O)

$C_{5-6}$ aryl, or C(O)$C_{1-6}$ heteroaryl, wherein $C_{1-6}$ alkyl, $C_{1-6}$ alkoxy, $C_{3-6}$ cycloalkyl, $C_{5-10}$ aryl, $C_{1-10}$ heterocyclyl, and $C_{1-10}$ heteroaryl, is optionally substituted with one or more of the groups selected from hydrogen, $C_{1-6}$ alkyl, $C_{1-6}$ haloalkyl, $C_{1-6}$ alkoxy, $C_{3-6}$ cycloalkyl, $C_{5-6}$ aryl, $C_{1-6}$ heteroaryl, $C_{1-6}$ heterocyclyl, oxo, halogen, hydroxyl, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano; and $R_{15}$ is selected from the group consisting of hydrogen, $C_{1-6}$ alkyl, and combinations thereof.

In an embodiment of the present disclosure, there is provided a compound of Formula I as described herein, wherein X is selected from O or S; Z is N; A is selected from N or $CR_1$; B is selected from N or $CR_2$; $R_1$, $R_2$, and $R_3$ are independently selected from hydrogen, hydroxyl, cyano, amino, halogen, $C_{1-4}$ alkyl, $C_{1-4}$ alkoxy, $C_{3-5}$ cycloalkyl, $C_{1-4}$ haloalkyl, $C_{1-4}$ haloalkoxy, $C_{5-6}$ aryl, $C_{1-6}$ heterocyclyl, and $C_{1-6}$ heteroaryl; $R_4$ is selected from hydrogen, hydroxyl, cyano, amino, halogen, $C_{1-4}$ alkyl, $C_{1-4}$ alkoxy, $C_{3-5}$ cycloalkyl, $C_{1-4}$ haloalkyl, $C_{1-4}$ haloalkoxy, $C_{5-6}$ aryl, $C_{1-4}$ heterocyclyl, $C_{1-4}$ heteroaryl, C(O)$C_{1-4}$ alkyl, C(O)$C_{1-4}$ haloalkyl, C(O)$NR_{15}$, C(O)$C_{1-4}$ alkylamino, C(O)$C_{5-6}$ aryl, C(O)$C_{1-4}$ heteroaryl, $SO_2C_{1-4}$ alkyl, $SO_2C_{1-4}$ haloalkyl, $SO_2C_{3-6}$ cycloalkyl, $SO_2NR_{15}$, $SO_2NC_{1-4}$ alkylamino, $SO_2C_{5-6}$ aryl, $SO_2C_{1-4}$ heteroaryl, $C_{1-4}$ acylamino, or $C_{1-4}$ alkylamino, wherein $C_{1-4}$ alkyl, $C_{1-4}$ alkoxy, $C_{1-4}$ heteroaryl, and $C_{1-4}$ haloalkoxy, is optionally substituted with one or more of the groups selected from hydrogen, oxo, $C_{1-4}$ alkyl, $C_{1-4}$ alkoxy, $C_{1-4}$ haloalkyl, $C_{3-5}$ cycloalkyl, $C_{5-6}$ aryl, $C_{1-4}$ heterocyclyl, $C_{1-4}$ heteroaryl, cyano, and hydroxyl; $R_{11}$ is hydrogen; $R_{12}$ is selected from $C_{1-4}$ alkylamino, and 5-10 membered monocyclic or bicyclic saturated heterocyclic ring with 1-3 heteroatoms selected from N, S or O, or $R_{11}$ and $R_{12}$ can be taken together to form a 5-10 membered monocyclic or bicyclic saturated heterocyclic ring with 1-5 heteroatoms selected from N, S or O, wherein the 5-10 membered monocyclic or bicyclic saturated heterocyclic ring is optionally substituted with the substituents selected from amino, $C_{1-4}$ alkylamino, $C_{1-4}$ acylamino, —NHC(NH)$CH_2Cl$, NH(CO)CH═CH—$CH_2$—$N(CH_3)_2$, $C_{1-4}$ alkyl, halogen, $C_{1-4}$ alkoxy, or hydroxyl; $R_{13}$ is selected from hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-10}$ heterocyclyl, $C_{1-10}$ heteroaryl, C(O)$C_{1-6}$ alkyl, C(O)$C_{1-6}$ haloalkyl, C(O)$NR_{15}$, C(O)$C_{1-6}$ alkylamino, C(O)$C_{5-6}$ aryl, or C(O)$C_{1-6}$ heteroaryl, wherein $C_{1-6}$ alkyl, $C_{1-6}$ alkoxy, $C_{3-6}$ cycloalkyl, $C_{5-10}$ aryl, $C_{1-10}$ heterocyclyl, and $C_{1-10}$ heteroaryl, is optionally substituted with one or more of the groups selected from hydrogen, $C_{1-6}$ alkyl, $C_{1-6}$ haloalkyl, $C_{1-6}$ alkoxy, $C_{3-6}$ cycloalkyl, $C_{5-6}$ aryl, $C_{1-6}$ heteroaryl, $C_{1-6}$ heterocyclyl, oxo, halogen, hydroxyl, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano; and $R_{15}$ is selected from the group consisting of hydrogen, $C_{1-6}$ alkyl, and combinations thereof.

In an embodiment of the present disclosure, there is provided a compound of Formula I as described herein, wherein X is selected from O or S; Z is N; A is selected from N or $CR_1$; B is selected from N or $CR_2$; $R_1$, $R_2$, and $R_3$ are independently selected from hydrogen, hydroxyl, cyano, amino, halogen, $C_{1-4}$ alkyl, $C_{1-4}$ alkoxy, $C_{3-5}$ cycloalkyl, $C_{1-4}$ haloalkyl, $C_{1-4}$ haloalkoxy, $C_{5-6}$ aryl, $C_{1-6}$ heterocyclyl, or $C_{1-6}$ heteroaryl, and combinations thereof; $R_4$ is selected from hydrogen, hydroxyl, cyano, amino, halogen, $C_{1-4}$ alkyl, $C_{1-4}$ alkoxy, $C_{3-5}$ cycloalkyl, $C_{1-4}$ haloalkyl, $C_{1-4}$ haloalkoxy, $C_{5-6}$ aryl, $C_{1-4}$ heterocyclyl, $C_{1-4}$ heteroaryl, C(O)$C_{1-4}$ alkyl, C(O)$C_{1-4}$ haloalkyl, C(O)$NR_{15}$, C(O)$C_{1-4}$ alkylamino, C(O)$C_{5-6}$ aryl, C(O)$C_{1-4}$ heteroaryl, $SO_2C_{1-4}$ alkyl, $SO_2C_{1-4}$ haloalkyl, $SO_2C_{3-6}$ cycloalkyl, $SO_2NR_{15}$, $SO_2NC_{1-4}$ alkylamino, $SO_2C_{5-6}$ aryl, $SO_2C_{1-4}$ heteroaryl, $C_{1-4}$ acylamino, or $C_{1-4}$ alkylamino, wherein $C_{1-4}$ alkyl, $C_{1-4}$ alkoxy, $C_{1-4}$ heteroaryl, and $C_{1-4}$ haloalkoxy, is optionally substituted with one or more of the groups selected from hydrogen, oxo, $C_{1-4}$ alkyl, $C_{1-4}$ alkoxy, $C_{1-4}$ haloalkyl, $C_{3-5}$ cycloalkyl, $C_{5-6}$ aryl, $C_{1-4}$ heterocyclyl, $C_{1-4}$ heteroaryl, cyano, and hydroxyl; $R_{11}$ is hydrogen; $R_{12}$ is selected from $C_{1-4}$ alkylamino, and 5-10 membered monocyclic or bicyclic saturated heterocyclic ring with 1-3 heteroatoms selected from N, S or O, or $R_{11}$ and $R_{12}$ can be taken together to form a 5-10 membered monocyclic or bicyclic saturated or unsaturated heterocyclic ring with 1-5 heteroatoms selected from N, S or O, wherein the 5-10 membered monocyclic or bicyclic saturated or unsaturated heterocyclic ring is optionally substituted with the substituents selected from amino, $C_{1-6}$ alkylamino, $C_{1-6}$ acylamino, —NHC(NH)$CH_2Cl$, NH(CO)CH═CH—$CH_2$—$N(CH_3)_2$, $C_{1-6}$ alkyl, halogen, $C_{1-6}$ alkoxy, and hydroxyl, and combinations thereof; $R_{13}$ is selected from hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-10}$ heterocyclyl, $C_{1-10}$ heteroaryl, C(O)$C_{1-4}$ alkyl, C(O)$C_{1-4}$ haloalkyl, C(O)$NR_{15}$, C(O)$C_{1-4}$ alkylamino, C(O)$C_{5-6}$ aryl, and C(O)$C_{1-6}$ heteroaryl, wherein $C_{1-6}$ alkyl, $C_{1-6}$ alkoxy, $C_{3-6}$ cycloalkyl, $C_{5-10}$ aryl, $C_{1-10}$ heterocyclyl, and $C_{1-10}$ heteroaryl, is optionally substituted with one or more of the groups selected from hydrogen, $C_{1-6}$ alkyl, $C_{1-6}$ haloalkyl, $C_{1-6}$ alkoxy, $C_{3-6}$ cycloalkyl, $C_{5-6}$ aryl, $C_{1-6}$ heteroaryl, $C_{1-6}$ heterocyclyl, oxo, halogen, hydroxyl, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano; and $R_{15}$ is independently selected from the group consisting of hydrogen, $C_{1-6}$ alkyl, and combinations thereof.

In an embodiment of the present disclosure, there is provided a compound of Formula I as described herein, wherein X is selected from O or S; Z is N; A is selected from N or $CR_1$; B is selected from N or $CR_2$; D is selected from N or $CR_3$; $R_1$, $R_2$, and $R_3$ are independently selected from hydrogen, hydroxyl, cyano, amino, halogen, $C_{1-4}$ alkyl, $C_{1-4}$ alkoxy, $C_{3-5}$ cycloalkyl, $C_{1-4}$ haloalkyl, $C_{1-4}$ haloalkoxy, $C_{5-6}$ aryl, $C_{1-6}$ heterocyclyl, or $C_{1-6}$ heteroaryl; $R_4$ is selected from hydrogen, hydroxyl, cyano, amino, halogen, $C_{1-4}$ alkyl, $C_{1-4}$ alkoxy, $C_{3-5}$ cycloalkyl, $C_{1-4}$ haloalkyl, $C_{1-4}$ haloalkoxy, $C_{5-6}$ aryl, $C_{1-6}$ heterocyclyl, $C_{1-6}$ heteroaryl, C(O)$C_{1-4}$ alkyl, C(O)$C_{1-4}$ haloalkyl, C(O)$NR_{15}$, C(O)$C_{1-4}$ alkylamino, C(O)$C_{5-6}$ aryl, C(O)$C_{1-6}$ heteroaryl, $SO_2C_{1-4}$ alkyl, $SO_2C_{1-4}$ haloalkyl, $SO_2C_{3-6}$ cycloalkyl, $SO_2NR_{15}$, $SO_2NC_{1-4}$ alkylamino, $SO_2C_{5-6}$ aryl, $SO_2C_{1-6}$ heteroaryl, $C_{1-4}$ acylamino, or $C_{1-4}$ alkylamino, wherein $C_{1-4}$ alkyl, $C_{1-4}$ alkoxy, $C_{1-6}$ heteroaryl, and $C_{1-4}$ haloalkoxy, is optionally substituted with one or more of the groups selected from hydrogen, oxo, $C_{1-4}$ alkyl, $C_{1-4}$ alkoxy, $C_{1-4}$ haloalkyl, $C_{3-5}$ cycloalkyl, $C_{5-6}$ aryl, $C_{1-6}$ heterocyclyl, $C_{1-6}$ heteroaryl, cyano, and hydroxyl; $R_{11}$ and $R_{12}$ are taken together to form a 5-10 membered monocyclic or bicyclic saturated or unsaturated heterocyclic ring with 1-5 heteroatoms selected from N or O, wherein the 5-10 membered monocyclic or bicyclic saturated or unsaturated heterocyclic ring is optionally substituted with the substituents selected from amino, $C_{1-4}$ alkylamino, $C_{1-4}$ acylamino, —NHC(NH)$CH_2Cl$, NH(CO)CH═CH—$CH_2$—N$(CH_3)_2$, $C_{1-4}$ alkyl, halogen, $C_{1-4}$ alkoxy, or hydroxyl; $R_{13}$ is selected from hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from halogen, $C_{1-4}$ alkyl, $C_{1-4}$ alkoxy, $C_{3-6}$ cycloalkyl, $C_{1-4}$ haloalkyl, $C_{1-4}$ haloalkoxy, $C_{1-4}$ acylamino, $C_{1-4}$ alkylamino, $C_{5-9}$ aryl, $C_{1-9}$ heterocyclyl, and $C_{1-9}$ heteroaryl, wherein $C_{1-4}$ alkyl, $C_{1-4}$ alkoxy, $C_{3-6}$ cycloalkyl, $C_{5-9}$ aryl, $C_{1-9}$ heterocyclyl, and $C_{1-9}$ heteroaryl, is optionally substituted with one or more of the groups selected from hydrogen, $C_{1-4}$ alkyl, $C_{1-4}$ haloalkyl, $C_{1-4}$ alkoxy, $C_{3-6}$ cycloalkyl, $C_{5-6}$ aryl, $C_{1-6}$ heteroaryl, $C_{1-6}$ heterocyclyl, oxo, halogen, hydroxyl, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano; and $R_{15}$ is selected from the group consisting of hydrogen, $C_{1-6}$ alkyl, and combinations thereof.

In an embodiment of the present disclosure, there is provided a compound of Formula I as described herein, wherein X is selected from O or S; Z is N; A is $CR_1$; B is $CR_2$; D is $CR_3$; $R_1$, $R_2$, and $R_3$ are independently selected from hydrogen, hydroxyl, cyano, amino, halogen, $C_{1-4}$ alkyl, $C_{1-4}$ alkoxy, $C_{3-5}$ cycloalkyl, $C_{1-4}$ haloalkyl, $C_{1-4}$ haloalkoxy, $C_{5-6}$ aryl, $C_{1-6}$ heterocyclyl, or $C_{1-6}$ heteroaryl; $R_4$ is selected from hydrogen, hydroxyl, cyano, amino, halogen, $C_{1-4}$ alkyl, $C_{1-4}$ alkoxy, $C_{3-5}$ cycloalkyl, $C_{1-4}$ haloalkyl, $C_{1-4}$ haloalkoxy, $C_{5-6}$ aryl, $C_{1-6}$ heterocyclyl, $C_{1-6}$ heteroaryl, C(O)$C_{1-4}$ alkyl, C(O)$C_{1-4}$ haloalkyl, C(O)$NR_{15}$, C(O)$C_{1-4}$ alkylamino, C(O)$C_{5-6}$ aryl, C(O)$C_{1-6}$ heteroaryl, $SO_2C_{1-4}$ alkyl, $SO_2C_{1-4}$ haloalkyl, $SO_2C_{3-6}$ cycloalkyl, $SO_2NR_{15}$, $SO_2NC_{1-4}$ alkylamino, $SO_2C_{5-6}$ aryl, $SO_2C_{1-6}$ heteroaryl, $C_{1-4}$ acylamino, or $C_{1-4}$ alkylamino, wherein $C_{1-4}$ alkyl, $C_{1-4}$ alkoxy, $C_{1-6}$ heteroaryl, and $C_{1-4}$ haloalkoxy, is optionally substituted with one or more of the groups selected from hydrogen, oxo, $C_{1-4}$ alkyl, $C_{1-4}$ alkoxy, $C_{1-4}$ haloalkyl, $C_{3-5}$ cycloalkyl, $C_{5-6}$ aryl, $C_{1-6}$ heterocyclyl, $C_{1-6}$ heteroaryl, cyano, and hydroxyl; $R_{11}$ and $R_{12}$ are taken together to form a 5-10 membered monocyclic or bicyclic saturated or unsaturated heterocyclic ring with 1-5 heteroatoms selected from N or O, wherein the 5-10 membered monocyclic or bicyclic saturated or unsaturated heterocyclic ring is optionally substituted with the substituents selected from amino, $C_{1-4}$ alkylamino, $C_{1-4}$ acylamino, —NHC(NH)$CH_2Cl$, NH(CO)CH═CH—$CH_2$—N$(CH_3)_2$, $C_{1-4}$ alkyl, halogen, $C_{1-4}$ alkoxy, or hydroxyl; $R_{13}$ is selected from hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from halogen, $C_{1-4}$ alkyl, $C_{1-4}$ alkoxy, $C_{3-6}$ cycloalkyl, $C_{1-4}$ haloalkyl, $C_{1-4}$ haloalkoxy, $C_{1-4}$ acylamino, $C_{1-4}$ alkylamino, $C_{5-9}$ aryl, $C_{1-9}$ heterocyclyl, or $C_{1-9}$ heteroaryl, wherein $C_{1-4}$ alkyl, $C_{1-4}$ alkoxy, $C_{3-6}$ cycloalkyl, $C_{5-9}$ aryl, $C_{1-9}$ heterocyclyl, and $C_{1-6}$ heteroaryl, is optionally substituted with one or more of the groups selected from hydrogen, $C_{1-4}$ alkyl, $C_{1-4}$ haloalkyl, $C_{1-4}$ alkoxy, $C_{3-6}$ cycloalkyl, $C_{5-6}$ aryl, $C_{1-6}$ heteroaryl, $C_{1-6}$ heterocyclyl, oxo, halogen, hydroxyl, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano; and $R_{15}$ is selected from the group consisting of hydrogen, $C_{1-6}$ alkyl, and combinations thereof.

In an embodiment of the present disclosure, there is provided a compound of Formula I as described herein, wherein X is selected from O or S; Z is N; A is selected from N or $CR_1$; B is selected from N or $CR_2$; D is selected from N or $CR_3$; $R_1$, $R_2$, and $R_3$ are independently selected from hydrogen, hydroxyl, cyano, amino, halogen, $C_{1-4}$ alkyl, or $C_{1-4}$ alkoxy; $R_4$ is selected from hydrogen, hydroxyl, cyano, amino, halogen, $C_{1-4}$ alkyl, $C_{1-4}$ alkoxy, $C_{3-5}$ cycloalkyl, $C_{1-4}$ haloalkyl, $C_{1-4}$ haloalkoxy, $C_{5-6}$ aryl, $C_{1-6}$ heterocyclyl, $C_{1-6}$ heteroaryl, C(O)$C_{1-4}$ alkyl, C(O)$C_{1-4}$ haloalkyl, C(O)$NR_{15}$, C(O)$C_{1-4}$ alkylamino, C(O)$C_{5-6}$ aryl, C(O)$C_{1-6}$ heteroaryl, $SO_2C_{1-4}$ alkyl, $SO_2C_{1-4}$ haloalkyl, $SO_2C_{3-6}$ cycloalkyl, $SO_2NR_{15}$, $SO_2NC_{1-4}$ alkylamino, $SO_2C_{5-6}$ aryl, $SO_2C_{1-6}$ heteroaryl, $C_{1-4}$ acylamino, or $C_{1-4}$ alkylamino, wherein $C_{1-4}$ alkyl, $C_{1-4}$ alkoxy, $C_{1-6}$ heteroaryl, and $C_{1-4}$ haloalkoxy, is optionally substituted with one or more of the groups selected from hydrogen, oxo, $C_{1-4}$ alkyl, $C_{1-4}$ alkoxy, $C_{1-4}$ haloalkyl, $C_{3-5}$ cycloalkyl, $C_{5-6}$ aryl, $C_{1-6}$ heterocyclyl, $C_{1-6}$ heteroaryl, cyano, and hydroxyl; $R_{11}$ and $R_{12}$ are taken together to form a 5-10 membered monocyclic or bicyclic saturated or unsaturated heterocyclic ring with 1-5 heteroatoms selected from N or O, wherein the 5-10 membered monocyclic or bicyclic saturated or unsaturated heterocyclic ring is optionally substituted with the substituents selected from amino, $C_{1-4}$ alkylamino, $C_{1-4}$ acylamino, —NHC(NH)$CH_2Cl$, NH(CO)CH═CH—$CH_2$—N$(CH_3)_2$, $C_{1-4}$ alkyl, halogen, $C_{1-4}$ alkoxy, or hydroxyl; $R_{13}$ is selected from hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from halogen, $C_{1-4}$ alkyl, $C_{1-4}$ alkoxy, $C_{3-6}$ cycloalkyl, $C_{1-4}$ haloalkyl, $C_{1-4}$ haloalkoxy, $C_{1-4}$ acylamino, $C_{1-4}$ alkylamino, $C_{5-9}$ aryl, $C_{1-9}$ heterocyclyl, and $C_{1-9}$ heteroaryl, wherein $C_{1-4}$ alkyl, $C_{1-4}$ alkoxy, $C_{3-6}$ cycloalkyl, $C_{5-9}$ aryl, $C_{1-9}$ heterocyclyl, and $C_{1-9}$ heteroaryl, is optionally substituted with one or more of the groups selected from hydrogen, $C_{1-4}$ alkyl, $C_{1-4}$ haloalkyl, $C_{1-4}$ alkoxy, $C_{3-6}$ cycloalkyl, $C_{5-6}$ aryl, $C_{1-6}$ heteroaryl, $C_{1-6}$ heterocyclyl, oxo, halogen, hydroxyl, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano; and $R_{15}$ is selected from the group consisting of hydrogen, $C_{1-6}$ alkyl, and combinations thereof.

In an embodiment of the present disclosure, there is provided a compound of Formula I as described herein, wherein X is selected from O or S; Z is N; A is selected from N or $CR_1$; B is selected from N or $CR_2$; D is selected from N or $CR_3$; $R_1$, $R_2$, and $R_3$ are independently selected from hydrogen, hydroxyl, cyano, amino, halogen, $C_{1-4}$ alkyl, $C_{1-4}$ alkoxy, $C_{3-5}$ cycloalkyl, $C_{1-4}$ haloalkyl, $C_{1-4}$ haloalkoxy, $C_{5-6}$ aryl, $C_{1-6}$ heterocyclyl, or $C_{1-6}$ heteroaryl; $R_4$ is selected from hydrogen, hydroxyl, cyano, amino, halogen, $C_{1-4}$ alkyl, $C_{1-4}$ alkoxy, $C_{3-5}$ cycloalkyl, $C_{1-4}$ haloalkyl, $C_{1-4}$ haloalkoxy, and $C_{5-6}$ aryl, wherein $C_{1-4}$ alkyl, $C_{1-4}$ alkoxy, and $C_{1-4}$ haloalkoxy, is optionally substituted with one or more of the groups selected from hydrogen, oxo, $C_{1-4}$ alkyl, $C_{1-4}$ alkoxy, $C_{1-4}$ haloalkyl, $C_{3-5}$ cycloalkyl, $C_{5-6}$ aryl, cyano, and hydroxyl; $R_{11}$ and $R_{12}$ are taken together to form a 5-10 membered monocyclic or bicyclic saturated or unsaturated heterocyclic ring with 1-5 heteroatoms selected from N or O, wherein the 5-10 membered monocyclic or bicyclic saturated or unsaturated heterocyclic ring is optionally substituted with the substituents selected from amino, $C_{1-4}$ alkylamino, $C_{1-4}$ acylamino, —NHC(NH)$CH_2Cl$, NH(CO)CH═CH—$CH_2$—N$(CH_3)_2$, $C_{1-4}$ alkyl, halogen, $C_{1-4}$ alkoxy, or hydroxyl; $R_{13}$ is selected from hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from halogen, $C_{1-4}$ alkyl, $C_{1-4}$ alkoxy, $C_{3-6}$ cycloalkyl, $C_{1-4}$ haloalkyl, $C_{1-4}$ haloalkoxy, $C_{1-4}$ acylamino, $C_{1-4}$ alkylamino, $C_{5-9}$ aryl, $C_{1-9}$ heterocyclyl, or $C_{1-9}$ heteroaryl, wherein $C_{1-4}$ alkyl, $C_{1-4}$ alkoxy, $C_{3-6}$ cycloalkyl, $C_{5-9}$ aryl, $C_{1-9}$ heterocyclyl, and $C_{1-9}$ heteroaryl, is optionally substituted with one or more of the groups selected from hydrogen, $C_{1-4}$ alkyl, $C_{1-4}$ haloalkyl, $C_{1-4}$ alkoxy, $C_{3-6}$ cycloalkyl, $C_{5-6}$ aryl, $C_{1-6}$ heteroaryl, $C_{1-6}$ heterocyclyl, oxo, halogen, hydroxyl, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano; and $R_{15}$ is selected from the group consisting of hydrogen, $C_{1-6}$ alkyl, and combinations thereof.

In an embodiment of the present disclosure, there is provided a compound of Formula I as described herein, wherein X is selected from O or S; Z is N; A is selected from N or $CR_1$; B is selected from N or $CR_2$; D is selected from N or $CR_3$; $R_1$, $R_2$, and $R_3$ are independently selected from hydrogen, hydroxyl, cyano, amino, halogen, $C_{1-4}$ alkyl, $C_{1-4}$ alkoxy, $C_{3-5}$ cycloalkyl, $C_{1-4}$ haloalkyl, $C_{1-4}$ haloalkoxy, $C_{5-6}$ aryl, $C_{1-6}$ heterocyclyl, or $C_{1-6}$ heteroaryl; $R_4$ is selected from hydrogen, hydroxyl, cyano, amino, halogen, $C_{1-4}$ alkyl, $C_{1-4}$ alkoxy, $C_{3-5}$ cycloalkyl, $C_{1-4}$ haloalkyl, $C_{1-4}$ haloalkoxy, $C_{5-6}$ aryl, $C_{1-6}$ heterocyclyl, $C_{1-6}$ heteroaryl, C(O)$C_{1-4}$ alkyl, C(O)$C_{1-4}$ haloalkyl, C(O)$NR_{15}$, C(O)$C_{1-4}$ alkylamino, C(O)$C_{5-6}$ aryl, C(O)$C_{1-6}$ heteroaryl, $SO_2C_{1-4}$ alkyl, $SO_2C_{1-4}$ haloalkyl, $SO_2C_{3-6}$ cycloalkyl, $SO_2NR_{15}$, $SO_2NC_{1-4}$ alkylamino, $SO_2C_{5-6}$ aryl, $SO_2C_{1-6}$ heteroaryl, $C_{1-4}$ acylamino, or $C_{1-4}$ alkylamino, wherein $C_{1-4}$ alkyl, $C_{1-4}$ alkoxy, $C_{1-6}$ heteroaryl, and $C_{1-4}$ haloalkoxy, is optionally substituted with one or more of the groups selected from hydrogen, oxo, $C_{1-4}$ alkyl, $C_{1-4}$ alkoxy, $C_{1-4}$ haloalkyl, $C_{3-5}$ cycloalkyl, $C_{5-6}$ aryl, $C_{1-6}$ heterocyclyl, $C_{1-6}$ heteroaryl, cyano, and hydroxyl; $R_{11}$ and $R_{12}$ are taken together to form a 5-10 membered monocyclic or bicyclic saturated or unsaturated heterocyclic ring with 1-5 heteroatoms selected from N or O, wherein the 5-10 membered monocyclic or bicyclic saturated or unsaturated heterocyclic ring is optionally substituted with the substituents selected from amino, $C_{1-4}$ alkylamino, $C_{1-4}$ acylamino, —NHC(NH)$CH_2Cl$, NH(CO)CH═CH—$CH_2$—N$(CH_3)_2$, $C_{1-4}$ alkyl, halogen, $C_{1-4}$ alkoxy, or hydroxyl; $R_{13}$ is selected from hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from halogen, $C_{1-4}$ alkyl, $C_{1-4}$ alkoxy, $C_{3-6}$ cycloalkyl, $C_{1-4}$ haloalkyl, $C_{5-9}$ aryl, $C_{1-9}$ heterocyclyl, or $C_{1-9}$ heteroaryl, wherein $C_{1-4}$ alkyl, $C_{1-4}$ alkoxy, $C_{3-6}$ cycloalkyl, $C_{5-9}$ aryl, $C_{1-9}$ heterocyclyl, and $C_{1-9}$ heteroaryl, is optionally substituted with one or more of the groups selected from hydrogen, $C_{1-4}$ alkyl, $C_{1-4}$ haloalkyl, $C_{1-4}$ alkoxy, $C_{3-6}$ cycloalkyl, $C_{5-6}$ aryl, $C_{1-6}$ heteroaryl, $C_{1-6}$ heterocyclyl, oxo, halogen, hydroxyl, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano; and $R_{15}$ is selected from the group consisting of hydrogen, $C_{1-6}$ alkyl, and combinations thereof.

In an embodiment of the present disclosure, there is provided a compound of Formula I as described herein, wherein X is selected from O or S; Z is N; A is $CR_1$; B is $CR_2$; D is $CR_3$; $R_1$, $R_2$, and $R_3$ are independently selected from hydrogen, or $C_{1-2}$ alkyl; $R_4$ is selected from hydrogen, $C_{1-4}$ alkyl, $C_{1-4}$ alkoxy, $C_{3-5}$ cycloalkyl, or $C_{5-6}$ aryl, wherein $C_{1-4}$ alkyl, and $C_{1-4}$ alkoxy, is optionally substituted with one or more of the groups selected from $C_{1-4}$ alkyl, and $C_{1-4}$ alkoxy; $R_{11}$ and $R_{12}$ are taken together to form a 5-10 membered monocyclic or bicyclic saturated heterocyclic ring with 1-5 heteroatoms selected from N, S or O, wherein the 5-10 membered monocyclic or bicyclic saturated heterocyclic ring is optionally substituted with the substituents selected from amino, NH(CO)CH═CH—$CH_2$—N$(CH_3)_2$, or $C_{1-2}$ alkylamino; and $R_{13}$ is selected from hydrogen, 5-9 membered monocyclic or bicyclic aryl, and 5-9 membered monocyclic or bicyclic heteroaryl with 1-5 heteroatoms selected from N, S or O, wherein 5-9 membered monocyclic or bicyclic aryl, and 5-9 membered monocyclic or bicyclic heteroaryl are optionally substituted with 1-5 substituents selected from hydroxyl, cyano, fluoro, bromo, chloro, $C_{1-4}$ alkyl, $C_{1-4}$ alkoxy, $C_{1-4}$ haloalkyl, $C_{3-5}$ cycloalkyl, $C_{5-9}$ aryl, $C_{1-9}$ heterocyclyl, or $C_{1-9}$ heteroaryl, wherein $C_{1-4}$ alkyl, $C_{1-4}$ alkoxy, $C_{3-5}$ cycloalkyl, $C_{5-9}$ aryl, $C_{1-9}$ heterocyclyl, and $C_{1-9}$ heteroaryl, is optionally substituted with one or more of the groups selected from hydrogen, $C_{1-4}$ alkyl, $C_{1-4}$ alkoxy, $C_{1-4}$ haloalkyl, $C_{3-5}$ cycloalkyl, $C_{5-6}$ aryl, $C_{1-6}$ heteroaryl, $C_{1-6}$ heterocyclyl, oxo, halogen, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano.

In an embodiment of the present disclosure, there is provided a compound of Formula I as described herein, wherein X is selected from O or S; Z is N; A is $CR_1$; B is $CR_2$; D is $CR_3$; $R_1$, $R_2$, and $R_3$ are independently selected from hydrogen, or $C_{1-2}$ alkyl; $R_4$ is selected from hydrogen, $C_1$ alkyl, $C_1$ alkoxy, $C_3$ cycloalkyl, or $C_6$ aryl, wherein $C_1$ alkyl, and $C_1$ alkoxy, is optionally substituted with one or more of the groups selected from $C_1$ alkyl, and $C_1$ alkoxy; $R_1$ and $R_{12}$ are taken together to form a 5-10 membered monocyclic or bicyclic saturated heterocyclic ring with 1-5 heteroatoms selected from N, S or O, wherein the 5-10 membered monocyclic or bicyclic saturated heterocyclic ring is optionally substituted with the substituents selected from amino, NH(CO)CH═CH—$CH_2$—N$(CH_3)_2$, or $C_{1-2}$ alkylamino; and $R_{13}$ is selected from hydrogen, 5-9 membered monocyclic or bicyclic aryl, and 5-9 membered monocyclic or bicyclic heteroaryl with 1-5 heteroatoms selected from N, S or O, wherein 5-9 membered monocyclic or bicyclic aryl, and 5-9 membered monocyclic or bicyclic heteroaryl are optionally substituted with 1-5 substituents selected from hydroxyl, cyano, fluoro, bromo, chloro, $C_{1-4}$ alkyl, $C_{1-4}$ alkoxy, $C_{1-4}$ haloalkyl, $C_{3-5}$ cycloalkyl, $C_{5-9}$ aryl, $C_{1-9}$ heterocyclyl, or $C_{1-9}$ heteroaryl, wherein $C_{1-4}$ alkyl, $C_{1-4}$ alkoxy, $C_{3-5}$ cycloalkyl, $C_{5-9}$ aryl, $C_{1-9}$ heterocyclyl, and $C_{1-9}$ heteroaryl, is optionally substituted with one or more of the groups selected from hydrogen, $C_{1-4}$ alkyl, $C_{1-4}$ alkoxy, $C_{1-4}$ haloalkyl, $C_{3-5}$ cycloalkyl, $C_{5-6}$ aryl, $C_{1-6}$ heteroaryl, $C_{1-6}$ heterocyclyl, oxo, halogen, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano.

In an embodiment of the present disclosure, there is provided a compound of Formula I as described herein, wherein X is selected from O or S; Z is N; A is $CR_1$; B is $CR_2$; D is $CR_3$; $R_1$, $R_2$, and $R_3$ are independently selected from hydrogen, and $C_{1-2}$ alkyl; $R_4$ is selected from hydrogen, $C_{1-4}$ alkyl, $C_{1-4}$ alkoxy, $C_{3-5}$ cycloalkyl, and $C_{5-6}$ aryl, wherein $C_{1-4}$ alkyl, and $C_{1-4}$ alkoxy, is optionally substituted with one or more of the groups selected from $C_{1-4}$ alkyl, and $C_{1-4}$ alkoxy; $R_{11}$ and $R_{12}$ are taken together to form a 5-10 membered monocyclic or bicyclic saturated heterocyclic ring with 1-5 heteroatoms selected from N, S or O, wherein the 5-10 membered monocyclic or bicyclic saturated heterocyclic ring is optionally substituted with amino, and $NH(CO)CH{=}CH{-}CH_2{-}N(CH_3)_2$; and $R_{13}$ is selected from hydrogen, 5-9 membered monocyclic or bicyclic aryl, and 5-9 membered monocyclic or bicyclic heteroaryl with 1-5 heteroatoms selected from N, S or O, wherein 5-9 membered monocyclic or bicyclic aryl, and 5-9 membered monocyclic or bicyclic heteroaryl are optionally substituted with 1-5 substituents selected from hydroxyl, cyano, fluoro, bromo, chloro, $C_{1-4}$ alkyl, $C_{1-4}$ alkoxy, $C_{1-4}$ haloalkyl, $C_{3-5}$ cycloalkyl, $C_{5-9}$ aryl, $C_{1-9}$ heterocyclyl, and $C_{1-9}$ heteroaryl, wherein $C_{1-4}$ alkyl, $C_{1-4}$ alkoxy, $C_{3-5}$ cycloalkyl, $C_{5-9}$ aryl, $C_{1-9}$ heterocyclyl, and $C_{1-9}$ heteroaryl, is optionally substituted with one or more of the groups selected from hydrogen, $C_{1-4}$ alkyl, $C_{1-4}$ alkoxy, $C_{1-4}$ haloalkyl, $C_{3-5}$ cycloalkyl, $C_{5-6}$ aryl, $C_{1-6}$ heteroaryl, $C_{1-6}$ heterocyclyl, oxo, halogen, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano.

In an embodiment of the present disclosure, there is provided a compound of Formula I as described herein, wherein X is selected from O or S; Z is N; A is $CR_1$; B is $CR_2$; D is $CR_3$; $R_1$, $R_2$, and $R_3$ are independently selected from hydrogen, and $C_1$ alkyl; $R_4$ is selected from hydrogen, $C_1$ alkyl, $C_1$ alkoxy, $C_3$ cycloalkyl, and $C_6$ aryl, wherein $C_1$ alkyl, and $C_1$ alkoxy, is optionally substituted with one or more of the groups selected from $C_1$ alkyl, and $C_1$ alkoxy; $R_{11}$ and $R_{12}$ are taken together to form a 5-10 membered monocyclic or bicyclic saturated heterocyclic ring with 1-5 heteroatoms selected from N, S or O, wherein the 5-10 membered monocyclic or bicyclic saturated heterocyclic ring is optionally substituted with amino, and $NH(CO)CH{=}CH{-}CH_2{-}N(CH_3)_2$; and $R_{13}$ is selected from hydrogen, 5-9 membered monocyclic or bicyclic aryl, and 5-9 membered monocyclic or bicyclic heteroaryl with 1-5 heteroatoms selected from N, S or O, wherein 5-9 membered monocyclic or bicyclic aryl, and 5-9 membered monocyclic or bicyclic heteroaryl are optionally substituted with 1-5 substituents selected from hydroxyl, cyano, fluoro, bromo, chloro, $C_{1-4}$ alkyl, $C_{1-4}$ alkoxy, $C_{1-4}$ haloalkyl, $C_{3-5}$ cycloalkyl, $C_{5-9}$ aryl, $C_{1-9}$ heterocyclyl, and $C_{1-9}$ heteroaryl, wherein $C_{1-4}$ alkyl, $C_{1-4}$ alkoxy, $C_{3-5}$ cycloalkyl, $C_{5-9}$ aryl, $C_{1-9}$ heterocyclyl, and $C_{1-9}$ heteroaryl, is optionally substituted with one or more of the groups selected from hydrogen, $C_{1-4}$ alkyl, $C_{1-4}$ alkoxy, $C_{1-4}$ haloalkyl, $C_{3-5}$ cycloalkyl, $C_{5-6}$ aryl, $C_{1-6}$ heteroaryl, $C_{1-6}$ heterocyclyl, oxo, halogen, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano.

In an embodiment of the present disclosure, there is provided a compound of Formula I as described herein, wherein X is selected from O or S; Z is N; A is $CR_1$; B is $CR_2$; D is $CR_3$; $R_1$, $R_2$, and $R_3$ are independently selected from hydrogen, or $C_1$ alkyl; $R_4$ is selected from hydrogen, $C_1$ alkyl, $C_1$ alkoxy, $C_3$ cycloalkyl, or $C_6$ aryl, wherein $C_1$ alkyl, and $C_1$ alkoxy, is optionally substituted with one or more of the groups selected from $C_1$ alkyl, and $C_1$ alkoxy; $R_1$ and $R_{12}$ are taken together to form a 5-6 membered monocyclic saturated heterocyclic ring with 1-5 heteroatoms selected from N, S or O, wherein the 5-6 membered monocyclic saturated heterocyclic ring is optionally substituted with amino, and $NH(CO)CH{=}CH{-}CH_2{-}N(CH_3)_2$; and $R_{13}$ is selected from hydrogen, 5-9 membered monocyclic or bicyclic aryl, and 5-9 membered monocyclic or bicyclic heteroaryl with 1-5 heteroatoms selected from N, S or O, wherein 5-9 membered monocyclic or bicyclic aryl, and 5-9 membered monocyclic or bicyclic heteroaryl are optionally substituted with 1-5 substituents selected from hydroxyl, cyano, fluoro, bromo, chloro, $C_{1-4}$ alkyl, $C_{1-4}$ alkoxy, $C_{1-4}$ haloalkyl, $C_{3-5}$ cycloalkyl, $C_5$-9 aryl, $C_{1-9}$ heterocyclyl, or $C_{1-9}$ heteroaryl, wherein $C_{1-4}$ alkyl, $C_{1-4}$ alkoxy, $C_{3-5}$ cycloalkyl, $C_{5-9}$ aryl, $C_{1-9}$ heterocyclyl, and $C_{1-9}$ heteroaryl, is optionally substituted with one or more of the groups selected from hydrogen, $C_{1-4}$ alkyl, $C_{1-4}$ alkoxy, $C_{1-4}$ haloalkyl, $C_{3-5}$ cycloalkyl, $C_{5-6}$ aryl, $C_{1-6}$ heteroaryl, $C_{1-6}$ heterocyclyl, oxo, halogen, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano.

In an embodiment of the present disclosure, there is provided a compound of Formula I as described herein, wherein X is selected from O or S; Z is N; A is $CR_1$; B is $CR_2$; D is $CR_3$; $R_1$, $R_2$, and $R_3$ are independently selected from hydrogen, or $C_1$ alkyl; $R_4$ is selected from hydrogen, $C_1$ alkyl, $C_1$ alkoxy, $C_3$ cycloalkyl, or $C_6$ aryl, wherein $C_1$ alkyl, and $C_1$ alkoxy, is optionally substituted with one or more of the groups selected from $C_1$ alkyl, and $C_1$ alkoxy; $R_{11}$ and $R_{12}$ are taken together to form a 5-10 membered bicyclic saturated heterocyclic ring with 1-5 heteroatoms selected from N, S or O; and $R_{13}$ is selected from hydrogen, 5-9 membered monocyclic or bicyclic aryl, and 5-9 membered monocyclic or bicyclic heteroaryl with 1-5 heteroatoms selected from N, S or O, wherein 5-9 membered monocyclic or bicyclic aryl, and 5-9 membered monocyclic or bicyclic heteroaryl are optionally substituted with 1-5 substituents selected from hydroxyl, cyano, fluoro, bromo, chloro, $C_{1-4}$ alkyl, $C_{1-4}$ alkoxy, $C_{1-4}$ haloalkyl, $C_{3-5}$ cycloalkyl, $C_{5-9}$ aryl, $C_{1-9}$ heterocyclyl, or $C_{1-9}$ heteroaryl, wherein $C_{1-4}$ alkyl, $C_{1-4}$ alkoxy, $C_{3-5}$ cycloalkyl, $C_{5-9}$ aryl, $C_{1-9}$ heterocyclyl, and $C_{1-9}$ heteroaryl, is optionally substituted with one or more of the groups selected from hydrogen, $C_{1-4}$ alkyl, $C_{1-4}$ alkoxy, $C_{1-4}$ haloalkyl, $C_{3-5}$ cycloalkyl, $C_{5-6}$ aryl, $C_{1-6}$ heteroaryl, $C_{1-6}$ heterocyclyl, oxo, halogen, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano.

In an embodiment of the present disclosure, there is provided a compound of Formula I as described herein, wherein X is selected from O or S; Z is N; A is $CR_1$; B is $CR_2$; D is $CR_3$; $R_1$, $R_2$, and $R_3$ are independently selected from hydrogen, or $C_1$ alkyl; $R_4$ is selected from hydrogen, $C_1$ alkyl, $C_1$ alkoxy, $C_3$ cycloalkyl, or $C_6$ aryl, wherein $C_1$ alkyl, and $C_1$ alkoxy, is optionally substituted with one or more of the groups selected from $C_1$ alkyl, and $C_1$ alkoxy; $R_1$ and $R_{12}$ are taken together to form a 5 membered monocyclic saturated heterocyclic ring with 1-5 heteroatoms selected from N, S or O, wherein the 5 membered monocyclic saturated heterocyclic ring is optionally substituted with amino; and $R_{13}$ is selected from hydrogen, 5-9 membered monocyclic or bicyclic aryl, and 5-9 membered monocyclic or bicyclic heteroaryl with 1-5 heteroatoms selected from N, S or O, wherein 5-9 membered monocyclic or bicyclic aryl, and 5-9 membered monocyclic or bicyclic heteroaryl are optionally substituted with 1-5 substituents selected from hydroxyl, cyano, fluoro, bromo, chloro, $C_{1-4}$ alkyl, $C_{1-4}$ alkoxy, $C_{1-4}$ haloalkyl, $C_{3-5}$ cycloalkyl, $C_{5-9}$ aryl, $C_{1-9}$ heterocyclyl, or $C_{1-9}$ heteroaryl, wherein $C_{1-4}$ alkyl, $C_{1-4}$ alkoxy, $C_{3-5}$ cycloalkyl, $C_{5-9}$ aryl, $C_{1-9}$ heterocyclyl, and $C_{1-9}$ heteroaryl, is optionally substituted with one or more of the groups selected from hydrogen, $C_{1-4}$ alkyl, $C_{1-4}$ alkoxy, $C_{1-4}$ haloalkyl, $C_{3-5}$ cycloalkyl, $C_{5-6}$ aryl, $C_{1-6}$ heteroaryl, $C_{1-6}$ heterocyclyl, oxo, halogen, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano.

In an embodiment of the present disclosure, there is provided a compound of Formula I as described herein, wherein X is selected from O or S; Z is N; A is $CR_1$; B is $CR_2$; D is $CR_3$; $R_1$, $R_2$, and $R_3$ are independently selected from hydrogen, or $C_1$ alkyl; $R_4$ is selected from hydrogen, $C_1$ alkyl, $C_1$ alkoxy, $C_3$ cycloalkyl, or $C_6$ aryl, wherein $C_1$ alkyl, and $C_1$ alkoxy, is optionally substituted with one or more of the groups selected from $C_1$ alkyl, and $C_1$ alkoxy; $R_{11}$ and $R_{12}$ are taken together to form a 5-10 membered monocyclic or bicyclic saturated heterocyclic ring with 1-5 heteroatoms selected from N, S or O, wherein the 5-10 membered monocyclic or bicyclic saturated heterocyclic ring is optionally substituted with amino, and NH(CO)CH═CH—$CH_2$—$N(CH_3)_2$; and $R_{13}$ is selected from hydrogen, 5-9 membered monocyclic aryl, wherein 5-9 membered monocyclic aryl, is optionally substituted with 1-5 substituents selected from hydroxyl, cyano, fluoro, bromo, chloro, $C_{1-4}$ alkyl, $C_{1-4}$ alkoxy, $C_{1-4}$ haloalkyl, $C_{3-5}$ cycloalkyl, $C_{5-6}$ aryl, $C_{1-6}$ heterocyclyl, or $C_{1-6}$ heteroaryl.

In an embodiment of the present disclosure, there is provided a compound of Formula I as described herein, wherein X is selected from O or S; Z is N; A is $CR_1$; B is $CR_2$; D is $CR_3$; $R_1$, $R_2$, and $R_3$ are independently selected from hydrogen, or $C_1$ alkyl; $R_4$ is selected from hydrogen, $C_1$ alkyl, $C_1$ alkoxy, $C_3$ cycloalkyl, or $C_6$ aryl, wherein $C_1$ alkyl, and $C_1$ alkoxy, is optionally substituted with one or more of the groups selected from $C_1$ alkyl, and $C_1$ alkoxy; $R_1$ and $R_{12}$ are taken together to form a 5-6 membered monocyclic or bicyclic saturated heterocyclic ring with 1-5 heteroatoms selected from N, S or O, wherein the 5-6 membered monocyclic or bicyclic saturated heterocyclic ring is optionally substituted with amino; and $R_{13}$ is selected from hydrogen, 5-9 membered monocyclic or bicyclic aryl, and 5-9 membered monocyclic or bicyclic heteroaryl with 1 heteroatoms selected from S or O, wherein 5-9 membered monocyclic or bicyclic aryl, and 5-9 membered monocyclic or bicyclic heteroaryl are optionally substituted with 1-5 substituents selected from hydroxyl, cyano, fluoro, bromo, chloro, $C_{1-4}$ alkyl, $C_{1-4}$ alkoxy, $C_{1-4}$ haloalkyl, $C_{3-5}$ cycloalkyl, $C_{5-6}$ aryl, $C_{1-6}$ heterocyclyl, or $C_{1-6}$ heteroaryl.

In an embodiment of the present disclosure, there is provided a compound of Formula I as described herein, wherein X is selected from O or S; Z is N; A is $CR_1$; B is $CR_2$; D is $CR_3$; $R_1$, $R_2$, and $R_3$ are independently selected from hydrogen, or $C_1$ alkyl; $R_4$ is selected from hydrogen, $C_1$ alkyl, $C_1$ alkoxy, $C_3$ cycloalkyl, or $C_6$ aryl, wherein $C_1$ alkyl, and $C_1$ alkoxy, is optionally substituted with one or more of the groups selected from $C_1$ alkyl, and $C_1$ alkoxy; $R_{11}$ and $R_{12}$ are taken together to form a 5-6 membered monocyclic or bicyclic saturated heterocyclic ring with 1-5 heteroatoms selected from N, S or O, wherein the 5-6 membered monocyclic or bicyclic saturated heterocyclic ring is optionally substituted with amino; and $R_{13}$ is indole, wherein indole is optionally substituted with 1-5 substituents selected from hydroxyl, cyano, fluoro, bromo, chloro, $C_{1-4}$ alkyl, $C_{1-4}$ alkoxy, $C_{1-4}$ haloalkyl, $C_{3-5}$ cycloalkyl, $C_{5-9}$ aryl, $C_{1-9}$ heterocyclyl, or $C_{1-9}$ heteroaryl, wherein $C_{1-4}$ alkyl, $C_{1-4}$ alkoxy, $C_{3-5}$ cycloalkyl, $C_{5-9}$ aryl, $C_{1-9}$ heterocyclyl, and $C_{1-9}$ heteroaryl, is optionally substituted with one or more of the groups selected from hydrogen, $C_{1-4}$ alkyl, $C_{1-4}$ alkoxy, $C_{1-4}$ haloalkyl, $C_{3-5}$ cycloalkyl, $C_{5-6}$ aryl, $C_{1-6}$ heteroaryl, $C_{1-6}$ heterocyclyl, oxo, halogen, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano.

In an embodiment of the present disclosure, there is provided a compound of Formula I as described herein, wherein X is O; Z is N; A is $CR_1$; B is $CR_2$; D is $CR_3$; $R_1$, $R_2$, and $R_3$ are independently selected from hydrogen, or $C_{1-2}$ alkyl; $R_4$ is selected from hydrogen, $C_{1-4}$ alkyl, $C_{1-4}$ alkoxy, $C_{3-5}$ cycloalkyl, or $C_{5-6}$ aryl, wherein $C_{1-4}$ alkyl, and $C_{1-4}$ alkoxy, is optionally substituted with one or more of the groups selected from $C_{1-4}$ alkyl, and $C_{1-4}$ alkoxy; $R_{11}$ and $R_{12}$ are taken together to form a 5-10 membered monocyclic or bicyclic saturated heterocyclic ring with 1-5 heteroatoms selected from N, S or O, wherein the 5-10 membered monocyclic or bicyclic saturated heterocyclic ring is optionally substituted with the substituents selected from amino, $C_{1-2}$ alkylamino, and NH(CO)CH═CH—$CH_2$—$N(CH_3)_2$; and $R_{13}$ is selected from hydrogen, 5-9 membered monocyclic or bicyclic aryl, and 5-9 membered monocyclic or bicyclic heteroaryl with 1-5 heteroatoms selected from N, S or O, wherein 5-9 membered monocyclic or bicyclic aryl, and 5-9 membered monocyclic or bicyclic heteroaryl are optionally substituted with 1-5 substituents selected from hydroxyl, cyano, fluoro, bromo, chloro, $C_{1-4}$ alkyl, $C_{1-4}$ alkoxy, $C_{1-4}$ haloalkyl, $C_{3-5}$ cycloalkyl, $C_{5-9}$ aryl, $C_{1-9}$ heterocyclyl, or $C_{1-9}$ heteroaryl, wherein $C_{1-4}$ alkyl, $C_{1-4}$ alkoxy, $C_{3-5}$ cycloalkyl, $C_{5-9}$ aryl, $C_{1-9}$ heterocyclyl, and $C_{1-9}$ heteroaryl, is optionally substituted with one or more of the groups selected from hydrogen, $C_{1-4}$ alkyl, $C_{1-4}$ alkoxy, $C_{1-4}$ haloalkyl, $C_{3-5}$ cycloalkyl, $C_{5-6}$ aryl, $C_{1-6}$ heteroaryl, $C_{1-6}$ heterocyclyl, oxo, halogen, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano.

In an embodiment of the present disclosure, there is provided a compound of Formula I as described herein, wherein X is O; Z is N; A is $CR_1$; B is $CR_2$; D is $CR_3$; $R_1$, $R_2$, and $R_3$ are independently selected from hydrogen, or $C_{1-2}$ alkyl; $R_4$ is selected from hydrogen, $C_{1-4}$ alkyl, $C_{1-4}$ alkoxy, $C_{3-5}$ cycloalkyl, or $C_{5-6}$ aryl, wherein $C_{1-4}$ alkyl, and $C_{1-4}$ alkoxy, is optionally substituted with one or more of the groups selected from $C_{1-4}$ alkyl, and $C_{1-4}$ alkoxy; $R_{11}$ and $R_{12}$ are taken together to form a 5-10 membered monocyclic or bicyclic saturated heterocyclic ring with 1-5 heteroatoms selected from N, S or O, wherein the 5-10 membered monocyclic or bicyclic saturated heterocyclic ring is optionally substituted with the substituents selected from amino, $C_{1-2}$ alkylamino, and NH(CO)CH═CH—$CH_2$—$N(CH_3)_2$; and $R_{13}$ is selected from hydrogen, 5-9 membered monocyclic or bicyclic aryl, and 5-9 membered monocyclic or bicyclic heteroaryl with 1-5 heteroatoms selected from N, or O, wherein 5-9 membered monocyclic or bicyclic aryl, and 5-9 membered monocyclic or bicyclic heteroaryl are optionally substituted with 1-5 substituents selected from hydroxyl, cyano, fluoro, bromo, chloro, $C_{1-4}$ alkyl, $C_{1-4}$ alkoxy, $C_{1-4}$ haloalkyl, $C_{3-5}$ cycloalkyl, $C_{5-9}$ aryl, $C_{1-9}$ heterocyclyl, and $C_{1-9}$ heteroaryl, wherein $C_{1-4}$ alkyl, $C_{1-4}$ alkoxy, $C_{3-5}$ cycloalkyl, $C_{5-9}$ aryl, $C_{1-9}$ heterocyclyl, and $C_{1-9}$ heteroaryl, is optionally substituted with one or more of the groups selected from hydrogen, $C_{1-4}$ alkyl, $C_{1-4}$ alkoxy, $C_{1-4}$ haloalkyl, $C_{3-5}$ cycloalkyl, $C_{5-6}$ aryl, $C_{1-6}$ heteroaryl, $C_{1-6}$ heterocyclyl, oxo, halogen, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano.

In an embodiment of the present disclosure, there is provided a compound of Formula I as described herein, wherein X is O; Z is N; A is $CR_1$; B is $CR_2$; D is $CR_3$; $R_1$, $R_2$, and $R_3$ are independently selected from hydrogen, or $C_{1-2}$ alkyl; $R_4$ is selected from hydrogen, $C_{1-4}$ alkyl, $C_{1-4}$ alkoxy, $C_{3-5}$ cycloalkyl, and $C_{5-6}$ aryl, wherein $C_{1-4}$ alkyl, and $C_{1-4}$ alkoxy, is optionally substituted with one or more of the groups selected from $C_{1-4}$ alkyl, and $C_{1-4}$ alkoxy; $R_{11}$ and $R_{12}$ are taken together to form a 5-10 membered monocyclic or bicyclic saturated heterocyclic ring with 1-5 heteroatoms selected from N, S or O, wherein the 5-10 membered monocyclic or bicyclic saturated heterocyclic ring is optionally substituted with the substituents selected from amino, $C_{1-2}$ alkylamino, and NH(CO)CH═CH—$CH_2$—$N(CH_3)_2$; and $R_{13}$ is selected from hydrogen, 5-9 membered monocyclic or bicyclic heteroaryl with 1-5 heteroatoms selected from N, S or O, wherein 5-9 membered monocyclic or bicyclic heteroaryl are optionally substituted with 1-5 substituents selected from hydroxyl, cyano, fluoro, bromo, chloro, $C_{1-4}$ alkyl, $C_{1-4}$ alkoxy, $C_{1-4}$ haloalkyl, $C_{3-5}$ cycloalkyl, $C_{5-9}$ aryl, $C_{1-9}$ heterocyclyl, and $C_{1-9}$ heteroaryl, wherein $C_{1-4}$ alkyl, $C_{1-4}$ alkoxy, $C_{3-5}$ cycloalkyl, $C_{5-9}$ aryl, $C_{1-9}$ heterocyclyl, and $C_{1-9}$ heteroaryl, is optionally substituted with one or more of the groups selected from hydrogen, $C_{1-4}$ alkyl, $C_{1-4}$ alkoxy, $C_{1-4}$ haloalkyl, $C_{3-5}$ cycloalkyl, $C_{5-6}$ aryl, $C_{1-6}$ heteroaryl, $C_{1-6}$ heterocyclyl, oxo, halogen, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano.

In an embodiment of the present disclosure, there is provided a compound of Formula I as described herein, wherein X is O; Z is N; A is $CR_1$; B is $CR_2$; D is $CR_3$; $R_1$, $R_2$, and $R_3$ are independently selected from hydrogen, or $C_{1-2}$ alkyl; $R_4$ is selected from hydrogen, $C_{1-4}$ alkyl, $C_{1-4}$ alkoxy, $C_{3-5}$ cycloalkyl, or $C_{5-6}$ aryl, wherein $C_{1-4}$ alkyl, and $C_{1-4}$ alkoxy, is optionally substituted with one or more of the groups selected from $C_{1-4}$ alkyl, and $C_{1-4}$ alkoxy; $R_{11}$ and $R_{12}$ are taken together to form a 5-10 membered monocyclic or bicyclic saturated heterocyclic ring with 1-5 heteroatoms selected from N, S or O, wherein the 5-10 membered monocyclic or bicyclic saturated heterocyclic ring is optionally substituted with the substituents selected from amino, $C_{1-2}$ alkylamino, and NH(CO)CH═CH—$CH_2$—$N(CH_3)_2$; and $R_{13}$ is selected from hydrogen, 5-9 membered monocyclic aryl, and 5-9 membered bicyclic heteroaryl with 1-5 heteroatoms selected from N, S or O, wherein 5-9 membered monocyclic aryl, and 5-9 membered bicyclic heteroaryl are optionally substituted with 1-5 substituents selected from hydroxyl, cyano, fluoro, bromo, chloro, $C_{1-4}$ alkyl, $C_{1-4}$ alkoxy, $C_{1-4}$ haloalkyl, $C_{3-5}$ cycloalkyl, $C_{5-9}$ aryl, $C_{1-9}$ heterocyclyl, and $C_{1-9}$ heteroaryl, wherein $C_{1-4}$ alkyl, $C_{1-4}$ alkoxy, $C_{3-5}$ cycloalkyl, $C_{5-9}$ aryl, $C_{1-9}$ heterocyclyl, and $C_{1-9}$ heteroaryl, is optionally substituted with one or more of the groups selected from hydrogen, $C_{1-4}$ alkyl, $C_{1-4}$ alkoxy, $C_{1-4}$ haloalkyl, $C_{3-5}$ cycloalkyl, $C_{5-6}$ aryl, $C_{1-6}$ heteroaryl, $C_{1-6}$ heterocyclyl, oxo, halogen, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano.

In an embodiment of the present disclosure, there is provided a compound of Formula I as described herein, wherein X selected from O or S; Z is N; A is $CR_1$; B is $CR_2$; D is $CR_3$; $R_1$, $R_2$, and $R_3$ are independently selected from hydrogen, or $C_{1-2}$ alkyl; $R_4$ is selected from hydrogen, $C_{1-4}$ alkyl, $C_{1-4}$ alkoxy, $C_{3-5}$ cycloalkyl, or $C_{5-6}$ aryl, wherein $C_{1-4}$ alkyl, and $C_{1-4}$ alkoxy, is optionally substituted with one or more of the groups selected from $C_{1-4}$ alkyl, and $C_{1-4}$ alkoxy; $R_{11}$ and $R_{12}$ are taken together to form a 5-10 membered monocyclic or bicyclic saturated heterocyclic ring with 1-5 heteroatoms selected from N, S or O, wherein the 5-10 membered monocyclic or bicyclic saturated heterocyclic ring is optionally substituted with the substituents selected from amino, $C_{1-2}$ alkylamino, and NH(CO)CH═CH—$CH_2$—$N(CH_3)_2$; and $R_{13}$ is selected from hydrogen, 5-9 membered bicyclic heteroaryl with 1-5 heteroatoms selected from N, or O, wherein 5-9 membered bicyclic heteroaryl are optionally substituted with 1-5 substituents selected from hydroxyl, cyano, fluoro, bromo, chloro, $C_{1-4}$ alkyl, $C_{1-4}$ alkoxy, $C_{1-4}$ haloalkyl, $C_{3-5}$ cycloalkyl, $C_{5-9}$ aryl, $C_{1-9}$ heterocyclyl, or $C_{1-9}$ heteroaryl, wherein $C_{1-4}$ alkyl, $C_{1-4}$ alkoxy, $C_{3-5}$ cycloalkyl, $C_{5-9}$ aryl, $C_{1-9}$ heterocyclyl, and $C_{1-9}$ heteroaryl, is optionally substituted with one or more of the groups selected from hydrogen, $C_{1-4}$ alkyl, $C_{1-4}$ alkoxy, $C_{1-4}$ haloalkyl, $C_{3-5}$ cycloalkyl, $C_{5-6}$ aryl, $C_{1-6}$ heteroaryl, $C_{1-6}$ heterocyclyl, oxo, halogen, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano.

In an embodiment of the present disclosure, there is provided a compound of Formula I as described herein, wherein X is O; Z is N; A is $CR_1$; B is $CR_2$; D is $CR_3$; $R_1$, $R_2$, and $R_3$ are independently selected from hydrogen, or $C_{1-2}$ alkyl; $R_4$ is selected from hydrogen, $C_{1-4}$ alkyl, $C_{1-4}$ alkoxy, $C_{3-5}$ cycloalkyl, or $C_{5-6}$ aryl, wherein $C_{1-4}$ alkyl, and $C_{1-4}$ alkoxy, is optionally substituted with one or more of the groups selected from $C_{1-4}$ alkyl, and $C_{1-4}$ alkoxy; $R_{11}$ and $R_{12}$ are taken together to form a 5-10 membered monocyclic or bicyclic saturated heterocyclic ring with 1-5 heteroatoms selected from N, S or O, wherein the 5-10 membered monocyclic or bicyclic saturated heterocyclic ring is optionally substituted with the substituents selected from amino, $C_{1-2}$ alkylamino, or NH(CO)CH═CH—$CH_2$—$N(CH_3)_2$; and $R_{13}$ is selected from hydrogen, 5-9 membered monocyclic or bicyclic aryl, and 5-9 membered monocyclic or bicyclic heteroaryl with 1 heteroatom selected from N, S or O, wherein 5-9 membered monocyclic or bicyclic aryl, and 5-9 membered monocyclic or bicyclic heteroaryl are optionally substituted with 1-5 substituents selected from hydroxyl, cyano, fluoro, bromo, chloro, $C_{1-4}$ alkyl, $C_{1-4}$ alkoxy, $C_{1-4}$ haloalkyl, $C_{3-5}$ cycloalkyl, $C_{5-9}$ aryl, $C_{1-9}$ heterocyclyl, or $C_{1-9}$ heteroaryl, wherein $C_{1-4}$ alkyl, $C_{1-4}$ alkoxy, $C_{3-5}$ cycloalkyl, $C_{5-9}$ aryl, $C_{1-9}$ heterocyclyl, and $C_{1-9}$ heteroaryl, is optionally substituted with one or more of the groups selected from hydrogen, $C_{1-4}$ alkyl, $C_{1-4}$ alkoxy, $C_{1-4}$ haloalkyl, $C_{3-5}$ cycloalkyl, $C_{5-6}$ aryl, $C_{1-6}$ heteroaryl, $C_{1-6}$ heterocyclyl, oxo, halogen, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano.

In an embodiment of the present disclosure, there is provided a compound of Formula I as described herein, wherein X is S; Z is N; A is $CR_1$; B is $CR_2$; D is $CR_3$; $R_1$, $R_2$, and $R_3$ are independently selected from hydrogen, or $C_{1-2}$ alkyl; $R_4$ is selected from hydrogen, $C_{1-4}$ alkyl, $C_{1-4}$ alkoxy, $C_{3-5}$ cycloalkyl, or $C_{5-6}$ aryl, wherein $C_{1-4}$ alkyl, and $C_{1-4}$ alkoxy, is optionally substituted with one or more of the groups selected from $C_{1-4}$ alkyl, and $C_{1-4}$ alkoxy; $R_{11}$ and $R_{12}$ are taken together to form a 5-10 membered monocyclic or bicyclic saturated heterocyclic ring with 1-5 heteroatoms selected from N, S or O, wherein the 5-10 membered monocyclic or bicyclic saturated heterocyclic ring is optionally substituted with the substituents selected from amino, $C_{1-2}$ alkylamino, or NH(CO)CH═CH—$CH_2$—$N(CH_3)_2$; and $R_{13}$ is selected from hydrogen, 5-9 membered monocyclic or bicyclic aryl, and 5-9 membered monocyclic or bicyclic heteroaryl with 1-5 heteroatoms selected from N, S or O, wherein 5-9 membered monocyclic or bicyclic aryl, and 5-9 membered monocyclic or bicyclic heteroaryl are optionally substituted with 1-5 substituents selected from hydroxyl, cyano, fluoro, bromo, chloro, $C_{1-4}$ alkyl, $C_{1-4}$ alkoxy, $C_{1-4}$ haloalkyl, $C_{3-5}$ cycloalkyl, $C_{5-9}$ aryl, $C_{1-9}$ heterocyclyl, or $C_{1-9}$ heteroaryl, wherein $C_{1-4}$ alkyl, $C_{1-4}$ alkoxy, $C_{3-5}$ cycloalkyl, $C_{5-9}$ aryl, $C_{1-9}$ heterocyclyl, and $C_{1-9}$ heteroaryl, is optionally substituted with one or more of the groups selected from hydrogen, $C_{1-4}$ alkyl, $C_{1-4}$ alkoxy, $C_{1-4}$ haloalkyl, $C_{3-5}$ cycloalkyl, $C_{5-6}$ aryl, $C_{1-6}$ heteroaryl, $C_{1-6}$ heterocyclyl, oxo, halogen, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano.

In an embodiment of the present disclosure, there is provided a compound of Formula II their polymorphs, stereoisomers, prodrugs, solvates, co-crystals, intermediates, pharmaceutically acceptable salts, and metabolites thereof, wherein Formula (II)

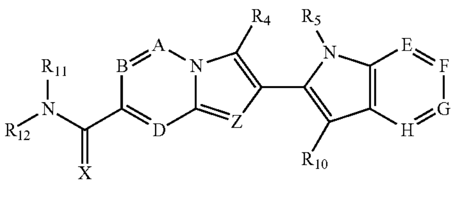

X is selected from O or S; Z is N; A is selected from N or $CR_1$; B is selected from N or $CR_2$; D is selected from N or $CR_3$; E is selected from N or $CR_6$; F is absent or is selected from N, and $CR_7$; G is absent or is selected from N, and $CR_8$; H is absent or is selected from N, and $CR_9$; $R_1$, $R_2$, $R_3$, $R_4$, $R_5$, $R_6$, $R_7$, $R_8$, $R_9$ and $R_{10}$ are independently selected from hydrogen, hydroxyl, cyano, amino, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-10}$ heterocyclyl, $C_{1-10}$ heteroaryl, $C(O)C_{1-6}$ alkyl, $C(O)C_{1-6}$ haloalkyl, $C(O)NR_{15}$, $C(O)C_{1-6}$ alkylamino, $C(O)C_{5-6}$ aryl, $C(O)C_{1-6}$ heteroaryl, $SO_2C_{1-6}$ alkyl, $SO_2C_{1-6}$ haloalkyl, $SO_2C_{3-6}$ cycloalkyl, $SO_2NR_{15}$, $SO_2NC_{1-6}$ alkylamino, $SO_2C_{5-6}$ aryl, or $SO_2C_{1-6}$ heteroaryl, wherein $C_{1-6}$ alkyl, $C_{1-6}$ alkoxy, $C_{1-10}$ heteroaryl, and $C_{1-6}$ haloalkoxy, is optionally substituted with one or more of the groups selected from hydrogen, oxo, $C_{1-6}$ alkyl, $C_{1-6}$ alkoxy, $C_{1-6}$ haloalkyl, $C_{1-6}$ alkylhydroxy, $C_{3-6}$ cycloalkyl, $C_{5-9}$ aryl, $C_{1-6}$ heterocyclyl, $C_{1-6}$ heteroaryl, cyano, halogen, and hydroxyl, wherein $C_{5-9}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano;

$R_{11}$ and $R_{12}$ are taken together to form a 5-10 membered monocyclic or bicyclic saturated or unsaturated heterocyclic ring with 1-5 heteroatoms selected from N, S or O, wherein the 5-10 membered monocyclic or bicyclic saturated or unsaturated heterocyclic ring is optionally substituted with the substituents selected from amino, $C_{1-6}$ alkylamino, $C_{1-6}$ acylamino, —NHC(NH)$CH_2Cl$, NH(CO)CH═CH—$CH_2$—$N(CH_3)_2$, $C_{1-6}$ alkyl, halogen, $C_{1-6}$ alkoxy, or hydroxyl; and $R_{15}$ is selected from the group consisting of hydrogen, $C_{1-6}$ alkyl, and combinations thereof.

In an embodiment of the present disclosure, there is provided a compound of Formula II as described herein, wherein X is selected from O or S; Z is N; A is selected from N or $CR_1$; B is selected from N or $CR_2$; D is selected from N or $CR_3$; E is selected from N or $CR_6$; F is absent or is selected from N, and $CR_7$; G is absent or is selected from N, and $CR_8$; H is absent or is selected from N, and $CR_9$; $R_1$, $R_2$, $R_3$, $R_6$, $R_7$, $R_8$, $R_9$, and $R_{10}$ are independently selected from hydrogen, hydroxyl, halogen, $C_{1-4}$ alkyl, $C_{1-4}$ alkoxy, $C_{1-4}$ haloalkyl, $C_{1-4}$ haloalkoxy, $C_{3-5}$ cycloalkyl, or $C_{5-6}$ aryl; $R_4$, and $R_5$ are independently selected from hydrogen, hydroxyl, cyano, amino, halogen, $C_{1-4}$ alkyl, $C_{1-4}$ alkoxy, $C_{3-6}$ cycloalkyl, $C_{1-4}$ haloalkyl, $C_{1-4}$ haloalkoxy, $C_{1-4}$ acylamino, $C_{1-4}$ alkylamino, $C_{5-9}$ aryl, $C_{1-9}$ heterocyclyl, $C_{1-9}$ heteroaryl, $C(O)C_{1-4}$ alkyl, $C(O)C_{1-4}$ haloalkyl, $C(O)NR_{15}$, $C(O)C_{1-4}$ alkylamino, $C(O)C_{5-6}$ aryl, $C(O)C_{1-6}$ heteroaryl, $SO_2C_{1-4}$ alkyl, $SO_2C_{1-4}$ haloalkyl, $SO_2C_{3-6}$ cycloalkyl, $SO_2NR_{15}$, $SO_2NC_{1-4}$ alkylamino, $SO_2C_{5-6}$ aryl, or $SO_2C_{1-6}$ heteroaryl, wherein $C_{1-4}$ alkyl, $C_{1-4}$ alkoxy, $C_{1-9}$ heteroaryl, and $C_{1-4}$ haloalkoxy, is optionally substituted with one or more of the groups selected from hydrogen, oxo, $C_{1-4}$ alkyl, $C_{1-4}$ alkoxy, $C_{1-4}$ haloalkyl, $C_{1-4}$ alkylhydroxy, $C_{3-6}$ cycloalkyl, $C_{5-6}$ aryl, $C_{1-6}$ heterocyclyl, $C_{1-6}$ heteroaryl, cyano, halogen, and hydroxyl, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano; $R_{11}$ and $R_{12}$ are taken together to form a 5-10 membered monocyclic or bicyclic saturated or unsaturated heterocyclic ring with 1-5 heteroatoms selected from N, S or O, wherein the 5-10 membered monocyclic or bicyclic saturated or unsaturated heterocyclic ring is optionally substituted with the substituents selected from amino, $C_{1-6}$ alkylamino, $C_{1-6}$ acylamino, —NHC(NH)$CH_2Cl$, NH(CO)CH═CH—$CH_2$—$N(CH_3)_2$, $C_{1-6}$ alkyl, halogen, $C_{1-6}$ alkoxy, or hydroxyl; and $R_{15}$ is selected from the group consisting of hydrogen, $C_{1-6}$ alkyl, and combinations thereof.

In an embodiment of the present disclosure, there is provided a compound of Formula II as described herein, wherein X is selected from O or S; Z is N; A is $CR_1$; B is $CR_2$; D is $CR_3$; E is selected from N or $CR_6$; F is absent or is $CR_7$; G is absent or is $CR_8$; H is absent or is $CR_9$; $R_1$, $R_2$, $R_3$, $R_6$, $R_7$, $R_8$, $R_9$, and $R_{10}$ are independently selected from hydrogen, halogen, $C_{1-2}$ alkyl, $C_{1-2}$ alkoxy, or $C_{5-6}$ aryl; $R_4$, and $R_5$ are independently selected from hydrogen, $C_{1-4}$ alkyl, $C_{1-4}$ alkoxy, $C_{3-6}$ cycloalkyl, $C_{1-4}$ haloalkyl, $C_{1-4}$ haloalkoxy, $C_{5-9}$ aryl, $C_{1-9}$ heterocyclyl, or $C_{1-9}$ heteroaryl, wherein $C_{1-4}$ alkyl, $C_{1-4}$ alkoxy, $C_{1-9}$ heteroaryl, and $C_{1-4}$ haloalkoxy, is optionally substituted with one or more of the groups selected from hydrogen, oxo, $C_{1-4}$ alkyl, $C_{1-4}$ alkoxy, $C_{1-4}$ haloalkyl, $C_{1-4}$ alkylhydroxy, $C_{3-6}$ cycloalkyl, $C_{5-6}$ aryl, $C_{1-6}$ heterocyclyl, $C_{1-6}$ heteroaryl, cyano, halogen, and hydroxyl, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano; $R_{11}$ and $R_{12}$ are taken together to form a 5-10 membered monocyclic or bicyclic saturated heterocyclic ring with 1-5 heteroatoms selected from N, S or O, wherein the 5-10 membered monocyclic or bicyclic saturated heterocyclic ring is optionally substituted with the substituents selected from amino, NH(CO)CH═CH—$CH_2$—$N(CH_3)_2$, or $C_{1-2}$ alkylamino.

In an embodiment of the present disclosure, there is provided a compound of Formula II as described herein, wherein X is selected from O or S; Z is N; A is $CR_1$; B is $CR_2$; D is $CR_3$; E is selected from N or $CR_6$; F is absent or is $CR_7$; G is absent or is $CR_8$; H is absent or is $CR_9$; $R_1$, $R_2$, $R_3$, $R_6$, $R_7$, $R_8$, $R_9$, and $R_{10}$ are independently selected from hydrogen, halogen, $C_1$ alkyl, or $C_1$ alkoxy; $R_4$ is selected from hydrogen, $C_1$ alkyl, $C_1$ alkoxy, $C_3$ cycloalkyl, or $C_6$ aryl, wherein $C_1$ alkyl, and $C_1$ alkoxy, is optionally substituted with one or more of the groups selected from $C_1$ alkyl, and $C_1$ alkoxy; $R_5$ is selected from hydrogen, $C_{1-4}$ alkyl, $C_{1-4}$ alkoxy, $C_{3-6}$ cycloalkyl, $C_{1-4}$ haloalkyl, $C_{1-4}$ haloalkoxy, $C_{5-9}$ aryl, $C_{1-9}$ heterocyclyl, or $C_{1-9}$ heteroaryl, wherein $C_{1-4}$ alkyl, $C_{1-4}$ alkoxy, $C_{1-9}$ heteroaryl, and $C_{1-4}$ haloalkoxy, is optionally substituted with one or more of the groups selected from hydrogen, oxo, $C_{1-4}$ alkyl, $C_{1-4}$ alkoxy, $C_{1-4}$ haloalkyl, $C_{1-4}$ alkylhydroxy, $C_{3-6}$ cycloalkyl, $C_{5-6}$ aryl, $C_{1-6}$ heterocyclyl, $C_{1-6}$ heteroaryl, cyano, halogen, and hydroxyl, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano; and $R_1$ and $R_{12}$ are taken together to form a 5-10 membered monocyclic or bicyclic saturated heterocyclic ring with 1-5 heteroatoms selected from N, S or O, wherein the 5-10 membered monocyclic or bicyclic saturated heterocyclic ring is optionally substituted with the substituents selected from amino, and NH(CO)CH═CH—$CH_2$—$N(CH_3)_2$.

In an embodiment of the present disclosure, there is provided a compound of Formula III their polymorphs, stereoisomers, prodrugs, solvates, co-crystals, intermediates, pharmaceutically acceptable salts, and metabolites thereof, wherein Formula (III)

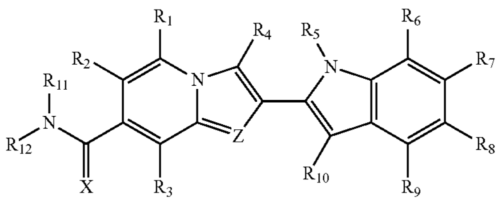

X is selected from O or S; Z is N; $R_1$, $R_2$, $R_3$, $R_4$, $R_5$, $R_6$, $R_7$, $R_8$, $R_9$ and $R_{10}$ are independently selected from hydrogen, hydroxyl, cyano, amino, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-10}$ heterocyclyl, $C_{1-10}$ heteroaryl, $C(O)C_{1-6}$ alkyl, $C(O)C_{1-6}$ haloalkyl, $C(O)NR_{15}$, $C(O)C_{1-6}$ alkylamino, $C(O)C_{5-6}$ aryl, $C(O)C_{1-6}$ heteroaryl, $SO_2C_{1-6}$ alkyl, $SO_2C_{1-6}$ haloalkyl, $SO_2C_{3-6}$ cycloalkyl, $SO_2NR_{15}$, $SO_2NC_{1-6}$ alkylamino, $SO_2C_{5-6}$ aryl, or $SO_2C_{1-6}$ heteroaryl, wherein $C_{1-6}$ alkyl, $C_{1-6}$ alkoxy, $C_{1-10}$ heteroaryl, and $C_{1-6}$ haloalkoxy, is optionally substituted with one or more of the groups selected from hydrogen, oxo, $C_{1-6}$ alkyl, $C_{1-6}$ alkoxy, $C_{1-6}$ haloalkyl, $C_{1-6}$ alkylhydroxy, $C_{3-6}$ cycloalkyl, $C_{5-9}$ aryl, $C_{1-6}$ heterocyclyl, $C_{1-6}$ heteroaryl, cyano, halogen, and hydroxyl, wherein $C_{5-9}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano; $R_{11}$ and $R_{12}$ are taken together to form a 5-10 membered monocyclic or bicyclic saturated or unsaturated heterocyclic ring with 1-5 heteroatoms selected from N, S or O, wherein the 5-10 membered monocyclic or bicyclic saturated or unsaturated heterocyclic ring is optionally substituted with the substituents selected from amino, $C_{1-6}$ alkylamino, $C_{1-6}$ acylamino, —$NHC(NH)CH_2Cl$, NH(CO)CH═CH—$CH_2$—$N(CH_3)_2$, $C_{1-6}$ alkyl, halogen, $C_{1-6}$ alkoxy, or hydroxyl; and $R_{15}$ is selected from the group consisting of hydrogen, $C_{1-6}$ alkyl, and combinations thereof.

In an embodiment of the present disclosure, there is provided a compound of Formula III as described herein, wherein X is selected from O or S; Z is N; $R_1$, $R_2$, $R_3$, $R_6$, $R_7$, $R_8$, $R_9$ and $R_{10}$ are independently selected from hydrogen, hydroxyl, cyano, amino, halogen, $C_{1-4}$ alkyl, $C_{1-4}$ alkoxy, $C_{1-4}$ haloalkyl, $C_{1-4}$ haloalkoxy, $C_{3-5}$ cycloalkyl, $C_{5-6}$ aryl, $C_{1-6}$ heterocyclyl, or $C_{1-6}$ heteroaryl; $R_4$, and $R_5$ are independently selected from hydrogen, hydroxyl, cyano, amino, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-10}$ heterocyclyl, $C_{1-10}$ heteroaryl, $C(O)C_{1-6}$ alkyl, $C(O)C_{1-6}$ haloalkyl, $C(O)NR_{15}$, $C(O)C_{1-6}$ alkylamino, $C(O)C_{5-6}$ aryl, $C(O)C_{1-6}$ heteroaryl, $SO_2C_{1-6}$ alkyl, $SO_2C_{1-6}$ haloalkyl, $SO_2C_{3-6}$ cycloalkyl, $SO_2NR_{15}$, $SO_2NC_{1-6}$ alkylamino, $SO_2C_{5-6}$ aryl, or $SO_2C_{1-6}$ heteroaryl, wherein $C_{1-6}$ alkyl, $C_{1-6}$ alkoxy, $C_{1-10}$ heteroaryl, and $C_{1-6}$ haloalkoxy, is optionally substituted with one or more of the groups selected from hydrogen, oxo, $C_{1-6}$ alkyl, $C_{1-6}$ alkoxy, $C_{1-6}$ haloalkyl, $C_{1-6}$ alkylhydroxy, $C_{3-6}$ cycloalkyl, $C_{5-9}$ aryl, $C_{1-6}$ heterocyclyl, $C_{1-6}$ heteroaryl, cyano, halogen, and hydroxyl, wherein $C_{5-9}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano; $R_{11}$ and $R_{12}$ are taken together to form a 5-10 membered monocyclic or bicyclic saturated or unsaturated heterocyclic ring with 1-5 heteroatoms selected from N, S or O, wherein the 5-10 membered monocyclic or bicyclic saturated or unsaturated heterocyclic ring is optionally substituted with the substituents selected from amino, $C_{1-6}$ alkylamino, $C_{1-6}$ acylamino, —NHC(NH)$CH_2$Cl, NH(CO)CH═CH—$CH_2$—$N(CH_3)_2$, $C_{1-6}$ alkyl, halogen, $C_{1-6}$ alkoxy, or hydroxyl; and $R_{15}$ is selected from the group consisting of hydrogen, $C_{1-6}$ alkyl, and combinations thereof.

In an embodiment of the present disclosure, there is provided a compound of Formula III as described herein, wherein X is selected from O or S; Z is N; $R_1$, $R_2$, $R_3$, $R_4$, $R_5$, $R_6$, $R_7$, $R_8$, $R_9$ and $R_{10}$ are independently selected from hydrogen, hydroxyl, cyano, amino, halogen, $C_{1-4}$ alkyl, $C_{1-4}$ alkoxy, $C_{3-6}$ cycloalkyl, $C_{1-4}$ haloalkyl, $C_{1-4}$ haloalkoxy, $C_{1-4}$ acylamino, $C_{1-4}$ alkylamino, $C_{5-9}$ aryl, $C_{1-9}$ heterocyclyl, $C_{1-9}$ heteroaryl, C(O)$C_{1-4}$ alkyl, C(O)$C_{1-4}$ haloalkyl, C(O)$NR_{15}$, C(O)$C_{1-4}$ alkylamino, C(O)$C_{5-6}$ aryl, C(O)$C_{1-6}$ heteroaryl, $SO_2C_{1-4}$ alkyl, $SO_2C_{1-4}$ haloalkyl, $SO_2C_{3-6}$ cycloalkyl, $SO_2NR_{15}$, $SO_2NC_{1-4}$ alkylamino, $SO_2C_{5-6}$ aryl, or $SO_2C_{1-6}$ heteroaryl, wherein $C_{1-4}$ alkyl, $C_{1-4}$ alkoxy, $C_{1-9}$ heteroaryl, and $C_{1-4}$ haloalkoxy, is optionally substituted with one or more of the groups selected from hydrogen, oxo, $C_{1-4}$ alkyl, $C_{1-4}$ alkoxy, $C_{1-4}$ haloalkyl, $C_{1-4}$ alkylhydroxy, $C_{3-6}$ cycloalkyl, $C_{5-6}$ aryl, $C_{1-6}$ heterocyclyl, $C_{1-6}$ heteroaryl, cyano, halogen, and hydroxyl, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2$OH, and cyano; $R_{11}$ and $R_{12}$ are taken together to form a 5-10 membered monocyclic or bicyclic saturated or unsaturated heterocyclic ring with 1-5 heteroatoms selected from N, S or O, wherein the 5-10 membered monocyclic or bicyclic saturated or unsaturated heterocyclic ring is optionally substituted with the substituents selected from amino, $C_{1-6}$ alkylamino, $C_{1-6}$ acylamino, —NHC(NH)$CH_2$Cl, NH(CO)CH═CH—$CH_2$—$N(CH_3)_2$, $C_{1-6}$ alkyl, halogen, $C_{1-6}$ alkoxy, and hydroxyl; and $R_{15}$ is selected from the group consisting of hydrogen, $C_{1-6}$ alkyl, and combinations thereof.

In an embodiment of the present disclosure, there is provided a compound of Formula III as described herein, wherein X is selected from O or S; Z is N; $R_1$, $R_2$, $R_3$, $R_6$, $R_7$, $R_8$, $R_9$, and $R_{10}$ are independently selected from hydrogen, hydroxyl, halogen, $C_{1-4}$ alkyl, $C_{1-4}$ alkoxy, $C_{1-4}$ haloalkyl, $C_{1-4}$ haloalkoxy, $C_{3-5}$ cycloalkyl, or $C_{5-6}$ aryl; $R_4$, and $R_5$ are independently selected from hydrogen, hydroxyl, cyano, amino, halogen, $C_{1-4}$ alkyl, $C_{1-4}$ alkoxy, $C_{3-6}$ cycloalkyl, $C_{1-4}$ haloalkyl, $C_{1-4}$ haloalkoxy, $C_{1-4}$ acylamino, $C_{1-4}$ alkylamino, $C_{5-9}$ aryl, $C_{1-9}$ heterocyclyl, $C_{1-9}$ heteroaryl, C(O)$C_{1-4}$ alkyl, C(O)$C_{1-4}$ haloalkyl, C(O)$NR_{15}$, C(O)$C_{1-4}$ alkylamino, C(O)$C_{5-6}$ aryl, C(O)$C_{1-6}$ heteroaryl, $SO_2C_{1-4}$ alkyl, $SO_2C_{1-4}$ haloalkyl, $SO_2C_{3-6}$ cycloalkyl, $SO_2NR_{15}$, $SO_2NC_{1-4}$ alkylamino, $SO_2C_{5-6}$ aryl, or $SO_2C_{1-6}$ heteroaryl, wherein $C_{1-4}$ alkyl, $C_{1-4}$ alkoxy, $C_{1-9}$ heteroaryl, and $C_{1-4}$ haloalkoxy, is optionally substituted with one or more of the groups selected from hydrogen, oxo, $C_{1-4}$ alkyl, $C_{1-4}$ alkoxy, $C_{1-4}$ haloalkyl, $C_{1-4}$ alkylhydroxy, $C_{3-6}$ cycloalkyl, $C_{5-6}$ aryl, $C_{1-6}$ heterocyclyl, $C_{1-6}$ heteroaryl, cyano, halogen, and hydroxyl, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2$OH, and cyano; $R_{11}$ and $R_{12}$ are taken together to form a 5-10 membered monocyclic or bicyclic saturated or unsaturated heterocyclic ring with 1-5 heteroatoms selected from N, S or O, wherein the 5-10 membered monocyclic or bicyclic saturated or unsaturated heterocyclic ring is optionally substituted with the substituents selected from amino, $C_{1-6}$ alkylamino, $C_{1-6}$ acylamino, —NHC(NH)$CH_2$Cl, NH(CO)CH═CH—$CH_2$—$N(CH_3)_2$, $C_{1-6}$ alkyl, halogen, $C_{1-6}$ alkoxy, or hydroxyl; and $R_{15}$ is selected from the group consisting of hydrogen, $C_{1-6}$ alkyl, and combinations thereof.

In an embodiment of the present disclosure, there is provided a compound of Formula III as described herein, wherein X is selected from O or S; Z is N; $R_1$, $R_2$, $R_3$, $R_6$, $R_7$, $R_8$, $R_9$, and $R_{10}$ are independently selected from hydrogen, halogen, $C_{1-4}$ alkyl, $C_{1-4}$ alkoxy, or $C_{5-6}$ aryl; $R_4$, and $R_5$ are independently selected from hydrogen, $C_{1-4}$ alkyl, $C_{1-4}$ alkoxy, $C_{3-6}$ cycloalkyl, $C_{1-4}$ haloalkyl, $C_{1-4}$ haloalkoxy, $C_{5-9}$ aryl, $C_{1-9}$ heterocyclyl, or $C_{1-9}$ heteroaryl, wherein $C_{1-4}$ alkyl, $C_{1-4}$ alkoxy, $C_{1-9}$ heteroaryl, and $C_{1-4}$ haloalkoxy, is optionally substituted with one or more of the groups selected from hydrogen, oxo, $C_{1-4}$ alkyl, $C_{1-4}$ alkoxy, $C_{1-4}$ haloalkyl, $C_{1-4}$ alkylhydroxy, $C_{3-6}$ cycloalkyl, $C_{5-6}$ aryl, $C_{1-6}$ heterocyclyl, $C_{1-6}$ heteroaryl, cyano, halogen, and hydroxyl, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2$OH, and cyano; and $R_{11}$ and $R_{12}$ are taken together to form a 5-10 membered monocyclic or bicyclic saturated heterocyclic ring with 1-5 heteroatoms selected from N, S or O, wherein the 5-10 membered monocyclic or bicyclic saturated heterocyclic ring is optionally substituted with the substituents selected from amino, $C_{1-4}$ alkylamino, and NH(CO)CH═CH—$CH_2$—$N(CH_3)_2$.

In an embodiment of the present disclosure there is provided a compound of Formula (I) or its polymorphs, stereoisomers, prodrugs, solvates, co-crystals, intermediates, pharmaceutically acceptable salts, and metabolites thereof, which is selected from a group consisting of:

1) (R)-(3-aminopiperidin-1-yl)(2-(3-bromo-1-(cyclopropylmethyl)-1H-indol-2-yl)-3-methylimidazo[1,2-a]pyridin-7-yl)methanone,
2) (R)-(3-aminopiperidin-1-yl)(2-(1-(cyclopropylmethyl)-1H-indol-2-yl)-3-methylimidazo[1,2-a]pyridin-7-yl)methanone,
3) (R)-(3-aminopiperidin-1-yl)(2-(1-benzyl-1H-indol-2-yl)-3-methylimidazo[1,2-a]pyridin-7-yl)methanone,
4) (R)-(3-aminopiperidin-1-yl)(2-(1-ethyl-1H-indol-2-yl)-3-methylimidazo[1,2-a]pyridin-7-yl)methanone,
5) (R)-(3-aminopiperidin-1-yl)(2-(1-ethyl-3-phenyl-1H-indol-2-yl)-3-methylimidazo[1,2-a]pyridin-7-yl)methanone,
6) (R)-(3-aminopyrrolidin-1-yl)(2-(1-ethyl-3-phenyl-1H-indol-2-yl)-3-methylimidazo[1,2-a]pyridin-7-yl)methanone,
7) (R)-(3-aminopyrrolidin-1-yl)(2-(1-ethyl-1H-indol-2-yl)-3-methylimidazo[1,2-a]pyridin-7-yl)methanone,
8) (R)-(3-aminopyrrolidin-1-yl)(2-(1-(cyclopropylmethyl)-1H-indol-2-yl)-3-methylimidazo[1,2-a]pyridin-7-yl)methanone,
9) (2-(1-(cyclopropylmethyl)-1H-indol-2-yl)-3-methylimidazo[1,2-a]pyridin-7-yl)(hexahydro-2H-pyrido[4,3-b][1,4]oxazin-6(5H)-yl)methanone,
10) (R)-(3-aminopiperidin-1-yl)(3-methyl-2-(1-(pyridin-4-ylmethyl)-1H-indol-2-yl)imidazo[1,2-a]pyridin-7-yl)methanone,
11) (R)-(3-Aminopiperidin-1-yl)(3-methyl-2-(1-((tetrahydro-2H-pyran-4-yl)methyl)-1H-indol-2-yl)imidazo[1,2-a]pyridin-7-yl)methanone,
12) (R)-(3-aminopiperidin-1-yl)(2-(1-(4-methoxybenzyl)-1H-indol-2-yl)-3-methylimidazo[1,2-a]pyridin-7-yl)methanone, 13) (R)-(3-aminopiperidin-1-yl)(2-(1-(4-fluorobenzyl)-1H-indol-2-yl)-3-methylimidazo[1,2-a]pyridin-7-yl)methanone, 14) (R)-4-((2-(7-(3-aminopiperidine-1-carbonyl)-3-methylimidazo[1,2-a]pyridin-2-yl)-1H-indol-1-yl)methyl)benzonitrile, 15) (R)-(3-aminopiperidin-1-yl)(3-methyl-2-(1-(pyridin-3-ylmethyl)-1H-indol-2-yl)imidazo[1,2-a]pyridin-7-yl)methanone, 16) (R)-(3-aminopiperidin-1-yl)(3-methyl-2-(1-(pyridin-2-ylmethyl)-1H-indol-2-yl)imidazo[1,2-a]pyridin-7-yl)methanone, 17) (R)-(3-aminopiperidin-1-yl)(3-methyl-2-(1-(2,2,2-trifluoroethyl)-1H-indol-2-yl)imidazo[1,2-a]pyridin-7-yl)methanone, 18) (R)-4-((2-(7-(3-aminopiperidine-1-carbonyl)-3-methylimidazo[1,2-a]pyridin-2-yl)-1H-indol-1-yl)methyl)-1-methylpyridin-2(1H)-one, 19) (R)-(3-aminopiperidin-1-yl)(2-(3-ethylbenzo[b]thiophen-2-yl)-3-methylimidazo[1,2-a]pyridin-7-yl)methanone, 20) (R)-(3-aminopiperidin-1-yl)(2-(1-(4-chlorobenzyl)-1H-indol-2-yl)-3-methylimidazo[1,2-a]pyridin-7-yl)methanone, 21) (R)-(3-aminopiperidin-1-yl)(2-(1-(2-fluorobenzyl)-1H-indol-2-yl)-3-methylimidazo[1,2-a]pyridin-7-yl)methanone, 22) (R)-(3-aminopiperidin-1-yl)(2-(1-ethyl-5-phenyl-1H-pyrrol-2-yl)-3-methylimidazo[1,2-a]pyridin-7-yl)methanone, 23) (R)-(3-aminopiperidin-1-yl)(2-(1-(cyclopropylmethyl)-6-methoxy-1H-indol-2-yl)-3-methylimidazo[1,2-a]pyridin-7-yl)methanone, 24) (R)-(3-aminopiperidin-1-yl)(2-(1-ethyl-1H-pyrrolo[2,3-b]pyridin-2-yl)-3-methylimidazo[1,2-a]pyridin-7-yl)methanone, 25) (R)-(3-aminopiperidin-1-yl)(2-(1-(cyclopropylmethyl)-1H-indol-2-yl)-3,5-dimethylimidazo[1,2-a]pyridin-7-yl)methanone, 26) (R)-(3-aminopiperidin-1-yl)(2-(1-benzyl-1H-indol-2-yl)-3,5-dimethylimidazo[1,2-a]pyridin-7-yl)methanone, 27) (R)-(3-aminopiperidin-1-yl)(3,5-dimethyl-2-(1-(pyridin-2-ylmethyl)-1H-indol-2-yl)imidazo[1,2-a]pyridin-7-yl)methanone, 28) (R)-(3-aminopiperidin-1-yl)(2-(1-(cyclopropylmethyl)-6-fluoro-1H-indol-2-yl)-3-methylimidazo[1,2-a]pyridin-7-yl)methanone, 29) (R)-(3-aminopiperidin-1-yl)(2-(1-(cyclopropylmethyl)-5-fluoro-1H-indol-2-yl)-3-methylimidazo[1,2-a]pyridin-7-yl)methanone, 30) (R)-(3-aminopiperidin-1-yl)(2-(1-(cyclopropylmethyl)-7-methyl-1H-indol-2-yl)-3-methylimidazo[1,2-a]pyridin-7-yl)methanone, 31) (R)-(3-aminopiperidin-1-yl)(2-(2-ethylphenyl)-3-methylimidazo[1,2-a]pyridin-7-yl)methanone, 32) (R)-(3-aminopiperidin-1-yl)(2-(1-(cyclopropylmethyl)-1H-indol-2-yl)-3-phenylimidazo[1,2-a]pyridin-7-yl)methanone, 33) (R)-(3-aminopiperidin-1-yl)(3-cyclopropyl-2-(1-(cyclopropylmethyl)-1H-indol-2-yl)imidazo[1,2-a]pyridin-7-yl)methanone, 34) (R)-(3-aminopiperidin-1-yl)(2-(1-(cyclopropylmethyl)-1H-indol-2-yl)-3-(methoxymethyl)imidazo[1,2-a]pyridin-7-yl)methanone, 35) (R)-(3-aminopiperidin-1-yl)(2-(1-(3-fluorobenzyl)-1H-indol-2-yl)-3-methylimidazo[1,2-a]pyridin-7-yl)methanone, 36) (R)-(3-aminopiperidin-1-yl)(3-methyl-2-(1-(thiophen-3-ylmethyl)-1H-indol-2-yl)imidazo[1,2-a]pyridin-7-yl)methanone, 37) (R)-(3-aminopiperidin-1-yl)(2-(1-(furan-3-ylmethyl)-1H-indol-2-yl)-3-methylimidazo[1,2-a]pyridin-7-yl)methanone, 38) (R)-3-aminopiperidin-1-yl)(2-(1-(1-(4-fluorophenyl)ethyl)-1H-indol-2-yl)-3-methylimidazo[1,2-a]pyridin-7-yl)methanone, 39) (R)-(3-aminopiperidin-1-yl)(2-(1-ethyl-5-fluoro-1H-indol-2-yl)-3-methylimidazo[1,2-a]pyridin-7-yl)methanone, 40) (R)-(3-aminopiperidin-1-yl)(2-(1-(cyclopropylmethyl)-4-fluoro-1H-indol-2-yl)-3-methylimidazo[1,2-a]pyridin-7-yl)methanone, 41) (R)-(3-aminopiperidin-1-yl)(3-methyl-2-(1-((4-methylthiazol-2-yl)methyl)-1H-indol-2-yl)imidazo[1,2-a]pyridin-7-yl)methanone, 42) (R)-(3-aminopiperidin-1-yl)(2-(1-(3-methoxybenzyl)-1H-indol-2-yl)-3-methylimidazo[1,2-a]pyridin-7-yl)methanone, 43) (R)-(3-aminopiperidin-1-yl)(2-(5-bromo-1-(cyclopropylmethyl)-1H-indol-2-yl)-3-methylimidazo[1,2-a]pyridin-7-yl)methanone, 44) (R)-(3-aminopiperidin-1-yl)(2-(7-chloro-1-(cyclopropylmethyl)-1H-indol-2-yl)-3-methylimidazo[1,2-a]pyridin-7-yl)methanone, 45) (R)-(3-aminopiperidin-1-yl)(2-(1-(4-fluorobenzyl)-1H-indol-2-yl)-3-methylimidazo[1,2-a]pyridin-7-yl)methanethione, 46) (R)-(3-aminopiperidin-1-yl)(3-methyl-2-(1-methyl-1H-indol-2-yl)imidazo[1,2-a]pyridin-7-yl)methanone, 47) (R)-(3-aminopiperidin-1-yl)(2-(1-(cyclopropylmethyl)-7-methoxy-1H-indol-2-yl)-3-methylimidazo[1,2-a]pyridin-7-yl)methanone, 48) (R)-(3-aminopiperidin-1-yl)(2-(1-((2,4-dimethylthiazol-5-yl)methyl)-1H-indol-2-yl)-3-methylimidazo[1,2-a]pyridin-7-yl)methanone, 49) (R)-(3-aminopiperidin-1-yl)(3-methyl-2-(1-((2-methylthiazol-5-yl)methyl)-1H-indol-2-yl)imidazo[1,2-a]pyridin-7-yl)methanone, 50) (R)-(3-aminopiperidin-1-yl) (2-(1-(3-methoxybenzyl)-1H-indol-2-yl)-3-methylimidazo[1,2-a]pyridin-7-yl)methanone trifluoroacetic acid salt, 51) (R)-(3-aminopiperidin-1-yl)(2-(6-methoxy-1-(pyridin-3-ylmethyl)-1H-indol-2-yl)-3-methylimidazo[1,2-a]pyridin-7-yl)methanone, 52) (R)-(3-aminopiperidin-1-yl)(2-(1-(cyclopropylmethyl)-6-fluoro-1H-indol-2-yl)-3-methylimidazo[1,2-a]pyridin-7-yl)methanone trifluoroacetic acid salt, 53) (R)-(3-aminopiperidin-1-yl)(2-(5-fluoro-1-(3-methoxybenzyl)-1H-indol-2-yl)-3-methylimidazo[1,2-a]pyridin-7-yl)methanone, 54) (R)-(3-aminopiperidin-1-yl)(2-(6-fluoro-1-(4-fluorobenzyl)-1H-indol-2-yl)-3-methylimidazo[1,2-a]pyridin-7-yl)methanone, 55) (R)-(3-aminopiperidin-1-yl)(2-(5,6-difluoro-1-(3-methoxybenzyl)-1H-indol-2-yl)-3-methylimidazo[1,2-a]pyridin-7-yl)methanone, 56) (R,E)-4-(dimethylamino)-N-(1-(2-(1-(4-fluorobenzyl)-1H-indol-2-yl)-3-methylimidazo[1,2-a]pyridine-7-carbonyl)piperidin-3-yl)but-2-enamide, 57) (R)-(3-aminopiperidin-1-yl)(3-methyl-2-(1-(pyrazin-2-ylmethyl)-1H-indol-2-yl)imidazo[1,2-a]pyridin-7-yl)methanone, 58) (R)-(3-aminopiperidin-1-yl)(3-methyl-2-(1-(pyrimidin-5-ylmethyl)-1H-indol-2-yl)imidazo[1,2-a]pyridin-7-yl)methanone trifluoroacetic acid salt, 59) (R)-(3-aminopiperidin-1-yl)(3-methyl-2-(1-(pyridazin-3-ylmethyl)-1H-indol-2-yl)imidazo[1,2-a]pyridin-7-yl)methanone, 60) (R)-(3-aminopiperidin-1-yl)(2-(1-isobutyl-1H-indol-2-yl)-3-methylimidazo[1,2-a]pyridin-7-yl)methanone, 61) (R)-(3-aminopiperidin-1-yl)(2-(1-(cyclobutylmethyl)-1H-indol-2-yl)-3-methylimidazo[1,2-a]pyridin-7-yl)methanone, 62) (R)-(3-aminopiperidin-1-yl)(2-(1-((3-fluoropyridin-2-yl)methyl)-1H-indol-2-yl)-3-methylimidazo[1,2-a]pyridin-7-yl)methanone, 63) (R)-(3-aminopiperidin-1-yl)(2-(1-((5-methoxypyridin-2-yl)methyl)-1H-indol-2-yl)-3-methylimidazo[1,2-a]pyridin-7-yl)methanone, 64) (R)-(3-aminopiperidin-1-yl)(2-(1-(2-methoxyethyl)-1H-indol-2-yl)-3-methylimidazo[1,2-a]pyridin-7-yl)methanone, 65) (R)-(3-aminopiperidin-1-yl)(2-(1-(2-hydroxyethyl)-1H-indol-2-yl)-3-methylimidazo[1,2-a]pyridin-7-yl)methanone, 66) (R)-(3-aminopiperidin-1-yl)(2-(6-methoxy-1-(pyridin-4-ylmethyl)-1H-indol-2-yl)-3-methylimidazo[1,2-a]pyridin-7-yl)methanone, 67) (R)-(3-aminopiperidin-1-yl)(2-(1-ethyl-6-methoxy-1H-indol-2-yl)-3-methylimidazo[1,2-a]pyridin-7-yl)methanone, 68) (R)-(3-aminopiperidin-1-yl)(2-(6-fluoro-1-(pyridin-4-ylmethyl)-1H-indol-2-yl)-3-methylimidazo[1,2-a]pyridin-7-yl)methanone, 69) (R)-(3-aminopiperidin-1-yl)(2-(6-fluoro-1-(pyridin-3-ylmethyl)-1H-indol-2-yl)-3-methylimidazo[1,2-a]pyridin-7-yl)methanone, 70) (R)-(3-aminopiperidin-1-yl)(2-(6-fluoro-1-(3-methoxybenzyl)-1H-indol-2-yl)-3-methylimidazo[1,2-a]pyridin-7-yl)methanone, 71) (R)-(3-aminopiperidin-1-yl)(2-(6-fluoro-1-(4-methoxybenzyl)-1H-indol-2-yl)-3-methylimidazo[1,2-a]pyridin-7-yl)methanone, 72) (R)-(3-aminopiperidin-1-yl)(2-(1-ethyl-6-fluoro-1H-indol-2-yl)-3-methylimidazo[1,2-a]pyridin-7-yl)methanone, 73) (R)-(3-aminopiperidin-1-yl)(2-(6-fluoro-1-isobutyl-1H-indol-2-yl)-3-methylimidazo[1,2-a]pyridin-7-yl)methanone, 74) (R)-(3-aminopiperidin-1-yl)(2-(5-fluoro-1-(pyridin-4-ylmethyl)-1H-indol-2-yl)-3-methylimidazo[1,2-a]pyridin-7-yl)methanone, 75) (R)-(3-aminopiperidin-1-yl)(2-(5-fluoro-1-(4-methoxybenzyl)-1H-indol-2-yl)-3-methylimidazo[1,2-a]pyridin-7-yl)methanone, 76) (R)-(3-aminopiperidin-1-yl)(2-(5-fluoro-1-(4-fluorobenzyl)-1H-indol-2-yl)-3-methylimidazo[1,2-a]pyridin-7-yl)methanone, 77) (R)-(3-aminopiperidin-1-yl)(2-(7-chloro-1-(4-fluorobenzyl)-1H-indol-2-yl)-3-methylimidazo[1,2-a]pyridin-7-yl)methanone, 78) (R)-(3-aminopiperidin-1-yl)(2-(1-(2,2-difluoroethyl)-1H-indol-2-yl)-3-methylimidazo[1,2-a]pyridin-7-yl)methanone trifluoroacetic acid salt, 79) (R)-(3-aminopiperidin-1-yl)(2-(1-((5-fluoropyridin-2-yl)methyl)-1H-indol-2-yl)-3-methylimidazo[1,2-a]pyridin-7-yl)methanone, 80) (R)-(3-aminopiperidin-1-yl)(2-(1-(4-fluorobenzyl)-6-methoxy-1H-indol-2-yl)-3-methylimidazo[1,2-a]pyridin-7-yl)methanone, 81) (R)-(3-aminopiperidin-1-yl)(2-(1-(4-(hydroxymethyl)benzyl)-1H-indol-2-yl)-3-methylimidazo[1,2-a]pyridin-7-yl)methanone, 82) (R)-(3-aminopiperidin-1-yl)(2-(1-isobutyl-6-methoxy-1H-indol-2-yl)-3-methylimidazo[1,2-a]pyridin-7-yl)methanone, 83) (R)-(3-aminopiperidin-1-yl)(2-(1-(2,2-difluoroethyl)-6-methoxy-1H-indol-2-yl)-3-methylimidazo[1,2-a]pyridin-7-yl)methanone, 84) (R)-(3-aminopiperidin-1-yl)(2-(5-fluoro-1-isobutyl-1H-indol-2-yl)-3-methylimidazo[1,2-a]pyridin-7-yl)methanone and 85) (R)-(3-aminopiperidin-1-yl)(2-(1-(4-fluoro-3-methoxybenzyl)-1H-indol-2-yl)-3-methylimidazo[1,2-a]pyridin-7-yl)methanone, and 86) (R)-(3-aminopiperidin-1-yl)(2-(1-(cyclopropylmethyl)-6-methoxy-1H-indol-2-yl)-3-(methoxymethyl)imidazo[1,2-a]pyridin-7-yl)methanone.

In an embodiment, the disclosure relates to a process of preparation of compounds of Formula (I), Formula (II), and Formula (III) as claimed in any of claims 1-11 or its polymorphs, stereoisomers, prodrugs, solvates, co-crystals, intermediates, pharmaceutically acceptable salts, and metabolites thereof.

In an embodiment, the disclosure relates to a process of preparation of compounds of Formula (I), or its polymorphs, stereoisomers, prodrugs, solvates, co-crystals, intermediates, pharmaceutically acceptable salts, and metabolites thereof, the process comprising reacting $R_{13}CH(O)$ and $R_4CH_2NO_2$ with a compound selected from Formula (IVA) or Formula (IV)

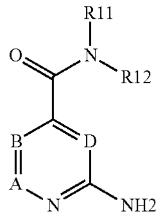

Formula (IVA)

+

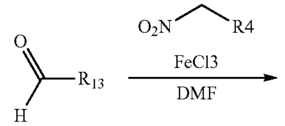

or

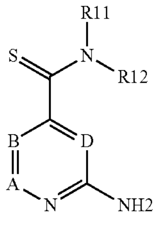

Formula (IV)

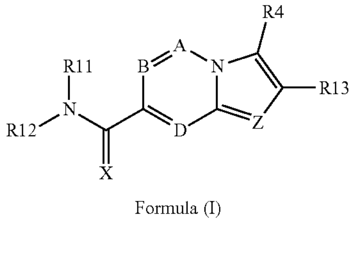

Formula (I)

wherein $R_{13}$ of $R_{13}CH(O)$ is selected from hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from the group consisting of hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-6}$ heterocyclyl, $C_{1-6}$ heteroaryl, $C(O)C_{1-6}$ alkyl, $C(O)C_{1-6}$ haloalkyl, $C(O)NR_{15}$, $C(O)C_{1-6}$ alkylamino, $C(O)C_{5-6}$ aryl, $C(O)C_{1-6}$ heteroaryl, $SO_2C_{1-6}$ alkyl, $SO_2C_{1-6}$ haloalkyl, $SO_2C_{3-6}$ cycloalkyl, $SO_2NR_{15}$, $SO_2NC_{1-6}$ alkylamino, $SO_2C_{5-6}$ aryl, or $SO_2C_{1-6}$ heteroaryl, wherein $C_{1-6}$ alkyl, $C_{1-6}$ alkoxy, $C_{3-6}$ cycloalkyl, $C_{5-10}$ aryl, $C_{1-6}$ heterocyclyl, and $C_{1-6}$ heteroaryl, is optionally substituted with one or more of the groups selected from hydrogen, $C_{1-6}$ alkyl, $C_{1-6}$ haloalkyl, $C_{1-6}$ alkoxy, $C_{3-6}$ cycloalkyl, $C_{5-6}$ aryl, $C_{1-6}$ heteroaryl, $C_{1-6}$ heterocyclyl, oxo, halogen, hydroxyl, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano; A of Formula (IVA) and (IV) is selected from N or $CR_1$; B is selected from N or $CR_2$; D is selected from N or $CR_3$; $R_{11}$ and $R_{12}$ are taken together to form a 5-10 membered monocyclic or bicyclic saturated or unsaturated heterocyclic ring optionally with 1-5 heteroatoms selected from N, S or O, wherein the 5-10 membered monocyclic or bicyclic saturated or unsaturated heterocyclic ring is optionally substituted with the substituents selected from amino, $C_{1-6}$ alkylamino, $C_{1-6}$ acylamino, —$NHC(NH)CH_2Cl$, —$NH(CO)CH{=}CH$—$CH_2$—$N(CH_3)_2$, $C_{1-6}$ alkyl, halogen, $C_{1-6}$ alkoxy, or hydroxyl; $R_4$ of $R_4CH_2NO_2$ is selected from hydrogen, hydroxyl, cyano, amino, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-6}$ heterocyclyl, $C_{1-6}$ heteroaryl, $C(O)C_{1-6}$ alkyl, $C(O)C_{1-6}$ haloalkyl, $C(O)NR_{15}$, $C(O)C_{1-6}$ alkylamino, $C(O)C_{5-6}$ aryl, $C(O)C_{1-6}$ heteroaryl, $SO_2C_{1-6}$ alkyl, $SO_2C_{1-6}$ haloalkyl, $SO_2C_{3-6}$ cycloalkyl, $SO_2NR_{15}$, $SO_2NC_{1-6}$ alkylamino, $SO_2C_{5-6}$ aryl, or $SO_2C_{1-6}$ heteroaryl, wherein $C_{1-6}$ alkyl, $C_{1-6}$ alkoxy, $C_{1-6}$ heteroaryl, and $C_{1-6}$ haloalkoxy, is optionally substituted with one or more of the groups selected from hydrogen, oxo, $C_{1-6}$ alkyl, $C_{1-6}$ alkoxy, $C_{1-6}$ haloalkyl, $C_{1-6}$ alkylhydroxy, $C_{3-6}$ cycloalkyl, $C_{5-10}$ aryl, $C_{1-6}$ heterocyclyl, $C_{1-6}$ heteroaryl, cyano, halogen, and hydroxyl, wherein $C_{5-10}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano; X of Formula (I) is selected from O or S; Z is N; A is selected from N or $CR_1$; B is selected from N or $CR_2$; D is selected from N or $CR_3$; $R_1$, $R_2$, $R_3$, and $R_4$ are independently selected from hydrogen, hydroxyl, cyano, amino, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-6}$ heterocyclyl, $C_{1-6}$ heteroaryl, $C(O)NR_{15}$, $C(O)C_{1-6}$ alkylamino, $C(O)C_{5-6}$ aryl, $C(O)C_{1-6}$ heteroaryl, $C(O)C_{1-6}$ alkyl, $C(O)C_{1-6}$ haloalkyl, $SO_2C_{1-6}$ alkyl, $SO_2C_{1-6}$ haloalkyl, $SO_2C_{3-6}$ cycloalkyl, $SO_2NR_{15}$, $SO_2NC_{1-6}$ alkylamino, $SO_2C_{5-6}$ aryl, or $SO_2C_{1-6}$ heteroaryl, wherein $C_{1-6}$ alkyl, $C_{1-6}$ alkoxy, $C_{1-6}$ heteroaryl, and $C_{1-6}$ haloalkoxy, is optionally substituted with one or more of the groups selected from hydrogen, oxo, $C_{1-6}$ alkyl, $C_{1-6}$ alkoxy, $C_{1-6}$ haloalkyl, $C_{3-6}$ cycloalkyl, $C_{5-10}$ aryl, $C_{1-6}$ heterocyclyl, $C_{1-6}$ heteroaryl, cyano, and hydroxyl; $R_{11}$ is hydrogen; $R_{12}$ is selected from $C_{1-6}$ alkylamino, and 5-10 membered monocyclic or bicyclic saturated heterocyclic ring with 1-3 heteroatoms selected from N, S or O, or $R_{11}$ and $R_{12}$ can be taken together to form a 5-10 membered monocyclic or bicyclic saturated or unsaturated heterocyclic ring with 1-5 heteroatoms selected from N, S or O, wherein the 5-10 membered monocyclic or bicyclic saturated or unsaturated heterocyclic ring is optionally substituted with the substituents selected from amino, $C_{1-6}$ alkylamino, $C_{1-6}$ acylamino, —$NHC(NH)CH_2Cl$, —$NH(CO)CH{=}CH$—$CH_2$—$N(CH_3)_2$, $C_{1-6}$ alkyl, halogen, $C_{1-6}$ alkoxy, or hydroxyl; $R_{13}$ is selected from hydrogen, 5-10 membered monocyclic or bicyclic aryl, and 5-10 membered monocyclic or bicyclic heteroaryl with 1-5 heteroatoms selected from N, S or O, wherein 5-10 membered monocyclic or bicyclic aryl, and 5-10 membered monocyclic or bicyclic heteroaryl are optionally substituted with 1-5 substituents selected from hydroxyl, cyano, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-6}$ heterocyclyl, $C_{1-6}$ heteroaryl, $C(O)C_{1-6}$ alkyl, $C(O)C_{1-6}$ haloalkyl, $C(O)NR_{15}$, $C(O)C_{1-6}$ alkylamino, $C(O)C_{5-6}$ aryl, $C(O)C_{1-6}$ heteroaryl, $SO_2C_{1-6}$ alkyl, $SO_2C_{1-6}$ haloalkyl, $SO_2C_{3-6}$ cycloalkyl, $SO_2NR_{15}$, $SO_2NC_{1-6}$ alkylamino, $SO_2C_{5-6}$ aryl, or $SO_2C_{1-6}$ heteroaryl, wherein $C_{1-6}$ alkyl, $C_{1-6}$ alkoxy, $C_{3-6}$ cycloalkyl, $C_{5-10}$ aryl, $C_{1-6}$ heterocyclyl, and $C_{1-6}$ heteroaryl, is optionally substituted with one or more of the groups selected from hydrogen, $C_{1-6}$ alkyl, $C_{1-6}$ haloalkyl, $C_{1-6}$ alkoxy, $C_{3-6}$ cycloalkyl, $C_{5-6}$ aryl, $C_{1-6}$ heteroaryl, $C_{1-6}$ heterocyclyl, oxo, halogen, hydroxyl, and cyano, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano; and $R_{15}$ is selected from the group consisting of hydrogen, $C_{1-6}$ alkyl, and combinations thereof.

In an embodiment, the disclosure relates to a process of preparation of compounds of Formula (II), or its polymorphs, stereoisomers, prodrugs, solvates, co-crystals, intermediates, pharmaceutically acceptable salts, and metabolites thereof, the process comprising reacting Formula (V) and $R_4CH_2NO_2$ with a compound selected from Formula (IVA) or Formula (IV)

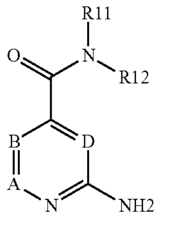

Formula (IVA)

+ or

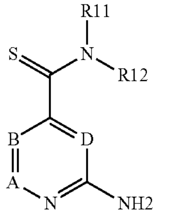

Formula (IV)

-continued

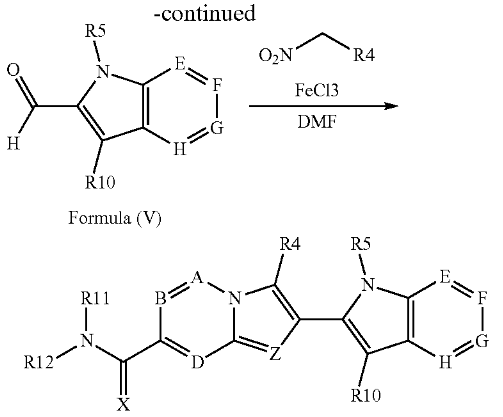

Formula (V)

Formula (II)

wherein A of Formula (IVA) and (IV) is selected from N or $CR_1$; B is selected from N or $CR_2$; D is selected from N or $CR_3$; $R_{11}$ and $R_{12}$ are taken together to form a 5-10 membered monocyclic or bicyclic saturated or unsaturated heterocyclic ring optionally with 1-5 heteroatoms selected from N, S or O, wherein the 5-10 membered monocyclic or bicyclic saturated or unsaturated heterocyclic ring is optionally substituted with the substituents selected from amino, $C_{1-6}$ alkylamino, $C_{1-6}$ acylamino, —NHC(NH)$CH_2Cl$, —NH(CO)CH═CH—$CH_2$—N$(CH_3)_2$, $C_{1-6}$ alkyl, halogen, $C_{1-6}$ alkoxy, or hydroxyl; $R_4$ of $R_4CH_2NO_2$ is selected from hydrogen, hydroxyl, cyano, amino, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-6}$ heterocyclyl, $C_{1-6}$ heteroaryl, C(O)$C_{1-6}$ alkyl, C(O)$C_{1-6}$ haloalkyl, C(O)$NR_{15}$, C(O)$C_{1-6}$ alkylamino, C(O)$C_{5-6}$ aryl, C(O)$C_{1-6}$ heteroaryl, $SO_2C_{1-6}$ alkyl, $SO_2C_{1-6}$ haloalkyl, $SO_2C_{3-6}$ cycloalkyl, $SO_2NR_{15}$, $SO_2NC_{1-6}$ alkylamino, $SO_2C_{5-6}$ aryl, or $SO_2C_{1-6}$ heteroaryl, wherein $C_{1-6}$ alkyl, $C_{1-6}$ alkoxy, $C_{1-6}$ heteroaryl, and $C_{1-6}$ haloalkoxy, is optionally substituted with one or more of the groups selected from hydrogen, oxo, $C_{1-6}$ alkyl, $C_{1-6}$ alkoxy, $C_{1-6}$ haloalkyl, $C_{1-6}$ alkylhydroxy, $C_{3-6}$ cycloalkyl, $C_{5-10}$ aryl, $C_{1-6}$ heterocyclyl, $C_{1-6}$ heteroaryl, cyano, halogen, and hydroxyl, wherein $C_{5-10}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano; E of Formula (V) is selected from N, $C_{5-6}$ aryl or $CR_6$; F is absent or is selected from N, and $CR_7$; G is absent or is selected from N, and $CR_8$; H is absent or is selected from N, and $CR_9$; $R_1$, $R_2$, $R_3$, $R_5$, $R_6$, $R_7$, $R_8$, $R_9$ and $R_{10}$ are independently selected from hydrogen, hydroxyl, cyano, amino, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-6}$ heterocyclyl, $C_{1-6}$ heteroaryl, C(O)$C_{1-6}$ alkyl, C(O)$C_{1-6}$ haloalkyl, C(O)$NR_{15}$, C(O)$C_{1-6}$ alkylamino, C(O)$C_{5-6}$ aryl, C(O)$C_{1-6}$ heteroaryl, $SO_2C_{1-6}$ alkyl, $SO_2C_{1-6}$ haloalkyl, $SO_2C_{3-6}$ cycloalkyl, $SO_2NR_{15}$, $SO_2NC_{1-6}$ alkylamino, $SO_2C_{5-6}$ aryl, or $SO_2C_{1-6}$ heteroaryl, wherein $C_{1-6}$ alkyl, $C_{1-6}$ alkoxy, $C_{1-6}$ heteroaryl, and $C_{1-6}$ haloalkoxy, is optionally substituted with one or more of the groups selected from hydrogen, oxo, $C_{1-6}$ alkyl, $C_{1-6}$ alkoxy, $C_{1-6}$ haloalkyl, $C_{1-6}$ alkylhydroxy, $C_{3-6}$ cycloalkyl, $C_{5-10}$ aryl, $C_{1-6}$ heterocyclyl, $C_{1-6}$ heteroaryl, cyano, halogen, and hydroxyl, wherein $C_{5-10}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano; X of Formula (II) is selected from O or S; Z is N; A is selected from N or $CR_1$; B is selected from N or $CR_2$; D is selected from N or $CR_3$; E is selected from N or $CR_6$; F is absent or is selected from N, and $CR_7$; G is absent or is selected from N, and $CR_8$; H is absent or is selected from N, and $CR_9$; $R_1$, $R_2$, $R_3$, $R_4$, $R_5$, $R_6$, $R_7$, $R_8$, $R_9$ and $R_{10}$ are independently selected from hydrogen, hydroxyl, cyano, amino, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-6}$ heterocyclyl, $C_{1-6}$ heteroaryl, C(O)$C_{1-6}$ alkyl, C(O)$C_{1-6}$ haloalkyl, C(O)$NR_{15}$, C(O)$C_{1-6}$ alkylamino, C(O)$C_{5-6}$ aryl, C(O)$C_{1-6}$ heteroaryl, $SO_2C_{1-6}$ alkyl, $SO_2C_{1-6}$ haloalkyl, $SO_2C_{3-6}$ cycloalkyl, $SO_2NR_{15}$, $SO_2NC_{1-6}$ alkylamino, $SO_2C_{5-6}$ aryl, or $SO_2C_{1-6}$ heteroaryl, wherein $C_{1-6}$ alkyl, $C_{1-6}$ alkoxy, $C_{1-6}$ heteroaryl, and $C_{1-6}$ haloalkoxy, is optionally substituted with one or more of the groups selected from hydrogen, oxo, $C_{1-6}$ alkyl, $C_{1-6}$ alkoxy, $C_{1-6}$ haloalkyl, $C_{1-6}$ alkylhydroxy, $C_{3-6}$ cycloalkyl, $C_{5-10}$ aryl, $C_{1-6}$ heterocyclyl, $C_{1-6}$ heteroaryl, cyano, halogen, and hydroxyl, wherein $C_{5-10}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano; $R_{11}$ and $R_{12}$ are taken together to form a 5-10 membered monocyclic or bicyclic saturated or unsaturated heterocyclic ring optionally with 1-5 heteroatoms selected from N, S or O, wherein the 5-10 membered monocyclic or bicyclic saturated or unsaturated heterocyclic ring is optionally substituted with the substituents selected from amino, $C_{1-6}$ alkylamino, $C_{1-6}$ acylamino, —NHC(NH)$CH_2Cl$, —NH(CO)CH═CH—$CH_2$—N$(CH_3)_2$, $C_{1-6}$ alkyl, halogen, $C_{1-6}$ alkoxy, or hydroxyl; and $R_{15}$ is selected from the group consisting of hydrogen, $C_{1-6}$ alkyl, and combinations thereof.

In an embodiment, the disclosure relates to a process of preparation of compounds of Formula (III), or its polymorphs, stereoisomers, prodrugs, solvates, co-crystals, intermediates, pharmaceutically acceptable salts, and metabolites thereof, the process comprising reacting Formula (VII) $R_4CH_2NO_2$ with a compound selected from Formula (VIA) or Formula (VI)

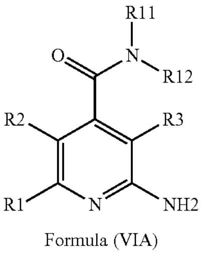

Formula (VIA)

+ or

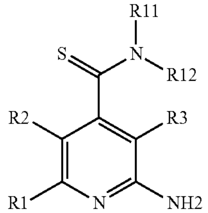

Formula (VI)

-continued

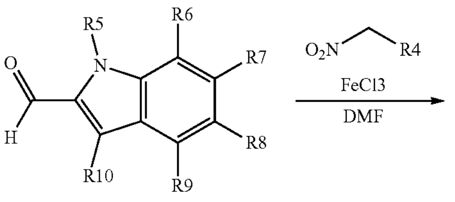

Formula (VII)

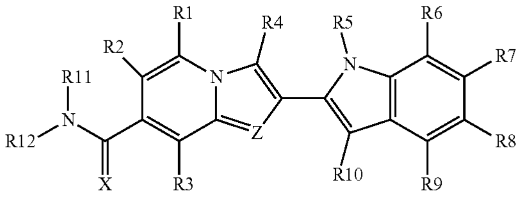

Formula (III)

wherein $R_1$, $R_2$, and $R_3$ of Formula (VIA) and Formula (VI) are independently selected from hydrogen, hydroxyl, cyano, amino, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-6}$ heterocyclyl, $C_{1-6}$ heteroaryl, C(O)$C_{1-6}$ alkyl, C(O)$C_{1-6}$ haloalkyl, C(O)$NR_{15}$, C(O)$C_{1-6}$ alkylamino, C(O)$C_{5-6}$ aryl, C(O)$C_{1-6}$ heteroaryl, $SO_2C_{1-6}$ alkyl, $SO_2C_{1-6}$ haloalkyl, $SO_2C_{3-6}$ cycloalkyl, $SO_2NR_{15}$, $SO_2NC_{1-6}$ alkylamino, $SO_2C_{5-6}$ aryl, or $SO_2C_{1-6}$ heteroaryl, wherein $C_{1-6}$ alkyl, $C_{1-6}$ alkoxy, $C_{1-6}$ heteroaryl, and $C_{1-6}$ haloalkoxy, is optionally substituted with one or more of the groups selected from hydrogen, oxo, $C_{1-6}$ alkyl, $C_{1-6}$ alkoxy, $C_{1-6}$ haloalkyl, $C_{1-6}$ alkylhydroxy, $C_{3-6}$ cycloalkyl, $C_{5-10}$ aryl, $C_{1-6}$ heterocyclyl, $C_{1-6}$ heteroaryl, cyano, halogen, and hydroxyl, wherein $C_{5-10}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano; $R_5$, $R_6$, $R_7$, $R_8$, $R_9$ and $R_{10}$ of Formula (VII) and $R_4$ of $R_4CH_2NO_2$ are independently selected from hydrogen, hydroxyl, cyano, amino, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-6}$ heterocyclyl, $C_{1-6}$ heteroaryl, C(O)$C_{1-6}$ alkyl, C(O)$C_{1-6}$ haloalkyl, C(O)$NR_{15}$, C(O)$C_{1-6}$ alkylamino, C(O)$C_{5-6}$ aryl, C(O)$C_{1-6}$ heteroaryl, $SO_2C_{1-6}$ alkyl, $SO_2C_{1-6}$ haloalkyl, $SO_2C_{3-6}$ cycloalkyl, $SO_2NR_{15}$, $SO_2NC_{1-6}$ alkylamino, $SO_2C_{5-6}$ aryl, or $SO_2C_{1-6}$ heteroaryl, wherein $C_{1-6}$ alkyl, $C_{1-6}$ alkoxy, $C_{1-6}$ heteroaryl, and $C_{1-6}$ haloalkoxy, is optionally substituted with one or more of the groups selected from hydrogen, oxo, $C_{1-6}$ alkyl, $C_{1-6}$ alkoxy, $C_{1-6}$ haloalkyl, $C_{1-6}$ alkylhydroxy, $C_{3-6}$ cycloalkyl, $C_{5-10}$ aryl, $C_{1-6}$ heterocyclyl, $C_{1-6}$ heteroaryl, cyano, halogen, and hydroxyl, wherein $C_{5-10}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano; X of Formula (III) is selected from O or S; Z is N; $R_1$, $R_2$, $R_3$, $R_4$, $R_5$, $R_6$, $R_7$, $R_8$, $R_9$ and $R_{10}$ are independently selected from hydrogen, hydroxyl, cyano, amino, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-6}$ heterocyclyl, $C_{1-6}$ heteroaryl, C(O)$C_{1-6}$ alkyl, C(O)$C_{1-6}$ haloalkyl, C(O)$NR_{15}$, C(O)$C_{1-6}$ alkylamino, C(O)$C_{5-6}$ aryl, C(O)$C_{1-6}$ heteroaryl, $SO_2C_{1-6}$ alkyl, $SO_2C_{1-6}$ haloalkyl, $SO_2C_{3-6}$ cycloalkyl, $SO_2NR_{15}$, $SO_2NC_{1-6}$ alkylamino, $SO_2C_{5-6}$ aryl, or $SO_2C_{1-6}$ heteroaryl, wherein $C_{1-6}$ alkyl, $C_{1-6}$ alkoxy, $C_{1-6}$ heteroaryl, and $C_{1-6}$ haloalkoxy, is optionally substituted with one or more of the groups selected from hydrogen, oxo, $C_{1-6}$ alkyl, $C_{1-6}$ alkoxy, $C_{1-6}$ haloalkyl, $C_{1-6}$ alkylhydroxy, $C_{3-6}$ cycloalkyl, $C_{5-10}$ aryl, $C_{1-6}$ heterocyclyl, $C_{1-6}$ heteroaryl, cyano, halogen, and hydroxyl, wherein $C_{5-10}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano; $R_{11}$ and $R_{12}$ are taken together to form a 5-10 membered monocyclic or bicyclic saturated or unsaturated heterocyclic ring optionally with 1-5 heteroatoms selected from N, S or O, wherein the 5-10 membered monocyclic or bicyclic saturated or unsaturated heterocyclic ring is optionally substituted with the substituents selected from amino, $C_{1-6}$ alkylamino, $C_{1-6}$ acylamino, —NHC(NH)$CH_2Cl$, —NH(CO)CH═CH—$CH_2$—$N(CH_3)_2$, $C_{1-6}$ alkyl, halogen, $C_{1-6}$ alkoxy, or hydroxyl; and $R_{15}$ is selected from the group consisting of hydrogen, $C_{1-6}$ alkyl, and combinations thereof.

In another embodiment, the disclosure relates to pharmaceutical composition comprising a compound of Formula (I), Formula (II), and Formula (III) or a pharmaceutically acceptable salt thereof as claimed in any of claims 1-11 together with a pharmaceutically acceptable carrier, optionally in combination with one or more other pharmaceutical compositions.

In yet another embodiment, the disclosure relates to the pharmaceutical composition as described herein, wherein the composition is in the form selected from a tablet, capsule, powder, syrup, solution, aerosol and suspension.

In an embodiment of the present disclosure, there is provided compounds of Formula (I), Formula (II), and Formula (III) or a pharmaceutically acceptable salt thereof as described herein, wherein the pharmaceutically acceptable salt selected derived from inorganic bases such as like Li, Na, K, Ca, Mg, Fe, Cu, Zn and Mn; salts of organic bases such as N, N'-diacetylethylenediamine, glucamine, triethylamine, choline, dicyclohexylamine, benzylamine, trialkylamine, thiamine, guanidine, diethanolamine, α-phenylethylamine, piperidine, morpholine, pyridine, hydroxyethylpyrrolidine, hydroxyethylpiperidine, ammonium, substituted ammonium salts, aluminum salts and the like. Salts also include amino acid salts such as glycine, alanine, cystine, cysteine, lysine, arginine, phenylalanine, and guanidine. Salts may include acid addition salts where appropriate which are sulphates, nitrates, phosphates, perchlorates, borates, hydrohalides, acetates, tartrates, maleates, citrates, succinates, palmoates, methanesulphonates, tosylates, benzoates, salicylates, hydroxynaphthoates, benzenesulfonates, ascorbates, glycerophosphates, ketoglutarates.

In an embodiment of the present disclosure, there is provided compounds of Formula (I), Formula (II), and Formula (III) or a pharmaceutically acceptable salt thereof for use in the manufacture of a medicament for inhibiting one or more PADs in a cell.

In an embodiment, the present disclosure relates to a method for inhibiting one or more PAD family in a cell with an effective amount of the compounds of Formula (I), Formula (II), and Formula (III) or a pharmaceutically acceptable salt thereof together with a pharmaceutically acceptable carrier, optionally in combination with one or more other pharmaceutical compositions.

In an embodiment, the present disclosure relates to a method for the treating a condition mediated by one or more PADs, the method comprising administering to a subject suffering from a condition mediated by one or more PAD family, a therapeutically effective amount of the compounds of Formula (I), Formula (II), and Formula (III) or a pharmaceutically acceptable salt thereof together with a pharmaceutically acceptable carrier, optionally in combination with one or more other pharmaceutical compositions.

In an embodiment of the present disclosure, there is provided a compound of Formula (I), Formula (II) and Formula (III) used for the treatment of rheumatoid arthritis, vasculitis, systemic lupus erythematosus, ulcerative colitis, cancer, cystic fibrosis, asthma, cutaneous lupus erythematosis, and psoriasis.

In an embodiment, the present disclosure relates to the use of the compound of Formula (I), Formula (II) and Formula (III) or a pharmaceutically acceptable salt or composition for the treatment of a condition mediated by one or more PAD family; or treatment and/or prevention of treatment of rheumatoid arthritis, vasculitis, systemic lupus erythematosus, ulcerative colitis, cancer, cystic fibrosis, asthma, cutaneous lupus erythematosis, and psoriasis together with other clinically relevant agents or biological agents.

In an embodiment, the present disclosure relates to the use of the compound of Formula (I), Formula (II) and Formula (III) or a pharmaceutically acceptable salt or composition for treatment of a condition mediated by one or more PAD family; or treatment and/or prevention of acid-induced lung injury, respiratory distress syndrome, allergen induced asthma, allergic bronchopulmonary, chronic lung disease of prematurity, chronic obstructive pulmonary disease, colitis, cystic fibrosis, gouty arthritis, inflammatory bowel disease, inflammatory lung disease, inflammatory pain, juvenile rheumatoid arthritis, kidney disease, kidney injury caused by parasitic infections, kidney transplant rejection prophylaxis, lung injury, lupus, lupus nephritis, multiple sclerosis, muscular dystrophy, non-allergen induced asthma, osterarthritis, periodontitis, peritoneal endometriosis, psoriasis, pulmonary disease, pulmonary fibrosis, pyogenic sterile arthritis, renal disease, rheumatic disease, rheumatoid arthritis, sepsis, severe pain and ulcerative colitis, together with other clinically relevant agents or biological agents.

In an embodiment, the disclosure relates to a method for the treatment and/or prevention of a condition mediated by one or more PAD family disorder, comprising administering to a subject suffering from the condition mediated by one or more PAD family a therapeutically effective amount of the compound of Formula (I), Formula (II), and Formula (III) or a pharmaceutically acceptable salt thereof together with a pharmaceutically acceptable carrier, optionally in combination with one or more other pharmaceutical compositions.

In an embodiment, the invention relates to a method for the treatment of rheumatoid arthritis, said method comprising administering a combination of the compounds of Formula (I), Formula (II), and Formula (III) or a pharmaceutically acceptable salt thereof together with a pharmaceutically acceptable carrier, optionally in combination with one or more other pharmaceutical compositions, with other clinically relevant agents or biological agents to a subject in need thereof.

In an embodiment, the disclosure relates to a method for the treatment of cancer, said method comprising administering a combination of compounds of Formula (I), Formula (II), and Formula (III) or a pharmaceutically acceptable salts thereof together with a pharmaceutically acceptable carrier, with other clinically relevant immune modulators agents to a subject in need of thereof.

EXAMPLES

As used herein the symbols and conventions used in these processes, schemes and examples are consistent with those used in the contemporary scientific literature, for example, the Journal of the American Chemical Society. Unless otherwise noted, all starting materials were obtained from commercial suppliers and used without further purification. Specifically, the following abbreviations may be used in the examples and throughout the specification:

Abbreviations

AcOH Acetic acid
$BOC_2O$ Di-tert-butyl dicarbonate
nBuLi n-Butyllithium
BuOH Butanol
Bz Benzyl
Cbz Carboxybenzyl
cHex Cyclohexane
$Cs_2CO_3$ Caesium carbonate
DCM/$CH_2Cl_2$ Dichloromethane
DIAD Diisopropyl azodicarboxylate
Dioxane 1,4-dioxane
DIPEA N, N-diisopropylethylamine
DMSO Dimethylsulfoxide
DMF N,N-dimethylformamide
$Et_3N$ Tri ethyl amine
Ether Diethyl ether
EtOAc Ethyl acetate
HATU o-(7-Azabenzotriazol-1-yl)-N,N,N',N'-tetramethyluronium hexafluorophosphate
HPLC High performance liquid chromatography
IPA Isopropyl alcohol
$K_2CO_3$ Potassium carbonate
KOH Potassium hydroxide
LiOH Lithium hydroxide
LCMS or LC/MS Liquid chromatography-mass spectroscopy
MeOH Methanol
min Minutes
$Na_2SO_4$ Sodium sulfate
$NaHCO_3$Sodium bicarbonate
$NH_4Cl$ Ammonium chloride
Palladium tetrakis palladium tetrakistriphenylphosphine
Pd/C Palladium on carbon
PTSA p-Toluenesulfonic acid
rb round-bottomed (flask)
r.t/rt. Room temperature
Rt Retention time
TFA Trifluoroacetic acid
TFAA Trifluoroacetic anhydride
THF/thf Tetrahydrofuran
TLC/tic Thin layer chromatography
TMEDA Tetramethyl ethyl enediamine
HOBt Hydroxybenzotriazole
EDC.HCl 1-Ethyl-3-(3-dimethylaminopropyl)carbodiimide Hydrochloride The following examples provide the details about the synthesis, activities, and applications of the compounds of the present disclosure. It should be understood the following is representative only, and that the invention is not limited by the details set forth in these examples.

The compounds of the invention may be made by a variety of methods, including standard chemistry. Any previously defined variable will continue to have the previously defined meaning unless otherwise indicated. Illustrative general synthetic methods are set out in the following schemes, and can be readily adapted to prepare other compounds of the invention.

There is also provided a process as shown in the following Scheme-1, for the preparation of compounds of the Formula (I, II, and III), wherein all the groups are as defined earlier.

Example 1

General Procedure for Synthesis of Compounds of Formula I, Formula II, and Formula III Scheme-1

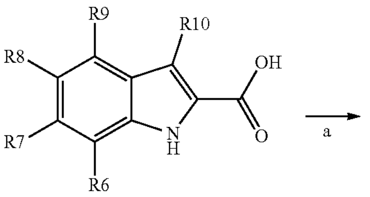

1

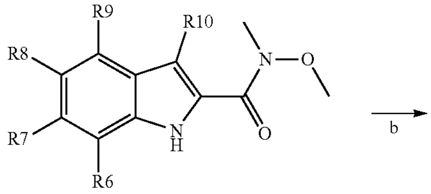

2

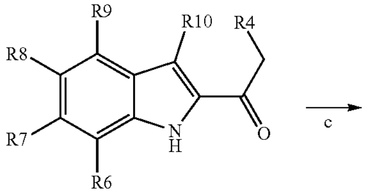

3

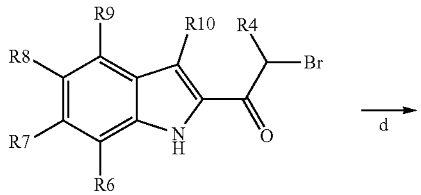

4

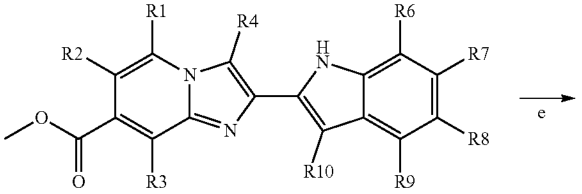

5

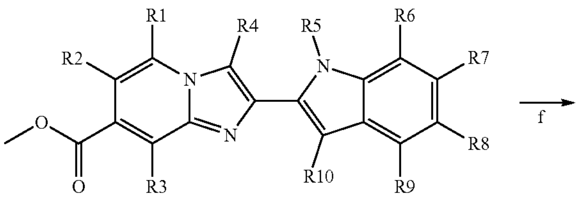

6

-continued

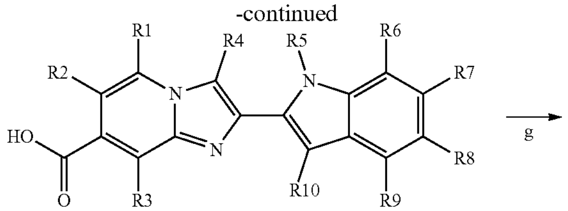

7

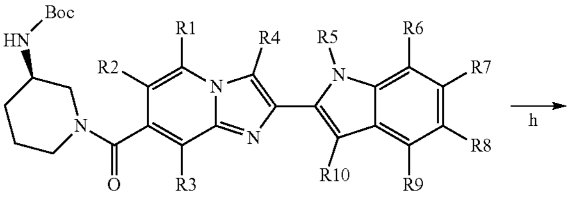

8

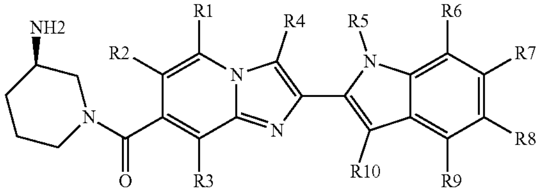

9

The said process for the preparation of the compounds of Formula (I, II, and III) comprises of the following steps:

Step 1: Compound 1 was converted to compound 2 under standard conditions using N,O-dimethylhydroxylamine hydrochloride, triethylamine, HOBt and EDC.HCl (Reaction condition a).

Step 2: Treatment of compound 2 with ethyl magnesium bromide (Reaction condition b) gave intermediate 3.

Step 3: Intermediate 3 was converted to compound 4 using phenyl trimethyl ammonium tribromide (Reaction condition c).

Step 4: Treatment of compound 4 with methyl 2-aminoisonicotinate or ethyl 2-chloro-6-methylisonicotinate and $NaHCO_3$(Reaction condition d) gave intermediate 5.

Step 5: Intermediate 5 was converted to compound 6 by reacting with substituted bromides (bromomethyl cyclopropane) and $Cs_2CO_3$ (Reaction condition e).

Step 6: Compound 6 was hydrolysed to give compound 7 under reaction condition f.

Step 7: Coupling of compound 7 with substituted carbamates, like tert-butyl (R)-piperidin-3-yl carbamate, (Reaction condition g) gave compound 8.

Step 8: Compound 8 was converted to final compound 9 by Boc deprotection (Reaction condition h).

General Considerations and Analytical Methods

The compounds used in the reaction processes, if not mentioned otherwise, were commercially available and purchased from Combi-Blocks, India. NMR data were obtained on Varian 400 MHz spectrometer. All compounds were characterized by $^1$H NMR, as well as, mass spectrometry (MS-ESI, Electrospray ionization Mass spectrometry). All $^1$H chemical shifts were reported in parts per million (ppm) and were measured relative to TMS or residual deuterated DMSO as solvent. MS (ESI) measurements were performed on Waters Mass spectrometer. The yields of the compounds provided refer to isolated compounds.

The examples given below are provided by the way of illustration only and therefore should not be construed to limit the scope of the invention.

Further, a class of compounds of Formula I, Formula II, and Formula III were prepared using the general procedure as described above.

Compound-1

Synthesis of (R)-(3-Aminopiperidin-1-yl)(2-(3-bromo-1-(cyclopropylmethyl)-1H-indol-2-yl)-3-methylimidazo[1,2-a]pyridin-7-yl)methanone (Compound-1)

Scheme-2

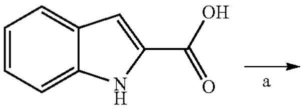

1

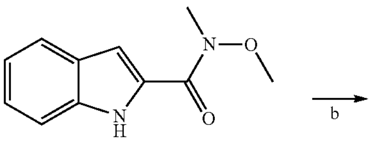

2

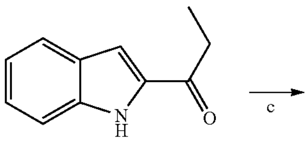

3

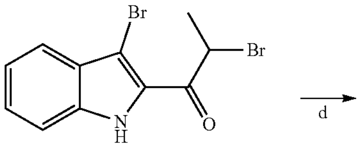

4

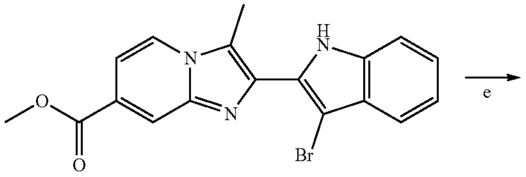

5

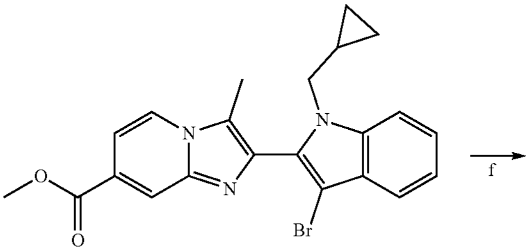

6

-continued

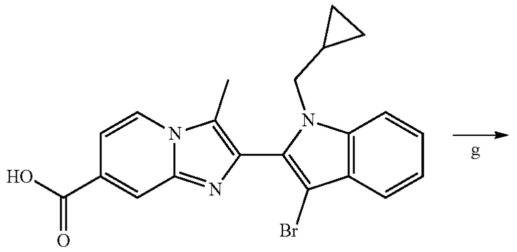

7

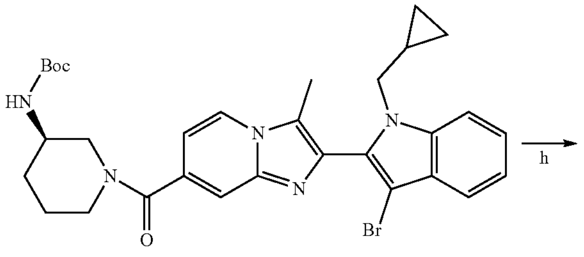

8

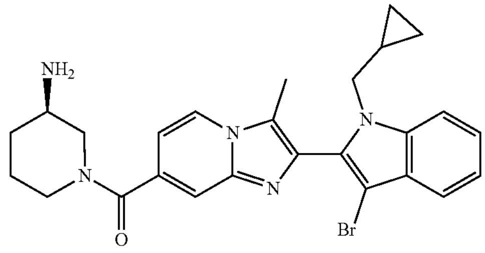

Compound 1

Step 1: Preparation of N-Methoxy-N-methyl-1H-indole-2-carboxamide (2)

2

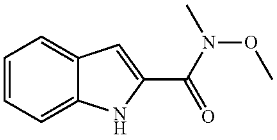

To a stirred solution of 1H-indole-2-carboxylic acid (1, 25 g, 155.5 mmol) and N,O-dimethylhydroxylamine hydrochloride (30.26 g, 310.2 mmol) in DCM (500 mL), was added triethylamine (107 mL, 775.6 mmol) and HOBt (36.7 g, 232.9 mmol), followed by EDC.HCl (44.4 g, 232.6 mmol) at 0° C. (Reaction condition a). The reaction mixture was stirred at rt for 4 h. To the reaction mixture, water and DCM were added. DCM layer was separated and washed with brine, dried over sodium sulphate and concentrated under reduced pressure. To the resulting crude, was added diethyl ether (200 mL), stirred for 30 min and filtered to give white solid. This solid was dissolved in EtOAc, passed through celite bed and evaporated to give title compound as off white solid (2) (27 g, 87% Yield). MS (ESI): Mass calcd. for $C_{11}H_{12}N_2O_2$, 204.23; m/z found, 205.1 $[M+H]^+$.

Step 2: Preparation of 1-(1H-Indol-2-yl)propan-1-one (3)

3

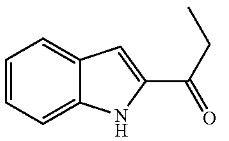

To a stirred solution of N-methoxy-N-methyl-1H-indole-2-carboxamide (2, 10 g, 49.01 mmol) in THF (200 mL), was added 3M solution of ethyl magnesium bromide (49 mL, 147 mmol) drop wise at 0° C. (Reaction condition b). The reaction mixture was stirred at rt for 16 h. The reaction mixture was quenched with saturated $NH_4Cl$ (100 mL) solution at 0° C. and extracted with EtOAc (500 mL). Organic layer was separated, washed with brine, dried over sodium sulphate and concentrated under reduced pressure. The crude was purified by flash column chromatography to give the title compound as off white solid (3) (53%, 4.5 g, 53% Yield). MS (ESI): Mass calcd. for $C_{11}H_{11}NO$, 173.22; m/z found, 174.1 $[M+H]^+$.

Step 3: Preparation of 2-Bromo-1-(3-bromo-1H-indol-2-yl)propan-1-one (4)

4

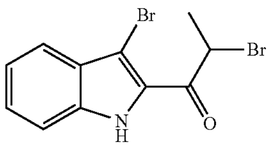

To the stirred solution of 1-(1H-indol-2-yl)propan-1-one (3, 2.5 g, 14.45 mmol) in THF (50 mL), was added phenyl trimethyl ammonium tribromide (16.3 g, 43.35 mmol) and stirred at reflux for 16 h (Reaction condition c). The reaction mixture was cooled to rt, added water (25 mL) and extracted with EtOAc (100 mL). Organic layer was washed with saturated $NaHCO_3$ (20 mL) solution, brine (20 mL) and evaporated. Crude product was purified by column chromatography to give the title compound as brown solid (4) (4 g, 86% Yield). MS (ESI): Mass calcd. for $C_{11}H_9Br_2NO$, 331.01; m/z found, 333.9 $[M+2H]^+$.

Step 4: Preparation of Methyl 2-(3-bromo-1H-indol-2-yl)-3-methylimidazo[1,2-a]pyridine-7-carboxylate (5)

5

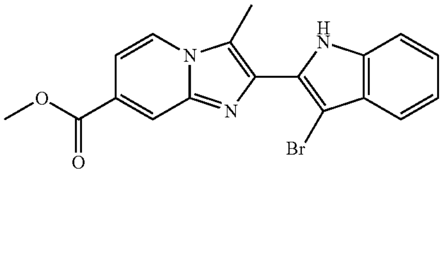

To the stirred solution of 2-bromo-1-(3-bromo-1H-indol-2-yl)propan-1-one (4, 2 g, 5.24 mmol) and methyl 2-aminoisonicotinate (0.92 g, 5.24 mmol) in EtOH (20 mL), was added $NaHCO_3$ (1.52 g, 26.2 mmol) and stirred at 90° C. for 16 h in seal tube (Reaction condition d). The reaction mixture was cooled to rt, added water (50 mL) and extracted with EtOAc (2×50 mL). Combined organic extracts were washed with brine, dried over sodium sulfate and evaporated to give the crude product. The crude product was purified by flash column chromatography using 25-30% EtOAc in hexane to afford title product as brown solid (5) (0.45 g, 20.5% Yield). MS (ESI): Mass calcd. for $C_{18}H_{14}BrN_3O_2$, 384.23; m/z found, 385.0 $[M+H]^+$.

Step 5: Preparation of Methyl 2-(3-bromo-1-(cyclopropylmethyl)-1H-indol-2-yl)-3-methylimidazo[1,2-a]pyridine-7-carboxylate (6)

6

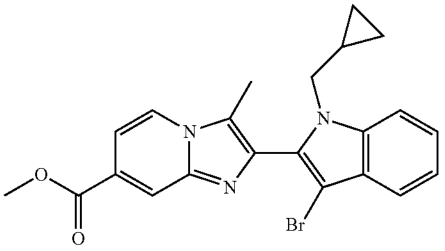

To the stirred solution of methyl 2-(3-bromo-1H-indol-2-yl)-3-methylimidazo[1,2-a]pyridine-7-carboxylate (5, 0.4 g, 1.01 mmol) in DMF (8 mL), was added $Cs_2CO_3$ (0.98 g, 3.01 mmol) followed by (bromomethyl) cyclopropane (0.24 mL, 1.51 mmol) and stirred at 80° C. for 16 h (Reaction condition e). The reaction mixture was cooled to rt, added water (20 mL) and extracted with EtOAc (50 mL). Combined organic extracts were washed with brine, dried over sodium sulfate and evaporated to give the crude product. The crude product was purified by flash column chromatography using 25-30% EtOAc in hexane to afford title product as brown gum (6) (0.42 g, 90% Yield). MS (ESI): Mass calcd. for $C_{22}H_{20}BrN_3O_2$, 438.33; m/z found, 440.1 $[M+2H]^+$.

Step 6: Preparation of 2-(3-Bromo-1-(cyclopropylmethyl)-1H-indol-2-yl)-3-methylimidazo[1,2-a]pyridine-7-carboxylic Acid (7)

7

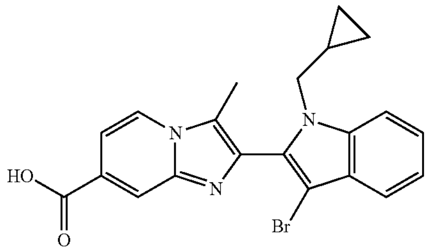

To the stirred solution of methyl 2-(3-bromo-1-(cyclopropylmethyl)-1H-indol-2-yl)-3-methylimidazo[1,2-a]pyridine-7-carboxylate (6, 0.42 g, 0.98 mmol) in MeOH (10 mL), was added 5N NaOH solution (0.2 mL, 4.51 mmol) and stirred at reflux for 1 h (Reaction condition f). The reaction mixture was cooled to rt, evaporated to dryness. Resulting crude was dissolved in water (10 mL), acidified using saturated citric acid solution and the compound was extracted with EtOAc (2×30 mL). Organic layer was separated, washed with brine (10 mL) solution, dried over anhydrous $Na_2SO_4$ and evaporated under vacuum to give the product as brown solid (7) (0.34 g, 83% Yield). MS (ESI): Mass calcd. for $C_{21}H_{18}BrN_3O_2$, 424.30; m/z found, 426.1 $(M+2H)^+$.

Step 7: Preparation of Tert-butyl (R)-(1-(2-(3-bromo-1-(cyclopropylmethyl)-1H-indol-2-yl)-3-methylimidazo[1,2-a]pyridine-7-carbonyl)piperidin-3-yl)carbamate (8)

8

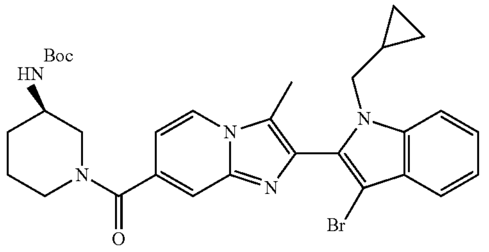

To a solution of tert-butyl (R)-piperidin-3-yl-12-azanecarboxylate (0.018 g, 0.09 mmol) and 2-(3-bromo-1-(cyclopropylmethyl)-1H-indol-2-yl)-3-methylimidazo[1,2-a]pyridine-7-carboxylic acid (7, 0.04 g, 0.09 mmol) in DCM (10 mL) at rt was added triethylamine (0.037 mL, 0.27 mmol) and propylphosphonic anhydride (T3P, 50% in ethylacetate solvent) (0.05 mL, 0.18 mmol). The reaction mixture was stirred at rt for 12 h (Reaction condition g). It was diluted with DCM and washed with saturated sodium bicarbonate solution. Organic layer was separated, dried over sodium sulphate and evaporated under reduced pressure to obtain crude. The crude product was purified by flash column chromatography using 5% methanol in DCM to afford desired product (8) (0.035 g, 82.5% Yield). MS (ESI): Mass calcd. for $C_{31}H_{36}BrN_5O_3$, 605.0; m/z found 606.3 $[M+H]^+$.

Step 8: Preparation of (R)-(3-Aminopiperidin-1-yl)(2-(3-bromo-1-(cyclopropylmethyl)-1H-indol-2-yl)-3-methylimidazo[1,2-a]pyridin-7-yl)methanone (Compound-1)

Compound-1

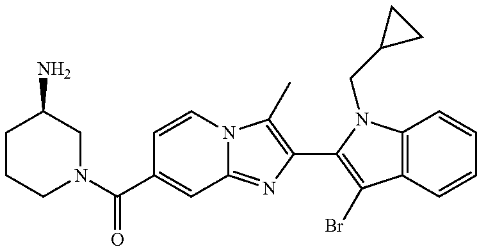

To a stirred solution tert-butyl (R)-(1-(2-(3-bromo-1-(cyclopropylmethyl)-1H-indol-2-yl)-3-methylimidazo[1,2-a]pyridine-7-carbonyl) piperidin-3-yl)carbamate (8, 0.035 g, 0.005 mmol) in DCM (10 mL) was added trifluroacetic acid (0.5 mL) at 0° C., then it was stirred at rt for 2 h (Reaction condition h). After completion of reaction, solvent was evaporated. The crude was dissolved in water (10 mL) and neutralized with saturated $NaHCO_3$ solution to give the crude product. The crude was purified by flash column chromatography using 3-5% methanol in DCM to afford desired product (Compound-1) (0.012 g, 60% Yield). $^1$HNMR (400 MHz, DMSO-$d_6$) δ (ppm): 8.45 (d, J=7.2 Hz, 1H), 7.67-7.61 (m, 2H), 7.49 (d, J=8 Hz, 1H), 7.29 (t, J=7.6 Hz, 1H), 7.20 (t, J=7.6 Hz, 1H), 7.02 (d, J=6.8 Hz, 1H), 4.49 (bs, 1H), 4.17 (d, J=7.2 Hz, 2H), 2.99 (bs, 1H), 1.97 (m, 2H), 1.69 (m, 2H), 1.50 (m, 2H), 1.31 (m, 1H), 1.26 (s, 3H), 1.00 (m, 1H), 0.87-0.84 (m, 2H), 0.26-0.25 (m, 2H), 0.04 (m, 2H). MS (ESI): Mass calcd. for $C_{26}H_{28}BrN_5O$, 506.1; m/z found 508.3 $[M+2H]^+$.

Compound-2

Synthesis of (R)-(3-Aminopiperidin-1-yl)(2-(1-(cyclopropylmethyl)-1H-indol-2-yl)-3-methylimidazo[1,2-a]pyridin-7-yl)methanone (Compound-2)

Intermediate 8 was synthesized using the procedure outlined in above scheme-2.

Scheme-3

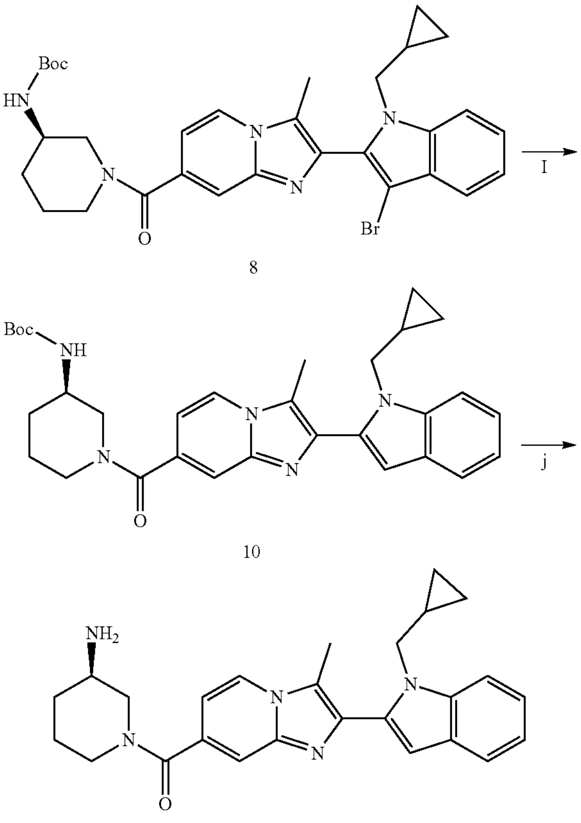

8

10

Compound 2

Step 1: Preparation of Tert-butyl (R)-(1-(2-(1-(cyclopropylmethyl)-1H-indol-2-yl)-3-methylimidazo[1,2-a]pyridine-7-carbonyl)piperidin-3-yl)carbamate (10)

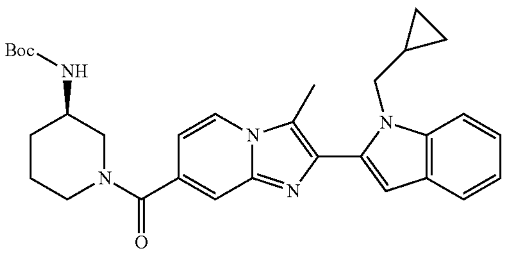

To the stirred solution of tert-butyl (R)-(1-(2-(3-bromo-1-(cyclopropylmethyl)-1H-indol-2-yl)-3-methylimidazo[1,2-a]pyridine-7-carbonyl) piperidin-3-yl)carbamate (8, 0.07 g, 0.33 mmol) in MeOH (6 mL), was added zinc powder (0.1 g, 3.33 mmol) followed by ammonium hydroxide (2 mL) and stirred at 90° C. for 16 h (Reaction condition i). The reaction mixture was cooled to rt, filtered through celite and the filtrate was evaporated. To the crude product water (10 mL) was added and extracted with DCM (30 mL). Organic layer was separated, dried over sodium sulfate and evaporated to give the crude product. The crude product was purified by flash column chromatography using 2-6% MeOH in DCM to afford the product as off white solid (10) (0.03 g, 35% Yield). MS (ESI): Mass calcd. for $C_{31}H_{37}N_5O_3$, 527.29; m/z found, 528.3 $(M+H)^+$.

Step 2: Preparation of (R)-(3-Aminopiperidin-1-yl)(2-(1-(cyclopropylmethyl)-1H-indol-2-yl)-3-methylimidazo[1,2-a]pyridin-7-yl)methanone (Compound 2)

Compound 2

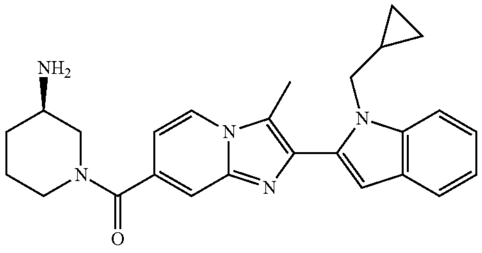

To a stirred solution tert-butyl (R)-(1-(2-(1-(cyclopropylmethyl)-1H-indol-2-yl)-3-methylimidazo[1,2-a]pyridine-7-carbonyl)piperidin-3-yl)carbamate (10, 0.03 g, 0.05 mmol) in 1,4-dioxane (1 mL), was added 4M HCl in dioxane (0.5 mL) and the reaction mixture was stirred at rt for 2 h (Reaction condition j). The reaction mixture was evaporated, dissolved in water (5 mL) and basified using saturated $NaHCO_3$ solution. Compound was extracted with EtOAc (2×15 mL). Combined organic layer was dried over anhydrous $Na_2SO_4$. The crude product was purified by flash column chromatography using 2-8% MeOH in DCM to afford the product as brown solid (Compound-2) (0.005 g, 20% Yield).

$^1$HNMR (400 MHz, DMSO-$d_6$) δ (ppm): 8.42 (d, J=6.8 Hz, 1H), 7.57 (t, J=6.8 Hz, 2H), 7.16-7.14 (m, 2H), 7.06-6.99 (m, 2H), 6.64 (s, 1H), 4.46 (d, J=6.8 Hz, 2H), 2.91 (s, 3H), 2.65-2.59 (m, 2H), 2.00-1.95 (m, 3H), 1.69-1.55 (m, 2H), 1.43-1.35 (m, 2H), 1.10 (m, 1H), 0.83-0.81 (m, 2H), 0.27-0.25 (m, 2H), 0.15-0.13 (m, 2H). MS (ESI): Mass calcd. for $C_{26}H_{29}N_5O$, 427.55; m/z found, 428.3 $[M+H]^+$.

Following compounds (Compounds 3, 4, 7, 8, 9, 10, 11, 12, 13, 14, 15, 16, 17, 18, 19, 35, 36, 37, 38, 41, 42, 45, 46, 48 and 49) were synthesized using the above procedure as exemplified for Compound-2 above.

Compound-3

(R)-(3-Aminopiperidin-1-yl)(2-(1-benzyl-1H-indol-2-yl)-3-methylimidazo[1,2-a]pyridin-7-yl)methanone

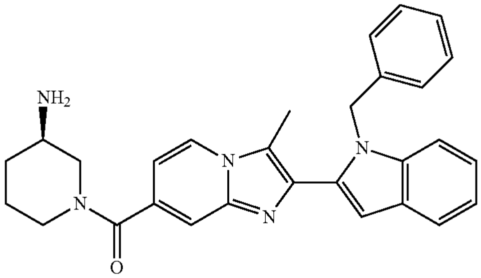 [SMILES: Cc1c(-c2cc3ccccc3n2Cc2ccccc2)nc2cc(C(=O)N3CCC[C@@H](N)C3)ccn12]

$^1$HNMR (400 MHz, DMSO-$d_6$) δ (ppm): 8.40 (d, J=6.8 Hz, 1H), 7.61-7.59 (m, 2H), 7.37 (d, J=7.6 Hz, 1H), 7.16-7.02 (m, 5H), 6.95-6.93 (m, 3H), 6.75 (s, 1H), 5.89 (s, 2H), 2.97-2.88 (m, 2H), 2.69-2.59 (m, 3H), 2.58-2.50 (m, 3H), 1.82-1.75 (m, 1H), 1.66-1.59 (m, 1H), 1.33-1.25 (m, 1H), 1.21-1.15 (m, 3H). MS (ESI): Mass calcd. for $C_{29}H_{29}N_5O$, 463.59; m/z found, 464.2 $(M+H)^+$.

Compound-4

(R)-(3-Aminopiperidin-1-yl)(2-(1-ethyl-1H-indol-2-yl)-3-methylimidazo[1,2-a]pyridin-7-yl)methanone

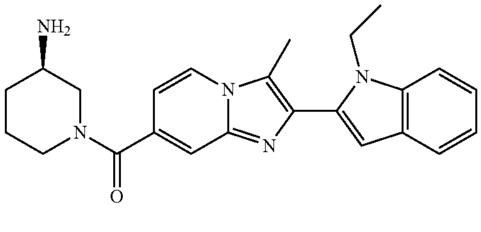 [SMILES: CCn1c(-c2nc3cc(C(=O)N4CCC[C@@H](N)C4)ccn3c2C)cc2ccccc21]

$^1$HNMR (400 MHz, DMSO-$d_6$) δ (ppm): 8.42 (d, J=6.8 Hz, 1H), 7.63 (s, 1H), 7.58 (d, J=8 Hz, 1H), 7.51 (d, J=8 Hz, 1H), 7.18 (t, J=7.6 Hz, 1H), 7.06 (t, J=8 Hz, 1H), 7.00 (d, J=7.2 Hz, 1H), 6.63 (s, 1H), 4.54 (t, J=7.2 Hz, 2H), 3.01 (bs, 1H), 2.84 (bs, 2H), 2.65 (s, 3H), 1.99-1.97 (m, 2H), 1.88 (bs, 1H), 1.69 (bs, 1H), 1.45 (bs, 2H), 1.33-1.31 (m, 2H), 1.32 (t, J=6.8 Hz, 3H). MS (ESI): Mass calcd. for $C_{24}H_{27}N_5O$, 401.22; m/z found, 402.2 $[M+H]^+$.

Compound-5

Synthesis of (R)-(3-Aminopiperidin-1-yl)(2-(1-ethyl-3-phenyl-1H-indol-2-yl)-3-methylimidazo[1,2-a]pyridin-7-yl)methanone (Compound-5)

Intermediate 1 is synthesized using the procedure outlined for Intermediate 6 in Scheme-2 above.

Scheme-4

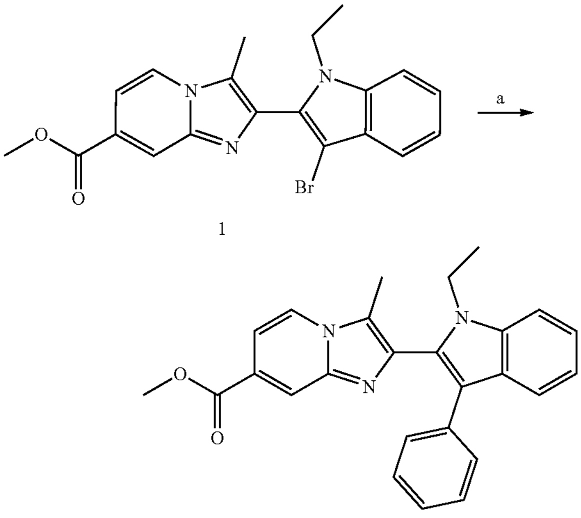

1

2

Step 6: Preparation of Methyl 2-(1-ethyl-3-phenyl-1H-indol-2-yl)-3-methylimidazo[1,2-a]pyridine-7-carboxylate (2)

2

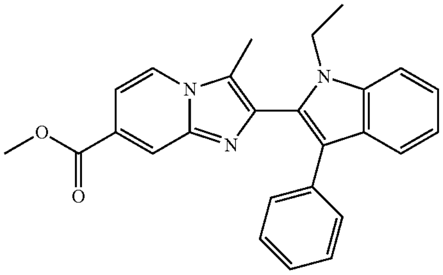

To the stirred solution of methyl 2-(3-bromo-1-ethyl-1H-indol-2-yl)-3-methylimidazo[1,2-a]pyridine-7-carboxylate (1, 0.27 g, 0.65 mmol) in dioxane:water (8:2, 10 mL), was added phenylboronic acid (0.12 g, 0.98 mmol), $K_2CO_3$ (0.27 g, 1.96 mmol), $Pd(PPh_3)_4$ (0.04 g, 0.03 mmol) and stirred at 85° C. for 16 h. The reaction mixture was cooled to rt, filtered through celite and dioxane was evaporated. To the resulting crude product was added water (10 mL), acidified using saturated citric acid solution and the compound was extracted with EtOAc (50 mL). Organic layer was washed with brine (10 mL) solution, dried over anhydrous $Na_2SO_4$ and evaporated under vacuum. The crude residue was purified by gradient column chromatography using 15-30% EtOAc in hexane to afford title product as brown gummy (2) (0.22 g, 78% Yield). MS (ESI): Mass calcd. for $C_{26}H_{23}N_3O_2$, 409.49; m/z found, 410.2 $(M+H)^+$.

Further steps for Compounds-5 and 6 were carried using the procedure as exemplified for Compound-1.

Compound-5

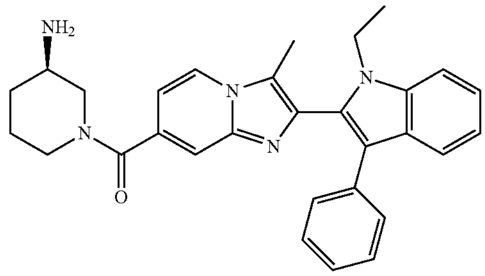 [SMILES: CCn1c(-c2nc3cc(C(=O)N4CCC[C@@H](N)C4)ccn3c2C)c(-c2ccccc2)c2ccccc21]

$^1$HNMR (400 MHz, DMSO-$d_6$) δ (ppm): 8.26 (d, J=7.2 Hz, 1H), 7.71-7.66 (m, 2H), 7.59 (d, J=8.0 Hz, 1H), 7.30-7.24 (m, 3H), 7.20-7.16 (m, 2H), 7.13-7.11 (m, 2H), 6.95-6.93-7.01 (m, 1H), 4.30-4.28 (m, 2H), 3.65-3.62 (m, 2H), 3.02-2.98 (m, 2H), 3.27-3.23 (m, 1H), 1.85 (s, 3H), 1.69-1.65 (m, 1H), 1.47-1.44 (m, 1H), 1.26-1.24 (m, 5H), 1.18-1.15 (m, 2H). MS (ESI): Mass calcd. for $C_{30}H_{31}N_5O$, 477.61; m/z found, 478.3 $(M+H)^+$.

Compound-6

(R)-(3-Aminopyrrolidin-1-yl)(2-(1-ethyl-3-phenyl-1H-indol-2-yl)-3-methylimidazo[1,2-a]pyridin-7-yl)methanone

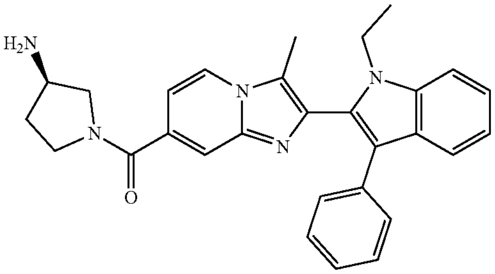 [SMILES: CCn1c(-c2nc3cc(C(=O)N4CC[C@@H](N)C4)ccn3c2C)c(-c2ccccc2)c2ccccc21]

$^1$HNMR (400 MHz, DMSO-$d_6$) δ (ppm): 8.25 (d, J=7.2 Hz, 1H), 7.81-7.78 (m, 1H), 7.69 (d, J=8.0 Hz, 1H), 7.60 (d, J=8.4 Hz, 1H), 7.30-7.24 (m, 3H), 7.19-7.13 (m, 4H), 7.06-7.01 (m, 1H), 4.31-4.28 (m, 2H), 3.65-3.62 (m, 2H), 3.51-3.47 (m, 2H), 3.27-3.23 (m, 1H), 1.96-1.94 (m, 2H), 1.86 (s, 3H), 1.65-1.62 (m, 1H), 1.26-1.24 (m, 3H), 1.18-1.15 (m, 1H). MS (ESI): Mass calcd. for $C_{29}H_{29}N_5O$, 463.59; m/z found, 464.2 $(M+H)^+$.

Compound-7

(R)-(3-Aminopyrrolidin-1-yl)(2-(1-ethyl-1H-indol-2-yl)-3-methylimidazo[1,2-a]pyridin-7-yl)methanone

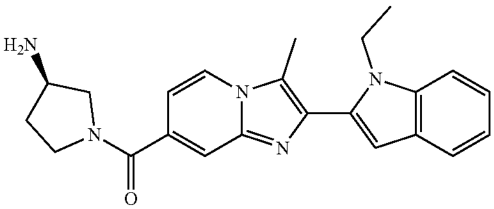 [SMILES: CCn1c(-c2nc3cc(C(=O)N4CC[C@@H](N)C4)ccn3c2C)cc2ccccc21]

$^1$HNMR (400 MHz, DMSO-$d_6$) δ (ppm): 8.41 (d, J=6.8 Hz, 1H), 7.76-7.74 (m, 1H), 7.58 (d, J=8.0 Hz, 1H), 7.51 (d, J=8.4 Hz, 1H), 7.17 (t, J=7.6 Hz, 1H), 7.11-7.03 (m, 2H), 6.64 (s, 1H), 4.58-4.53 (m, 2H), 3.67-3.63 (m, 2H), 3.55-3.49 (m, 2H), 3.27 (br s, 2H), 3.10-2.99 (m, 2H), 2.88-2.81 (m, 2H), 2.63 (s, 3H), 1.99-1.95 (m, 1H), 1.22 (t, J=6.8 Hz, 1H). MS (ESI): Mass calcd. for $C_{23}H_{25}N_5O$, 387.49; m/z found, 388.2 $(M+H)^+$.

Compound-8

(R)-(3-Aminopyrrolidin-1-yl)(2-(1-(cyclopropylmethyl)-1H-indol-2-yl)-3-methyl imidazo[1,2-a]pyridin-7-yl)methanone

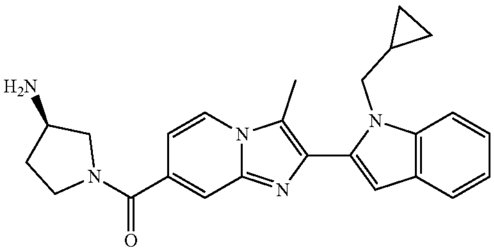 [SMILES: Cc1c(-c2cc3ccccc3n2CC2CC2)nc2cc(C(=O)N3CC[C@@H](N)C3)ccn12]

$^1$HNMR (400 MHz, DMSO-$d_6$) δ (ppm): 8.41 (d, J=7.2 Hz, 1H), 7.77-6.73 (m, 1H), 7.57 (t, J=7.6 Hz, 2H), 7.18-7.14 (m, 1H), 7.11-7.09 (m, 1H), 7.06-7.03 (m, 1H), 6.65 (s, 1H), 4.49 (d, J=6.8 Hz, 2H), 3.67-3.60 (m, 2H), 3.57-3.50 (m, 2H), 3.23-3.19 (m, 1H), 2.63 (s, 3H), 1.96-1.89 (m, 1H), 1.65-1.60 (m, 1H), 1.23-1.15 (m, 2H), 1.09 (m, 1H), 0.26-0.25 (m, 2H), 0.15-0.13 (m, 2H). MS (ESI): Mass calcd. for $C_{25}H_{27}N_5O$, 413.53; m/z found, 414.2 $(M+H)^+$.

Compound-9

(2-(1-(Cyclopropylmethyl)-1H-indol-2-yl)-3-methyl-imidazo[1,2-a]pyridin-7-yl) (hexahydro-2H-pyrido[4,3-b][1,4]oxazin-6(5H)-yl)methanone

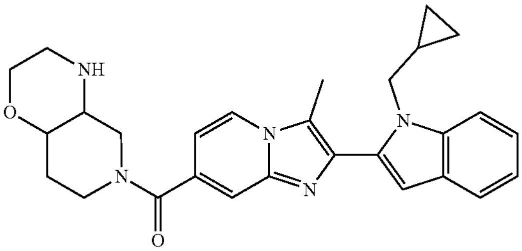 [SMILES: Cc1c(-c2cc3ccccc3n2CC2CC2)nc2cc(C(=O)N3CCC4OCCNC4C3)ccn12]

$^1$HNMR (400 MHz, DMSO-$d_6$) δ (ppm): 8.41 (d, J=7.2 Hz, 1H), 7.62 (s, 1H), 7.57 (t, J=6.8 Hz, 2H), 7.18-7.14 (m, 1H), 7.06-6.99 (m, 2H), 6.64 (s, 1H), 4.48 (d, J=7.2 Hz, 2H), 3.76-3.72 (m, 2H), 3.44-3.40 (m, 2H), 2.85-2.78 (m, 2H), 2.65 (s, 3H), 2.01-1.97 (m, 2H), 1.85-1.81 (m, 1H), 1.67-1.61 (m, 1H), 1.21-1.19 (m, 3H), 1.10-1.05 (m, 1H), 0.27-0.25 (m, 2H), 0.15-0.13 (m, 2H). MS (ESI): Mass calcd. for $C_{28}H_{31}N_5O_2$, 469.59; m/z found, 470.3 $(M+H)^+$.

Compound-10

(R)-(3-Aminopiperidin-1-yl)(3-methyl-2-(1-(pyridin-4-ylmethyl)-1H-indol-2-yl) imidazo[1,2-a]pyridin-7-yl)methanone

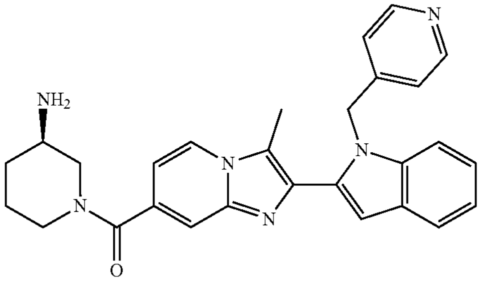 [SMILES: Cc1c(-c2cc3ccccc3n2Cc2ccncc2)nc2cc(C(=O)N3CCC[C@@H](N)C3)ccn12]

$^1$HNMR (400 MHz, DMSO-$d_6$) δ (ppm): 8.40 (d, J=6.8 Hz, 1H), 7.35-7.33 (m, 2H), 7.63 (d, J=7.6 Hz, 1H), 7.57 (s, 1H), 7.35 (d, J=8.0 Hz, 1H), 7.13-7.07 (m, 2H), 6.98-6.96 (m, 1H), 6.90-6.88 (m, 2H), 6.78 (s, 1H), 5.95 (s, 2H), 4.19-4.11 (m, 1H), 3.65-3.61 (m, 2H), 2.99-2.95 (m, 1H), 2.80-2.79 (m, 2H), 2.64 (s, 3H), 1.86-1.83 (m, 1H), 1.66-1.63 (m, 1H), 1.45-1.42 (m, 1H), 1.31-1.29 (m, 1H), 1.21-1.18 (m, 1H). MS (ESI): Mass calcd. for $C_{28}H_{28}N_6O$, 464.57; m/z found, 465.3 $(M+H)^+$.

Compound-11

(R)-(3-Aminopiperidin-1-yl)(3-methyl-2-(1-((tetrahydro-2H-pyran-4-yl)methyl)-1H-indol-2-yl)imidazo[1,2-a]pyridin-7-yl)methanone

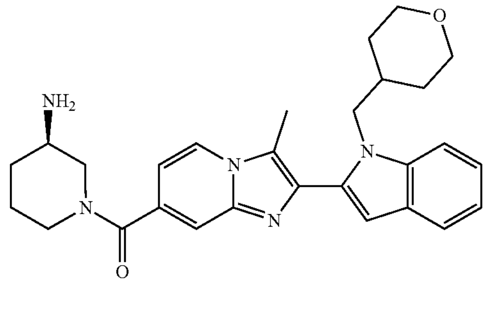 [SMILES: Cc1c(-c2cc3ccccc3n2CC2CCOCC2)nc2cc(C(=O)N3CCC[C@@H](N)C3)ccn12]

$^1$HNMR (400 MHz, DMSO-$d_6$) δ (ppm): 8.41 (d, J=6.8 Hz, 1H), 7.62 (s, 1H), 7.56 (t, J=7.2 Hz, 2H), 7.18-7.14 (m, 1H), 7.06-7.00 (m, 1H), 6.98-6.95 (m, 1H), 6.65 (s, 1H), 4.52 (d, J=7.2 Hz, 1H), 4.19-4.11 (m, 1H), 3.65-3.62 (m, 2H), 3.48-3.41 (m, 1H), 3.07-3.01 (m, 2H), 2.78-2.75 (m, 2H), 2.67-2.63 (m, 2H), 2.61 (s, 3H), 1.99-1.95 (m, 2H), 1.70-1.67 (m, 1H), 1.1.65-1.61 (m, 1H), 1.28-1.21 (m, 1H), 1.18-1.11 (m, 4H), 1.03-1.00 (m, 2H). MS (ESI): Mass calcd. for $C_{28}H_{33}N_5O_2$, 471.61; m/z found, 472.3 $(M+H)^+$.

Compound-12

(R)-(3-Aminopiperidin-1-yl)(2-(1-(4-methoxybenzyl)-1H-indol-2-yl)-3-methyl imidazo[1,2-a]pyridin-7-yl)methanone

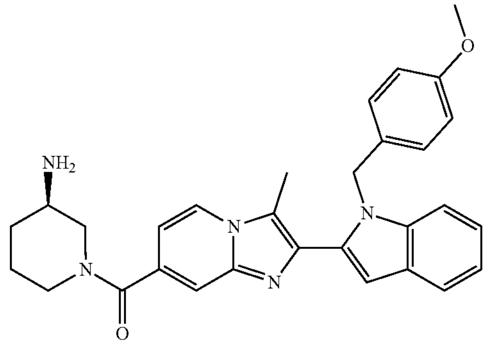 [SMILES: COc1ccc(Cn2c(-c3nc4cc(C(=O)N5CCC[C@@H](N)C5)ccn4c3C)cc3ccccc32)cc1]

$^1$HNMR (400 MHz, DMSO-$d_6$) δ (ppm): 8.40 (s, 1H), 7.60-7.57 (m, 2H), 7.41-7.39 (m, 2H), 7.11-7.07 (m, 1H), 7.05-7.01 (m, 1H), 6.99-6.97 (m, 1H), 6.92-6.90 (m, 2H), 6.72-6.70 (m, 2H), 5.80 (s, 2H), 3.63 (s, 3H), 2.83-2.81 (m, 2H), 2.68-2.65 (m, 2H), 2.64 (s, 3H), 2.06-2.01 (m, 2H), 1.88-1.85 (m, 1H), 1.68-1.65 (m, 1H), 1.44-1.41 (m, 1H), 1.21-1.18 (m, 2H). MS (ESI): Mass calcd. for $C_{30}H_{31}N_5O_2$, 493.61; m/z found, 494.3 $(M+H)^+$.

Compound-13

(R)-(3-Aminopiperidin-1-yl)(2-(1-(4-fluorobenzyl)-1H-indol-2-yl)-3-methylimidazo[1,2-a]pyridin-7-yl)methanone

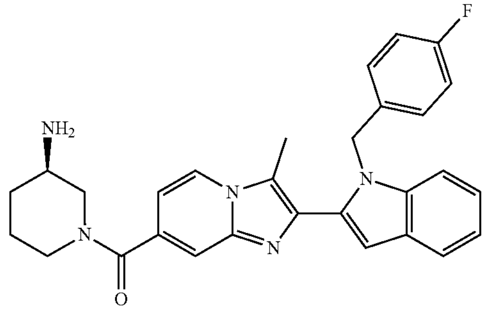 [SMILES: Cc1c(-c2cc3ccccc3n2Cc2ccc(F)cc2)nc2cc(C(=O)N3CCC[C@@H](N)C3)ccn12]

$^1$HNMR (400 MHz, DMSO-$d_6$) δ (ppm): 8.40 (d, J=7.2 Hz, 1H), 7.61-7.59 (m, 2H), 7.40 (d, J=7.2 Hz, 1H), 7.12-7.08 (m, 1H), 7.02-6.98 (m, 6H), 6.75 (s, 1H), 5.86 (s, 2H), 4.05-4.01 (m, 1H), 3.57-3.51 (m, 1H), 2.97-2.94 (m, 1H), 2.78-2.71 (m, 1H), 2.62 (s, 3H), 2.02-1.98 (m, 2H), 1.84-1.81 (m, 1H), 1.67-1.61 (m, 1H), 1.44-1.41 (m, 1H), 1.25-1.21 (m, 2H). MS (ESI): Mass calcd. for $C_{29}H_{28}FN_5O$, 481.58; m/z found, 482.2 $(M+H)^+$.

Compound-14

(R)-4-((2-(7-(3-Aminopiperidine-1-carbonyl)-3-methylimidazo[1,2-a]pyridin-2-yl)-1H-indol-1-yl)methyl)benzonitrile

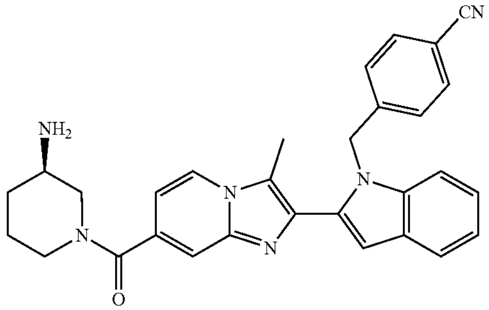 [SMILES: Cc1c(-c2cc3ccccc3n2Cc2ccc(C#N)cc2)nc2cc(C(=O)N3CCC[C@@H](N)C3)ccn12]

$^1$HNMR (400 MHz, DMSO-$d_6$) δ (ppm): 8.41 (d, J=7.2 Hz, 1H), 7.66-7.59 (m, 4H), 7.35 (d, J=8.0 Hz, 1H), 7.14-7.12 (m, 2H), 7.08-7.05 (m, 2H), 6.97 (d, J=7.2 Hz, 1H), 6.81 (s, 1H), 5.99 (s, 2H), 2.93-2.89 (m, 2H), 2.64 (s, 3H), 1.99-1.97 (m, 1H), 1.88-1.85 (m, 1H), 1.68-1.65 (m, 1H), 1.45-1.41 (m, 3H), 1.33-1.29 (m, 1H), 1.22-1.19 (m, 2H). MS (ESI): Mass calcd. for $C_{30}H_{28}N_6O$, 488.60; m/z found, 489.2 $(M+H)^+$.

Compound-15

(R)-(3-Aminopiperidin-1-yl)(3-methyl-2-(1-(pyridin-3-ylmethyl)-1H-indol-2-yl) imidazo[1,2-a]pyridin-7-yl)methanone

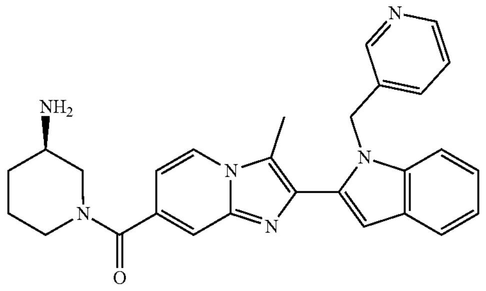 [SMILES: Cc1c(-c2cc3ccccc3n2Cc2cccnc2)nc2cc(C(=O)N3CCC[C@@H](N)C3)ccn12]

$^1$HNMR (400 MHz, DMSO-$d_6$) δ (ppm): 8.41 (d, J=6.8 Hz, 1H), 8.32 (d, J=4.0 Hz, 1H), 8.26 (s, 1H), 7.62-7.59 (m, 2H), 7.46-7.44 (m, 1H), 7.37-7.35 (m, 1H), 7.20-7.18 (m, 1H), 7.13-7.07 (m, 2H), 6.99-6.97 (m, 1H), 6.78 (s, 1H), 5.93 (s, 2H), 4.19-4.11 (m, 1H), 3.65-3.61 (m, 2H), 2.98-2.95 (m, 1H), 2.70-2.67 (m, 2H), 2.63 (s, 3H), 1.85-1.83 (m, 1H), 1.66-1.63 (m, 1H), 1.45-1.42 (m, 1H), 1.27-1.21 (m, 2H). MS (ESI): Mass calcd. for $C_{28}H_{28}N_6O$, 464.23; m/z found, 465.2 $(M+H)^+$.

Compound-16

(R)-(3-Aminopiperidin-1-yl)(3-methyl-2-(1-(pyridin-2-ylmethyl)-1H-indol-2-yl) imidazo[1,2-a]pyridin-7-yl)methanone

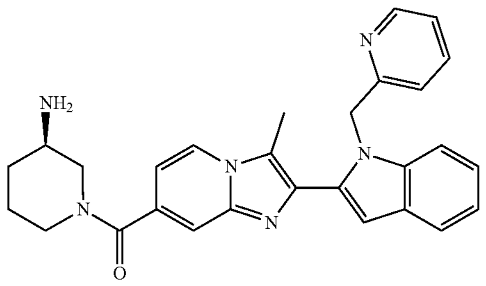 [SMILES: Cc1c(-c2cc3ccccc3n2Cc2ccccn2)nc2cc(C(=O)N3CCC[C@@H](N)C3)ccn12]

$^1$HNMR (400 MHz, DMSO-$d_6$) δ (ppm): 8.42-8.38 (m, 2H), 7.62 (d, J=6.8 Hz, 1H), 7.57-7.52 (m, 2H), 7.34 (d, J=8.0 Hz, 1H), 7.15-7.05 (m, 3H), 7.04-6.95 (m, 1H), 6.78 (s, 1H), 6.64 (d, J=8.0 Hz, 1H), 5.96 (s, 2H), 4.19-4.11 (m, 1H), 3.55-3.49 (m, 1H), 2.97-2.95 (m, 2H), 2.79-2.73 (m, 2H), 2.63 (s, 3H), 1.87-1.82 (m, 1H), 1.66-1.63 (m, 1H), 1.45-1.42 (m, 1H), 1.28-1.22 (m, 2H). MS (ESI): Mass calcd. for $C_{28}H_{28}N_6O$, 464.23; m/z found, 465.2 $(M+H)^+$.

Compound-17

(R)-(3-Aminopiperidin-1-yl)(3-methyl-2-(1-(2,2,2-trifluoroethyl)-1H-indol-2-yl) imidazo[1,2-a]pyridin-7-yl)methanone

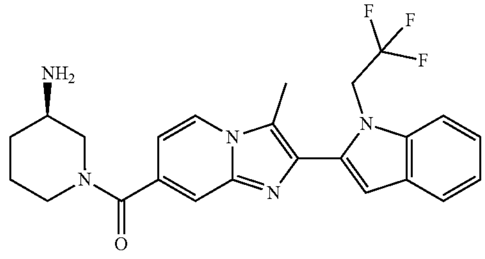 [SMILES: Cc1c(-c2cc3ccccc3n2CC(F)(F)F)nc2cc(C(=O)N3CCC[C@@H](N)C3)ccn12]

$^1$HNMR (400 MHz, DMSO-$d_6$) δ (ppm): 8.43 (d, J=7.2 Hz, 1H), 7.66-7.61 (m, 3H), 7.24 (t, J=7.2 Hz, 1H), 7.12 (t, J=7.4 Hz, 1H), 7.01 (d, J=7.2 Hz, 1H), 6.83 (s, 1H), 5.85-5.80 (m, 2H), 4.1 (bs, 1H), 3.60 (bs, 1H), 3.00 (bs, 1H), 2.66-2.63 (m, 4H), 1.88-1.83 (m, 2H), 1.67 (bs, 2H), 1.46 (bs, 1H), 1.27-1.22 (m, 2H). MS (ESI): Mass calcd. for $C_{24}H_{24}F_3N_5O$, 455.49; m/z found, 456.2 $(M+H)^+$.

Compound-18

(R)-4-((2-(7-(3-Aminopiperidine-1-carbonyl)-3-methylimidazo[1,2-a]pyridin-2-yl)-1H-indol-1-yl) methyl)-1-methylpyridin-2(1H)-one

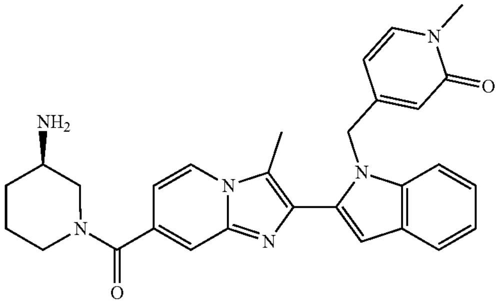 [SMILES: Cc1c(-c2cc3ccccc3n2Cc2ccn(C)c(=O)c2)nc2cc(C(=O)N3CCC[C@@H](N)C3)ccn12]

$^1$HNMR (400 MHz, DMSO-$d_6$) δ (ppm): 8.41 (d, J=6.8 Hz, 1H), 7.61 (d, J=8.0 Hz, 1H), 7.57 (s, 1H), 7.47 (d, J=6.8 Hz, 1H), 7.37 (d, J=8.0 Hz, 1H), 7.16-7.10 (m, 2H), 6.98 (d, J=7.2 Hz, 1H), 6.80 (s, 1H), 5.87 (d, J=5.6 Hz, 1H), 5.77 (s, 2H), 5.65 (s, 1H), 4.19-4.11 (m, 1H), 3.65-3.61 (m, 1H), 3.24 (s, 3H), 2.97-2.93 (m, 1H), 2.65 (s, 3H), 2.64-2.61 (m, 2H), 1.86-1.83 (m, 2H), 1.66-1.63 (m, 2H), 1.44-1.41 (m, 1H), 1.24-1.19 (m, 1H). MS (ESI): Mass calcd. for $C_{29}H_{30}N_6O_2$, 494.24; m/z found, 495.4 $(M+H)^+$.

Compound-19

(R)-(3-Aminopiperidin-1-yl)(2-(3-ethylbenzo[b]thiophen-2-yl)-3-methylimidazo[1,2-a]pyridin-7-yl)methanone

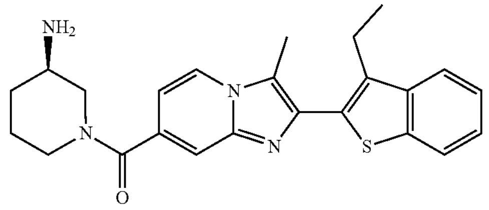 [SMILES: CCc1c(-c2nc3cc(C(=O)N4CCC[C@@H](N)C4)ccn3c2C)sc2ccccc12]

$^1$HNMR (400 MHz, DMSO-$d_6$) δ (ppm): 8.38 (d, J=6.8 Hz, 1H), 7.96 (d, J=7.2 Hz, 1H), 7.87 (d, J=7.5 Hz, 1H), 7.59 (s, 1H), 7.45-7.36 (m, 2H), 6.97 (d, J=7.2 Hz, 1H), 4.02-3.99 (m, 1H), 3.49-3.45 (m, 1H), 3.03-2.97 (m, 3H), 2.69-2.60 (m, 2H), 2.58 (s, 3H), 2.14-2.08 (m, 1H), 1.88-1.83 (m, 1H), 1.69-1.61 (m, 1H), 1.46-1.39 (m, 1H), 1.31-1.26 (m, 2H), 1.19-1.12 (m, 3H). MS (ESI): Mass calcd. for $C_{24}H_{26}N_4OS$, 418.56; m/z found, 419.2 $(M+H)^+$.

Compound-20

Synthesis of (R)-(3-Aminopiperidin-1-yl)(2-(1-(4-chlorobenzyl)-1H-indol-2-yl)-3-methylimidazo[1,2-a]pyridin-7-yl)methanone (Compound-20)

Scheme-5

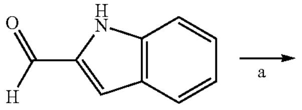

1

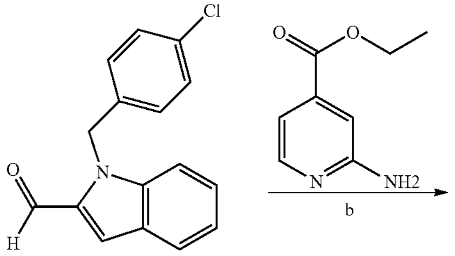

2

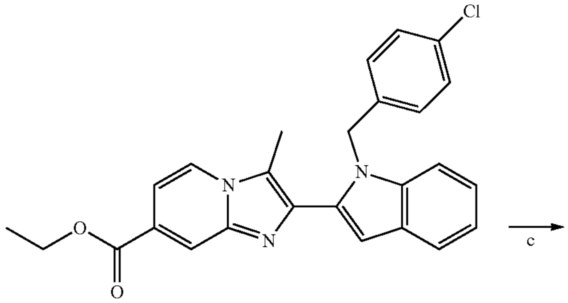

3

-continued

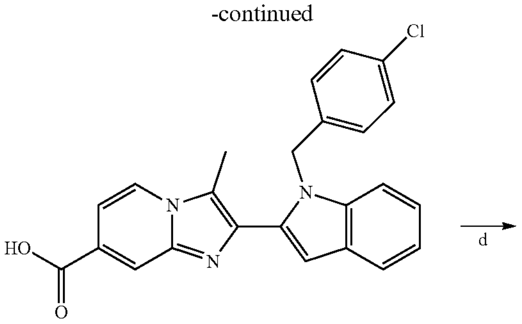

4

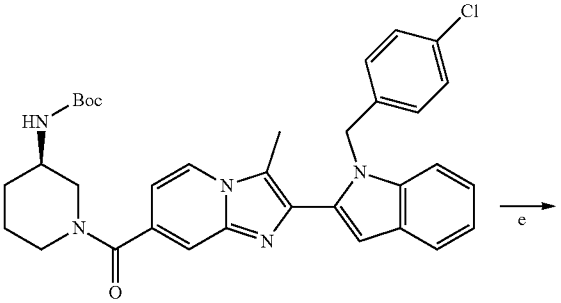

5

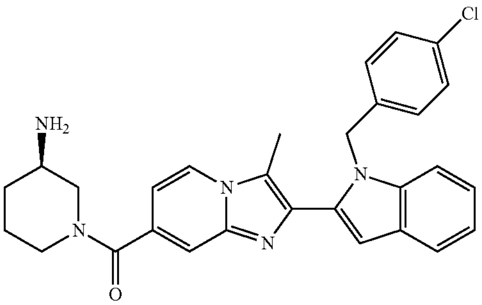

Compound-20

Step 1: Preparation of Ethyl 2-(1-(4-chlorobenzyl)-1H-indol-2-yl)-3-methylimidazo[1,2-a]pyridine-7-carboxylate (2)

2

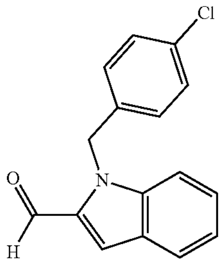

To a stirred solution 1H-indole-2-carbaldehyde (1, 0.5 g, 3.44 mmol) in DMF (10 mL), was added potassium carbonate (1.42 g, 10.3 mmol) followed by 1-(bromomethyl)-4-chlorobenzene (0.84 g, 4.13 mmol) and then the reaction mixture was stirred at rt for 4 h (Reaction condition a). Reaction mixture was poured into crushed ice which resulted in the formation of precipitate. The precipitate was filtered through sintered funnel and dried over vacuum to get the title compound as beige colour solid (2) (0.86 g, 93.4% Yield). MS (ESI): Mass calcd. for $C_{16}H_{12}ClNO$, 269.73; m/z found 270.1 $(M+H)^+$.

Step 2: Preparation of Ethyl 2-(1-(4-chlorobenzyl)-1H-indol-2-yl)-3-methylimidazo[1,2-a]pyridine-7-carboxylate (3)

3

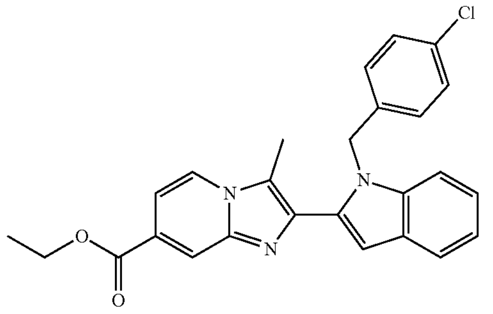

To the stirred solution of 1-(4-chlorobenzyl)-1H-indole-2-carbaldehyde (2, 0.38 g, 1.44 mmol) and ethyl 2-aminoisonicotinate (0.2 g, 1.2 mmol) in DMF was added nitro ethane (1.1 g, 14.3 mmol) followed by $FeCl_3$ (0.04 g, 0.28 mmol) and stirred at 90° C. under air for 5 h (Reaction condition b). The reaction mixture was cooled to rt, diluted with ethyl acetate and evaporated under vacuum to get crude compound. Crude was purified by flash column chromatography using ethylacetate in hexane as an eluent to afford the product as pale yellow gummy solid (3) (0.07 g, 10.9% Yield). MS (ESI): Mass calcd. for $C_{26}H_{22}ClN_3O_2$, 443.93; m/z found, 444.1 $(M+H)^+$.

Step 3: Preparation of 2-(1-(4-Chlorobenzyl)-1H-indol-2-yl)-3-methylimidazo[1,2-a]pyridine-7-carboxylic acid (4)

4

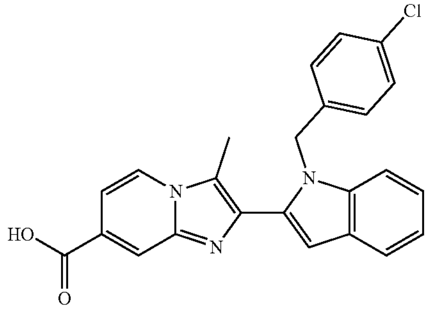

To the stirred solution of ethyl 2-(1-(4-chlorobenzyl)-1H-indol-2-yl)-3-methylimidazo[1,2-a]pyridine-7-carboxylate (3, 0.08 g, 0.18 mmol) in ethanol (5 mL), was added 5N sodium hydroxide solution (0.18 mL, 9.0 mmol) and was heated at 80° C. for 1 h (Reaction condition c). The reaction mixture was cooled to rt and evaporated to dryness. Resulting crude product was dissolved in water (10 mL), acidified using saturated citric acid solution and extracted with dichloromethane (40 mL). Organic layer was dried over anhydrous sodium sulfate and evaporated under vacuum to afford the product as colourless gummy solid (4) (0.06 g, 80.3% Yield). MS (ESI): Mass calcd. for $C_{24}H_{18}ClN_3O_2$, 415.88; m/z found, 416.1 $(M+H)^+$.

Step 4: Preparation of Tert-butyl (R)-(1-(2-(1-(4-chlorobenzyl)-1H-indol-2-yl)-3-methylimidazo[1,2-a]pyridine-7-carbonyl)piperidin-3-yl)carbamate (5)

5

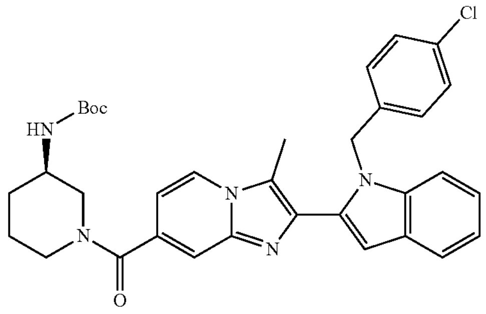

To a stirred solution 2-(1-ethyl-1H-pyrrolo[2,3-b]pyridin-2-yl)-3-methylimidazo[1,2-a]pyridine-7-carboxylic acid (4, 0.06 g, 0.144 mmol) in DCM (3 mL), was added tert-butyl (R)-piperidin-3-ylcarbamate (0.043 g, 0.216 mmol), $Et_3N$ (0.06 mL, 0.432 mmol), 50% solution of T3P in ethyl acetate (0.068 mL, 0.216 mmol) and the reaction mixture was stirred at rt for 5 h (Reaction condition d). The reaction mixture was quenched with water (10 mL) and extracted with ethyl acetate (25 mL). Organic layer was dried over anhydrous $Na_2SO_4$ and evaporated under vacuum. Crude was purified by column chromatography using ethylacetate in hexane to afford the product as off white solid (5) (0.09 g, 61% Yield). MS (ESI): Mass calcd. for $C_{34}H_{36}ClN_5O_3$, 598.14; m/z found, 599.2 $(M+H)^+$.

Step 5: Preparation of (R)-(3-Aminopiperidin-1-yl)(2-(1-(4-chlorobenzyl)-1H-indol-2-yl)-3-methylimidazo[1,2-a]pyridin-7-yl)methanone (6, Compound-20)

Compound-20

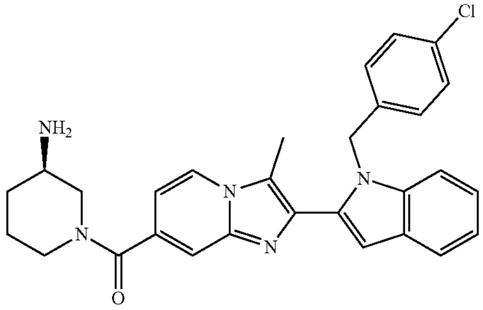

To a stirred solution tert-butyl (R)-(1-(2-(1-ethyl-1H-pyrrolo[2,3-b]pyridin-2-yl)-3-methylimidazo[1,2-a]pyridine-7-carbonyl)piperidin-3-yl)carbamate (5, 0.05 g, 0.083 mmol) in DCM (3 mL), was added TFA (0.5 mL) and the reaction mixture was stirred at rt for 2 h (Reaction condition e). The reaction mixture was basified using saturated sodium bicarbonate solution and extracted with MeOH/DCM (2×25 mL). Combined organic layer was dried over anhydrous sodium sulphate. Crude product was purified by flash column chromatography using 7% MeOH in DCM to give the title compound as brown colour solid (0.007 g, 26.8% Yield) (6, Compound-20) $^1$HNMR (400 MHz, DMSO-$d_6$) δ (ppm): 8.41 (d, J=6.8 Hz, 1H), 7.62-7.59 (m, 2H), 7.37 (d, J=8.0 Hz, 1H), 7.23 (d, J=8.4 Hz, 2H), 7.12-7.00 (m, 2H), 6.99-6.98 (m, 3H), 6.76 (s, 1H), 5.91 (s, 2H), 4.12 (bs, 1H), 3.6 (bs, 1H), 3.00 (bs, 1H), 2.79 (bs, 1H), 2.65-2.63 (m, 1H), 1.88-1.84 (m, 2H), 1.68 (bs, 2H), 1.46-1.43 (m, 2H), 1.28-1.12 (m, 3H). MS (ESI): Mass calcd. for $C_{29}H_{28}ClN_5O$, 498.03; m/z found, 499.2 $(M+H)^+$.

Following compounds (Compounds 21, 22, 23, 24, 25, 26, 27, 28, 29, 30, 39, 40, 43, 44 and 47) were synthesized using the above procedure as exemplified for Compound-20.

Compound-21

(R)-(3-Aminopiperidin-1-yl)(2-(1-(2-fluorobenzyl)-1H-indol-2-yl)-3-methylimidazo[1,2-a]pyridin-7-yl) methanone

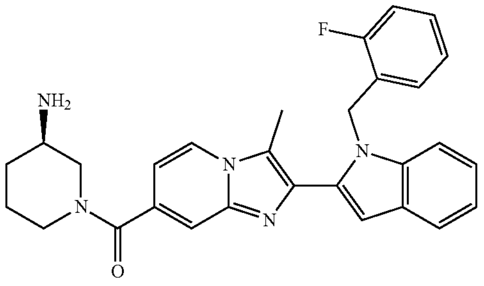 [SMILES: Cc1c(-c2cc3ccccc3n2Cc2ccccc2F)nc2cc(C(=O)N3CCC[C@@H](N)C3)ccn12]

$^1$HNMR (400 MHz, DMSO-$d_6$) δ (ppm): 8.39 (d, J=7.2 Hz, 1H), 7.62-7.59 (m, 2H), 7.37 (d, J=8 Hz, 1H), 7.17-7.05 (m, 4H), 7.14 (d, J=6.8 Hz, 1H), 6.96-6.89 (m, 1H), 6.78 (s, 1H), 6.52-6.48 (m, 1H), 5.97 (s, 2H), 4.10 (bs, 1H), 2.99 (bs, 1H), 2.80 (bs, 2H), 2.62 (s, 3H), 1.88 (bs, 2H), 1.68 (bs, 1H), 1.46 1.68 (bs, 1H), 1.31-1.21 (m, 3H). MS (ESI): Mass calcd. for $C_{29}H_{28}FN_5O$, 481.58; m/z found, 482.4 $(M+H)^+$.

Compound-22

(R)-(3-Aminopiperidin-1-yl)(2-(1-ethyl-5-phenyl-1H-pyrrol-2-yl)-3-methylimidazo[1,2-a]pyridin-7-yl) methanone

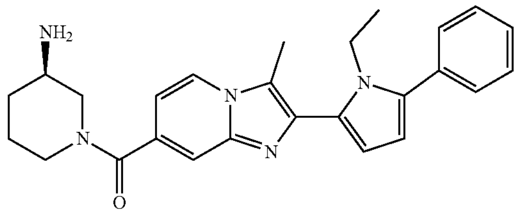 [SMILES: CCn1c(-c2ccccc2)ccc1-c1nc2cc(C(=O)N3CCC[C@@H](N)C3)ccn2c1C]

$^1$HNMR (400 MHz, DMSO-$d_6$) δ (ppm): 8.35 (d, J=7.2 Hz, 1H), 7.56 (s, 1H), 7.46-7.44 (m, 4H), 7.36-7.34 (m, 1H), 6.95 (d, J=6.8 Hz, 1H), 6.30 (d, J=3.6 Hz, 1H), 6.21 (d, J=3.6 Hz, 1H), 4.40-4.38 (m, 2H), 3.05 (bs, 1H), 2.73 (bs, 2H), 2.57 (s, 3H), 1.88-1.84 (m, 2H), 1.68 (bs, 2H), 1.46 (bs, 1H), 1.28-1.22 (m, 3H), 0.90-0.83 (m, 3H). MS (ESI): Mass calcd. for $C_{26}H_{29}N_5O$, 427.55; m/z found, 428.3 $(M+H)^+$.

Compound-23

(R)-(3-Aminopiperidin-1-yl)(2-(1-(cyclopropylmethyl)-6-methoxy-1H-indol-2-yl)-3-methylimidazo [1,2-a]pyridin-7-yl)methanone

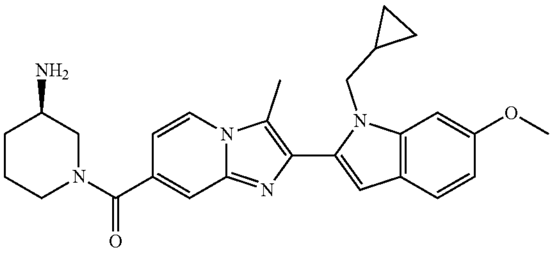 [SMILES: COc1ccc2cc(-c3nc4cc(C(=O)N5CCC[C@@H](N)C5)ccn4c3C)n(CC3CC3)c2c1]

$^1$HNMR (400 MHz, DMSO-$d_6$) δ (ppm): 8.41 (d, J=6.8 Hz, 1H), 7.63 (s, 1H), 7.45 (d, J=8.8 Hz, 1H), 7.08 (s, 1H), 6.99 (d, J=6.4 Hz, 1H), 6.71 (d, J=7.6 Hz, 1H), 6.55 (s, 1H), 5.15 (bs, 2H), 4.46 (d, J=6.8 Hz, 2H), 3.82 (s, 3H), 3.08-2.92 (m, 3H), 2.61 (s, 3H), 1.97-1.88 (m, 2H), 1.71 (bs, 1H), 1.48-1.36 (bs, 3H), 1.09 (m, 1H), 0.26 (d, J=7.6 Hz, 2H), 0.13 (d, J=4 Hz, 2H). MS (ESI): Mass calcd. for $C_{27}H_{31}N_5O_2$, 457.58; m/z found, 458.58 (M+H).

Compound-24

(R)-(3-Aminopiperidin-1-yl)(2-(1-ethyl-1H-pyrrolo [2,3-b]pyridin-2-yl)-3-methyl imidazo[1,2-a]pyridin-7-yl)methanone

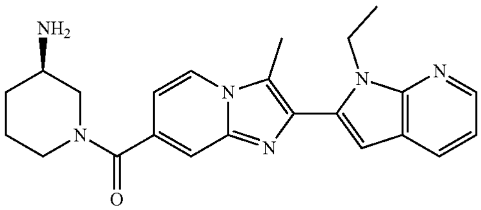 [SMILES: CCn1c(-c2nc3cc(C(=O)N4CCC[C@@H](N)C4)ccn3c2C)cc2cccnc21]

$^1$HNMR (400 MHz, DMSO-$d_6$) δ (ppm): 8.43 (d, J=6.4 Hz, 1H), 8.28-8.25 (m, 1H), 7.98 (d, J=7.2 Hz, 1H), 7.63 (s, 1H), 7.13-7.11 (m, 1H), 7.01-6.99 (m, 1H), 6.67 (s, 1H), 4.71-4.65 (m, 2H), 4.24-4.21 (m, 1H), 3.55-3.49 (m, 1H), 3.00-2.96 (m, 1H), 2.69-2.66 (m, 1H), 2.65 (s, 3H), 2.21-2.19 (m, 2H), 1.87-1.83 (m, 2H), 1.68-1.65 (m, 1H), 1.45-1.42 (m, 1H), 1.35-1.33 (m, 1H), 1.26-1.24 (m, 3H). MS (ESI): Mass calcd. for $C_{23}H_{26}N_6O$, 402.22; m/z found, 403.1 $(M+H)^+$.

Compound-25

(R)-(3-Aminopiperidin-1-yl)(2-(1-(cyclopropylmethyl)-1H-indol-2-yl)-3,5-dimethyl imidazo[1,2-a]pyridin-7-yl)methanone

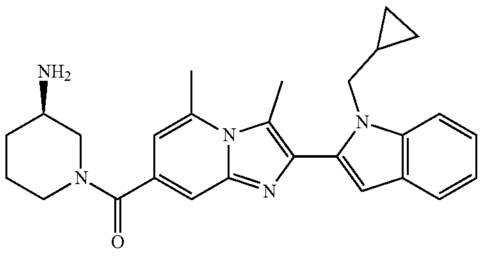 [SMILES: Cc1cc(C(=O)N2CCC[C@@H](N)C2)cc2nc(-c3cc4ccccc4n3CC3CC3)c(C)n12]

$^1$HNMR (400 MHz, DMSO-$d_6$) δ (ppm): 7.57 (t, J=7.2 Hz, 2H), 7.40 (s, 1H), 7.16 (t, J=7.6 Hz, 1H), 7.04 (t, J=7.6 Hz, 1H), 6.66 (s, 1H), 6.53 (s, 1H), 4.33 (d, J=6.8 Hz, 2H), 4.09-4.04 (m, 1H), 2.95 (s, 3H), 2.88 (s, 3H), 2.65-2.61 (m, 2H), 1.88-1.85 (m, 2H), 1.67-1.64 (m, 1H), 1.43-1.39 (m, 1H), 1.27-1.24 (m, 2H), 1.21-1.19 (m, 2H), 1.06-1.02 (m, 1H), 0.27-0.25 (m, 2H), 0.11-0.09 (m, 2H). MS (ESI): Mass calcd. for $C_{27}H_{31}N_5O$, 441.25; m/z found, 442.3 $(M+H)^+$.

Compound-26

(R)-(3-Aminopiperidin-1-yl)(2-(1-benzyl-1H-indol-2-yl)-3,5-dimethylimidazo[1,2-a]pyridin-7-yl)methanone

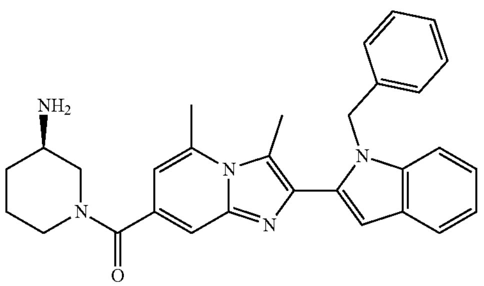 [SMILES: Cc1cc(C(=O)N2CCC[C@@H](N)C2)cc2nc(-c3cc4ccccc4n3Cc3ccccc3)c(C)n12]

$^1$HNMR (400 MHz, DMSO-$d_6$) δ (ppm): 7.62 (d, J=8.0 Hz, 1H), 7.40-7.37 (m, 2H), 7.19-7.09 (m, 5H), 6.94 (d, J=6.8 Hz, 2H), 6.66 (s, 2H), 5.75 (s, 2H), 4.19-4.14 (m, 1H), 3.75-3.71 (m, 1H), 2.94 (s, 3H), 2.89 (s, 3H), 1.89-1.87 (m, 2H), 1.86-1.85 (m, 2H), 1.67-1.64 (m, 1H), 1.43-1.39 (m, 2H), 1.27-1.24 (m, 2H). MS (ESI): Mass calcd. for $C_{30}H_{31}N_5O$, 477.25; m/z found, 478.5 $(M+H)^+$.

Compound-27

(R)-(3-Aminopiperidin-1-yl)(3,5-dimethyl-2-(1-(pyridin-2-ylmethyl)-1H-indol-2-yl)imidazo[1,2-a]pyridin-7-yl)methanone

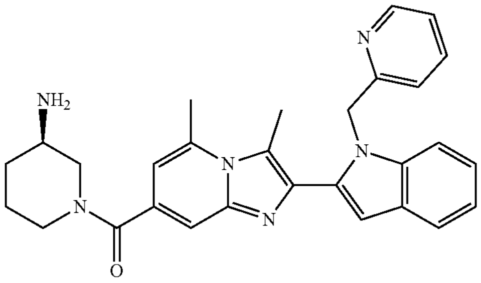 [SMILES: Cc1cc(C(=O)N2CCC[C@@H](N)C2)cc2nc(-c3cc4ccccc4n3Cc3ccccn3)c(C)n12]

$^1$HNMR (400 MHz, DMSO-$d_6$) δ (ppm): 8.40 (d, J=6.8 Hz, 1H), 7.63-7.61 (m, 1H), 7.55-7.51 (m, 1H), 7.37-7.35 (m, 2H), 7.15-7.10 (m, 4H), 6.67-6.64 (m, 2H), 5.80 (s, 2H), 3.75-3.71 (m, 1H), 2.92 (s, 3H), 2.88 (s, 3H), 2.65-2.61 (m, 1H), 2.01-1.98 (m, 1H), 1.97-1.94 (m, 2H), 1.88-1.85 (m, 2H), 1.43-1.39 (m, 2H), 1.27-1.24 (m, 2H). MS (ESI): Mass calcd. for $C_{29}H_{30}N_6O$, 478.25; m/z found, 479.2 $(M+H)^+$.

Compound-28

(R)-(3-Aminopiperidin-1-yl)(2-(1-(cyclopropylmethyl)-6-fluoro-1H-indol-2-yl)-3-methylimidazo[1,2-a]pyridin-7-yl)methanone

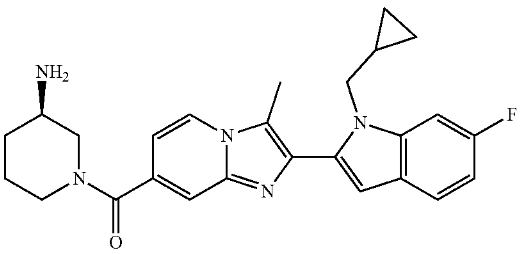 [SMILES: Cc1c(-c2cc3ccc(F)cc3n2CC2CC2)nc2cc(C(=O)N3CCC[C@@H](N)C3)ccn12]

$^1$HNMR (400 MHz, DMSO-$d_6$) δ (ppm): 8.41 (d, J=6.4 Hz, 1H), 7.60-7.55 (m, 2H), 7.44 (d, J=9.6 Hz, 1H), 6.9 (d, J=7.2 Hz, 1H), 6.92-6.88 (m, 1H), 6.54 (s, 1H), 4.46 (d, J=6.8 Hz, 2H), 4.25 (m, 1H), 3.28 (m, 2H), 2.83 (m, 1H), 2.62 (s, 3H), 1.99-1.95 (m, 1H), 1.82 (m, 2H), 1.68 (m, 2H), 1.46 (m, 2H), 1.07 (m, 1H), 0.27-0.25 (m, 2H), 0.14-013 (m, 2H). MS (ESI): Mass calcd. for $C_{26}H_{28}FN_5O$, 445.23; m/z found, 446.2 $(M+H)^+$.

Compound-29

(R)-(3-Aminopiperidin-1-yl)(2-(1-(cyclopropylmethyl)-5-fluoro-1H-indol-2-yl)-3-methylimidazo[1,2-a]pyridin-7-yl)methanone

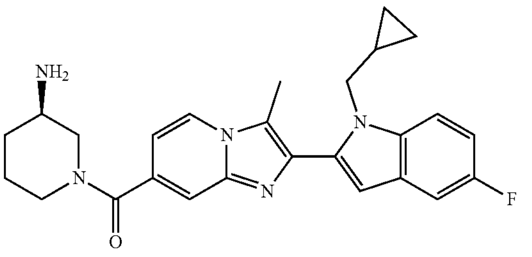 [SMILES: Cc1c(-c2cc3cc(F)ccc3n2CC2CC2)nc2cc(C(=O)N3CCC[C@@H](N)C3)ccn12]

$^1$HNMR (400 MHz, DMSO-$d_6$) δ (ppm): 8.41 (d, J=7.2 Hz, 1H), 7.61-7.57 (m, 2H), 7.35-7.32 (m, 1H), 7.03-6.98 (m, 2H), 6.64 (s, 1H), 4.48 (d, J=6.8 Hz, 2H), 4.21-4.11 (m, 2H), 3.63-3.60 (m, 1H), 2.99-2.95 (m, 1H), 2.78-2.74 (m, 1H), 2.65 (s, 3H), 1.86-1.83 (m, 1H), 1.71-1.68 (m, 3H), 1.46-1.43 (m, 1H), 1.28-1.25 (m, 1H), 1.09-1.03 (m, 1H), 0.27-0.25 (m, 2H), 0.14-0.11 (m, 2H). MS (ESI): Mass calcd. for $C_{26}H_{28}FN_5O$, 445.23; m/z found, 446.2 $(M+H)^+$.

Compound-30

(R)-(3-Aminopiperidin-1-yl)(2-(1-(cyclopropylmethyl)-7-methyl-1H-indol-2-yl)-3-methylimidazo[1,2-a]pyridin-7-yl)methanone

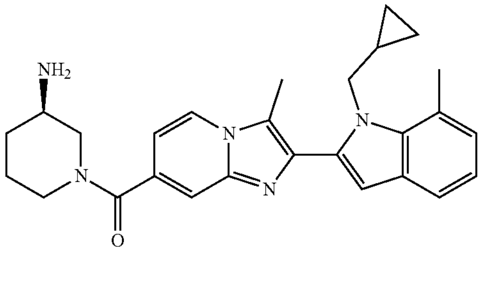 [SMILES: Cc1cccc2cc(-c3nc4cc(C(=O)N5CCC[C@@H](N)C5)ccn4c3C)n(CC3CC3)c12]

$^1$HNMR (400 MHz, DMSO-$d_6$) δ (ppm): 8.41 (d, J=7.2 Hz, 1H), 7.60 (s, 1H), 7.42 (d, J=6.4 Hz, 1H), 7.00-6.98 (m, 1H), 6.96-6.93 (m, 2H), 6.60 (s, 1H), 4.65 (d, J=6.0 Hz, 2H), 4.21-4.11 (m, 2H), 3.01-2.98 (m, 1H), 2.79-2.77 (m, 2H), 2.76 (s, 3H), 2.65 (s, 3H), 1.89-1.85 (m, 2H), 1.69-1.66 (m, 1H), 1.46-1.43 (m, 1H), 1.32-1.27 (m, 2H), 0.89-0.85 (m, 1H), 0.15-0.14 (m, 2H), 0.24-0.25 (m, 2H). MS (ESI): Mass calcd. for $C_{27}H_{31}N_5O$, 441.25; m/z found, 442.4 $(M+H)^+$.

Compound-31

Synthesis of (R)-(3-Aminopiperidin-1-yl)(2-(2-ethylphenyl)-3-methylimidazo[1,2-a]pyridin-7-yl)methanone (Compound-31)

Scheme-6

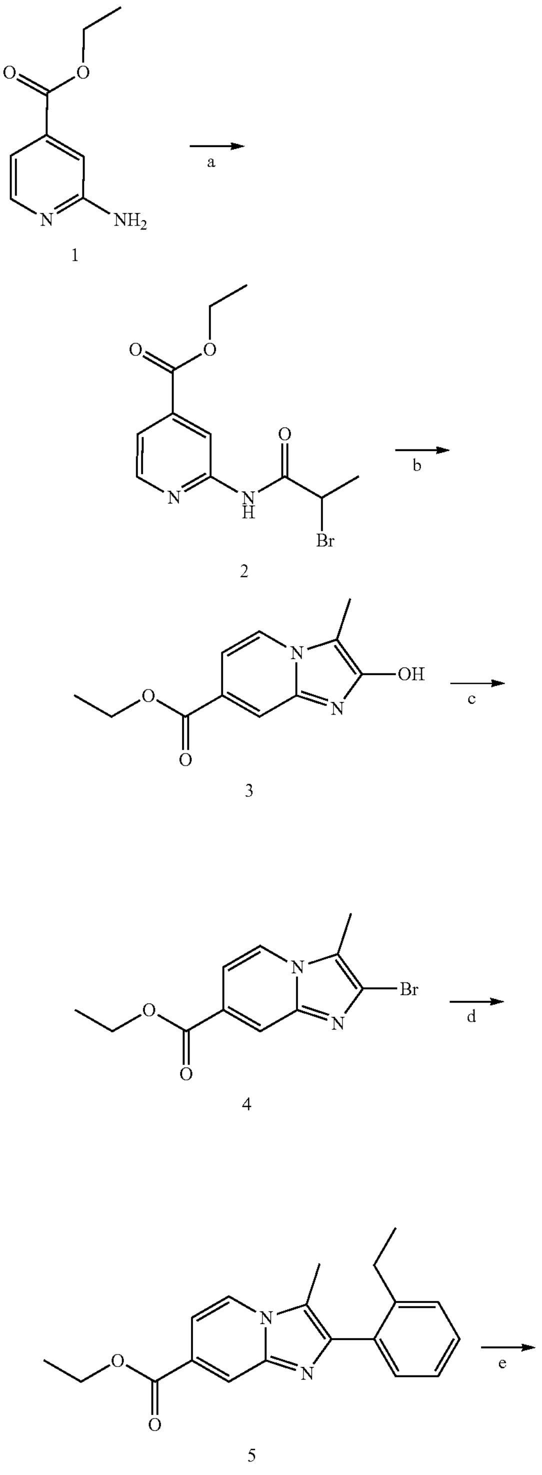

-continued

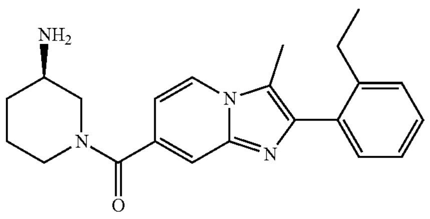

Compound-31

Step 1: Ethyl 2-(2-bromopropanamido)isonicotinate

2

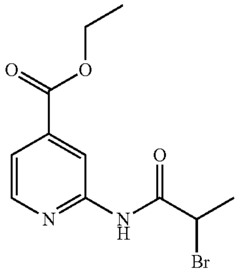

To the stirred solution of ethyl 2-aminoisonicotinate (1, 2 g, 12.0 mmol) in DCM (20 mL was added 2-bromopropanoic acid (2.2 g, 14.4 mmol), $Et_3N$ (3.3 mL, 24.1 mmol), 50% solution of T3P in ethyl acetate (12.1 mL, 18.1 mmol) and the reaction mixture was stirred at rt for 16 h. To the reaction mixture, water (50 mL) was added and the compound was extracted with DCM (100 mL). Organic layer was dried over anhydrous $Na_2SO_4$ and evaporated under vacuum. Crude product was purified by column chromatography using 20-30% EtOAc in hexane to afford the product as yellow solid (2.3 g, 64% Yield). MS (ESI): Mass calcd. for $C_1H_{13}BrN_2O_3$, 301.14; m/z found, 303.0 $(M+2H)^+$.

Step 2: Ethyl 2-hydroxy-3-methylimidazo[1,2-a]pyridine-7-carboxylate

3

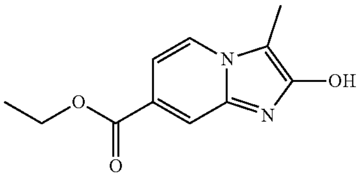

To the stirred solution of ethyl 2-(2-bromopropanamido) isonicotinate (2, 1 g, 3.33 mmol) in EtOH (20 mL), was added $K_2CO_3$ (1.37 g, 9.99 mmol) and stirred at 80° C. for 5 h. The reaction mixture was evaporated to dryness, triturated with diethyl ether and dried to get crude product as brown gummy solid (1.0 g, 80% Yield). MS (ESI): Mass calcd. for $C_{11}H_{12}N_2O_3$, 220.08; m/z found, 221.1 $(M+H)^+$.

Step 3: Ethyl 2-bromo-3-methylimidazo[1,2-a]pyridine-7-carboxylate

4

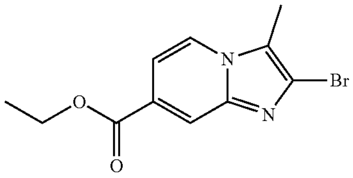

To the stirred solution of ethyl 2-hydroxy-3-methylimidazo[1,2-a]pyridine-7-carboxylate (4, 1.0 g, 5.45 mmol) in 1,2-dichloroethane (20 mL), was added $POBr_3$ (4.6 g, 16.3 mmol) and stirred at 90° C. for 16 h. The reaction mixture was cooled to rt, quenched with saturated $Na_2CO_3$ solution (50 mL) and extracted with EtOAc (100 mL). Organic layer was dried over anhydrous $Na_2SO_4$ and evaporated under vacuum. Crude product was purified by column chromatography using 30-40% EtOAc in hexane to afford the product as brown solid (0.2 g, 21% Yield). MS (ESI): Mass calcd. for $C_{11}H_{11}BrN_2O_2$, 283.13; m/z found, 285.0 $(M+2H)^+$.

Step 4: Ethyl 2-(2-ethylphenyl)-3-methylimidazo[1,2-a]pyridine-7-carboxylate

5

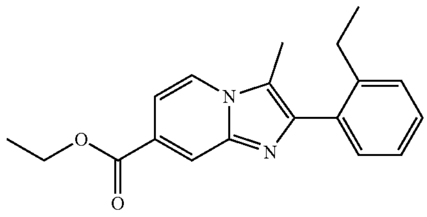

To a stirred solution ethyl 2-bromo-3-methylimidazo[1,2-a]pyridine-7-carboxylate (5, 0.2 g, 0.70 mmol) in dioxane (5 mL), was added (2-ethylphenyl)boronic acid (0.16 g, 1.06 mmol), $K_2CO_3$ (0.3 g, 2.12 mmol), $Pd(dppf)Cl_2$.DCM (0.03 g, 0.03 mmol) and the reaction mixture was stirred at 85° C. for 16 h. The reaction mixture was filtered through celite and the solvent was evaporated. To the resulting crude product, water (10 mL) was added and the compound was extracted with EtOAc (25 mL). Organic layer was dried over anhydrous $Na_2SO_4$ and evaporated under vacuum. Crude product was purified by column chromatography using 25-30% EtOAc in hexane to afford the product as brown solid (0.15 g, 71% Yield). MS (ESI): Mass calcd. for $C_{19}H_{20}N_2O_2$, 308.15; m/z found, 309.1 $(M+H)^+$.

Remaining steps for Compound-31 were carried using the procedure as exemplified for Compound-20.

Compound-31
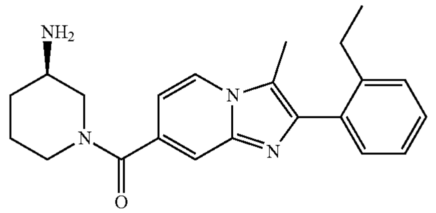
$^1$HNMR (400 MHz, DMSO-$d_6$) δ (ppm): 8.34 (d, J=6.8 Hz, 1H,), 7.57 (s, 1H), 7.35-7.31 (m, 2H), 7.27-7.24 (m, 2H), 6.96 (d, J=6.4 Hz, 1H), 4.01-3.98 (m, 2H), 3.66-3.61 (m, 1H), 3.49-3.41 (m, 1H), 3.02-2.97 (m, 1H), 2.83-2.79 (m, 2H), 2.67-2.61 (m, 1H), 2.38 (s, 3H), 1.88-1.82 (m, 1H), 1.69-1.62 (m, 1H), 1.48-1.42 (m, 1H), 1.33-1.29 (m, 1H), 1.21-1.19 (m, 1H), 1.02-0.98 (m, 3H). MS (ESI): Mass calcd. for $C_{22}H_{26}N_4O$, 362.21; m/z found, 363.2 $(M+H)^+$.
Compound-32
Synthesis of (R)-(3-Aminopiperidin-1-yl)(2-(1-(cyclopropylmethyl)-1H-indol-2-yl)-3-phenyl imidazo [1,2-a]pyridin-7-yl)methanone (Compound-32)
Scheme-7
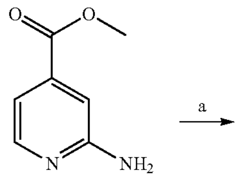
1
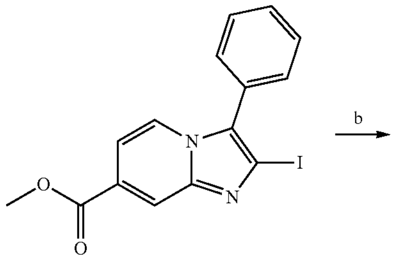
2
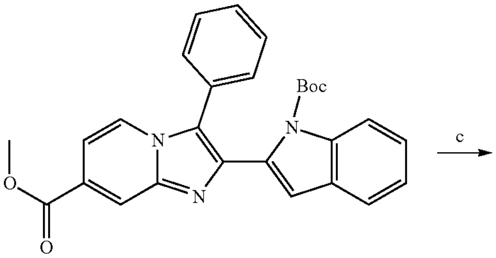
3
-continued
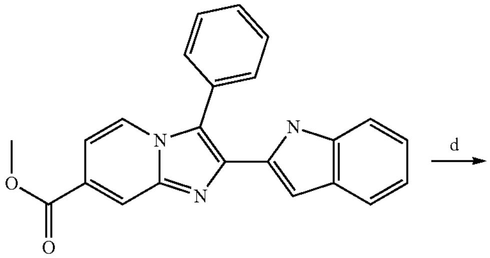
4
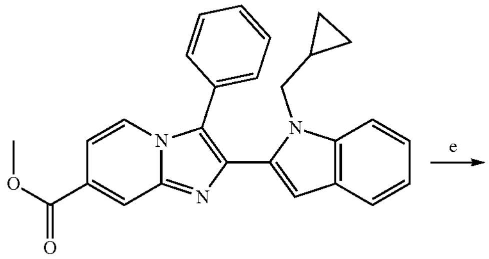
5
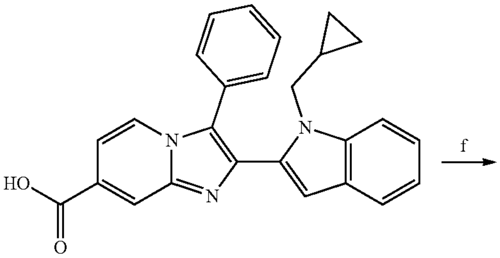
6
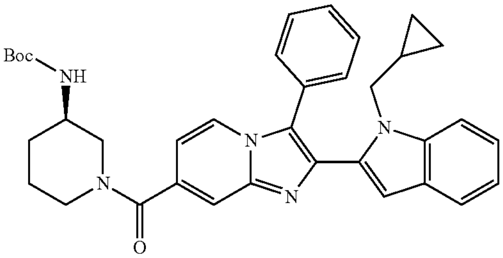
7
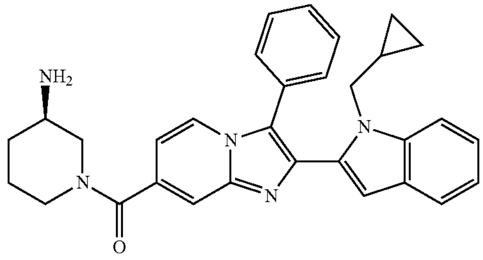
8

Step-1: Methyl 2-iodo-3-phenylimidazo[1,2-a]pyridine-7-carboxylate

2

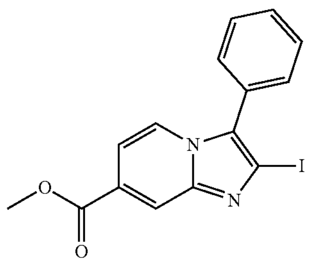

To a stirred solution of methyl 2-aminoisonicotinate (1, 1 g, 6.5 mmol) and phenyl acetylene (0.79 mL, 7.8 mmol) in 1, 2-dichlorobenzene (20 mL), was added iodine (1.6 g, 6.5 mol) and copper (II)acetate (0.1 g, 0.65 mmol). The reaction mixture was filled with 5 kg/$cm^2$ oxygen in steel bomb and stirred at 120° C. for 12 h. Then the reaction mixture was filtered and evaporated to give residue which was dissolved in water (50 mL). It was extracted with ethyl acetate (2×20 mL) and the organic layer was dried over $Na_2SO_4$, filtered, and concentrated to give the crude product. The crude product was purified by gradient column chromatography using 20% EtOAc/hexane as the eluent to yield desired product as pale yellow solid (0.3 g, 12.2% Yield). MS (ESI): Mass calcd for $C_{15}H_{11}IN_2O_2$, 377.99; m/z found, 380.0 $[M+H]^+$.

Step-2: Methyl 2-(1-(tert-butoxycarbonyl)-1H-indol-2-yl)-3-phenylimidazo[1,2-a]pyridine-7-carboxylate

3

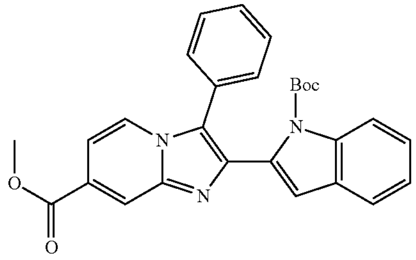

To a solution of methyl 2-iodo-3-phenylimidazo[1,2-a]pyridine-7-carboxylate (2, 0.17 g, 0.44 mmol) and (1-(tert-butoxycarbonyl)-1H-indol-2-yl)boronic acid (0.17 g, 0.66 mmol) in 1, 4 dioxane (10 mL) and water (2 mL), was added sodium carbonate (0.13 g, 1.3 mmol) and the mixture was purged with argon gas for 20 min. Then added $Pd(PPh_3)_4$ (0.015 g, 0.002 mmol) and continued purging for 5 min. Then the reaction mixture was stirred for 12 h at 90° C. in sealed tube. To the reaction mixture, water (10 mL) was added and extracted with EtOAc (2×20 mL). Organic layer was washed with saturated $NH_4Cl$ solution and brine, dried over sodium sulphate, filtered and concentrated under reduced pressure. The crude product was purified by gradient column chromatography using 20% EtOAc/hexane as the eluent to yield desired product as pale yellow solid (0.1 g, 53.5% Yield). MS (ESI): Mass calcd for $C_{28}H_{25}N_3O_4$, 467.18; m/z found, 468.3 $[M+H]^+$.

Step-3: Methyl 2-(1H-indol-2-yl)-3-phenylimidazo[1,2-a]pyridine-7-carboxylate

4

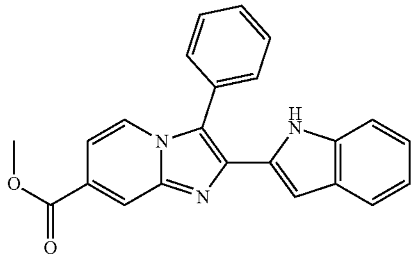

To a solution of methyl 2-(1-(tert-butoxycarbonyl)-1H-indol-2-yl)-3-phenylimidazo[1,2-a]pyridine-7-carboxylate (3, 0.08 g, 0.1 mmol) in DCM (2 mL) was added trifluoroacetic acid (0.04 mL, 0.5 mmol) at 0° C. Mixture was stirred for 2 h at rt under $N_2$ atmosphere. The reaction mixture was concentrated under vacuum and neutralized using aqueous sodium bicarbonate. The aqueous phase was then extracted with DCM (2×20 mL). Organic layer was dried over $Na_2SO_4$ and concentrated to give desired product as pale yellow solid (4; 0.06 g, 99% Yield). MS (ESI): Mass calcd for $C_{23}H_{17}N_3O_2$, 367.13; m/z found, 368.3 $[M+H]^+$.

Step-4: Methyl 2-(1-(cyclopropylmethyl)-1H-indol-2-yl)-3-phenylimidazo[1,2-a]pyridine-7-carboxylate

5

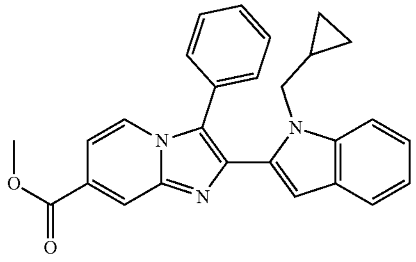

To a solution of methyl 2-(1H-indol-2-yl)-3-phenylimidazo[1,2-a]pyridine-7-carboxylate (4, 0.06 g, 0.16 mmol) in DMF (10 mL) was added cesium carbonate (0.025 g, 0.19 mmol) followed by (bromo methyl)cyclopropane (0.025 g, 0.19 mmol). Mixture was stirred for 12 h at rt. To the reaction mixture, water (20 mL) was added and extracted with EtOAc (2×20 mL). Organic layer was washed with water and brine, dried over sodium sulphate, filtered and concentrated under reduced pressure to obtain pale yellow solid (5; 0.06 g, 88.9% Yield). MS (ESI): Mass calcd for $C_{27}H_{23}N_3O_2$, 421.8; m/z found, 422.3 $[M+H]^+$.

Step-5: 2-(1-(Cyclopropylmethyl)-1H-indol-2-yl)-3-phenylimidazo[1,2-a]pyridine-7-carboxylic Acid

6

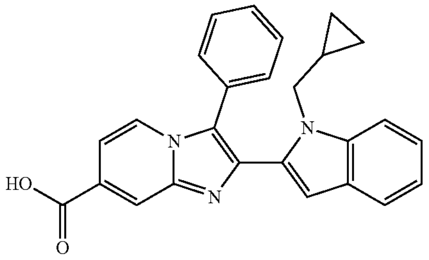

To a solution of methyl 2-(1-(cyclopropylmethyl)-1H-indol-2-yl)-3-phenylimidazo[1,2-a]pyridine-7-carboxylate (5, 0.06 g, 0.14 mmol) in ethanol (20 mL), was added 5M sodium hydroxide solution (0.14 mL, 0.72 mmol). The reaction mixture was allowed to stir at 80° C. for 45 min. After the completion of the reaction, the reaction mixture was evaporated to dryness. Then crude product was dissolved in water, neutralized with citric acid to precipitate the product. The mixture was filtered to obtain the desired product as off white solid (6; 0.04 g, 70.2% Yield). MS (ESI): Mass calcd for $C_{26}H_{21}N_3O_2$, 407.16; m/z found, 408.3 $[M+H]^+$.

Step-6: Tert-butyl (R)-(1-(2-(1-(cyclopropylmethyl)-1H-indol-2-yl)-3-phenylimidazo[1,2-a]pyridine-7-carbonyl)piperidin-3-yl)carbamate

7

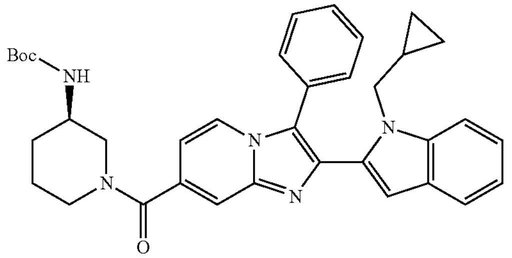

To a solution of tert-butyl (R)-piperidin-3-yl-12-azanecarboxylate (0.02 g, 0.1 mmol) 2-(1-(cyclopropylmethyl)-1H-indol-2-yl)-3-phenylimidazo[1,2-a]pyridine-7-carboxylic acid (6, 0.04 g, 0.09 mmol) in DCM (10 mL) at rt was added triethylamine (0.04 mL, 0.2 mmol) and propylphosphonic anhydride ($T_3P$, 50% in ethyl acetate) (0.67 mL, 0.2 mmol). The reaction mixture was stirred at rt for 12 h. It was diluted with DCM and washed with saturated sodium bicarbonate solution. Organic layer was separated, dried over sodium sulphate and evaporated under reduced pressure to obtain crude. The crude residue was purified by gradient column chromatography using 5% methanol in DCM to afford desired product (7; 0.04 g, 69.2% Yield). MS (ESI): Mass calcd for $C_{36}H_{39}N_5O_3$, 589.3; m/z found, 590.3 $[M+H]^+$.

Step-7: (R)-(3-Aminopiperidin-1-yl)(2-(1-(cyclopropylmethyl)-1H-indol-2-yl)-3-phenylimidazo[1,2-a]pyridin-7-yl)methanone (Compound-32)

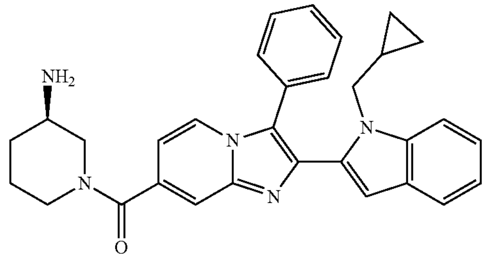 [SMILES: N[C@@H]1CCCN(C(=O)c2ccn3c(-c4ccccc4)c(-c4cc5ccccc5n4CC4CC4)nc3c2)C1]

To a stirred solution tert-butyl (R)-(1-(2-(1-(cyclopropylmethyl)-1H-indol-2-yl)-3-phenylimidazo[1,2-a]pyridine-7-carbonyl)piperidin-3-yl)carbamate (7, 0.04 g, 0.06 mmol) in DCM (10 mL) was added TFA (0.02 mL, 0.3 mmol) at 0° C., then it was stirred at rt for 2 h. After completion of reaction, solvent was evaporated. The crude was dissolved in water (10 mL) and neutralized with saturated $NaHCO_3$ solution to get crude. The crude product was purified by gradient column chromatography using 5% methanol in DCM followed by preparative HPLC Column: Inertsil ODS 3V (250 mm×4.6 mm×5 mic) Mobile phase(A): 0.1% ammonia in water, Mobile phase(B): acetonitrile, Flow rate: 1.0 mL/min to afford desired product as off white solid (0.02 g, 68.9% Yield). $^1$HNMR (400 MHz, DMSO-$d_6$) δ (ppm): 8.21 (d, J=7.2 Hz, 1H), 7.21 (s, 1H), 7.52 (m, 6H), 7.39 (d, J=8 Hz, 1H), 7.13 (d, J=7.2 Hz, 1H), 6.98-6.94 (m, 2H), 6.19 (s, 1H), 4.46 (d, J=8 Hz, 2H), 2.78 (m, 2H), 1.86 (m, 2H), 1.72 (m, 2H), 1.45 (m, 2H), 1.30 (m, 2H), 1.12 (m, 2H), 0.30 (d, J=7.6 Hz, 2H), 0.16 (d, J=3.6 Hz, 2H). MS (ESI): Mass calcd. for $C_{31}H_{31}N_5O$, 489.25; m/z found, 490.3 $[M+H]^+$.

Following compounds (Compounds-33 and 34) were synthesized using the above procedure as exemplified for Compound-32.

Compound-33

(R)-(3-Aminopiperidin-1-yl)(3-cyclopropyl-2-(1-(cyclopropylmethyl)-1H-indol-2-yl)imidazo[1,2-a]pyridin-7-yl)methanone

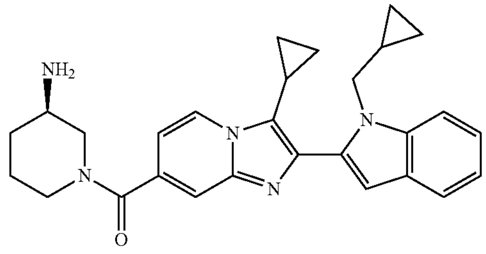 [SMILES: N[C@@H]1CCCN(C(=O)c2ccn3c(C4CC4)c(-c4cc5ccccc5n4CC4CC4)nc3c2)C1]

$^1$HNMR (400 MHz, DMSO-$d_6$) δ (ppm): 8.55 (d, J=7.2 Hz, 1H), 7.63 (s, 1H), 7.58 (t, J=7.6 Hz, 2H), 7.17 (t, J=7.2 Hz, 1H), 7.05 (t, J=8 Hz, 2H), 6.73 (s, 1H), 4.47 (d, J=7.2 Hz, 2H), 3.9 (bs, 2H), 3.03 (bs, 1H), 2.85 (m, 2H), 2.12-2.08 (m, 1H), 2.01-1.95 (m, 2H), 1.88 (m, 1H), 1.73-1.69 (m, 1H), 1.45-1.44 (m, 2H), 1.08-1.06 (m, 2H), 0.85-0.81 (m, 1H), 0.39 (d, J=4.4 Hz, 2H), 0.21 (d, J=8 Hz, 2H), 0.01 (d, J=4.4 Hz, 2H). MS (ESI): Mass calcd. for $C_{28}H_{31}N_5O$, 453.25; m/z found, 454.3 $[M+H]^+$.

Compound-34

(R)-(3-Aminopiperidin-1-yl)(2-(1-(cyclopropylmethyl)-1H-indol-2-yl)-3 (methoxymethyl) imidazo[1,2-a]pyridin-7-yl) methanone

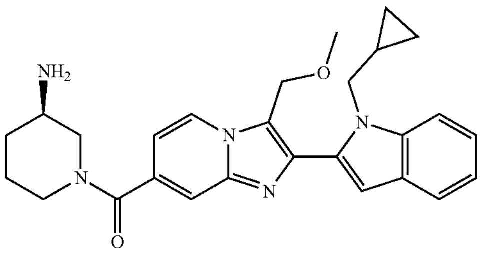 [SMILES: COCc1c(-c2cc3ccccc3n2CC2CC2)nc2cc(C(=O)N3CCC[C@@H](N)C3)ccn12]

$^1$HNMR (400 MHz, DMSO-$d_6$) δ (ppm): 8.52 (d, J=7.2 Hz, 1H), 7.66 (s, 1H), 7.59 (t, J=8.8 Hz, 2H), 7.19 (t, J=7.6 Hz, 1H), 7.07-7.02 (m, 2H), 6.47 (s, 1H), 4.87 (s, 2H), 4.47 (d, J=6.8 Hz, 2H), 3.8 (m, 3H), 3.04 (bs, 1H), 2.96-2.92 (m, 3H), 2.81 (s, 1H), 2.01-1.95 (m, 2H), 1.88 (m, 1H), 1.73-1.69 (m, 2H), 1.45-1.44 (m, 2H), 0.21 (d, J=8 Hz, 2H), 0.01 (d, J=4.4 Hz, 2H). MS (ESI): Mass calcd. for $C_{27}H_{31}N_5O_2$, 457.25; m/z found, 458.2 $[M+H]^+$.

Compound-35

(R)-(3-aminopiperidin-1-yl)(2-(1-(3-fluorobenzyl)-1H-indol-2-yl)-3-methylimidazo[1,2-a]pyridin-7-yl) methanone

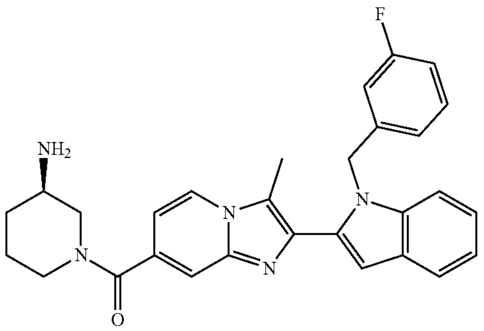 [SMILES: Cc1c(-c2cc3ccccc3n2Cc2cccc(F)c2)nc2cc(C(=O)N3CCC[C@@H](N)C3)ccn12]

$^1$HNMR (400 MHz, DMSO-$d_6$) δ (ppm): 8.41 (d, J=6.8 Hz, 1H), 7.61-7.59 (m, 2H), 7.39 (d, J=8.0 Hz, 1H), 7.23-7.18 (m, 1H), 7.13-7.04 (m, 2H), 6.99-6.97 (m, 1H), 6.93-6.91 (m, 1H), 6.80-6.76 (m, 3H), 5.91 (s, 2H), 4.05-4.01 (m, 1H), 3.49-3.45 (m, 1H), 2.99-2.95 (m, 1H), 2.73-2.71 (m, 2H), 2.63 (s, 3H), 1.86-1.83 (m, 2H), 1.67-1.61 (m, 1H), 1.44-1.41 (m, 1H), 1.26-1.21 (m, 2H). MS (ESI): Mass calcd. for $C_{29}H_{28}FN_5O$, 481.23; m/z found, 482.2 $(M+H)^+$.

Compound-36

(R)-(3-aminopiperidin-1-yl)(3-methyl-2-(1-(thiophen-3-ylmethyl)-1H-indol-2-yl)imidazo[1,2-a]pyridin-7-yl)methanone

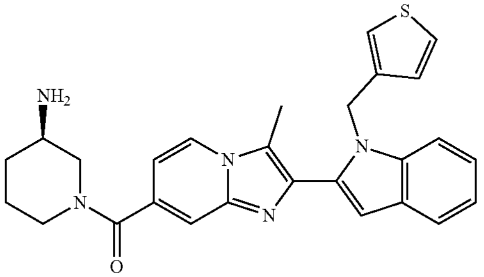 [SMILES: Cc1c(-c2cc3ccccc3n2Cc2ccsc2)nc2cc(C(=O)N3CCC[C@@H](N)C3)ccn12]

$^1$HNMR (400 MHz, DMSO-$d_6$) δ (ppm): 8.43 (d, J=7.2 Hz, 1H), 7.63 (s, 1H), 7.58 (d, J=8.0 Hz, 1H), 7.53 (d, J=8.0 Hz, 1H), 7.31-7.29 (m, 1H), 7.13-7.11 (m, 2H), 7.06-7.00 (m, 2H), 6.76 (d, J=4.4 Hz, 1H), 6.71 (s, 1H), 5.85 (s, 2H), 4.22-4.16 (m, 1H), 3.66-3.61 (m, 1H), 2.97-2.95 (m, 1H), 2.64-2.61 (m, 5H), 1.84-1.81 (m, 2H), 1.66-1.59 (m, 2H), 1.44-1.42 (m, 2H). MS (ESI): Mass calcd. for $C_{27}H_{27}N_5OS$, 469.19; m/z found, 470.2 $(M+H)^+$.

Compound-37

(R)-(3-aminopiperidin-1-yl)(2-(1-(furan-3-ylmethyl)-1H-indol-2-yl)-3-methylimidazo[1,2-a]pyridin-7-yl)methanone

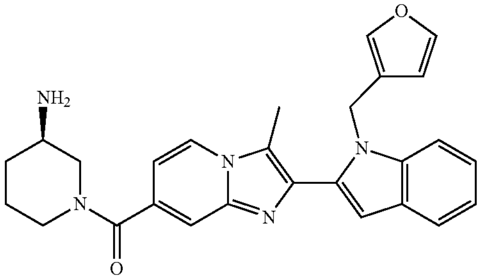 [SMILES: Cc1c(-c2cc3ccccc3n2Cc2ccoc2)nc2cc(C(=O)N3CCC[C@@H](N)C3)ccn12]

$^1$HNMR (400 MHz, DMSO-$d_6$) δ (ppm): 8.43 (d, J=7.2 Hz, 1H), 7.65 (s, 1H), 7.58 (d, J=8.0 Hz, 2H), 7.48 (s, 1H), 7.40 (s, 1H), 7.16-7.12 (m, 1H), 7.06-7.00 (m, 2H), 6.69 (s, 1H), 6.15 (s, 1H), 5.67 (s, 2H), 4.22-4.16 (m, 1H), 3.57-3.55 (m, 1H), 3.02-2.99 (m, 1H), 2.76-2.73 (m, 2H), 2.64 (s, 3H), 1.84-1.81 (m, 2H), 1.69-1.65 (m, 2H), 1.30-1.28 (m, 1H), 1.21-1.18 (m, 1H). MS (ESI): Mass calcd. for $C_{27}H_{27}N_5O_2$, 453.22; m/z found, 454.2 $(M+H)^+$.

Compound-38

(R)-3-aminopiperidin-1-yl)(2-(1-(1-(4-fluorophenyl) ethyl)-1H-indol-2-yl)-3 methylimidazo[1,2-a]pyridin-7-yl)methanone

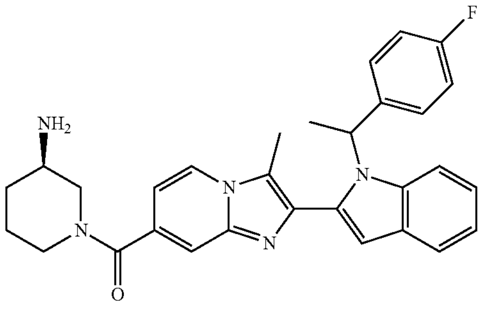 [SMILES: Cc1c(-c2cc3ccccc3n2C(C)c2ccc(F)cc2)nc2cc(C(=O)N3CCC[C@@H](N)C3)ccn12]

$^1$HNMR (400 MHz, DMSO-$d_6$) δ (ppm): 8.42 (d, J=6.4 Hz, 1H), 7.61-7.57 (m, 2H), 7.32-7.30 (m, 2H), 7.11-7.08 (m, 2H), 6.98-6.95 (m, 4H), 6.74 (s, 1H), 6.48-6.45 (m, 1H), 4.22-4.18 (m, 1H), 3.59-3.55 (m, 1H), 2.97-2.94 (m, 1H), 2.72-2.70 (m, 2H), 2.63 (s, 3H), 1.88-1.86 (m, 4H), 1.68-1.65 (m, 2H), 1.44-1.41 (m, 1H), 1.27-1.25 (m, 2H). MS (ESI): Mass calcd. for $C_{30}H_{30}FN_5O$, 495.24; m/z found, 496.2 $(M+H)^+$.

Compound-39

(R)-(3-aminopiperidin-1-yl)(2-(1-ethyl-5-fluoro-1H-indol-2-yl)-3-methyl imidazo[1,2-a]pyridin-7-yl) methanone

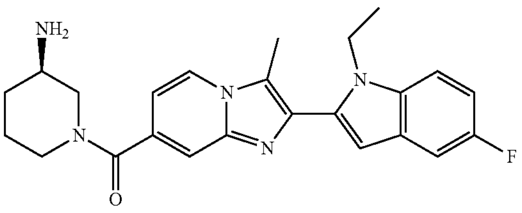 [SMILES: CCn1c(-c2nc3cc(C(=O)N4CCC[C@@H](N)C4)ccn3c2C)cc2cc(F)ccc21]

$^1$HNMR (400 MHz, DMSO-$d_6$) δ (ppm): 8.36 (d, J=7.2 Hz, 1H), 7.60 (s, 1H), 7.5-7.750 (m, 1H), 7.33 (d, J=9.6 Hz, 1H), 7.02-6.97 (m, 2H), 6.62 (s, 1H), 4.7-4.46 (m, 2H), 4.20 (m, 2H), 2.65 (s, 4H), 1.84 (m, 2H), 1.69 (m, 1H), 1.41 (m, 1H), 1.29-1.13 (m, 7H). MS (ESI): Mass calcd. for $C_{24}H_{26}FN_5O$, 419.2; m/z found 420.2 $(M+H)^+$.

Compound-40

(R)-(3-aminopiperidin-1-yl)(2-(1-(cyclopropylmethyl)-4-fluoro-1H-indol-2-yl)-3-methylimidazo[1,2-a]pyridin-7-yl)methanone

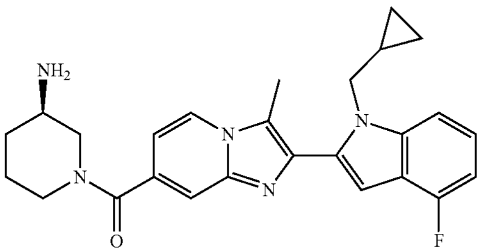 [SMILES: Cc1c(-c2cc3c(F)cccc3n2CC2CC2)nc2cc(C(=O)N3CCC[C@@H](N)C3)ccn12]

$^1$HNMR (400 MHz, DMSO-$d_6$) δ (ppm): 8.43 (d, J=6.8 Hz, 1H), 7.63 (s, 1H), 7.44 (d, J=8.4 Hz, 1H), 7.17-7.11 (m, 1H), 7.01 (d, J=6.4 Hz, 1H), 6.82 (t, J=8.4 Hz, 1H), 6.69 (s, 1H), 4.50 (d, J=6.4 Hz, 2H), 4.20 (m, 1H), 3.49 (m, 1H), 3.02 (m, 1H), 2.79 (m, 2H), 2.63 (s, 3H), 1.88 (m, 2H), 1.70 (m, 2H), 1.48-1.45 (m, 1H), 1.31-1.28 (m, 1H), 1.10 (m, 1H), 0.27 (m, 2H), 0.15 (m, 2H). MS (ESI): Mass calcd. for $C_{26}H_{28}FN_5O$, 445.2; m/z found, 446 $(M+H)^+$.

Compound-41

(R)-(3-aminopiperidin-1-yl)(3-methyl-2-(1-((4-methylthiazol-2-yl)methyl)-1H-indol-2-yl)imidazo[1,2-a] pyridin-7-yl)methanone

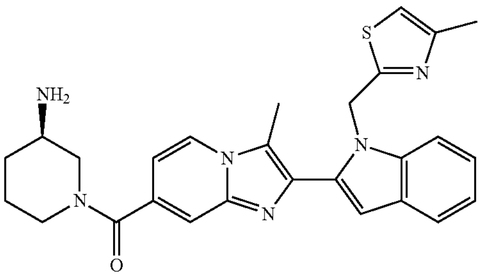 [SMILES: Cc1csc(Cn2c(-c3nc4cc(C(=O)N5CCC[C@@H](N)C5)ccn4c3C)cc3ccccc32)n1]

$^1$HNMR (400 MHz, DMSO-$d_6$) δ (ppm): 8.43 (d, J=4.4 Hz, 1H), 7.61 (d, J=8 Hz, 2H), 7.52 (d, J=8.4 Hz, 1H), 7.17 (t, J=7.6 Hz, 1H), 7.09 (t, J=7.6 Hz, 1H), 7.0 (d, J=7.2 Hz, 1H), 7.44 (d, J=8.4 Hz, 1H), 7.17-7.11 (m, 1H), 7.01 (d, J=6.4 Hz, 1H), 6.80 (s, 1H), 3.02 (m, 2H), 2.80 (m, 2H), 2.65 (s, 3H), 2.23 (s, 3H), 1.68 (m, 2H), 1.47-1.45 (m, 2H), 1.1-1.22 (m, 3H). MS (ESI): Mass calcd. for $C_{27}H_{28}N_6OS$, 484.2; m/z found, 485.2 $(M+H)^+$.

Compound-42

(R)-(3-aminopiperidin-1-yl)(2-(1-(3-methoxybenzyl)-1H-indol-2-yl)-3-methyl imidazo[1,2-a]pyridin-7-yl)methanone

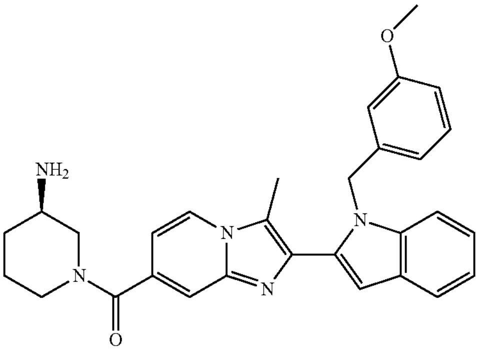 [SMILES: COc1cccc(Cn2c(-c3nc4cc(C(=O)N5CCC[C@@H](N)C5)ccn4c3C)cc3ccccc32)c1]

$^1$HNMR (400 MHz, DMSO-$d_6$) δ (ppm): 8.41 (d, J=6.8 Hz, 1H), 7.61 (t, J=8.8 Hz, 2H), 7.39 (d, J=8.0 Hz, 1H), 7.12-7.03 (m, 3H), 6.69 (d, J=5.2 Hz, 1H), 6.75 (s, 1H), 6.67-6.64 (m, 1H), 6.51 (s, 2H), 5.86 (s, 2H), 4.71-4.67 (m, 1H), 4.22-4.19 (m, 1H), 3.55 (s, 3H), 3.09-2.99 (m, 1H), 2.91-2.88 (m, 2H), 2.63 (s, 3H), 1.89-1.86 (m, 1H), 1.68-1.65 (m, 1H), 1.48-1.41 (m, 2H), 1.21-1.18 (m, 2H). MS (ESI): mass calcd. for $C_{30}H_{31}N_5O_2$, 493.25; m/z found, 494.2 $(M+H)^+$.

Compound-43

(R)-(3-aminopiperidin-1-yl)(2-(5-bromo-1-(cyclopropylmethyl)-1H-indol-2-yl)-3-methylimidazo[1,2-a]pyridin-7-yl)methanone

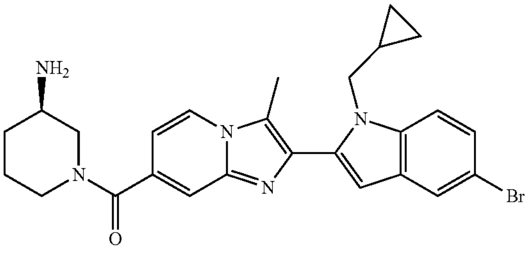 [SMILES: Cc1c(-c2cc3cc(Br)ccc3n2CC2CC2)nc2cc(C(=O)N3CCC[C@@H](N)C3)ccn12]

$^1$HNMR (400 MHz, DMSO-$d_6$) δ (ppm): 8.45 (d, J=7.2 Hz, 1H), 7.77 (s, 1H), 7.70 (s, 1H), 7.57 (d, J=8.4 Hz, 1H), 7.28 (bs, 1H), 6.71 (bs, 1H), 6.65 (s, 1H), 4.49 (bs, 2H), 3.16 (bs, 3H), 2.06-1.89 (m, 2H), 1.53 (bs, 2H), 1.31-1.28 (m, 5H), 1.09 (bs, 1H), 0.83 (bs, 2H), 0.28 (bs, 2H), 0.15 (bs, 2H). MS (ESI): Mass calcd. for $C_{26}H_{28}BrN_5O$, 506.45; m/z found, 508.1 $[M+H]^{2+}$.

Compound-44

(R)-(3-aminopiperidin-1-yl)(2-(7-chloro-1-(cyclopropylmethyl)-1H-indol-2-yl)-3-methylimidazo[1,2-a]pyridin-7-yl)methanone

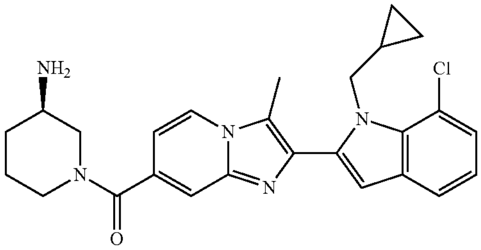 [SMILES: Cc1c(-c2cc3cccc(Cl)c3n2CC2CC2)nc2cc(C(=O)N3CCC[C@@H](N)C3)ccn12]

$^1$HNMR (400 MHz, DMSO-$d_6$) δ (ppm): 8.41 (d, J=7.2 Hz, 1H), 7.67 (s, 1H), 7.58 (d, J=8 Hz, 1H), 7.22 (d, J=7.6 Hz, 1H), 7.08-7.02 (m, 2H), 6.74 (s, 1H), 4.80 (d, J=6.8 Hz, 2H), 4.0 (bs, 2H), 2.98 (m, 3H), 2.61 (s, 3H), 1.89 (m, 2H), 1.71 (m, 1H), 1.48-1.46 (m, 2H), 1.22 (m, 1H), 1.02 (m, 1H), 0.20-0.18 (m, 2H), −0.08 (m, 2H). MS (ESI): mass calcd. for $C_{26}H_{28}ClN_5O$, 461.20; m/z found, 462.1 $(M+H)^+$.

Compound-45

Synthesis of (R)-(3-aminopiperidin-1-yl)(2-(1-(4-fluorobenzyl)-1H-indol-2-yl)-3-methylimidazo[1,2-a]pyridin-7-yl)methanethione Compound-45 was prepared from Compound-13 according to the step provided below.

Scheme 8

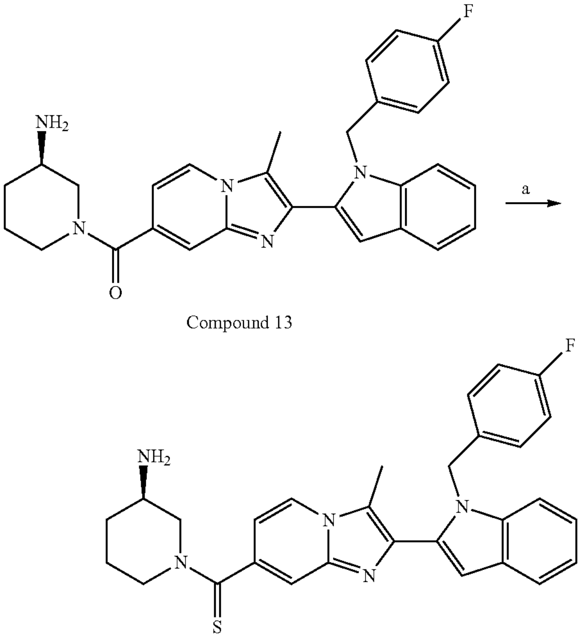

Compound 13

Compound 45

To the stirred solution of (R)-(3-aminopiperidin-1-yl)(2-(1-(4-fluorobenzyl)-1H-indol-2-yl)-3-methylimidazo[1,2-a]

pyridin-7-yl)methanone (Compound-13, 0.05 g, 0.11 mmol) in toluene (2 mL), was added Lawesson's reagent (0.06 g, 0.15 mmol) and stirred at 100° C. for 16 h (Reaction condition a). The reaction mixture was cooled to rt, added saturated $NaHCO_3$ (10 mL) and compound was extracted with EtOAc (30 mL). Organic extract was washed with brine solution (10 mL), dried over sodium sulfate and evaporated. Crude product was purified by column chromatography using 2-6% MeOH in DCM followed by prep. HPLC (Analytical Conditions: —Column: Inertsil ODS 3V (250 mm×4.6 mm×5 mic), Mobile phase (A): 0.1% ammonium acetate in water, Mobile phase(B): ACN, Flow rate: 1.0 mL/min, Rt: 14.43) to afford the product as yellow solid (Compound-45) (0.015 g, 29% Yield). $^1$HNMR (400 MHz, DMSO-$d_6$) δ (ppm): 8.36 (d, J=5.2 Hz, 1H), 7.61-7.59 (m, 1H), 7.42-7.38 (m, 2H), 7.12-7.00 (m, 6H), 6.92-6.90 (m, 1H), 6.74 (s, 1H), 5.86 (s, 2H), 5.08-4.90 (m, 2H), 3.84-3.76 (m, 1H), 3.45-3.42 (m, 1H), 3.10-3.05 (m, 1H), 2.84-2.81 (m, 1H), 2.62 (s, 3H), 1.85-1.81 (m, 2H), 1.67-1.59 (m, 2H), 1.32-1.29 (m, 1H). MS (ESI): Mass calcd. for $C_{29}H_{28}FN_5S$, 497.20; m/z found, 498.1 $(M+H)^+$.

Compound-46

(R)-(3-aminopiperidin-1-yl)(3-methyl-2-(1-methyl-1H-indol-2-yl)imidazo[1,2-a]pyridin-7-yl)methanone

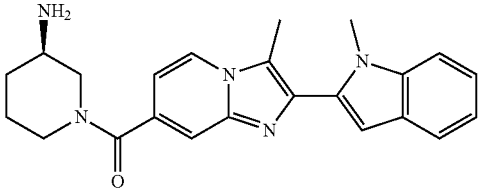 [SMILES: Cc1c(-c2cc3ccccc3n2C)nc2cc(C(=O)N3CCC[C@@H](N)C3)ccn12]

$^1$HNMR (400 MHz, DMSO-$d_6$) δ (ppm): 8.42 (d, J=7.2 Hz, 1H), 7.64 (s, 1H), 7.59 (d, J=8 Hz, 1H), 7.49 (d, J=8.4 Hz, 1H), 7.20 (t, J=6.4 Hz, 1H), 7.07 (t, J=7.6 Hz, 1H), 6.99 (d, J=6.8 Hz, 1H), 6.66 (s, 1H), 4.12 (m, 1H), 3.96 (s, 3H), 2.65 (s, 3H), 1.87 (m, 1H), 1.68 (m, 2H), 1.47 (m, 1H), 1.26-1.22 (m, 4H), 0.88-0.84 (m, 2H). MS (ESI): Mass calcd. for $C_{23}H_{25}N_5O$, 387.20; m/z found 388.2 $(M+H)^+$.

Compound-47

(R)-(3-aminopiperidin-1-yl)(2-(1-(cyclopropylmethyl)-7-methoxy-1H-indol-2-yl)-3-methylimidazo[1,2-a]pyridin-7-yl)methanone

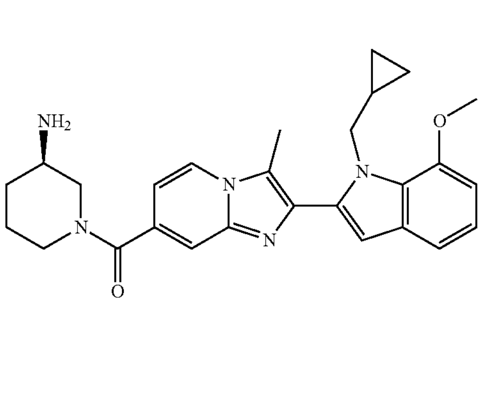 [SMILES: COc1cccc2cc(-c3nc4cc(C(=O)N5CCC[C@@H](N)C5)ccn4c3C)n(CC3CC3)c12]

$^1$HNMR (400 MHz, DMSO-$d_6$) δ (ppm): 8.41 (d, J=7.2 Hz, 1H), 7.67 (s, 1H), 7.58 (d, J=8 Hz, 1H), 7.22 (d, J=7.6 Hz, 1H), 7.08-7.02 (m, 2H), 6.74 (s, 1H), 4.80 (d, J=6.8 Hz, 2H), 4.0 (bs, 2H), 3.95 (s, 3H), 2.98 (m, 3H), 2.61 (s, 3H), 1.89 (m, 2H), 1.71 (m, 1H), 1.48-1.46 (m, 2H), 1.22 (m, 1H), 1.02 (m, 1H), 0.20-0.18 (m, 2H), −0.08 (m, 2H). MS (ESI): Mass calcd. for $C_{27}H_{31}N_5O_2$, 457.2; m/z found, 458.1 $(M+H)^+$.

Compound-48

(R)-(3-aminopiperidin-1-yl)(2-(1-((2,4-dimethylthiazol-5-yl)methyl)-1H-indol-2-yl)-3-methylimidazo[1,2-a]pyridin-7-yl)methanone

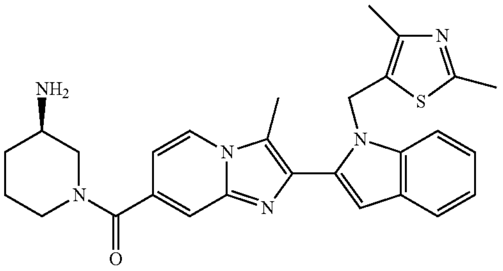 [SMILES: Cc1nc(C)c(Cn2c(-c3nc4cc(C(=O)N5CCC[C@@H](N)C5)ccn4c3C)cc3ccccc32)s1]

$^1$HNMR (400 MHz, DMSO-$d_6$) δ (ppm): 8.43 (d, J=6.8 Hz, 1H), 7.62-7.58 (m, 2H), 7.49 (d, J=8.0 Hz, 1H), 7.18 (t, J=6.8 Hz, 1H), 7.07 (t, J=6.8 Hz, 1H), 7.00 (d, J=7.2 Hz, 1H), 6.72 (s, 1H), 6.00 (s, 2H), 4.22-4.16 (m, 1H), 3.66-3.61 (m, 1H), 2.99-2.95 (m, 1H), 2.64-2.63 (m, 1H), 2.62 (s, 3H), 2.56 (s, 3H), 2.17 (s, 3H), 2.01-1.95 (m, 1H), 1.84-1.81 (m, 2H), 1.66-1.59 (m, 2H), 1.44-1.42 (m, 1H), 1.22-1.20 (m, 1H). MS (ESI): Mass calcd. for $C_{28}H_{30}N_6OS$, 498.22; m/z found, 499.2 $(M+H)^+$.

Compound-49

(R)-(3-aminopiperidin-1-yl)(3-methyl-2-(1-((2-methylthiazol-5-yl)methyl)-1H-indol-2-yl)imidazo[1,2-a]pyridin-7-yl)methanone

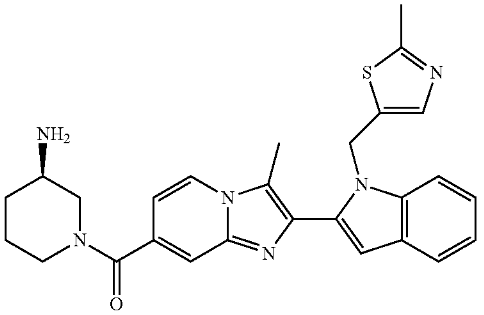 [SMILES: Cc1ncc(Cn2c(-c3nc4cc(C(=O)N5CCC[C@@H](N)C5)ccn4c3C)cc3ccccc32)s1]

$^1$HNMR (400 MHz, DMSO-$d_6$) δ (ppm): 8.46 (d, J=7.2 Hz, 1H), 7.67-7.64 (m, 2H), 7.58 (d, J=7.6 Hz, 1H), 7.51 (s, 1H), 7.17 (t, J=7.2 Hz, 1H), 7.08-7.02 (m, 2H), 6.74 (s, 1H), 6.07 (s, 2H), 4.66-4.61 (m, 1H), 4.12-4.08 (m, 1H), 3.05-3.01 (m, 1H), 2.94-2.91 (m, 2H), 2.66 (s, 3H), 2.41 (s, 3H), 1.90-1.87 (m, 1H), 1.70-1.67 (m, 1H), 1.49-1.45 (m, 1H), 1.37-1.33 (m, 1H), 1.26-1.21 (m, 2H). MS (ESI): Mass calcd. for $C_{27}H_{28}N_6OS$, 484.20; m/z found 485.1 $(M+H)^+$.

Compound-50

Synthesis of (R)-(3-aminopiperidin-1-yl) (2-(1-(3-methoxybenzyl)-1H-indol-2-yl)-3-methylimidazo[1,2-a]pyridin-7-yl)methanone Trifluoroacetic Acid Salt (Compound-50)

Scheme-9

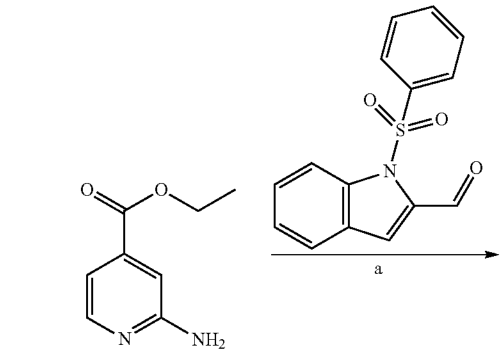

1

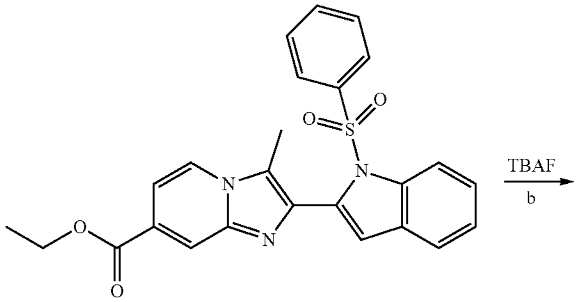

2

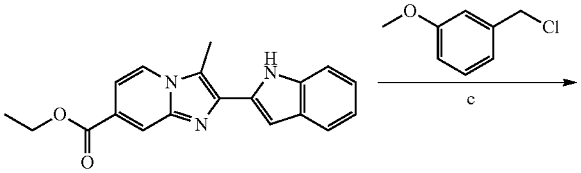

3

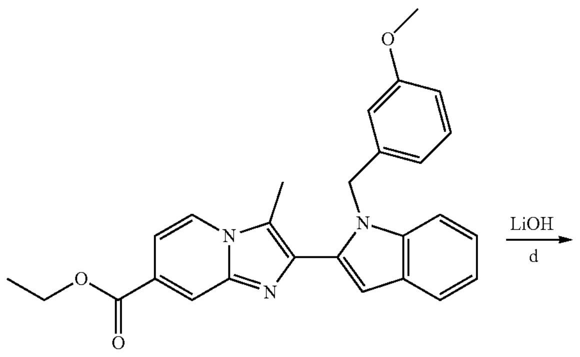

4

-continued

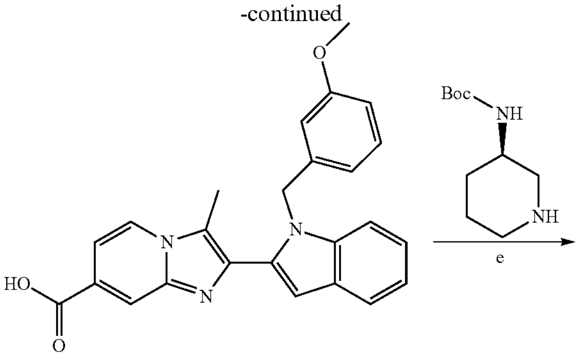

5

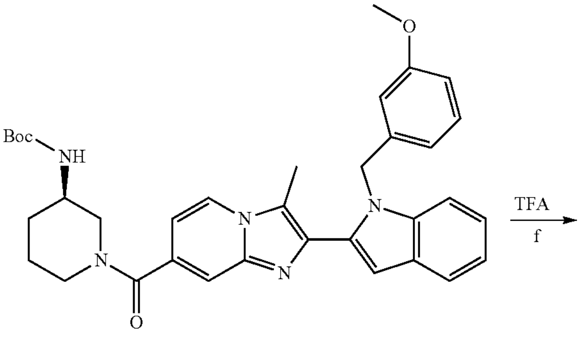

6

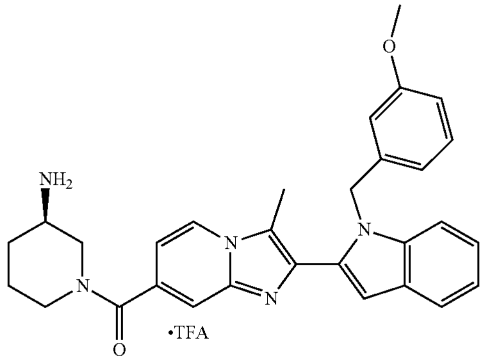

Compound 50

Step-1: Synthesis of ethyl-3-methyl-2-(1-(phenylsulfonyl)-1H-indol-2-yl) imidazo[1,2-a]pyridine-7-carboxylate (2)

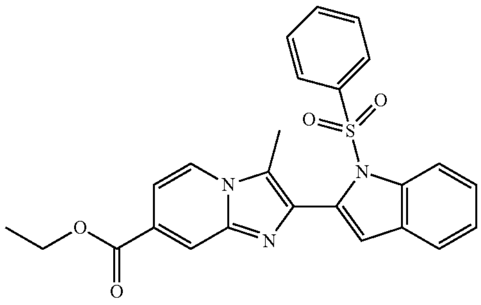 [SMILES: CCOC(=O)c1ccn2c(C)c(-c3cc4ccccc4n3S(=O)(=O)c3ccccc3)nc2c1]

To a stirred solution of ethyl-2-aminoisonicotinate (1, 6.0 g, 36.11 mmol) and 1-(phenylsulfonyl)-1H-indole-2-carbaldehyde (11.3 g, 40.44 mmol) in nitro ethane (60 mL), ferric chloride (0.55 g, 3.37 mmol) was added and then reaction mixture was reflux at 90° C. for 5 h. After completion of reaction, ice cold water was added and the reaction mixture was extracted with ethyl acetate. The organic layer was dried over anhydrous sodium sulfate, filtered and concentrated under reduced pressure to get the crude. The crude was purified by CombiFlash using 12.0 g RediSep column and 0-30% ethyl acetate in hexane as eluent. The desired fractions were concentrated under reduced pressure to afford ethyl-3-methyl-2-(1-(phenylsulfonyl)-1H-indol-2-yl)imidazo[1,2 a]pyridine-7-carboxylate (2) as yellow solid. Yield: 3.4 g (35%). MS (ESI): 459.22; m/z found: 460.39 $[M+H]^+$.

Step-2: Synthesis of ethyl-2-(1H-indol-2-yl)-3-methylimidazo[1, 2-a]pyridine-7-carboxylate (3)

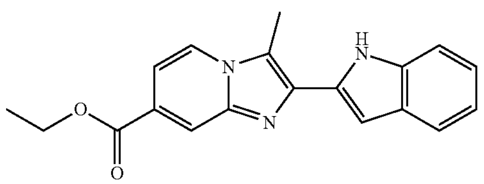 [SMILES: CCOC(=O)c1ccn2c(C)c(-c3cc4ccccc4[nH]3)nc2c1]

To a stirred solution of ethyl-3-methyl-2-(1-(phenylsulfonyl)-1H-indol-2-yl)imidazo[1,2 a]pyridine-7-carboxylate (2, 3.40 g 7.40 mmol) in tetrahydrofuran (10 mL), 1M tetra butyl ammonium fluoride in tetrahydrofuran (30 mL) was added under 0° C. slowly. The reaction mixture was refluxed at 60° C. for about 12 h. After completion of reaction, ice cold water was added and the reaction mixture was extracted with ethyl acetate. The organic layer was dried over anhydrous sodium sulfate, filtered and concentrated under reduced pressure to get the crude. The crude was purified by CombiFlash using 12.0 g RediSep column and 30% ethyl acetate in hexane as eluent to afford of ethyl-2-(1H-indol-2-yl)-3-methylimidazo[1,2-a]pyridine-7-carboxylate (3) as yellow solid. Yield: 2.2 g (93%), MS (ESI): 319.11; m/z found, 320.34 $[M+H]^+$.

Step-3: Synthesis of ethyl-2-(1-(3-methoxybenzyl)-1H-indol-2-yl)-3-methylimidazo[1,2-a]pyridine-7-carboxylate (4)

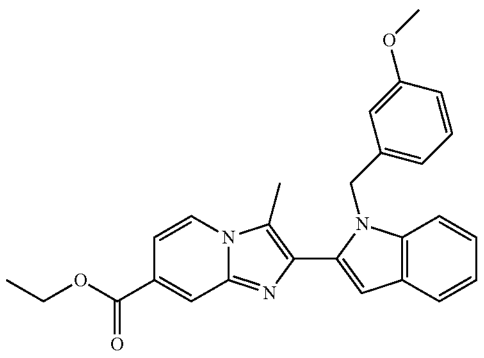 [SMILES: CCOC(=O)c1ccn2c(C)c(-c3cc4ccccc4n3Cc3cccc(OC)c3)nc2c1]

To a stirred solution of ethyl-2-(1H-indol-2-yl)-3-methylimidazo[1,2-a]pyridine-7-carboxylate (3, 2.20 g, 6.89 mmol) in N,N-dimethylformamide (20 mL), cesium carbonate (6.72 g, 20.68 mmol) was added at rt. 1-(chloromethyl)-3-methoxybenzene (1.20 g, 20.68 mmol) was added and stirred for about 10 min at rt and then resulting mixture was heated to 90° C. for 3 h. After completion of reaction, the reaction mixture was cooled to rt and diluted with ethyl acetate (50 mL×3). The organic phase was washed with water and brine, dried over anhydrous sodium sulfate and concentrated under reduced pressure to afford the crude compound. The crude was purified by CombiFlash using 12.0 g RediSep column and 30-50% ethyl acetate in hexane as eluent to afford ethyl-2-(1-(3-methoxybenzyl)-1H-indol-2-yl)-3-methylimidazo[1,2-a]pyridine-7-carboxylate (4) as yellow solid. Yield: 1.2 g (40%). MS (ESI): 439.50; m/z found, 440.04 $[M+H]^{+1}$.

Step-4: Synthesis of 2-(1-(3-methoxybenzyl)-1H-indol-2-yl)-3-methylimidazo[1,2-a]pyridine-7-carboxylic Acid (5)

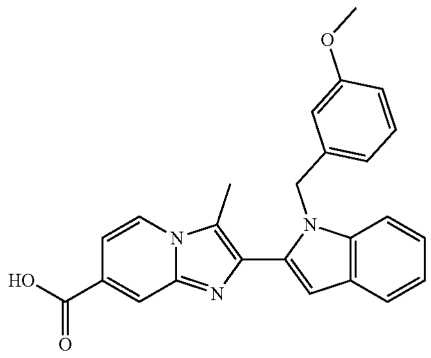 [SMILES: COc1cccc(Cn2c(-c3nc4cc(C(=O)O)ccn4c3C)cc3ccccc32)c1]

To a stirred solution of ethyl-2-(1-(3-methoxybenzyl)-1H-indol-2-yl)-3-methylimidazo[1,2-a]pyridine-7-carboxylate (1.20 g, 2.73 mmol) in tetrahydrofuran (10 mL) was added methanol (4 mL) and 5N sodium hydroxide solution (4 mL) and the resulting mixture was heated to 60° C. for 3 h. After completion of reaction, the reaction mixture was evaporated under reduced pressure and acidify to pH 2-3 with citric acid at 0° C. The crude was extracted with dichloromethane (30 mL×2), washed with brine, dried over anhydrous sodium sulfate, filtered and concentrated under reduced pressure to 2-(1-(3-methoxybenzyl)-1H-indol-2-yl)-3-methylimidazo[1,2-a]pyridine-7-carboxylic acid (5) as pale yellow color solid. Yield: 0.850 g (78%). MS (ESI): 412; m/z found, 413 $[M+H]^+$.

Step-5: Synthesis of tert-butyl (R)-(1-(2-(1-(3-methoxybenzyl)-1H-indol-2-yl)-3-methylimidazo[1,2-a]pyridine-7-carbonyl)piperidin-3-yl)carbamate (6)

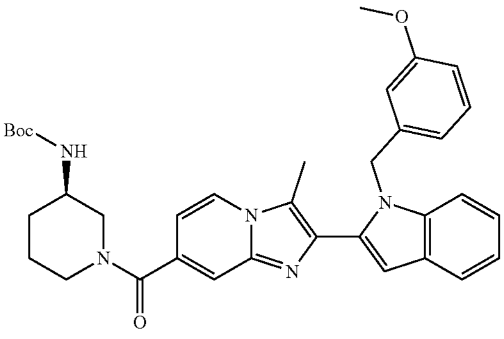 [SMILES: COc1cccc(Cn2c(-c3nc4cc(C(=O)N5CCC[C@@H](NC(=O)OC(C)(C)C)C5)ccn4c3C)cc3ccccc32)c1]

To a stirred solution of 2-(1-(3-methoxybenzyl)-1H-indol-2-yl)-3-methylimidazo[1,2-a]pyridine-7-carboxylic acid (5, 0.85 g, 2.06 mmol) in dichloromethane (20 mL), tert-butyl (R)-piperidin-3-ylcarbamate (0.49 g, 2.47 mmol), triethylamine (0.8 mL, 6.18 mmol) and propyl phosphoric anhydride in 50% ethyl acetate (2.1 mL, 6.80 mmol) were added at 0° C. The reaction mixture was allowed to stir at rt for 1 h. After completion of reaction, the reaction mixture was quenched with sodium bicarbonate solution (20 mL) and extracted with dichloromethane (20 mL×2). The combined organic layers were washed with brine, dried over anhydrous sodium sulfate, filtered and concentrated under reduced pressure to get crude product. The crude was purified by CombiFlash using 40.0 g Redisep column and 30-50% ethyl acetate in hexane as eluent to tert-butyl (R)-(1-(2-(1-(3-methoxybenzyl)-1H-indol-2-yl)-3-methylimidazo[1,2-a]pyridine-7-carbonyl)piperidin-3-yl)carbamate (6) as brown solid. Yield: 0.640 g (86%). MS (ESI): 594.30; m/z found, 595.41$[M+H]^{+1}$.

Step-6: Synthesis of (R)-(3-aminopiperidin-1-yl)(2-(1-(3-methoxybenzyl)-1H-indol-2-yl)-3-methylimidazo[1,2-a]pyridin-7-yl)methanone Trifluoroacetic Acid Salt (Compound 50)

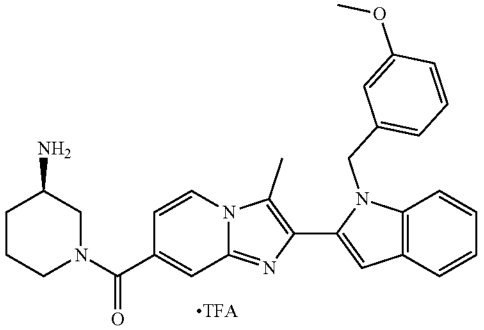 [SMILES: COc1cccc(Cn2c(-c3nc4cc(C(=O)N5CCC[C@@H](N)C5)ccn4c3C)cc3ccccc32)c1]

To the stirred solution of mixture tert-butyl (R)-(1-(2-(1-(3-methoxybenzyl)-1H-indol-2-yl)-3-methylimidazo[1,2-a]pyridine-7-carbonyl)piperidin-3-yl)carbamate (0.64 g, 1.08 mmol) in dichloromethane (60 mL), trifluoroacetic acid (10 mL) was added at 0° C. The reaction mixture was stirred at rt for 2 h. After completion of reaction, the reaction mixture was concentrated under reduced pressure to remove trifluoroacetic acid. The crude was dissolved in minimum volume of water and basified by saturated sodium bicarbonate solution (20 mL) and was extracted with dichloromethane (50 mL×2). The organic layer was washed with brine, dried over anhydrous sodium sulfate and concentrated to get crude product. The crude was purified by reverse prep HPLC to afford (R)-(3-aminopiperidin-1-yl)(2-(1-(3-methoxybenzyl)-1H-indol-2-yl)-3-methylimidazo[1,2-a]pyridin-7-yl)methanone trifluoroacetate as off yellow solid. Yield: 0.49 g (93%).

$^1H$ NMR (400 MHz, DMSO-$d_6$) δ (ppm): 8.49 (d, J=7.0 Hz, 1H), 7.76 (s, 1H), 7.63 (d, J=7.6 Hz, 1H), 7.42 (d, J=8.04 Hz, 1H)), 7.15-7.07 (m, 4H), 6.80 (s, 1H), 6.69 (d J=8.2 Hz, 1H), 6.53 (s, 2H), 5.83 (s, 2H), 4.11 (bs, 2H), 3.57 (s, 3H), 3.27 (bs, 3H), 2.65 (s, 3H), 1.98 (m, 1H), 1.73 (m, 1H), 1.58 (m, 2H). MS (ESI): Mass calcd. for $C_{30}H_{31}N_5O_2$, 494.11; m/z found, 495.07 $[M+H]^{+1}$.

Following compounds were synthesized using the above procedure as exemplified for Compound-50.

Compound-51

(R)-(3-aminopiperidin-1-yl) (2-(6-methoxy-1-(pyridin-3-ylmethyl)-1H-indol-2-yl)-3-methylimidazo[1,2-a]pyridin-7-yl)methanone

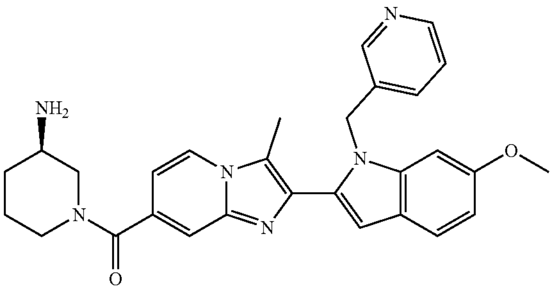 [SMILES: COc1ccc2cc(-c3nc4cc(C(=O)N5CCC[C@@H](N)C5)ccn4c3C)n(Cc3cccnc3)c2c1]

$^1H$ NMR (400 MHz, DMSO-$d_6$) δ (ppm): 8.41 (d, J=7.08 Hz, 1H), 8.33 (d, J=4.52 Hz, 1H), 8.26 (s, 1H), 7.59 (s, 1H), 7.50 (d, J=8.6 Hz, 1H), 7.36 (d J=7.81 Hz, 1H), 7.22-7.19 (m, 1H), 7.03 (s, 1H), 6.98 (d, J=7.08 Hz, 1H), 6.74 (d, J=8.01 Hz, 1H), 6.70 (s, 1H), 5.92 (bs, 2H), 4.27-4.10 (m, 1H), 3.75 (s, 3H), 3.56 (bs, 1H), 2.98-2.95 (m, 2H), 2.66 (m, 1H), 2.62 (s, 3H), 1.85-1.82 (m, 1H), 1.71-1.67 (m, 3H), 1.44-1.42 (m, 1H), 1.27-1.23 (m, 1H). MS (ESI): Mass calcd. for $C_{29}H_{30}N_6O_2$, 494.43; m/z found, 495.07 $[M+H]^+$.

Compound-52

(R)-(3-aminopiperidin-1-yl)(2-(1-(cyclopropylmethyl)-6-fluoro-1H-indol-2-yl)-3-methylimidazo[1,2-a]pyridin-7-yl)methanone Trifluoroacetic Acid Salt

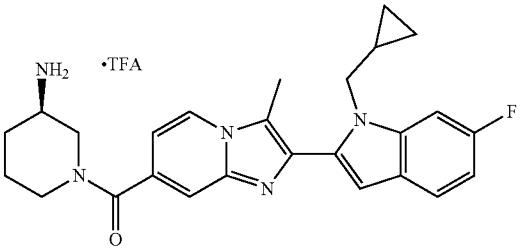 [SMILES: Cc1c(-c2cc3ccc(F)cc3n2CC2CC2)nc2cc(C(=O)N3CCC[C@@H](N)C3)ccn12]

$^1$HNMR (400 MHz, DMSO-$d_6$) δ (ppm): 8.51 (d, J=7.08 Hz, 1H), 7.95 (s, 1H), 7.76 (s, 1H), 7.62-7.58 (m, 1H), 7.49 (d, J=10.3 Hz, 1H), 7.10 (d, J=6.56 Hz, 1H), 6.94 (t, J=8.04 Hz, 1H), 6.70 (s, 1H), 4.45 (d, J=6.64 Hz, 2H), 3.29 (s, 4H), 2.64 (s, 3H), 2.01 (s, 1H), 1.75 (s, 1H), 1.60 (s, 2H), 1.06 (s, 1H), 0.28 (d, J=7.48 Hz, 2H), 0.15 (d, J=3.88 Hz, 2H). MS (ESI): Mass calcd. for $C_{26}H_{28}FN_5O$, 445; m/z found, 446.45 $[M+H]^+$.

Compound-53

(R)-(3-aminopiperidin-1-yl)(2-(5-fluoro-1-(3-methoxybenzyl)-1H-indol-2-yl)-3-methylimidazo[1,2-a]pyridin-7-yl)methanone

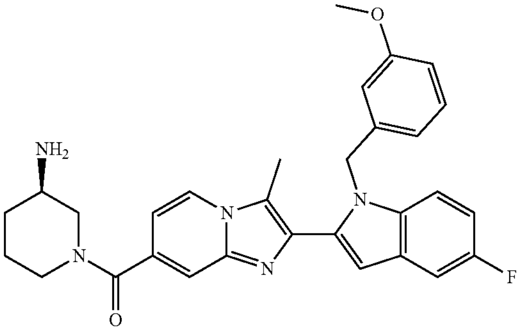 [SMILES: COc1cccc(Cn2c(-c3nc4cc(C(=O)N5CCC[C@@H](N)C5)ccn4c3C)cc3cc(F)ccc32)c1]

$^1$H NMR (400 MHz, DMSO-$d_6$) δ (ppm): 8.42 (d, J=6.9 Hz, 1H), 7.62 (s, 1H), 7.43-7.36 (m, 2H), 7.08 (t, J=7.3 Hz, 1H), 7.01-6.94 (m, 2H), 6.76 (s, 1H), 6.67 (d, J=6.9 Hz, 1H), 6.53-6.51 (m, 2H), 5.87 (s, 2H), 4.30-4.08 (m, 1H), 3.57 (s, 4H), 2.98 (s, 1H), 2.80 (s, 1H), 2.64 (s, 5H), 2.01 (bs, 1H), 1.85-1.83 (m, 1H), 1.68 (m, 1H), 1.45-1.42 (m, 1H), 1.26-1.23 (s, 1H). MS (ESI): Mass calcd. for $C_{30}H_{30}FN_5O_2$, 511.51; m/z found 512.67 $[M+1]^+$.

Compound-54

(R)-(3-aminopiperidin-1-yl)(2-(6-fluoro-1-(4-fluorobenzyl)-1H-indol-2-yl)-3-methylimidazo[1,2-a]pyridin-7-yl)methanone

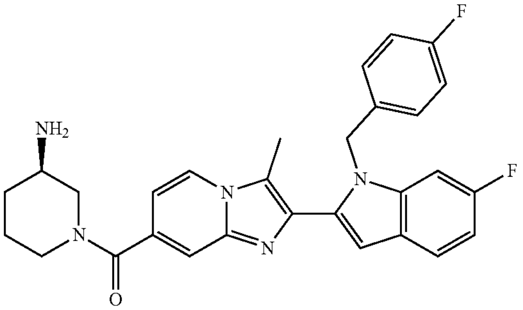 [SMILES: Cc1c(-c2cc3ccc(F)cc3n2Cc2ccc(F)cc2)nc2cc(C(=O)N3CCC[C@@H](N)C3)ccn12]

$^1$H NMR (400 MHz, DMSO-$d_6$) δ (ppm): 8.42 (d, J=6.96 Hz, 1H), 7.63-7.60 (m, 2H), 7.31 (d, J=10.04 Hz, 1H), 7.03-6.99 (m, 5H), 6.93 (t, J=8.6 Hz, 1H), 6.78 (s, 1H), 5.86 (s, 2H), 4.25-4.10 (m, 1H), 3.56 (m, 1H), 2.98 (bs, 1H), 2.82 (m, 1H), 2.62 (m, 5H), 1.85-1.82 (m, 1H), 1.69 (bs, 2H), 1.45-1.42 (m, 1H), 1.24-1.22 (m, 1H). MS (ESI): Mass calcd. for $C_{29}H_{27}F_2N_5O$, 499.22; m/z found, 500.37 $[M+H]^+$.

Compound-55

(R)-(3-aminopiperidin-1-yl)(2-(5,6-difluoro-1-(3-methoxybenzyl)-1H-indol-2-yl)-3-methylimidazo[1,2-a]pyridin-7-yl)methanone

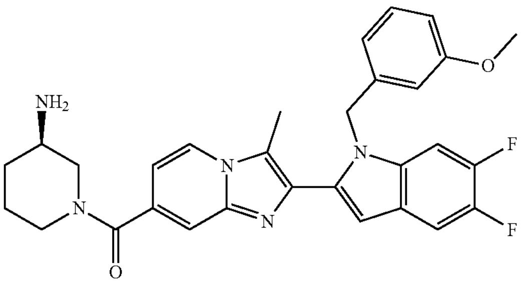 [SMILES: COc1cccc(Cn2c(-c3nc4cc(C(=O)N5CCC[C@@H](N)C5)ccn4c3C)cc3cc(F)c(F)cc32)c1]

$^1$H NMR (400 MHz, DMSO-$d_6$) δ (ppm): 8.42 (d, J=6.84 Hz, 1H), 7.63-7.54 (m, 2H), 7.08 (t, J=7.8 Hz, 1H), 6.99 (d, J=6.76 1H), 6.77 (s, 1H), 6.69 (d, J=7.56 2H), 6.50 (m, 2H), 5.86 (s, 2H), 4.24-4.01 (bs, 2H), 3.56 (s, 3H), 2.97 (bs, 2H), 2.62 (m, 4H), 1.82 (m, 1H), 1.69 (m, 2H), 1.43 (d, J=9.08, 1H), 1.23-1.09 (m, 2H). MS (ESI): Mass calcd. for $C_{30}H_{29}F_2N_5O_2$, 529.59; m/z found, 530.29$[M+H]^{+1}$.

Compound-56

Synthesis of (R,E)-4-(dimethylamino)-N-(1-(2-(1-(4-fluorobenzyl)-1H-indol-2-yl)-3-methylimidazo[1,2-a]pyridine-7-carbonyl)piperidin-3-yl)but-2-enamide Scheme-10

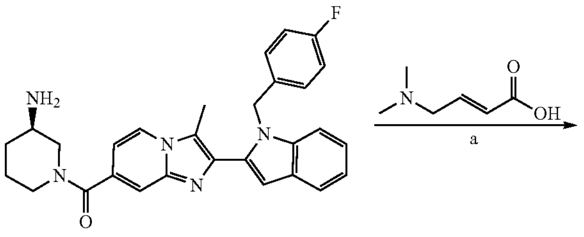

Compound-13

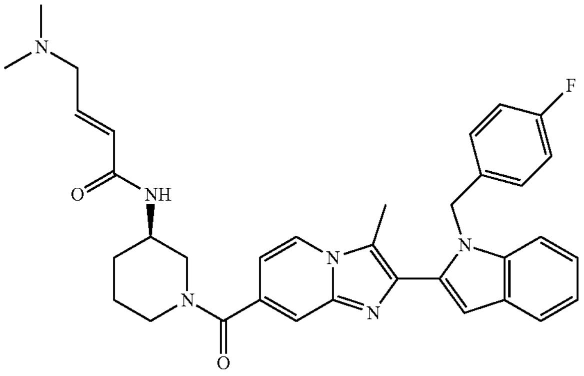

Compound-56

To a stirred solution of (E)-4-(dimethylamino)but-2-enoic acid (0.103 g, 0.623 mmol) in dichloromethane (10 mL), (R)-(3-aminopiperidin-1-yl)(2-(1-(4-fluorobenzyl)-1H-indol-2-yl)-3-methylimidazo[1,2-a]pyridin-7-yl)methanone (0.200 g, 0.415 mmol), triethylamine (0.18 mL, 1.28 mmol), propyl phosphonic anhydride in 50% ethyl acetate (0.85 mL, 1.33 mmol) were added at 0° C. The reaction mixture was allowed to stir at rt for 2 h. After completion of reaction, the reaction mixture was quenched with sodium bicarbonate solution (20 mL) and extracted with dichloromethane (50 mL×2). The combined organic layers were washed with brine, dried over anhydrous sodium sulfate, filtered and concentrated under reduced pressure to get crude product. The crude product was purified by prep HPLC to afford (R,E)-4-(dimethylamino)-N-(1-(2-(1-(4-fluorobenzyl)-1H-indol-2-yl)-3-methylimidazo[1,2-a]pyridine-7-carbonyl)piperidin-3-yl)but-2-enamide as off-white solid. Yield: 0.12 g (49%).

$^1$H NMR (400 MHz, DMSO-$d_6$) δ (ppm): 8.40 (s, 1H), 8.01 (s, 1H), 7.62 (d, J=7.6 Hz, 2H), 7.44 (d, J=7.6 Hz, 1H), 7.14-7.11 (m, 1H), 7.06-6.99 (m, 6H), 6.76 (s, 1H), 6.55-6.43 (m, 1H), 6.06 (d, J=14.2 Hz, 1H), 5.88 (s, 2H), 4.13-3.68 (m, 3H), 3.11-2.94 (m, 4H), 2.63 (s, 3H), 2.11 (s, 6H), 1.87 (d, J=9.2 Hz, 1H), 1.79 (m, 1H), 1.53-1.51 (m, 2H). MS (ESI): Mass calcd. for $C_{35}H_{37}FN_6O_2$, 592.30; m/z found 593.4 $[M+H]^{+1}$.

Compound-57

Synthesis of (R)-(3-aminopiperidin-1-yl)(3-methyl-2-(1-(pyrazin-2-ylmethyl)-1H-indol-2-yl)imidazo[1,2-a]pyridin-7-yl)methanone (Compound-57)

Scheme: 11

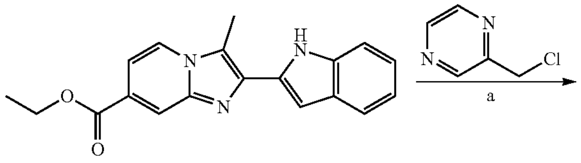

1

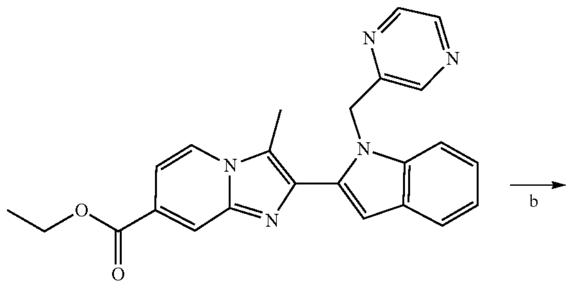

2

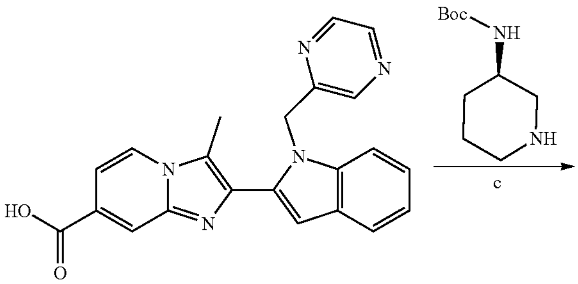

3

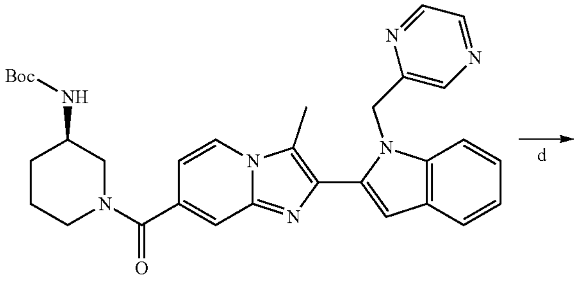

4

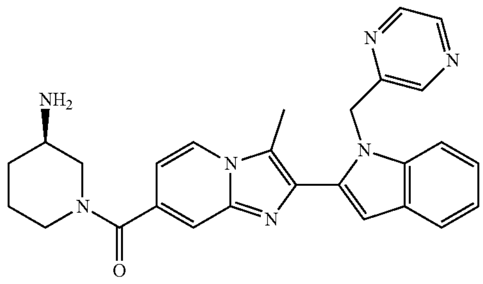

Compound 57

Step-1: ethyl-3-methyl-2-(1-(pyrazin-2-ylmethyl)-1H-indol-2-yl)imidazo[1,2-a]pyridine-7-carboxylate (2)

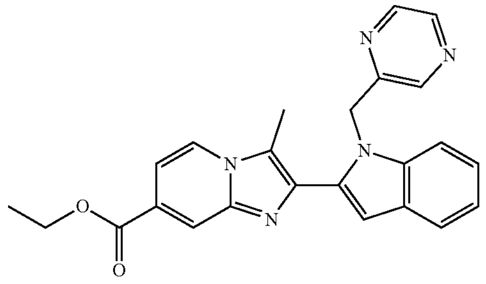 [SMILES: CCOC(=O)c1ccn2c(C)c(-c3cc4ccccc4n3Cc3cnccn3)nc2c1]

To a stirred solution of ethyl-2-(1H-indol-2-yl)-3-methylimidazo[1,2-a]pyridine-7-carboxylate (1, 0.3 g, 0.94 mmol) in N,N-dimethylformamide (10 mL), was added cesium carbonate (1.5 g, 4.7 mmol) and 2-(chloromethyl) pyrazine (0.15 g, 1.13 mmol), and stirred at 60° C. for 3 h. After completion of reaction, the reaction mixture was cooled to rt and diluted with ethyl acetate (10 mL×3). The organic phase was washed with water, brine, dried over anhydrous sodium sulfate and concentrated under reduced pressure to afford the crude compound. The crude was purified by using CombiFlash, 12 g RediSep and 50-70% ethyl acetate in hexane as eluent to afford ethyl 3-methyl-2-(1-(pyrazin-2-ylmethyl)-1H-indol-2-yl)imidazo[1,2-a] pyridine-7-carboxylate (2) as light brown solid. Yield: 0.108 g (28%). MS (ESI): 411.17; m/z found, 412.21.

Step-2: Synthesis of 3-methyl-2-(1-(pyrazin-2-ylmethyl)-1H-indol-2-yl)imidazo[1,2-a]pyridine-7-carboxylic Acid (3)

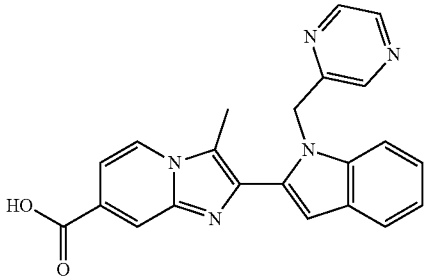 [SMILES: Cc1c(-c2cc3ccccc3n2Cc2cnccn2)nc2cc(C(=O)O)ccn12]

To a stirred solution of ethyl3-methyl-2-(1-(pyrazin-2-ylmethyl)-1H-indol-2-yl)imidazo[1,2-a]pyridine-7-carboxylate (2, 0.108 g, 0.267 mmol) in tetrahydrofuran (4 mL), was added methanol (2 mL) and 5N sodium hydroxide solution in water (2 mL) and the resulting mixture was heated to 60° C. for 1 h. After completion of reaction, the reaction mixture was evaporated under reduced pressure and acidified to pH 2-3 with citric acid at 0° C. The crude was extracted with dichloromethane (50 mL×2), washed with brine, dried over anhydrous sodium sulfate, filtered and concentrated under reduced pressure to afford 3-methyl-2-(1-(pyrazin-2-ylmethyl)-1H-indol-2-yl)imidazo[1,2-a]pyridine-7-carboxylic acid (3) as off white solid. Yield: 0.10 g, 99%. MS (ESI): 383.14; m/z found, 382.11 $[M-H]^{-1}$.

Step-3: Synthesis of tert-butyl (R)-(1-(3-methyl-2-(1-(pyrazin-2-ylmethyl)-1H-indol-2-yl)imidazo[1,2-a]pyridine-7-carbonyl)piperidin-3-yl)carbamate (4)

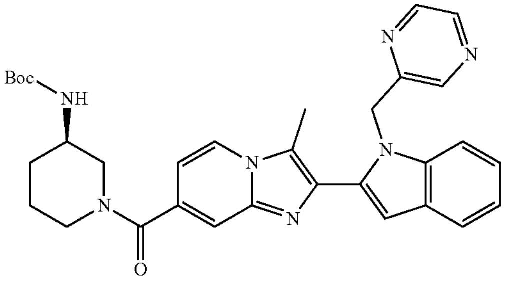 [SMILES: Cc1c(-c2cc3ccccc3n2Cc2cnccn2)nc2cc(C(=O)N3CCC[C@@H](NC(=O)OC(C)(C)C)C3)ccn12]

To a stirred solution of 3-methyl-2-(1-(pyrazin-2-ylmethyl)-1H-indol-2-yl)imidazo[1,2-a]pyridine-7-carboxylic acid (3, 0.10 g, 0.261 mmol) in dichloromethane (10 mL), tert-butyl (R)-piperidin-3-ylcarbamate (0.06 g, 0.313 mmol), triethylamine (0.11 mL, 0.80 mmol), propyl phosphonic anhydride in 50% ethyl acetate (0.50 mL, 0.83 mmol) were added at 0° C. The reaction mixture was allowed to stir at rt for 3 h. After completion of reaction, the reaction mixture was quenched with sodium bicarbonate solution (20 mL) and extracted with dichloromethane (5 mL×2). The combined organic layers were washed with brine, dried over anhydrous sodium sulfate, filtered and concentrated under reduced pressure to get crude product. The crude was purified by using CombiFlash, 4.0 g RediSep and 1-5% methanol in dichloromethane as eluent to afford tert-butyl (R)-(1-(3-methyl-2-(1-(pyrazin-2-ylmethyl)-1H-indol-2-yl)imidazo[1,2-a]pyridine-7-carbonyl)piperidin-3-yl)carbamate (4) as off white solid. Yield: 0.07 g, 47%. MS (ESI): 565.28; m/z found, 566.18 $[M+H]^{+1}$.

Step-4: Synthesis of (R)-(3-aminopiperidin-1-yl)(3-methyl-2-(1-(pyrazin-2-ylmethyl)-1H-indol-2-yl) imidazo[1,2-a]pyridin-7-yl)methanon (Compound 57)

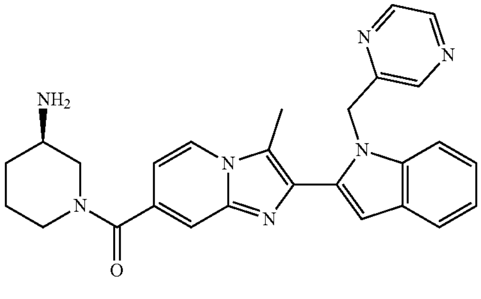 [SMILES: Cc1c(-c2cc3ccccc3n2Cc2cnccn2)nc2cc(C(=O)N3CCC[C@@H](N)C3)ccn12]

To the stirred solution of mixture tert-butyl (R)-(1-(3-methyl-2-(1-(pyrazin-2-ylmethyl)-1H-indol-2-yl)imidazo [1,2-a]pyridine-7-carbonyl)piperidin-3-yl)carbamate (4, 0.07 g, 0.123 mmol) in dichloromethane (2.0 mL), trifluoroacetic acid (0.5 mL) was added at 0° C. The reaction mixture was stirred at rt for 3 h. After completion of reaction, the reaction mixture was concentrated under reduced pressure to remove trifluoroacetic acid. The crude was dissolved in minimum volume of water and basified by saturated sodium bicarbonate solution (20 mL) and was extracted with dichloromethane (10 mL×2). The organic layer was washed with brine, dried over anhydrous sodium sulfate and concentrated to afford (R)-(3-aminopiperidin-1-yl)(3-methyl-2-(1-(pyrazin-2-ylmethyl)-1H-indol-2-yl)imidazo[1,2-a]pyridin-7-yl)methanone as white solid. Yield: 0.05 g (87%).

$^{1}$H NMR (400 MHz, DMSO-$d_6$) δ (ppm): 8.49 (s, 1H), 8.43-8.40 (m, 2H), 8.15 (s, 1H), 7.64 (d, J=7.56 Hz, 1H), 7.57 (s, 1H), 7.47 (d, J=8.12 Hz, 1H), 7.16-7.07 (m, 2H), 6.99 (d, J=7.04 Hz, 1H), 6.82 (s, 1H), 6.05 (s, 2H), 4.26-4.09 (m, 2H), 3.59-3.51 (m, 2H), 3.00 (bs, 2H), 2.64 (s, 3H), 1.85 (bs, 1H), 1.68 (bs, 1H), 1.46-1.43 (m, 1H), 1.35-1.23 (m, 2H). MS (ESI): Mass calcd. for $C_{27}H_{27}N_{7}O$, 465.23; m/z found, 466.17[M+H]$^{+1}$.

Following compounds were synthesized using the above procedure as exemplified for Compound-57.

Compound-58

(R)-(3-aminopiperidin-1-yl) (3-methyl-2-(1-(pyrimidin-5-ylmethyl)-1H-indol-2-yl) imidazo[1,2-a]pyridin-7-yl)methanone Trifluoroacetic Acid Salt

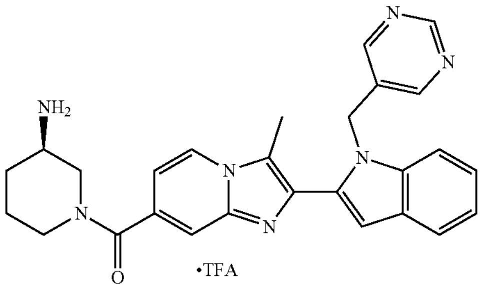 [SMILES: Cc1c(-c2cc3ccccc3n2Cc2cncnc2)nc2cc(C(=O)N3CCC[C@@H](N)C3)ccn12]

$^{1}$H NMR (400 MHz, DMSO-$d_6$) δ (ppm): 8.99 (s, 1H), 8.54 (s, 2H), 8.48 (d, J=6.5 Hz, 1H), 7.70 (s, 1H), 7.65 (d, J=7.6 Hz, 1H), 7.55 (d, J=8.0 Hz, 1H), 7.20-7.16 (m, 1H), 7.13-7.09 (m, 1H), 7.05 (d, J=11.4 Hz, 1H), 6.84 (s, 1H), 5.93 (s, 2H), 4.09 (s, 2H), 3.29 (m, 3H), 2.67 (s, 3H), 1.99 (s, 2H), 1.74 (s, 1H), 1.58 (m, 2H), 1.23 (s, 1H). MS (ESI): Mass calcd. for $C_{27}H_{27}N_{7}O$, 465.11; m/z found, 466.07 [M+H]$^{+1}$.

Compound-59

(R)-(3-aminopiperidin-1-yl) (3-methyl-2-(1-(pyridazin-3-ylmethyl)-1H-indol-2-yl)imidazo[1,2-a] pyridin-7-yl)methanone

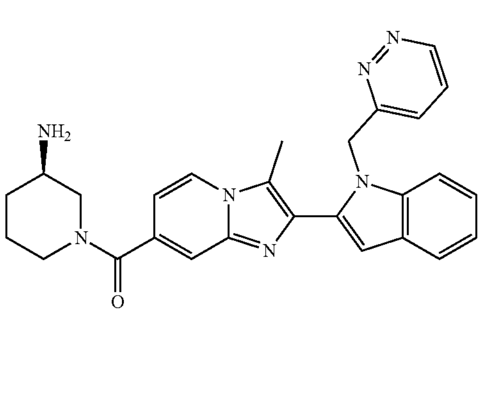 [SMILES: Cc1c(-c2cc3ccccc3n2Cc2cccnn2)nc2cc(C(=O)N3CCC[C@@H](N)C3)ccn12]

$^{1}$H NMR (400 MHz, DMSO-$d_6$) δ (ppm): 9.06 (d, J=4.76 Hz, 1H), 8.43 (d, J=7.0 Hz, 1H), 7.64 (d, J=7.25 Hz, 1H), 7.57 (s, 1H), 7.55-7.51 (m, 1H), 7.43 (d, J=7.68 Hz, 1H), 7.18 (d, J=7.31 Hz, 1H), 7.13-7.07 (m, 2H), 7.00 (d, J=6.96 Hz, 1H), 6.83 (s, 1H), 6.17 (s, 2H), 4.25-4.08 (s, 1H), 3.54 (bs, 1H), 2.96 (bs, 1H), 2.66 (s, 3H), 1.88-1.83 (m, 4H), 1.70 (m, 2H), 1.44-1.41 (m, 1H), 1.28-1.23 (m, 1H). MS (ESI): Mass calcd. for $C_{27}H_{27}N_{7}O$, 465.34; m/z found, 466.67 [M+H]$^{+1}$.

Compound-60

(R)-(3-aminopiperidin-1-yl)(2-(1-isobutyl-1H-indol-2-yl)-3-methylimidazo[1,2-a]pyridin-7-yl)methanone

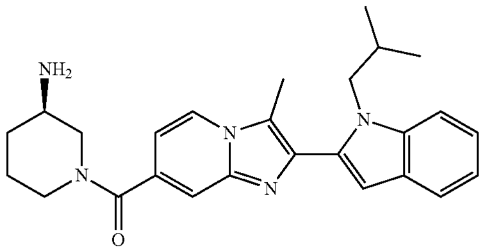 [SMILES: Cc1c(-c2cc3ccccc3n2CC(C)C)nc2cc(C(=O)N3CCC[C@@H](N)C3)ccn12]

$^{1}$H NMR (400 MHz, DMSO-$d_6$) δ (ppm): 8.45 (d, J=2.9 Hz, 1H), 7.71 (s, 1H), 7.59 (d, J=7.8 Hz, 1H), 7.54 (d, J=8.2 Hz, 1H), 7.17 (t, J=7.2 Hz, 1H), 7.07-7.02 (m, 2H), 6.65 (s, 1H), 4.45 (d, J=7.0 Hz, 2H), 4.18 (m, 2H), 3.12 (bs, 2H), 2.63 (s, 3H), 1.98-1.95 (m, 2H), 1.73 (m, 1H), 1.53 (m, 2H), 1.23 (s, 2H), 0.84 (m, 1H), 0.64 (d, J=6.4 Hz, 6H). MS (ESI): Mass calcd. for $C_{26}H_{31}N_{5}O$, 429.31; m/z found, 430.24 [M+H]$^{+}$.

Compound-61

(R)-(3-aminopiperidin-1-yl)(2-(1-(cyclobutylmethyl)-1H-indol-2-yl)-3-methylimidazo[1,2-a]pyridin-7-yl)methanone

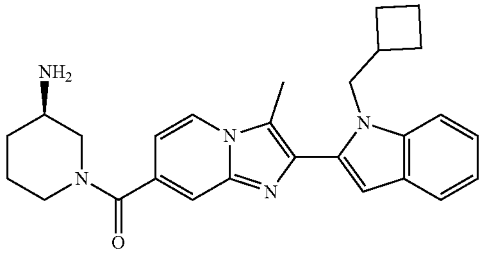 [SMILES: Cc1c(-c2cc3ccccc3n2CC2CCC2)nc2cc(C(=O)N3CCC[C@@H](N)C3)ccn12]

$^{1}$H NMR (400 MHz, DMSO-$d_6$) δ (ppm): 8.43 (d, J=6.92 Hz, 1H), 7.65 (s, 1H), 7.57 (t, J=7.56 Hz, 2H), 7.17 (t, J=7.20 Hz, 1H), 7.07-7.00 (m, 2H), 6.63 (s, 1H), 4.67 (d, J=6.76 Hz, 2H), 4.30-4.14 (m, 1H), 3.63 (bs, 1H), 3.01 (bs, 2H), 2.72 (m, 1H), 2.63 (s, 3H), 2.59-2.55 (m, 1H), 1.87 (d, J=9.8 Hz, 1H), 1.70-1.62 (m, 6H), 1.53-1.48 (m, 4H), 1.35-1.23 (m, 1H). MS (ESI): Mass calcd. for $C_{27}H_{31}N_{5}O$, 441.25; m/z found, 442.27 [M+H]$^{+1}$.

Compound-62

(R)-(3-aminopiperidin-1-yl)(2-(1-((3-fluoropyridin-2-yl)methyl)-1H-indol-2-yl)-3-methylimidazo[1,2-a]pyridin-7-yl)methanone

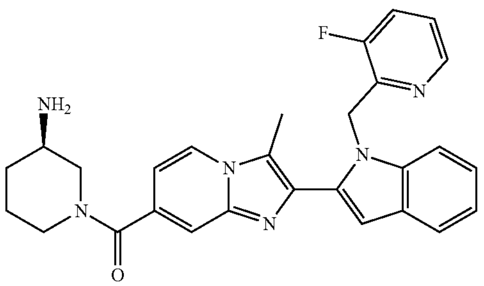 [SMILES: Cc1c(-c2cc3ccccc3n2Cc2ncccc2F)nc2cc(C(=O)N3CCC[C@@H](N)C3)ccn12]

$^1$H NMR (400 MHz, DMSO-$d_6$) δ (ppm): 8.39 (d, J=6.92 Hz, 1H), 8.14 (d, J=4.44 Hz, 1H), 7.61-7.54 (m, 3H), 7.44 (d, J=8.08 Hz, 1H), 7.27-7.23 (m, 1H), 7.13-7.09 (m, 1H), 7.07-7.03 (m, 1H), 6.97 (d, J=6.04 Hz, 1H), 6.73 (s, 1H), 6.09 (s, 2H), 4.25-4.07 (m, 1H), 3.57 (bs, 1H), 2.98 (m, 2H), 2.66 (m, 1H), 2.61 (s, 3H), 1.85 (d, J=9.68 Hz, 1H), 1.69-1.58 (m, 2H), 1.45-1.42 (m, 1H), 1.23 (m, 2H). MS (ESI): Mass calcd. for $C_{27}H_{31}N_5O$, 482.22; m/z found, 483.30 $[M+H]^{+1}$.

Compound-63

(R)-(3-aminopiperidin-1-yl)(2-(1-((5-methoxypyridin-2-yl)methyl)-1H-indol-2-yl)-3-methylimidazo[1,2-a]pyridin-7-yl)methanone

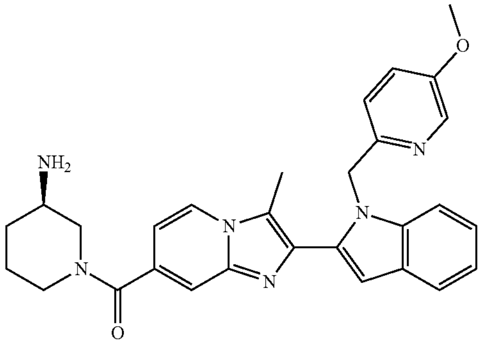 [SMILES: COc1ccc(Cn2c(-c3nc4cc(C(=O)N5CCC[C@@H](N)C5)ccn4c3C)cc3ccccc32)nc1]

$^1$H NMR (400 MHz, DMSO-$d_6$) δ (ppm): 8.42 (d, J=6.96 Hz, 1H), 8.13 (d, J=2.72 Hz, 1H), 7.63-7.60 (m, 1H), 7.38 (d, J=7.96 Hz, 1H), 7.19-7.16 (dd, J=2.8 Hz, 8.6 Hz, 1H), 7.13-7.04 (m, 2H), 7.00 (d, J=6.24 Hz, 1H), 6.77 (s, 1H), 6.70 (d, J=8.64 Hz, 2H), 5.90 (s, 2H), 4.26-4.01 (s, 2H), 3.71 (s, 3H), 3.58 (m, 1H), 2.96 (bs, 2H), 2.65 (s, 3H), 1.85-1.69 (m, 4H), 1.45-1.42 (m, 1H), 1.26-1.23 (m, 1H). MS (ESI): Mass calcd. for $C_{29}H_{30}N_6O_2$, 494.23; m/z found, 495.29 $[M+H]^{+1}$.

Compound-64

(R)-(3-aminopiperidin-1-yl) (2-(1-(2-methoxyethyl)-1H-indol-2-yl)-3-methylimidazo[1,2-a]pyridin-7-yl) methanone

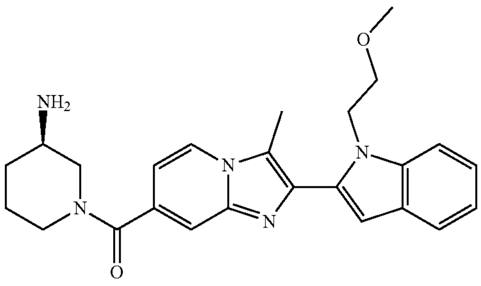 [SMILES: COCCn1c(-c2nc3cc(C(=O)N4CCC[C@@H](N)C4)ccn3c2C)cc2ccccc21]

$^1$H NMR (400 MHz, DMSO-$d_6$) δ (ppm): 8.43 (d, J=7.0 Hz, 1H), 7.62 (s, 1H), 7.60-7.54 (m, 2H), 7.18 (t, J=7.6 Hz, 1H), 7.06 (t, J=7.4 Hz, 1H), 7.00 (d, J=6.8 Hz, 1H), 6.67 (s, 1H), 4.72 (t, J=5.6 Hz, 2H), 4.28-4.12 (m, 1H), 3.58 (t, J=5.8 Hz, 2H), 3.07 (s, 3H), 2.98-2.74 (m, 2H), 2.64 (s, 5H), 1.86-1.84 (m, 1H), 1.72 (m, 2H), 1.47-1.44 (m, 1H), 1.29-1.24 (m, 1H). MS (ESI): Mass calcd. for $C_{25}H_{29}N_5O_2$, 431.23; m/z found, 432.27$[M+H]^{+1}$.

Compound-65

Synthesis of (R)-(3-aminopiperidin-1-yl)(2-(1-(2-hydroxyethyl)-1H-indol-2-yl)-3-methylimidazo[1,2-a]pyridin-7-yl)methanone Scheme 12

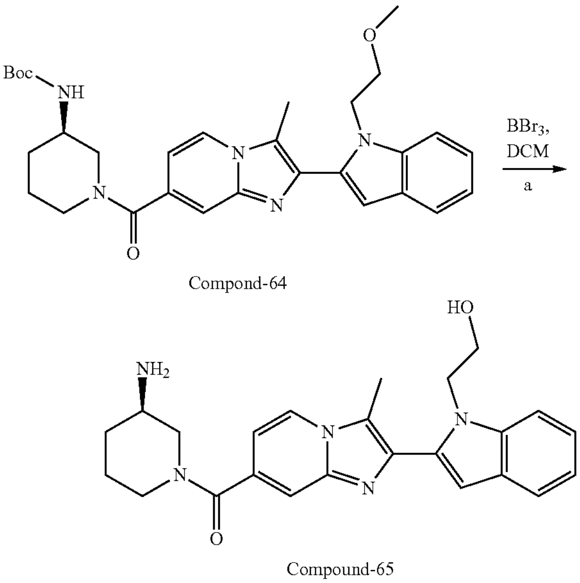

To the stirred solution of tert-butyl (R)-(1-(2-(1-(2-methoxyethyl)-1H-indol-2-yl)-3-methylimidazo[1,2-a]pyridine-7-carbonyl)piperidin-3-yl)carbamate (4, 0.20 g, 0.30 mmol) in dichloromethane (4 mL), boron tribromide (1M solution in dichloromethane) (5 mL) was added at 0° C. The reaction mixture was stirred at rt for 3 h. After completion of reaction, the reaction mixture was concentrated under reduced pressure to remove boron tribromide. The crude product was dissolved in minimum volume of water and basified by saturated sodium bicarbonate solution (20 mL) and was extracted with dichloromethane (20 mL×2). The organic layer was washed with brine, dried over anhydrous sodium sulfate and concentrated to get crude product. The crude product was purified by prep HPLC to afford (R)-(3-aminopiperidin-1-yl)(2-(1-(2-hydroxyethyl)-1H-indol-2-yl)-3-methylimidazo[1,2-a]pyridin-7-yl)methanone as off-white solid.

$^1$H NMR (400 MHz, DMSO-$d_6$) δ (ppm): 8.45 (d, J=6.8 Hz, 1H), 7.64 (s, 1H), 7.60 (d, J=7.2 Hz, 1H), 7.55 (d, J=6.9 Hz, 1H), 7.18 (t, J=7.4 Hz, 1H), 7.08 (d, J=7.44 Hz, 1H), 7.05-7.02 (m, 1H), 6.66 (s, 1H), 5.24 (bs, 1H), 4.56 (t, J=5.80 Hz, 2H), 4.25-4.06 (m, 1H), 3.69 (t, J=5.8 Hz, 2H), 3.07 (bs, 1H), 2.80 (bs, 2H), 2.64 (s, 3H), 1.87 (s, 4H), 1.75-1.72 (m, 1H), 1.49 (m, 1H), 1.32 (m, 1H). MS (ESI): Mass calcd. for $C_{24}H_{27}N_5O_2$, 417.22; m/z found, 418.39 $[M+H]^{+1}$.

Compound-66

(R)-(3-aminopiperidin-1-yl)(2-(6-methoxy-1-(pyridin-4-ylmethyl)-1H-indol-2-yl)-3-methylimidazo[1,2-a]pyridin-7-yl)methanone

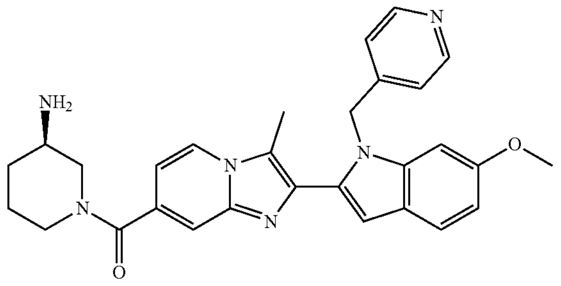 [SMILES: COc1ccc2cc(-c3nc4cc(C(=O)N5CCC[C@@H](N)C5)ccn4c3C)n(Cc3ccncc3)c2c1]

$^1$H NMR (400 MHz, DMSO-$d_6$) δ (ppm): 8.35 (s, 2H), 7.55 (s, 2H), 6.90 (s, 4H), 6.74 (s, 3H), 5.94 (s, 2H), 4.21-4.05 (m, 1H), 3.72 (s, 3H), 2.97 (bs, 2H), 2.63-2.49 (m, 4H), 1.84 (m, 2H), 1.69 (m, 2H), 1.44 (bs, 1H), 1.24 (m, 2H). MS (ESI): Mass calcd. for $C_{29}H_{30}N_6O_2$, 494.22; m/z found, 495.07 $[M+H]^{+1}$.

Compound-67

(R)-(3-aminopiperidin-1-yl)(2-(1-ethyl-6-methoxy-1H-indol-2-yl)-3-methylimidazo[1,2-a]pyridin-7-yl)methanone

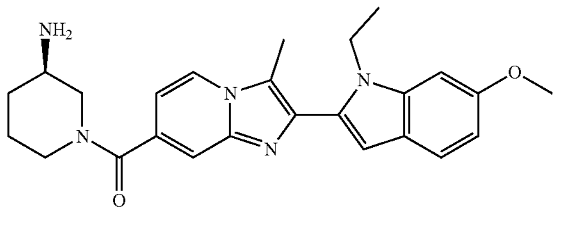 [SMILES: CCn1c(-c2nc3cc(C(=O)N4CCC[C@@H](N)C4)ccn3c2C)cc2ccc(OC)cc21]

$^1$H NMR (400 MHz, DMSO-$d_6$) δ (ppm): 8.41 (d, J=6.96 Hz, 1H), 7.61 (s, 1H), 7.46 (d, J=8.56 Hz, 1H), 7.04 (s, 1H), 6.99 (d, J=6.56 Hz, 1H), 6.72 (d, J=8.56 Hz, 1H), 6.56 (s, 1H), 4.54 (d, J=7.0 Hz, 2H), 4.28-4.08 (m, 2H), 3.83 (s, 3H), 3.63 (m, 1H), 3.00 (bs, 2H), 2.67 (m, 1H), 2.62 (s, 3H), 1.85 (d, J=9.80 Hz, 1H), 1.71 (bs, 2H), 1.45 (d, J=10.08 Hz, 2H), 1.23-1.20 (t, J=6.8 Hz, 3H). MS (ESI): Mass calcd. for $C_{25}H_{29}N_5O_2$, 431.23; m/z found, 432.32 $[M+H]^+$.

Compound-68

(R)-(3-aminopiperidin-1-yl)(2-(6-fluoro-1-(pyridin-4-ylmethyl)-1H-indol-2-yl)-3-methylimidazo[1,2-a]pyridin-7-yl)methanone

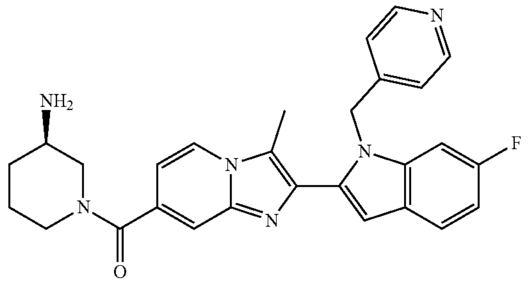 [SMILES: Cc1c(-c2cc3ccc(F)cc3n2Cc2ccncc2)nc2cc(C(=O)N3CCC[C@@H](N)C3)ccn12]

$^1$HNMR (400 MHz, DMSO-$d_6$) δ (ppm): 8.36 (s, 3H), 7.65 (s, 1H), 7.56 (s, 1H), 7.28 (d, J=8.4 Hz, 1H), 6.97-6.84 (m, 5H), 5.95 (s, 2H), 4.21-4.10 (m, 2H), 3.50 (m, 1H), 2.97 (bs, 2H), 2.64 (s, 3H), 1.83 (m, 2H), 1.67 (m, 2H), 1.23 (s, 2H). MS (ESI): Mass calcd. for $C_{28}H_{27}FN_6O$, 482; m/z found, 483.33 $[M+H]^+$.

Compound-69

(R)-(3-aminopiperidin-1-yl)(2-(6-fluoro-1-(pyridin-3-ylmethyl)-1H-indol-2-yl)-3-methylimidazo[1,2-a]pyridin-7-yl)methanone

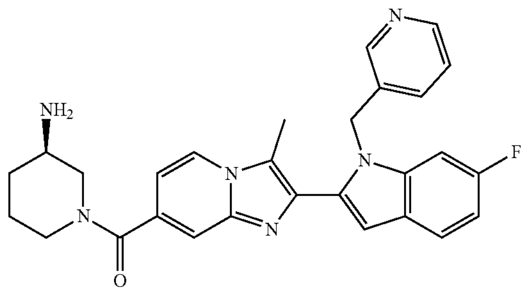 [SMILES: Cc1c(-c2cc3ccc(F)cc3n2Cc2cccnc2)nc2cc(C(=O)N3CCC[C@@H](N)C3)ccn12]

$^1$H NMR (400 MHz, DMSO-$d_6$) δ (ppm): 8.43 (d, J=7.0 Hz, 1H), 8.34 (d, J=3.8 Hz, 1H), 8.27 (s, 1H), 7.63 (t, J=6.2 Hz, 2H), 7.39-7.36 (m, 2H), 7.23-7.19 (m, 1H), 7.02 (d, J=7.0 Hz, 1H), 6.94 (t, J=6.3 Hz, 1H), 6.81 (s, 1H), 5.92 (s, 2H), 4.08 (bs, 2H), 3.5 (bs, 1H), 3.02 (bs, 1H), 2.85 (bs, 2H), 2.63 (s, 3H), 1.88-1.87 (m, 1H), 1.69 (bs, 1H), 1.48-1.45 (m, 1H), 1.35-1.33 (m, 1H), 1.22 (s, 1H). MS (ESI): Mass calcd. for $C_{28}H_{27}FN_6O$, 482.22; m/z found, 483.14$[M+H]^{+1}$.

Compound-70

(R)-(3-aminopiperidin-1-yl)(2-(6-fluoro-1-(3-methoxybenzyl)-1H-indol-2-yl)-3-methylimidazo[1,2-a]pyridin-7-yl)methanone

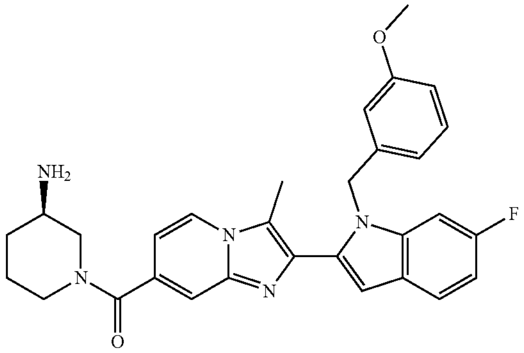 [SMILES: COc1cccc(Cn2c(-c3nc4cc(C(=O)N5CCC[C@@H](N)C5)ccn4c3C)cc3ccc(F)cc32)c1]

$^1$H NMR (400 MHz, DMSO-$d_6$) δ (ppm): 8.42 (d, J=7.96 Hz, 1H), 7.63-7.60 (m, 2H), 7.29 (d, J=9.36 Hz, 1H), 7.08 (t, J=8.12 Hz, 1H), 6.99 (d, J=6.4 Hz, 1H), 6.92 (t, J=8.3 Hz, 1H), 6.78 (s, 1H), 6.69 (d, J=7.04 Hz, 1H), 6.53 (s, 2H), 5.85 (s, 2H), 4.26-4.08 (m, 1H), 3.56 (s, 4H), 2.98 (m, 1H), 2.62 (s, 3H), 1.84-1.83 (m, 2H), 1.71-1.70 (m, 2H), 1.46-1.42 (m, 1H), 1.23 (s, 3H). MS (ESI): Mass calcd. for $C_{30}H_{30}FN_5O_2$, 511.24; m/z found, 512.38$[M+H]^{+1}$.

Compound-71

(R)-(3-aminopiperidin-1-yl)(2-(6-fluoro-1-(4-methoxybenzyl)-1H-indol-2-yl)-3-methylimidazo[1,2-a]pyridin-7-yl)methanone

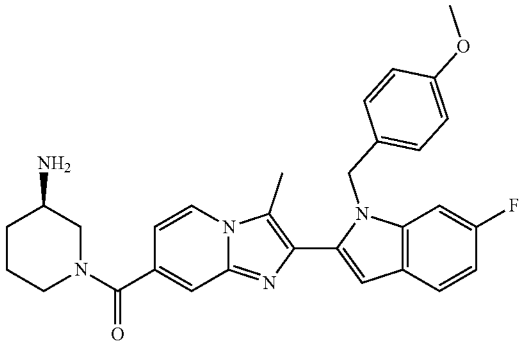 [SMILES: COc1ccc(Cn2c(-c3nc4cc(C(=O)N5CCC[C@@H](N)C5)ccn4c3C)cc3ccc(F)cc32)cc1]

$^1$H NMR (400 MHz, DMSO-$d_6$) δ (ppm): 8.43 (d, J=6.96 Hz, 1H), 7.62-7.58 (m, 2H), 7.29 (d, J=10.24 Hz, 1H), 7.00 (d, J=6.72 Hz, 1H), 6.94-6.88 (m, 3H), 6.75-6.72 (m, 3H), 5.79 (s, 2H), 4.27-4.08 (m, 1H), 3.62 (s, 3H), 2.98 (bs, 2H), 2.63 (m, 5H), 1.85-1.73 (m, 4H), 1.45-1.42 (m, 1H), 1.25-1.22 (m, 1H). MS (ESI): Mass calcd. for $C_{30}H_{30}FN_5O_2$, 511.24; m/z found, 512.25$[M+H]^{+1}$.

Compound-72

(R)-(3-aminopiperidin-1-yl)(2-(1-ethyl-6-fluoro-1H-indol-2-yl)-3-methylimidazo[1,2-a]pyridin-7-yl)methanone

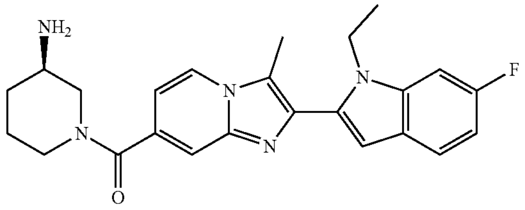 [SMILES: CCn1c(-c2nc3cc(C(=O)N4CCC[C@@H](N)C4)ccn3c2C)cc2ccc(F)cc21]

$^1$H NMR (400 MHz, DMSO-$d_6$) δ (ppm): 8.43 (d, J=6.96 Hz, 1H), 7.62-7.57 (m, 2H), 7.42 (d, J=9.2 Hz, 1H), 7.00 (d, J=6.52 Hz, 1H), 6.92 (t, J=8.24 Hz, 1H), 6.66 (s, 1H), 4.54 (d, J=7.04 Hz, 2H), 4.28-4.03 (m, 2H), 3.60 (bs, 1H), 3.00 (bs, 2H), 2.80 (m, 1H), 2.63 (s, 3H), 1.86-1.83 (m, 1H), 1.68-1.56 (m, 2H), 1.46-1.44 (m, 1H), 1.23-1.19 (s, 4H). MS (ESI): Mass calcd. for $C_{24}H_{26}FN_5O$, 419.21; m/z found, 420.31 $[M+H]^{+1}$.

Compound-73

(R)-(3-aminopiperidin-1-yl)(2-(6-fluoro-1-isobutyl-1H-indol-2-yl)-3-methylimidazo[1,2-a]pyridin-7-yl)methanone

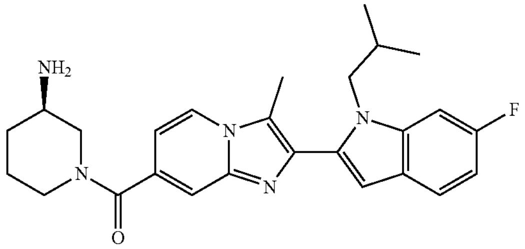 [SMILES: Cc1c(-c2cc3ccc(F)cc3n2CC(C)C)nc2cc(C(=O)N3CCC[C@@H](N)C3)ccn12]

$^1$H NMR (400 MHz, DMSO-$d_6$) δ (ppm): 8.42 (d, J=7.0 Hz, 1H), 7.63 (s, 1H), 7.60-7.56 (m, 1H), 7.43 (d, J=9.44 Hz, 1H), 7.00 (d, J=6.16 Hz, 1H), 6.91 (t, J=7.6 Hz, 1H), 6.66 (s, 1H), 4.41 (d, J=7.28 Hz, 2H), 4.27-4.11 (m, 1H), 3.00 (bs, 2H), 2.83-2.66 (m, 2H), 2.62 (s, 3H), 1.93-1.92 (m, 1H), 1.88 (s, 2H), 1.75-1.72 (m, 2H), 1.47-1.45 (m, 1H), 1.28-1.25 (m, 1H), 0.64 (d, J=6.64 Hz, 6H). MS (ESI): Mass calcd. for $C_{26}H_{30}FN_5O$, 447.24; m/z found, 448.45 $[M+H]^{+1}$.

Compound-74

(R)-(3-aminopiperidin-1-yl)(2-(5-fluoro-1-(pyridin-4-ylmethyl)-1H-indol-2-yl)-3-methylimidazo[1,2-a]pyridin-7-yl)methanone

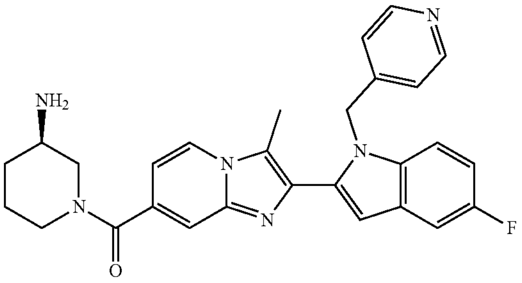 [SMILES: Cc1c(-c2cc3cc(F)ccc3n2Cc2ccncc2)nc2cc(C(=O)N3CCC[C@@H](N)C3)ccn12]

$^1$H NMR (400 MHz, DMSO-$d_6$) δ (ppm): 8.42 (d, J=6.9 Hz, 1H), 8.37 (d, J=4.8 Hz, 2H), 7.57 (s, 1H), 7.36-7.42 (m, 2H), 6.99-6.96 (m, 2H), 6.91 (d, J=4.7 Hz, 2H), 6.82 (s, 1H), 5.97 (s, 2H), 4.24-4.08 (m, 1H), 3.50 (m, 1H), 3.38 (m, 1H), 2.96 (bs, 1H), 2.65 (s, 3H), 1.82 (m, 2H), 1.71 (m, 1H), 1.60 (m, 1H), 1.41 (m, 1H), 1.23 (m, 2H). MS (ESI): Mass calcd. for $C_{28}H_{27}FN_6O$, 482.21; m/z found, 483.21[M+H]$^{+1}$.

Compound-75

(R)-(3-aminopiperidin-1-yl)(2-(5-fluoro-1-(4-methoxybenzyl)-1H-indol-2-yl)-3-methylimidazo[1,2-a]pyridin-7-yl)methanone

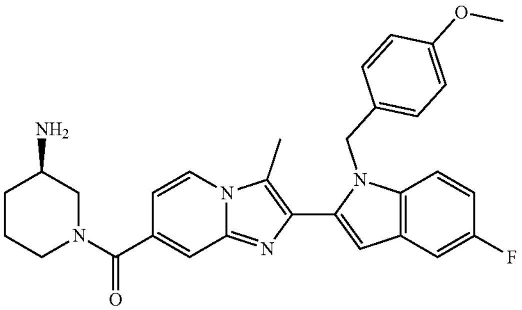 [SMILES: COc1ccc(Cn2c(-c3nc4cc(C(=O)N5CCC[C@@H](N)C5)ccn4c3C)cc3cc(F)ccc32)cc1]

$^1$H NMR (400 MHz, DMSO-$d_6$) δ (ppm): 8.44 (d, J=6.96 Hz, 1H), 7.63 (s, 1H), 7.44-7.41 (m, 1H), 7.36 (d, J=7.6 Hz, 1H), 7.01-6.91 (m, 4H), 6.74-6.72 (m, 3H), 5.82 (s, 2H), 4.27-4.10 (m, 1H), 3.62 (s, 3H), 2.97 (bs, 2H), 2.79 (m, 2H), 2.64 (s, 3H), 1.83 (m, 1H), 1.70 (m, 2H), 1.45-1.43 (m, 1H), 1.27-1.24 (m, 1H). MS (ESI): Mass calcd. for $C_{30}H_{30}FN_5O_2$, 511.32; m/z found, 512.32 [M+H]$^{+1}$.

Compound-76

(R)-(3-aminopiperidin-1-yl)(2-(5-fluoro-1-(4-fluorobenzyl)-1H-indol-2-yl)-3-methylimidazo[1,2-a]pyridin-7-yl)methanone

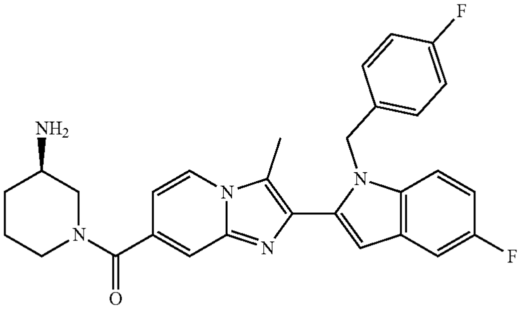 [SMILES: Cc1c(-c2cc3cc(F)ccc3n2Cc2ccc(F)cc2)nc2cc(C(=O)N3CCC[C@@H](N)C3)ccn12]

$^1$H NMR (400 MHz, DMSO-$d_6$) δ (ppm): 8.43 (d, J=6.92 Hz, 1H), 7.61 (s, 1H), 7.44-7.37 (m, 2H), 7.03-7.37 (m, 6H), 6.77 (s, 1H), 5.88 (s, 2H), 4.27-4.09 (m, 1H), 3.60 (bs, 1H), 2.98 (bs, 1H), 2.83 (bs, 1H), 2.64 (s, 3H), 1.85-1.83 (m, 1H), 1.69 (bs, 3H), 1.45-1.42 (m, 1H), 1.31-1.20 (m, 2H). MS (ESI): Mass calcd. for $C_{29}H_{27}F_2N_5O$, 499.22; m/z found, 500.38 [M+H]$^{+1}$.

Compound-77

(R)-(3-aminopiperidin-1-yl)(2-(7-chloro-1-(4-fluorobenzyl)-1H-indol-2-yl)-3-methylimidazo[1,2-a]pyridin-7-yl)methanone

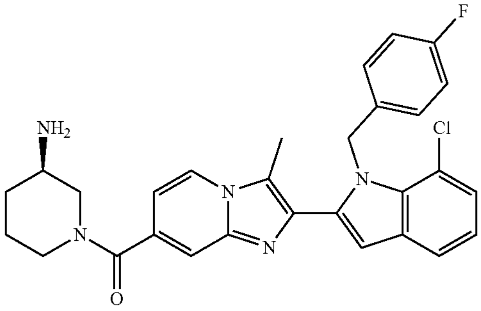 [SMILES: Cc1c(-c2cc3cccc(Cl)c3n2Cc2ccc(F)cc2)nc2cc(C(=O)N3CCC[C@@H](N)C3)ccn12]

$^1$H NMR (400 MHz, DMSO-$d_6$) δ (ppm): 8.41 (d, J=6.96 Hz, 1H), 7.63 (d, J=7.72 Hz, 1H), 7.61 (s, 1H), 7.16 (d, J=7.44 Hz, 1H), 7.08 (t, J=7.68 Hz, 1H), 6.99-6.97 (m, 3H), 6.89 (s, 1H), 6.73-6.70 (m, 2H), 6.15 (s, 2H), 4.26-4.09 (m, 2H), 2.98 (bs, 2H), 2.66 (m, 1H), 2.59 (s, 3H), 1.88 (s, 2H), 1.83 (m, 1H), 1.75-1.65 (m, 1H), 1.45-1.42 (m, 1H), 1.28-1.23 (m, 1H). MS (ESI): Mass calcd. for $C_{29}H_{27}ClFN_5O$, 515.19; m/z found, 516.18 [M+H]$^{+1}$.

Compound-78

Synthesis of (R)-(3-aminopiperidin-1-yl)(2-(1-(2,2-difluoroethyl)-1H-indol-2-yl)-3-methylimidazo[1,2-a]pyridin-7-yl)methanone Trifluoroacetic Acid Salt Scheme 13

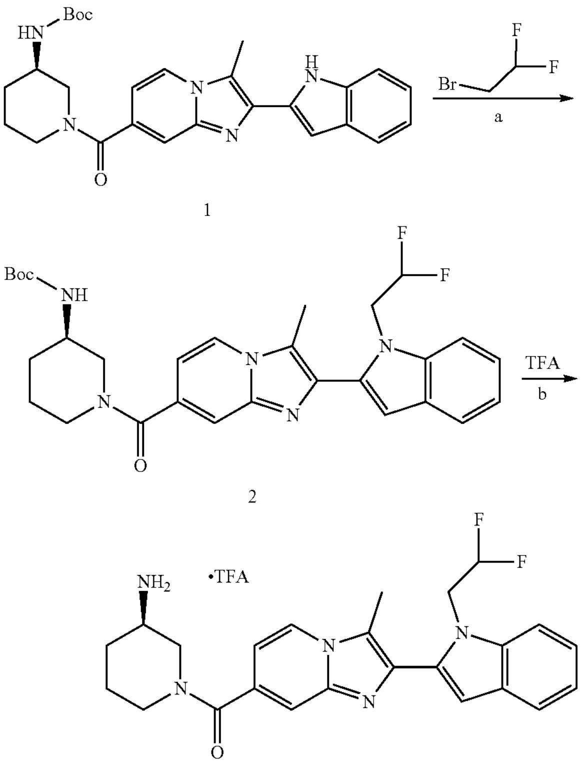

1

2

Compound 78

Step-1: Synthesis of tert-butyl (R)-(1-(2-(1-(2,2-difluoroethyl)-1H-indol-2-yl)-3-methylimidazo[1,2-a]pyridine-7-carbonyl)piperidin-3-yl)carbamate (2)

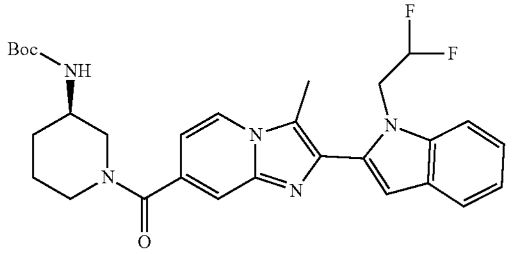 [SMILES: Cc1c(-c2cc3ccccc3n2CC(F)F)nc2cc(C(=O)N3CCC[C@@H](NC(=O)OC(C)(C)C)C3)ccn12]

To a stirred solution of tert-butyl (R)-(1-(2-(1H-indol-2-yl)-3-methylimidazo[1,2-a]pyridine-7-carbonyl)piperidin-3-yl)carbamate (1, 0.50 g, 1.05 mmol) in N, N-dimethylformamide (5.0 mL), cesium carbonate (1.7 g, 5.28 mmol) and 2-bromo-1,1-difluoroethane (0.22 mL, 2.64 mmol) were added at rt. The reaction mixture was stirred at 60° C. for 4 h. After completion of reaction, reaction mixture was diluted with water and extracted with ethyl acetate (200 mL×2). The combined organic extracts were washed with brine, dried over anhydrous sodium sulfate, filtered and concentrated under reduced pressure. The crude was purified by Combi-Flash using 12.0 g RediSep column and 70% ethyl acetate in hexane as eluent to afford the tert-butyl (R)-(1-(2-(1-(2,2-difluoroethyl)-1H-indol-2-yl)-3-methylimidazo[1,2-a]pyridine-7-carbonyl)piperidin-3-yl)carbamate as brown solid (2). Yield: 0.13 g (26%), MS (ESI): 537; m/z found 538.32 $[M+1]^{+1}$.

Step-2: Synthesis of (R)-(3-aminopiperidin-1-yl)(2-(1-(2,2-difluoroethyl)-1H-indol-2-yl)-3-methylimidazo[1,2-a]pyridin-7-yl)methanone Trifluoroacetic Acid Salt (Compound-78)

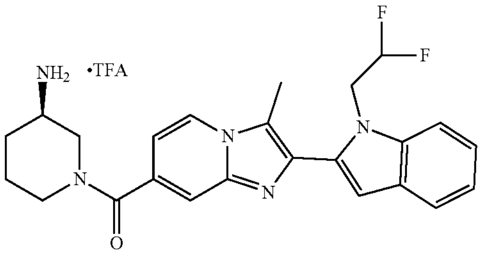 [SMILES: Cc1c(-c2cc3ccccc3n2CC(F)F)nc2cc(C(=O)N3CCC[C@@H](N)C3)ccn12]

To a stirred solution of tert-butyl (R)-(1-(2-(1-(2,2-difluoroethyl)-1H-indol-2-yl)-3-methylimidazo[1,2-a]pyridine-7-carbonyl)piperidin-3-yl)carbamate (2, 0.13 g, 0.24 mmol) in dichloromethane (2.0 mL), trifluoroacetic acid (1.0 mL) was added at 0° C. The reaction mixture was stirred at rt for 2 h. After completion of reaction, the reaction mixture was concentrated under reduced pressure to remove trifluoroacetic acid. The crude was dissolved in minimum volume of water and basified by saturated sodium bicarbonate solution and was extracted with dichloromethane. The organic layer was washed with brine, dried over anhydrous sodium sulfate and concentrated to get the crude. The crude was purified by prep HPLC to afford (R)-(3-aminopiperidin-1-yl) (2-(1-(2,2-difluoroethyl)-1H-indol-2-yl)-3-methylimidazo[1,2-a]pyridin-7-yl)methanone trifluoroacetic acid salt as white solid. Yield: 0.007 g (7%).

$^1$HNMR (400 MHz, DMSO-$d_6$) δ (ppm): 8.50 (d, J=6.9 Hz, 1H), 7.75 (s, 1H), 7.64-7.60 (m, 2H), 7.23 (t, J=7.3 Hz, 1H), 7.14-7.07 (m, 2H), 6.81 (s, 1H), 6.47 (t, J=55.6 Hz, 1H), 5.05 (t, J=14.4 Hz, 2H), 3.29 (m, 4H), 2.68 (s, 3H), 2.58 (s, 1H), 2.00 (m, 2H), 1.76 (m, 2H), 1.60-1.59 (m, 2H). MS (ESI): Mass calcd. for $C_{24}H_{25}F_2N_5O$, 437.23; m/z found, 438.27 $[M+1]^{+1}$.

Following compounds 79-82 were synthesized using the above procedure as exemplified for Compound-78.

Compound-79

(R)-(3-aminopiperidin-1-yl)(2-(1-((5-fluoropyridin-2-yl)methyl)-1H-indol-2-yl)-3-methylimidazo[1,2-a]pyridin-7-yl)methanone

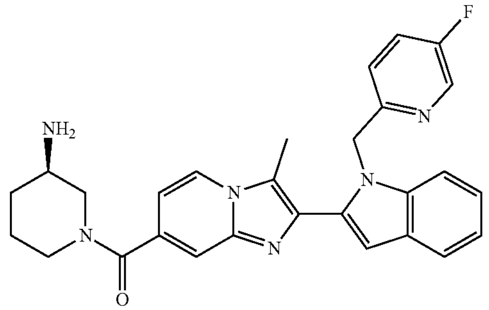

$^1$HNMR (400 MHz, DMSO-$d_6$) δ (ppm): 8.44 (s, 1H), 8.42 (s, 1H), 7.62 (t, J=7.96 Hz, 2H), 7.53 (t, J=9.00 Hz, 1H), 7.38 (d, J=7.92 Hz, 1H), 7.14-7.06 (m, 2H), 7.00 (d, J=6.96 Hz, 1H), 6.84-6.80 (m, 2H), 5.97 (s, 2H), 4.14 (s, 2H), 3.65 (bs, 1H), 3.12 (bs, 2H), 2.96 (m, 2H), 2.65 (s, 3H), 1.90-1.87 (m, 1H), 1.69 (bs, 1H), 1.48-1.46 (m, 1H), 1.36-1.23 (m, 1H). MS (ESI): Mass calcd. for $C_{28}H_{27}FN_6O$, 482; m/z found, 483.30 $[M+1]^{+1}$.

Compound-80

(R)-(3-aminopiperidin-1-yl)(2-(1-(4-fluorobenzyl)-6-methoxy-1H-indol-2-yl)-3-methylimidazo[1,2-a]pyridin-7-yl)methanone

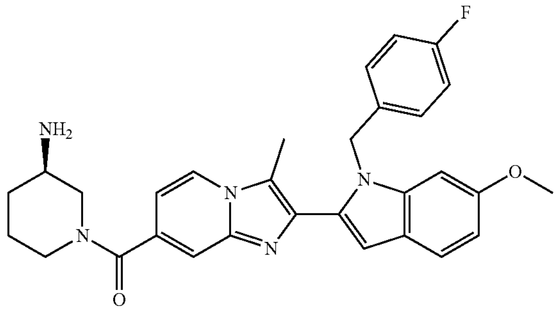 [SMILES: COc1ccc2cc(-c3nc4cc(C(=O)N5CCC[C@@H](N)C5)ccn4c3C)n(Cc3ccc(F)cc3)c2c1]

$^1$HNMR (400 MHz, DMSO-$d_6$) δ (ppm): 8.41 (d, J=6.96 Hz, 1H), 7.60 (s, 1H), 7.49 (d, J=8.6 Hz, 1H), 7.03-6.96 (m, 6H), 6.73 (d, J=8.56 Hz, 1H), 6.68 (s, 1H), 5.85 (s, 2H), 4.29-4.08 (m, 2H), 3.73 (s, 3H), 3.00 (bs, 2H), 2.71 (m, 1H), 2.61 (s, 3H), 1.8-1.84 (m, 2H), 1.68 (bs, 2H), 1.45-1.43 (m, 1H), 1.27-1.23 (m, 1H). MS (ESI): Mass calcd. for $C_{30}H_{30}FN_5O_2$, 511; found m/z 512.35 $[M+1]^+$.

Compound-81

(R)-(3-aminopiperidin-1-yl)(2-(1-(4-(hydroxymethyl)benzyl)-1H-indol-2-yl)-3-methylimidazo[1,2-a]pyridin-7-yl)methanone

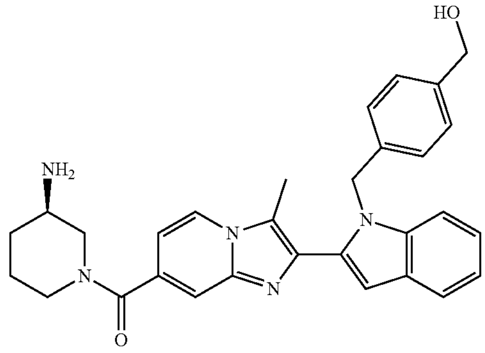 [SMILES: Cc1c(-c2cc3ccccc3n2Cc2ccc(CO)cc2)nc2cc(C(=O)N3CCC[C@@H](N)C3)ccn12]

$^1$H NMR (400 MHz, DMSO-$d_6$) δ (ppm): 8.42 (d, J=6.96 Hz, 1H), 7.61 (s, 2H), 7.38 (d, J=8.0 Hz, 1H), 7.11-7.03 (m, 4H), 6.99 (d, J=6.72 Hz, 1H), 6.91 (d, J=7.88 Hz, 2H), 6.76 (s, 1H), 5.89 (s, 2H), 5.02 (t, J=5.44 Hz, 1H), 4.33 (s, 2H), 4.09 (bs, 1H), 3.59 (bs, 1H), 3.00-2.95 (m, 2H), 2.65 (s, 3H), 2.17-1.99 (m, 2H), 1.83 (m, 1H), 1.69 (m, 1H), 1.45 (m, 1H), 1.26-1.24 (m, 1H). MS (ESI): Mass calcd. for $C_{30}H_{31}N_5O_2$, 493.25; m/z found, 494.39 $[M+H]^{+1}$.

Compound-82

(R)-(3-aminopiperidin-1-yl)(2-(1-isobutyl-6-methoxy-1H-indol-2-yl)-3-methylimidazo[1,2-a]pyridin-7-yl)methanone

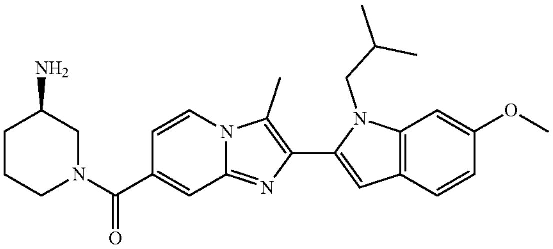 [SMILES: COc1ccc2cc(-c3nc4cc(C(=O)N5CCC[C@@H](N)C5)ccn4c3C)n(CC(C)C)c2c1]

$^1$H NMR (400 MHz, DMSO-$d_6$) δ (ppm): 8.40 (d, J=7.0 Hz, 1H), 7.61 (s, 1H), 7.46 (d, J=8.5 Hz, 1H), 7.04 (s, 1H), 6.98 (d, J=6.9 Hz, 1H), 6.72 (dd, J=8.7, 1.5 Hz, 1H), 6.55 (s, 1H), 4.41 (d, J=7.1 Hz, 2H), 4.11 (bs, 1H), 3.82 (s, 3H), 3.61 (bs, 1H), 2.98 (bs, 1H), 2.66 (m, 1H), 2.61 (s, 3H), 1.98-1.91 (m, 1H), 1.88 (m, 3H), 1.75-1.70 (m, 1H), 1.47-1.44 (m, 1H), 1.29-1.24 (m, 1H), 0.64 (d, J=6.6 Hz, 6H). MS (ESI): Mass calcd. for $C_{27}H_{33}N_5O_2$, 459.59; m/z found, 460.41 $[M+H]^{+1}$.

Compound-83

(R)-(3-aminopiperidin-1-yl)(2-(1-(2,2-difluoro-ethyl)-6-methoxy-1H-indol-2-yl)-3-methylimidazo[1,2-a]pyridin-7-yl)methanone

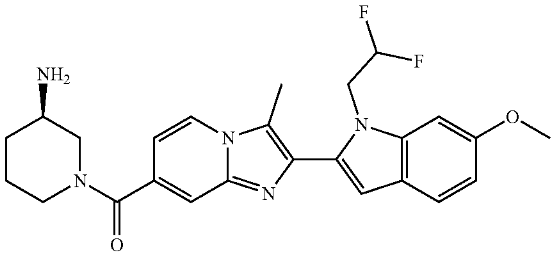 [SMILES: COc1ccc2cc(-c3nc4cc(C(=O)N5CCC[C@@H](N)C5)ccn4c3C)n(CC(F)F)c2c1]

$^1$H NMR (400 MHz, DMSO-d6) δ (ppm): 8.44 (d, J=7.0 Hz, 1H), 7.63 (s, 1H), 7.49 (d, J=8.5 Hz, 1H), 7.16 (s, 1H), 7.02 (d, J=6.8 Hz, 1H), 6.78-6.75 (m, 1H), 6.70 (s, 1H), 6.45 (t, J=56.0 Hz, 1H), 5.03 (t, J=14.5 Hz, 2H), 4.17 (bs, 1H), 3.83 (s, 3H), 3.04 (bs, 1H), 2.81 (m, 2H), 2.65 (s, 3H), 1.90 (m, 4H), 1.75-1.70 (m, 1H), 1.48-1.46 (m, 1H), 1.32-1.01 (m, 1H). MS (ESI): Mass calcd. for $C_{25}H_{27}F_2N_5O_2$, 467.52; m/z found, 468.17 $[M+H]^{+1}$.

Compound-84

(R)-(3-aminopiperidin-1-yl)(2-(5-fluoro-1-isobutyl-1H-indol-2-yl)-3-methylimidazo[1,2-a]pyridin-7-yl)methanone

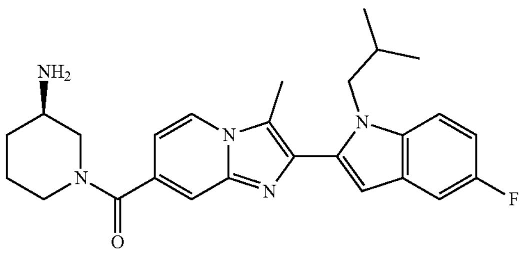 [SMILES: Cc1c(-c2cc3cc(F)ccc3n2CC(C)C)nc2cc(C(=O)N3CCC[C@@H](N)C3)ccn12]

$^1$H NMR (400 MHz, DMSO-$d_6$) δ (ppm): 8.42 (d, J=7.0 Hz, 1H), 7.63 (s, 1H), 7.58-7.55 (m, 1H), 7.36-7.33 (dd, J=2.3 Hz, 7.0 Hz, 1H), 7.03-6.99 (m, 2H), 6.64 (s, 1H), 4.44 (d, J=7.2 Hz, 2H), 4.28-4.11 (m, 1H), 3.60 (bs, 1H), 2.99-2.78 (m, 2H), 2.66 (m, 1H), 2.62 (s, 3H), 1.98-1.91 (m, 1H), 1.87-1.73 (m, 4H), 1.47-1.44 (m, 1H), 1.29-1.23 (m, 1H), 0.63 (d, J=6.6 Hz, 6H). MS (ESI): Mass calcd. for $C_{26}H_{30}FN_5O$, 447.24; m/z found, 448.39$[M+H]^{+1}$.

Compound-85

(R)-(3-aminopiperidin-1-yl)(2-(1-(4-fluoro-3-methoxybenzyl)-1H-indol-2-yl)-3-methylimidazo[1,2-a]pyridin-7-yl)methanone

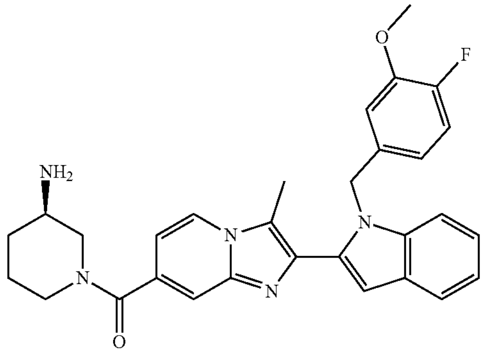 [SMILES: COc1cc(Cn2c(-c3nc4cc(C(=O)N5CCC[C@@H](N)C5)ccn4c3C)cc3ccccc32)ccc1F]

$^1$H NMR (400 MHz, DMSO-$d_6$) δ (ppm): 8.43 (d, J=7.0 Hz, 1H), 7.62 (d, J=7.9 Hz, 2H), 7.47 (d, J=8.0 Hz, 1H), 7.13 (t, J=7.84 Hz, 1H), 7.06 (t, J=7.32 Hz, 1H), 7.01-6.96 (m, 3H), 6.76 (s, 1H), 6.49 (bs, 1H), 5.83 (s, 2H), 4.29-4.10 (m, 1H), 3.62 (s, 3H), 2.98 (bs, 2H), 2.63 (s, 3H), 1.82 (m, 1H), 1.66 (m, 3H), 1.45 (m, 1H), 1.23 (m, 3H). MS (ESI): Mass calcd. for $C_{26}H_{30}FN_5O$, 511.24; m/z found, 512.48$[M+H]^{+1}$.

Compound-86

(R)-(3-aminopiperidin-1-yl)(2-(1-(cyclopropylm-ethyl)-6-methoxy-1H-indol-2-yl)-3-(methoxymethyl)imidazo[1,2-a]pyridin-7-yl)methanone Scheme-14

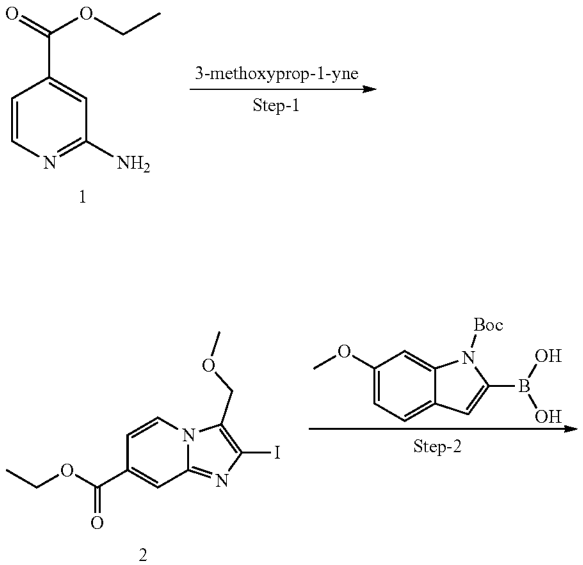

-continued

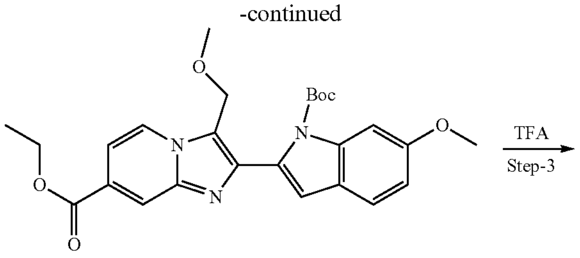

3

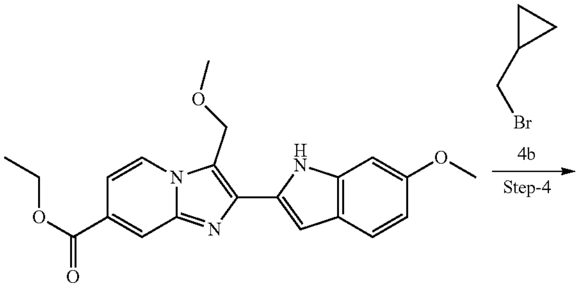

4

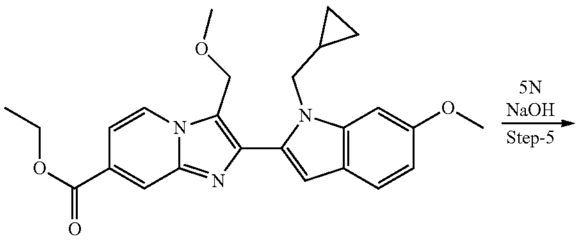

5

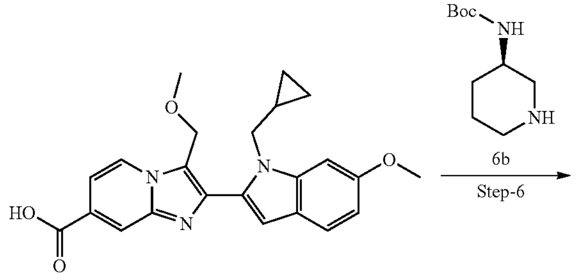

6

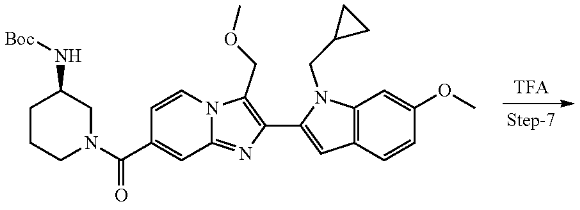

7

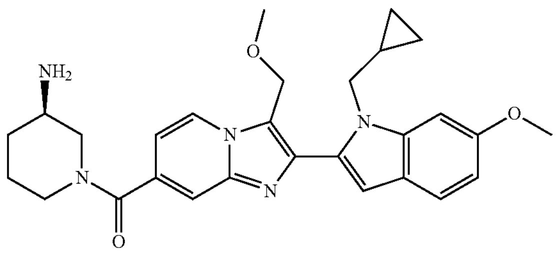

Compound 86

Step-1: Synthesis of ethyl-2-iodo-3-(methoxymethyl)imidazo[1,2-a]pyridine-7-carboxylate (2)

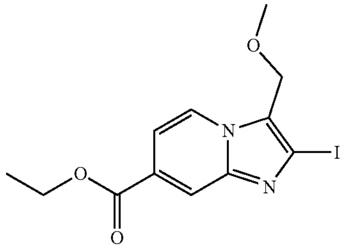 [SMILES: CCOC(=O)c1ccn2c(COC)c(I)nc2c1]

To a stirred solution of methyl-2-aminoisonicotinate (1, 5.0 g, 30.0 mmol) and 3-methoxyprop-1-yne (2.53 g, 36.1 mmol) in 1, 2-dichlorobenzene (100 mL), were added iodine (7.63 g, 30.0 mol) and copper (II) acetate (0.54 g, 3.0 mmol). The reaction mixture was filled with 5 kg/$cm^2$ oxygen in steel bomb and stirred at 120° C. for 12 h. After completion of reaction, The reaction mixture directly passed through 100-200 mesh size silica gel and eluted with hexane (2000 m L) followed by 20% ethyl acetate in hexane as eluent to afford ethyl 2-iodo-3-(methoxymethyl)imidazo[1,2-a]pyridine-7-carboxylate (2) as white solid. Yield 7.40 g (68.1%). MS (ESI): Mass 360.15; m/z found, 361.01 $[M+H]^{+1}$.

Step-2: Synthesis of ethyl-2-(1-(tert-butoxycarbonyl)-6-methoxy-1H-indol-2-yl)-3-(methoxymethyl) imidazo[1,2-a]pyridine-7-carboxylate (3)

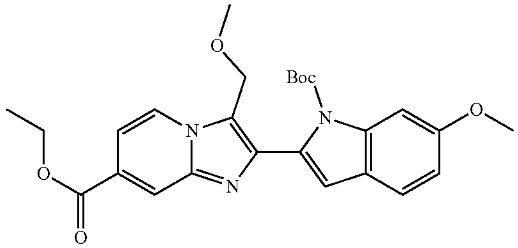 [SMILES: CCOC(=O)c1ccn2c(COC)c(-c3cc4ccc(OC)cc4n3C(=O)OC(C)(C)C)nc2c1]

To a solution of ethyl-2-iodo-3-(methoxymethyl)imidazo [1,2-a]pyridine-7-carboxylate (2, 0.8 g, 2.22 mmol) and (1-(tert-butoxycarbonyl)-6-methoxy-1H-indol-2-yl)boronic acid (0.97 g, 3.33 mmol) in 1, 4 dioxane (40 mL) and water (8 mL), was added potassium phosphate (1.4 g, 6.66 mmol) and the mixture was purged with argon gas for 20 min. Then added tetrakis(triphenylphosphine)palladium(0) (0.12 g, 0.11 mmol) and continued purging for 5 min. The reaction mixture was stirred for 4 h at 90° C. in sealed tube. After completion of reaction, water (100 mL) was added and extracted with ethyl acetate (200 mL×2). Organic layer was washed with saturated ammonium chloride solution, brine, dried over sodium sulfate, filtered and concentrated under reduced pressure. The crude was purified CombiFlash using 40.0 g RediSep column and 30-40% ethyl acetate in hexane as eluent to afford ethyl-2-(1-(tert-butoxycarbonyl)-6-methoxy-1H-indol-2-yl)-3-(methoxymethyl)imidazo[1,2-a] pyridine-7-carboxylate (3) as oily liquid. Yield 0.8 g (80%). MS (ESI): Mass 479.21; m/z found, 480.19 $[M+H]^+$.

Step-3: Synthesis of ethyl-2-(6-methoxy-1H-indol-2-yl)-3-(methoxymethyl)imidazo[1,2-a]pyridine-7-carboxylate (4)

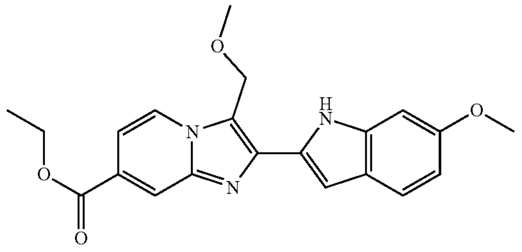 [SMILES: CCOC(=O)c1ccn2c(COC)c(-c3cc4ccc(OC)cc4[nH]3)nc2c1]

To a solution of ethyl-2-(1-(tert-butoxycarbonyl)-6-methoxy-1H-indol-2-yl)-3-(methoxymethyl)imidazo[1,2-a]pyridine-7-carboxylate (3, 0.8 g, 1.64 mmol) in dichloromethane (50 mL) was added trifluoroacetic acid (8.0 mL) at 0° C. The reaction mixture was stirred for 5 h at room temperature. After completion of reaction, mixture was concentrated under vacuum and neutralized using aqueous sodium bicarbonate. The aqueous phase was then extracted with dichloromethane (2×20 mL). Organic layer was dried over sodium sulfate and concentrated to afford ethyl-2-(6-methoxy-1H-indol-2-yl)-3-(methoxymethyl)imidazo[1,2-a]pyridine-7-carboxylate (4) as pale yellow solid. Yield 0.55 g. MS (ESI): Mass 379.15; m/z found, 380.24 $[M+H]^{+1}$.

Step 4: Synthesis of ethyl 2-(1-(cyclopropylmethyl)-6-methoxy-1H-indol-2-yl)-3-(methoxymethyl)imidazo[1,2-a]pyridine-7-carboxylate (5)

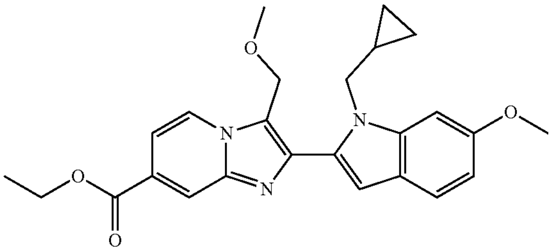 [SMILES: CCOC(=O)c1ccn2c(COC)c(-c3cc4ccc(OC)cc4n3CC3CC3)nc2c1]

To a stirred solution of ethyl-2-(6-methoxy-1H-indol-2-yl)-3-(methoxymethyl)imidazo[1,2-a]pyridine-7-carboxylate (4, 0.5 g, 1.32 mmol) in N,N, dimethylformamide (10 mL), was added cesium carbonate (1.23 g, 3.95 mmol) and (bromomethyl)cyclopropane (0.21 g, 1.58 mmol). The reaction mixture was stirred at 60° C. for 3 h. After completion of reaction, the reaction mixture was cooled to room temperature and diluted with ethyl acetate (100 mL×3). The organic phase was washed with water, brine, dried over anhydrous sodium sulfate and concentrated under reduced pressure to afford the crude compound. The crude was purified CombiFlash using 40.0 g RediSep column and 10-15% ethyl acetate in hexane as eluent to afford ethyl-2-(1-(cyclopropylmethyl)-6-methoxy-1H-indol-2-yl)-3-(methoxymethyl)imidazo[1,2-a]pyridine-7-carboxylate (5) as yellow solid. Yield: 0.30 g (52%). MS (ESI): 433.20; m/z found, 434.14 $[M+H]^{+1}$.

Step 5: Synthesis of 2-(1-(cyclopropylmethyl)-6-methoxy-1H-indol-2-yl)-3-(methoxymethyl)imidazo[1,2-a]pyridine-7-carboxylic acid (6)

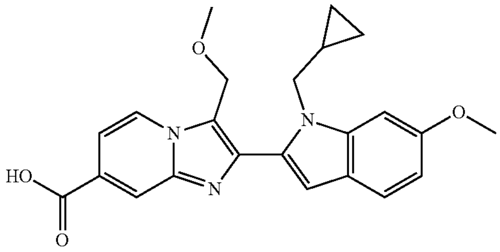 [SMILES: COCc1c(-c2cc3ccc(OC)cc3n2CC2CC2)nc2cc(C(=O)O)ccn12]

To a stirred solution of ethyl-2-(1-(cyclopropylmethyl)-6-methoxy-1H-indol-2-yl)-3-(methoxymethyl)imidazo[1,2-a]pyridine-7-carboxylate (5, 0.30 g, 0.629 mmol) in tetrahydrofuran (10 mL) were added methanol (5 mL) and 5N sodium hydroxide solution in water (5 mL) and the resulting mixture was heated to 60° C. for 3 h. After completion of reaction, the reaction mixture was evaporated under reduced pressure and acidified up to pH 2-3 with citric acid at 0° C. The crude was extracted with dichloromethane (10 mL×2), washed with brine, dried over anhydrous sodium sulfate, filtered and concentrated under reduced pressure to afford 2-(1-(cyclopropylmethyl)-6-methoxy-1H-indol-2-yl)-3-(methoxymethyl)imidazo[1,2-a]pyridine-7-carboxylic acid (6) as yellow solid. Yield: 0.20 g (71%). MS (ESI): 405.17; m/z found, 404.12 $[M-H]^{-1}$.

Step 6: Synthesis of tert-butyl (R)-(1-(2-(1-(cyclopropylmethyl)-6-methoxy-1H-indol-2-yl)-3-(methoxymethyl)imidazo[1,2-a]pyridine-7-carbonyl)piperidin-3-yl)carbamate (7)

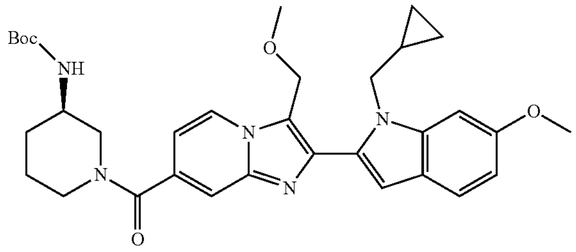 [SMILES: COCc1c(-c2cc3ccc(OC)cc3n2CC2CC2)nc2cc(C(=O)N3CCC[C@@H](NC(=O)OC(C)(C)C)C3)ccn12]

To a stirred solution of 2-(1-(cyclopropylmethyl)-6-methoxy-1H-indol-2-yl)-3-(methoxymethyl)imidazo[1,2-a]pyridine-7-carboxylic acid (6, 0.20 g, 0.508 mmol) in dichloromethane (10 mL) were added tert-butyl (R)-piperidin-3-ylcarbamate (0.122 g, 0.61 mmol), triethylamine (0.22 mL, 1.57 mmol) and propyl phosphonic anhydride in 50% ethyl acetate (1.2 mL, 1.62 mmol) at 0° C. The reaction mixture was allowed to stir at room temperature for 1 h. After completion of reaction, the reaction mixture was quenched with sodium bicarbonate solution (20 mL) and extracted with dichloromethane (20 mL×2). The combined organic layers were washed with brine, dried over anhydrous sodium sulfate, filtered and concentrated under reduced pressure to get crude product. The crude was purified by CombiFlash using 12.0 g RediSep column and 2-5% methanol in dichloromethane as eluent to afford tert-butyl (R)-(1-

(2-(1-(cyclopropylmethyl)-6-methoxy-1H-indol-2-yl)-3-(methoxymethyl)imidazo[1,2-a]pyridine-7-carbonyl) piperidin-3-yl)carbamate (7) as off-white solid. Yield: 0.14 g (48%). MS (ESI): 587.31; m/z found, 588.27 $[M+H]^{+1}$.

Step 7: Synthesis of (R)-(3-aminopiperidin-1-yl)(2-(1-(cyclopropylmethyl)-6-methoxy-1H-indol-2-yl)-3-(methoxymethyl)imidazo[1,2-a]pyridin-7-yl) methanone (Example 86)

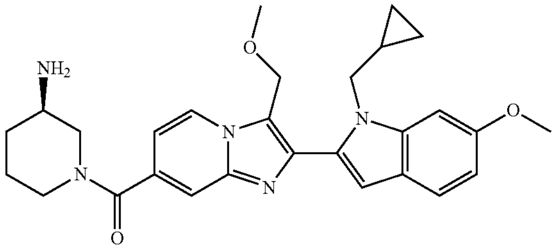 [SMILES: COCc1c(-c2cc3ccc(OC)cc3n2CC2CC2)nc2cc(C(=O)N3CCC[C@@H](N)C3)ccn12]

To a stirred solution of mixture of tert-butyl (R)-(1-(2-(1-(cyclopropylmethyl)-6-methoxy-1H-indol-2-yl)-3-(methoxymethyl)imidazo[1,2-a]pyridine-7-carbonyl)piperidin-3-yl)carbamate (7, 0.14 g, 0.24 mmol) in dichloromethane (5 mL), trifluoroacetic acid (1.0 mL) was added at 0° C. The reaction mixture was stirred at room temperature for 2 h. After completion of reaction, the reaction mixture was concentrated under reduced pressure to remove trifluoroacetic acid. The crude was dissolved in minimum volume of water and basified by saturated sodium bicarbonate solution (20 mL) and was extracted with dichloromethane (20 mL×2). The organic layer was washed with brine, dried over anhydrous sodium sulfate and concentrated and was purified by reverse prep to afford (R)-(3-aminopiperidin-1-yl)(2-(1-(cyclopropylmethyl)-6-methoxy-1H-indol-2-yl)-3-(methoxymethyl)imidazo[1,2-a]pyridin-7-yl) methanone as yellow solid. Yield: 0.03 g (30%).

$^1$HNMR (400 MHz, DMSO-d6) δ (ppm): 8.54 (d, J=7.0 Hz, 1H), 7.66 (s, 1H), 7.48 (d, J=8.56 Hz, 1H), 7.1 (s, 1H), 7.03 (d, J=7.21 Hz, 1H), 6.72 (d, J=8.56 Hz, 1H), 6.58 (s, 1H), 4.88 (s, 2H), 4.49 (d, J=6.64 Hz, 2H), 4.28-4.09 (m, 1H), 3.83 (s, 3H), 3.76-3.53 (m, 1H), 3.34-3.32 (m, 4H), 3.00-2.85 (m, 2H), 2.65 (s, 1H), 1.83 (m, 1H), 1.72 (bs, 2H), 1.47-1.44 (m, 1H), 1.26-1.23 (m, 1H), 1.09 (m, 1H), 0.27 (d, J=7.64 Hz, 2H), 0.15 (d, J=3.96 Hz, 2H). MS (ESI): Mass claudicated for $C_{28}H_{33}N_5O_3$, 487.26; m/z found, 488.41 $[M+H]^{+1}$.

SYNTHESIS OF INTERMEDIATES

Synthesis of 2-bromo-1-(3-ethylbenzo[b]thiophen-2-yl)propan-1-one (Intermediate for Compound-19)

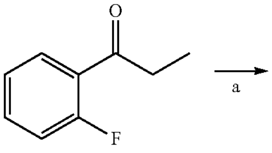

1

-continued

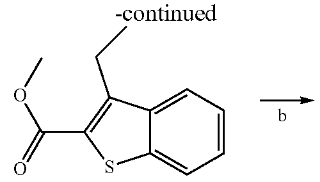

2

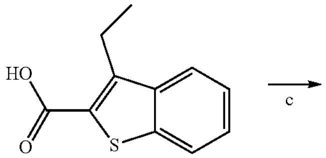

3

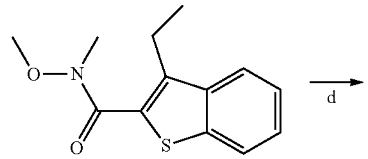

4

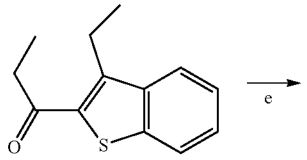

5

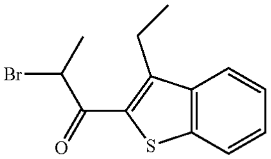

6

Step-1: Preparation of Methyl 3-ethylbenzo[b]thiophene-2-carboxylate (2)

2

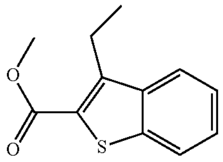

To a suspension of NaH (60% in oil, 1.7 g, 42.7 mmol) in THF (50 mL) was added methyl 2-mercaptoacetate (4.1 g, 39.4 mmol) at rt and stirred for 30 min. To the reaction was added solution of 1-(2-fluorophenyl)propan-1-one (1, 5.0 g, 32.8 mmol) in THF and allowed to reflux for 16 h (Reaction condition a). Completion of the reaction was monitored by LCMS since starting material and product come very close in TLC (2:8 EtOAc:Hexane). The reaction mixture was cooled to rt, diluted with EtOAc (100 mL) and washed with 1N NaOH (20 mL) and water (20 mL). Organic layer was dried over sodium sulphate, filtered and concentrated under reduced pressure. The obtained crude is purified by column chromatography to obtain the product as brown oil (2) (4.0 g, 57.14% Yield). MS (ESI): Mass calcd. for $C_{12}H_{12}O_2S$, 220.06; m/z found, 221.1 $(M+H)^+$.

Step 2: Preparation of 3-Ethylbenzo[b]thiophene-2-carboxylic Acid (3)

3

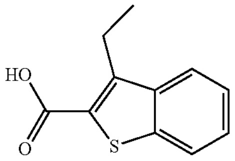

To a solution of methyl 3-ethylbenzo[b]thiophene-2-carboxylate (2, 4.0 g, 18.1 mmol) in THF:MeOH:$H_2O$ (8:2:1, 40 mL) was added LiOH (1.7 g, 72.7 mmol) at 0° C. and stirred at rt for 3 h (Reaction condition b). The reaction mixture was evaporated, dissolved in water (20 mL) and acidified using saturated citric acid solution. The white precipitate formed was collected by filtration and dried to obtain the product (3) (2.7 g, 73% Yield). MS (ESI): Mass calcd. for $C_{11}H_{10}O_2S$, 206.04; m/z found, 207.1 $(M+H)^+$.

Step 3: Preparation of 3-Ethyl-N-methoxy-N-methylbenzo[b]thiophene-2-carboxamide (4)

4

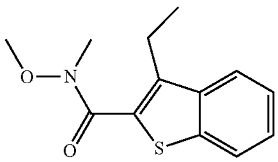

To a stirred solution of 3-ethylbenzo[b]thiophene-2-carboxylic acid (3, 2.5 g, 12.1 mmol) and N,O-dimethylhydroxylamine hydrochloride (1.8 g, 18.2 mmol) in DCM (30 mL), was added triethylamine (8.4 mL, 60.6 mmol), HOBt (2.4 g, 18.2 mmol) followed by EDC.HCl (2.8 g, 18.2 mmol) at 0° C. and the reaction mixture was stirred at rt for 4 h (Reaction condition c). To the reaction mixture, was added water (50 ml) and DCM layer was separated. The organic layer was washed with brine solution (20 mL), dried and evaporated to give the crude product. The crude was purified by gradient column chromatography using 20-25% ethyl acetate in hexane to afford the product as off white solid (4) (2.15 g, 72% Yield). MS (ESI): Mass calcd. for $C_{13}H_{15}NO_2S$, 249.08; m/z found, 250.2 $[M+H]^+$.

Step 4: Preparation of 1-(3-Ethylbenzo[b]thiophen-2-yl)propan-1-one (5)

5

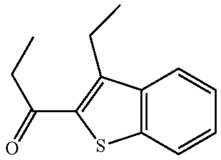

To a stirred solution of 3-ethyl-N-methoxy-N-methylbenzo[b]thiophene-2-carboxamide (4, 2.1 g, 8.43 mmol) in THF (20 mL), was added 3M solution of ethyl magnesium bromide (8.4 mL, 25.3 mmol) drop wise at 0° C. and the reaction mixture was stirred at rt for 16 h (Reaction condition d). The reaction mixture was quenched with saturated $NH_4Cl$ (10 mL) solution at 0° C. and extracted with EtOAc (50 mL). The organic layer was evaporated, purified by flash column chromatography to give the tittle compound as brown oil (5) (1.7 g, 92% Yield). MS (ESI): Mass calcd. for $C_{13}H_{14}OS$, 218.08; m/z found, 219.1 $[M+H]^+$.

Step 5: Preparation of 2-Bromo-1-(3-ethylbenzo[b]thiophen-2-yl)propan-1-one (6)

6

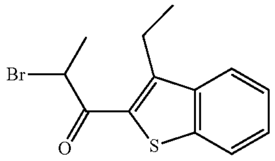

To the stirred solution of 1-(3-ethylbenzo[b]thiophen-2-yl)propan-1-one (5, 0.5 g, 2.29 mmol) in THF (5 mL), was added trimethylphenylammonium tribromide (0.95 g, 2.52 mmol) and stirred at 80° C. for 3 h (Reaction condition e). The reaction mixture was cooled to rt, added water (20 mL) and compound was extracted with EtOAc (50 mL). Organic extract was washed with saturated $NaHCO_3$ (20 mL), dried over sodium sulfate and evaporated. Crude was purified by column chromatography using 0-25% EtOAc in hexane to afford the product as pale yellow gummy solid (6) (0.6 g, 88% Yield). MS (ESI): mass calcd. for $C_{13}H_{13}BrOS$, 295.99; m/z found, 297.0 $(M+H)^+$.

Rest of the steps are similar to that given for Compound-1 (Step 4 onwards).

Synthesis of 1-(4-chlorobenzyl)-1H-indole-2-carbaldehyde (Intermediate for Compound-20)

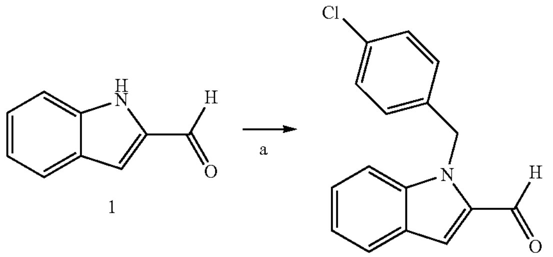

1 2

To a stirred solution 1H-pyrrolo[2,3-b]pyridine-2-carbaldehyde (1, 0.5 g, 3.44 mmol) in DMF (10 mL), was added potassium carbonate (1.42 g, 10.3 mmol) followed by 1-(bromomethyl)-4-chlorobenzene (0.84 g, 4.13 mmol) and the reaction mixture was stirred at same temperature for 4 h (Reaction condition a). The reaction mixture was quenched with water and extracted with ethyl acetate (30 mL×2). Combined organic extracts were washed with brine, dried over sodium sulfate, filtered and evaporated to give the crude product. Crude residue was purified by gradient column chromatography using 10-15% ethyl acetate in hexane to give the product as off white solid (2) (0.86 g, 93.4%, Yield). $^1$HNMR (400 MHz, DMSO) δ (ppm): 9.9 (s, 1H), 7.79 (d, J=8 Hz, 1H), 7.60-7.56 (m, 2H), 7.39-7.36 (m, 1H), 7.31 (d, J=8 Hz, 2H), 7.18-7.14 (m, 1H), 7.06 (d, J=8 Hz, 2H), 5.8 (s, 2H). MS (ESI): Mass calcd. for $C_{16}H_{12}ClNO$, 269.73; m/z found, 270.1 $(M+H)^+$.

Following compound below was synthesized using the above procedure as exemplified for 1-(4-chlorobenzyl)-1H-indole-2-carbaldehyde (Intermediate for Compound-20).

Synthesis of 1-(2-fluorobenzyl)-1H-indole-2-carbaldehyde (Intermediate for Compound-21)

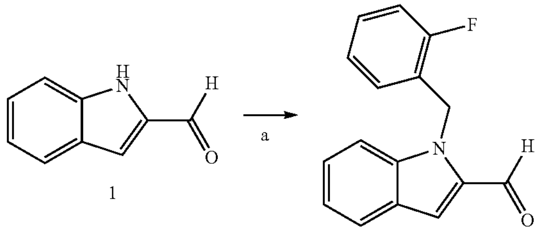

1

2

To a stirred solution 1H-indole-2-carbaldehyde (1, 1 g, 6.89 mmol) in DMF (15 mL), was added potassium carbonate (2.85 g, 20.6 mmol) followed by 1-(chloromethyl)-2-fluorobenzene (1.19 g, 8.26 mmol) and the reaction mixture was stirred at same temperature for 4 h (Reaction condition a). Reaction mixture was poured into crushed ice, diluted with water and extracted with ethyl acetate. Organic layer was dried over anhydrous sodium sulfate, evaporated under vacuum to give the crude. Crude was purified by flash column chromatography using ethyl acetate and hexane to afford the 1-(2-fluorobenzyl)-1H-indole-2-carbaldehyde as grey color solid (2) (Yield: 1.8 g, 96.5%). $^1$HNMR (400 MHz, DMSO) δ (ppm): 9.90 (s, 1H), 7.81 (d, J=8 Hz, 1H), 7.58-7.54 (m, 2H), 7.40-7.36 (m, 1H), 7.28-7.15 (m, 3H), 7.01-6.97 (m, 1H), 6.55-6.51 (m, 1H), 5.88 (s, 2H). MS (ESI): mass calcd. for $C_{16}H_{12}FNO$, 253.09; m/z found, 254.0 $(M+H)^+$.

Synthesis of 1-ethyl-5-phenyl-1H-pyrrole-2-carbaldehyde (Intermediate for Compound-22)

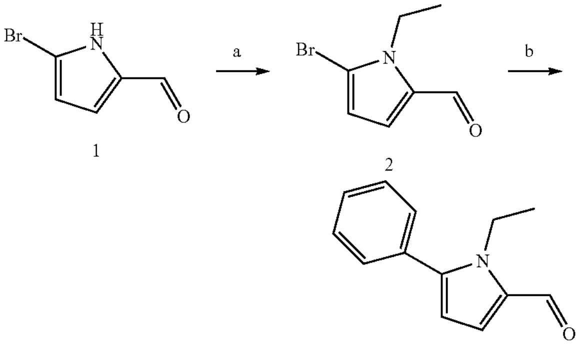

1

2

3

Step 1: Preparation of 5-Bromo-1-ethyl-1H-pyrrole-2-carbaldehyde (2)

2

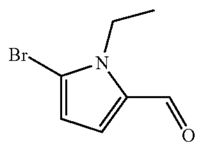

To a stirred solution 5-bromo-1H-pyrrole-2-carbaldehyde (1, 1 g, 5.7 mmol) in DMF (15 mL), was added potassium carbonate (3.14 g, 22 mmol) followed by ethyl iodide (1.33 g, 8.6 mmol) and the reaction mixture was stirred at same temperature for 16 h (Reaction condition a). Reaction mixture was diluted with water and extracted with ethyl acetate. Organic layer was dried over anhydrous sodium sulfate and evaporated under vacuum to obtain the crude. Crude was purified by flash column chromatography using ethylacetate in Hexane as an elutant to afford the title compound as orange color liquid (0.9 g, 77.58% Yield) (2) MS (ESI): Mass calcd. for $C_7H_8BrNO$, 202.05; m/z found 204.0 $(M+2H)^+$.

Step 2: Preparation of 1-Ethyl-5-phenyl-1H-pyrrole-2-carbaldehyde (3)

3

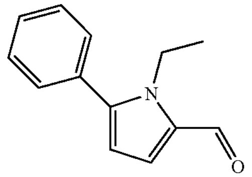

To a stirred solution of 5-bromo-1-ethyl-1H-pyrrole-2-carbaldehyde (2, 0.9 g, 4.45 mmol), in 1,4-dioxane in a seal tube was added phenyl boronic acid (0.8 g, 6.67 mmol), potassium carbonate (1.84 g, 13.3 mmol) then the reaction mixture was purged with nitrogen. After purging for few minutes, [1,1'-Bis(diphenylphosphino)ferrocene]dichloropalladium(II) complex with dichloromethane (0.18 g, 0.22 mmol) was added and then heated to 80° C. for 12 h (Reaction condition b). After completion of the reaction, reaction mixture was filtered through celite bed, filtrates were evaporated to dryness to give the crude product. The crude was purified by gradient column chromatography using 12% ethyl acetate in hexane to give the title compound as pale yellow colour solid (3) (0.52 g, 59.09% Yield). MS (ESI): Mass calcd. for $C_{13}H_{13}NO$, 199.25; m/z found 200.0 $(M+H)^+$.

Synthesis of 1-(cyclopropylmethyl)-6-methoxy-1H-indole-2-carbaldehyde (Intermediate for Compound-23)

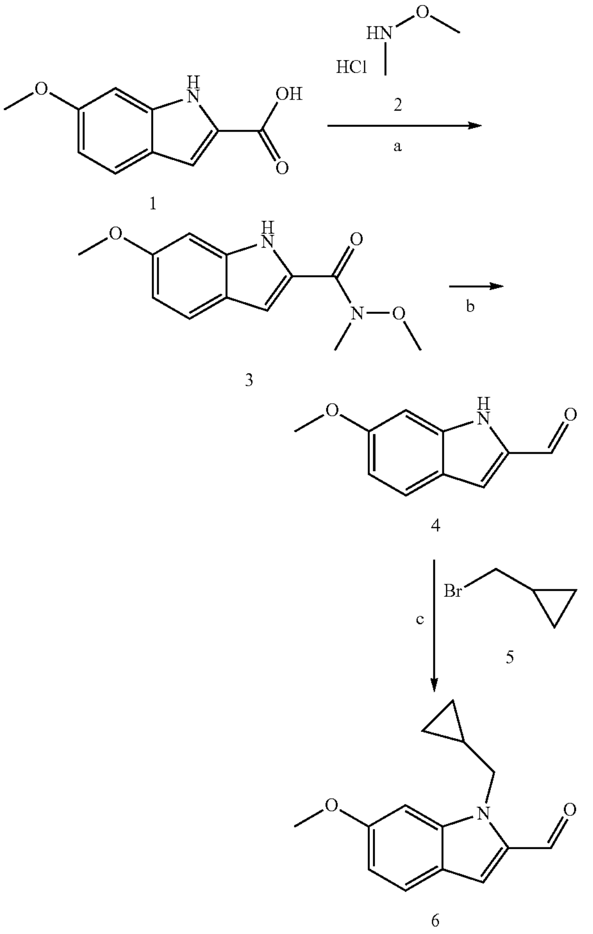

Step-1: Preparation of N,6-dimethoxy-N-methyl-1H-indole-2-carboxamide (3)

3

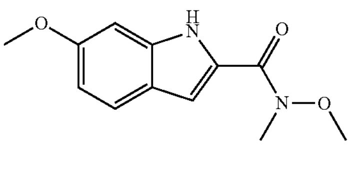

To a stirred solution 6-methoxy-1H-indole-2-carboxylic acid (1, 3 g, 15.69 mmol) in DCM (20 mL), was added N,O-dimethylhydroxylamine hydrochloride (2, 3 g, 31.38 mmol), followed by hydroxybenzotriazole (3.6 g, 23.5 mmol), N-(3-dimethylaminopropyl)-N'-ethylcarbodiimide hydrochloride (4.5 g, 23.5 mmol) and TEA (11.3 mL, 120.7 mmol), and the reaction mixture was stirred at same temperature for 5 h (Reaction condition a). The reaction mixture was quenched with water, extracted with ethyl acetate (50 mL×2). Combined organic extracts were washed with brine, dried over sodium sulfate, filtered and evaporated to get crude product. Crude residue was purified by gradient column chromatography using 25-30% ethyl acetate in hexane to get the product as beige colour solid (3) (Yield: 75%, 0.86 g). MS (ESI): mass calcd. for $C_{12}H_{14}N_2O_3$, 234.10; m/z found, 235 $(M+H)^+$.

Step-2: Preparation of 6-methoxy-1H-indole-2-carbaldehyde (4)

4

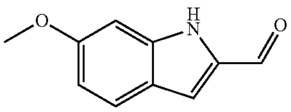

To a stirred solution of N,6-dimethoxy-N-methyl-1H-indole-2-carboxamide (3, 2 g, 8.54 mmol) in THF (20 mL), was added LAH 1M soln. in THF (12.8 mL, 12.75 mmol) slowly under cooling condition, and then the reaction mixture was allowed to stir at rt for 1 h (Reaction condition b). The reaction mixture was quenched with ammonium chloride, extracted with ethyl acetate (50 mL×2). Combined organic extracts were washed with brine, dried over sodium sulfate, filtered and evaporated to get crude product. Crude residue was purified by gradient column chromatography using 5-10% ethyl acetate in hexane to get the product as white solid (4) (Yield: 60%, 0.9 g). MS (ESI): mass calcd. for $C_{10}H_9NO_2$, 175.06; m/z found, 176.1 $(M+H)^+$.

Step-3: Preparation of 1-(cyclopropylmethyl)-6-methoxy-1H-indole-2-carbaldehyde (6)

6

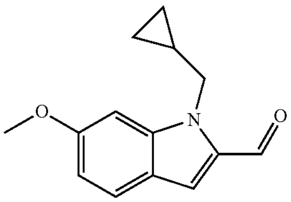

To a stirred solution of 6-methoxy-1H-indole-2-carbaldehyde (4, 0.28 g, 1.6 mmol) in DMF (5 mL), was added potassium carbonate (1.1 g, 8 mmol) followed by (bromomethyl)cyclopropane (5, 0.23 mL, 1.72 mmol) and the reaction mixture was stirred at same temperature for 4 h (Reaction condition c). The reaction mixture was quenched with water, extracted with ethyl acetate (20 mL×2). Combined organic extracts were washed with brine, dried over sodium sulfate, filtered and evaporated to get crude product. Crude residue was purified by gradient column chromatography using 5-10% ethyl acetate in hexane to get the product as brown liquid (6) (Yield: 63%, 0.23 g). $^1$HNMR (400 MHz, DMSO) δ (ppm): 9.72 (s, 1H), 7.62 (d, J=8 Hz, 1H), 7.3 (s, 1H), 7.07 (s, 1H), 6.78 (d, J=8 Hz, 1H), 4.43 (d, J=8 Hz, 2H), 3.84 (s, 3H), 1.26-1.21 (m, 1H), 0.40-0.38 (m, 4H). MS (ESI): mass calcd. for $C_{14}H_{15}NO_2$, 229.1; m/z found, 230.2 $(M+H)^+$.

Synthesis of 1-ethyl-1H-pyrrolo[2,3-b]pyridine-2-carbaldehyde (Intermediate for Compound-24)

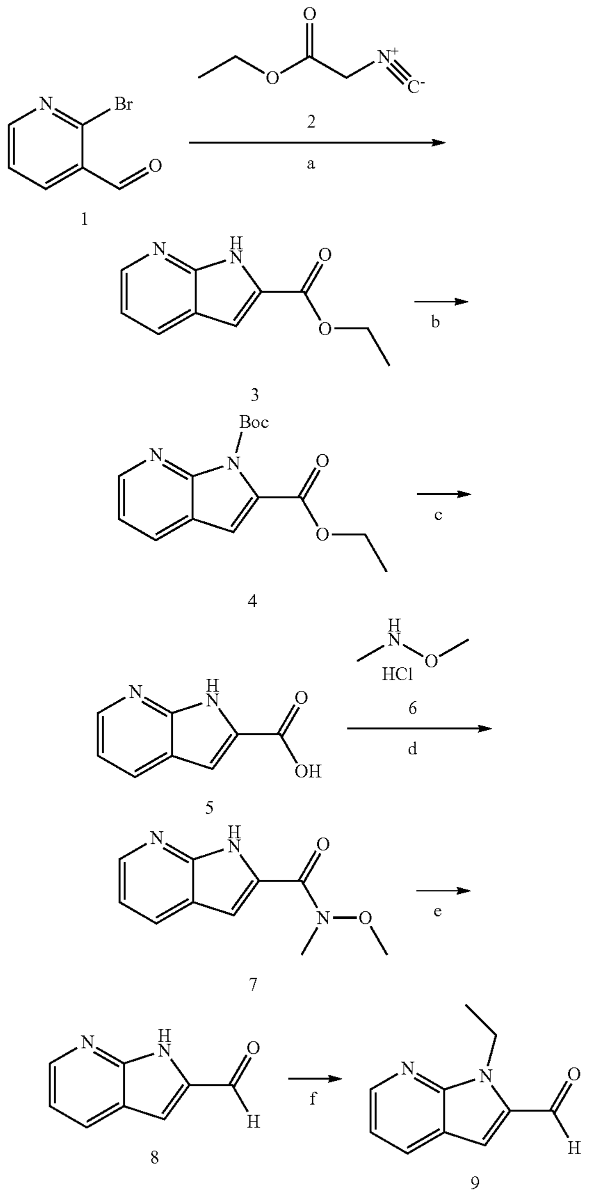

Step-1: Preparation of Ethyl 1H-pyrrolo[2,3-b]pyridine-2-carboxylate (3)

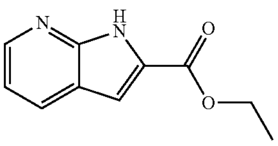
3

To the stirred solution of 2-bromonicotinaldehyde (1, 10.0 g, 53.7 mmol) in DMSO (100 mL), was added $Cs_2CO_3$ (35.0 g, 107 mmol), CuI (1.05 g, 5.37 mmol) followed by ethyl-2-isocyanoacetate (2, 7.9 mL, 69.8 mmol) and stirred at 80° C. for 16 h (Reaction condition a). The reaction mixture was cooled to rt and filtered through celite. To this water (100 mL) was added and the compound was extracted with EtOAc (200 mL). Organic layer was dried over anhydrous $Na_2SO_4$ and evaporated under vacuum. Crude was purified by column chromatography using 30-50% EtOAc in Hexane to afford the product as brown gummy solid (3) (4.5 g, 45% Yield). MS (ESI): Mass calcd. for $C_{10}H_{10}N_2O_2$, 190.20; m/z found 191.0 $(M+H)^+$.

Step-2: Preparation of 1-(Tert-butyl) 2-ethyl 1H-pyrrolo[2,3-b]pyridine-1,2-dicarboxylate (4)

4
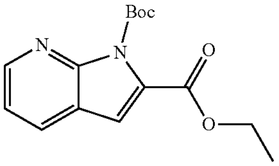

To the stirred solution of ethyl 1H-pyrrolo[2,3-b]pyridine-2-carboxylate (3, 34.5 g, 23.6 mmol) in THF (50 mL), was added triethylamine (6.5 mL, 47.3 mmol) followed by Boc anhydride (3.6 g, 35.5 mmol) and stirred at rt for 16 h (Reaction condition b). To the reaction mixture was added water (100 mL) and extracted with EtOAc (200 mL). Organic layer was dried over anhydrous $Na_2SO_4$ and evaporated under vacuum. Crude was purified by column chromatography using 20-30% EtOAc in Hexane to afford the product as brown gum (4) (5.5 g, 81% Yield). MS (ESI): Mass calcd. for $C_{15}H_{18}N_2O_4$, 290.32; m/z found, 291.1 $(M+H)^+$.

Step-3: Preparation of 1H-Pyrrolo[2,3-b]pyridine-2-carboxylic acid (5)

5
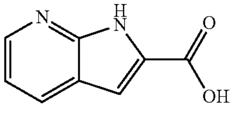

To a stirred solution 1-(tert-butyl) 2-ethyl 1H-pyrrolo[2,3-b]pyridine-1,2-dicarboxylate (4, 5.5 g, 18.9 mmol) in THF (40 mL), was added LiOH (3.9 g, 94.8 mmol) in water (10 mL) and stirred at rt for 4 h (Reaction condition c). The reaction mixture was evaporated, dissolved in minimum amount of water. To this added saturated citric acid solution till acidic and the precipitate formed was collected by filtration and dried to afford the product as white solid (5) (2.5 g, 81% Yield). MS (ESI): Mass calcd. for $C_8H_6N_2O_2$, 162.04; m/z found, 163.1 $(M+H)^+$.

Step-4: Preparation of N-Methoxy-N-methyl-1H-pyrrolo[2,3-b]pyridine-2-carboxamide (7)

7

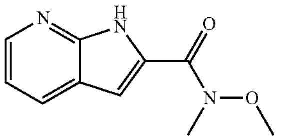

To the stirred solution of 1H-pyrrolo[2,3-b]pyridine-2-carboxylic acid (5, 2.5 g, 15.4 mmol) and N,O-dimethylhydroxylamine hydrochloride (6, 1.8 g, 18.5 mmol) in DCM (50 mL), was added triethylamine (10.6 mL, 77.1 mmol), HOBt (3.54 g, 23.14 mmol) followed by EDC.HCl (4.42 g, 23.18 mmol) at 0° C. and the reaction mixture was stirred at rt for 16 h (Reaction condition d). The reaction mixture was cooled to rt, filtered through celite and the filtrate was evaporated. To the crude, water (10 mL) was added and the compound was extracted with DCM (30 mL). Organic layer was dried over sodium sulfate and evaporated to give the crude product. The crude residue was purified by gradient column chromatography using 2-4% MeOH in DCM to afford the product as off white solid (7) (2.6 g, 82% Yield). MS (ESI): Mass calcd. for $C_{10}H_{11}N_3O_2$, 205.09; m/z found 206.1 $(M+H)^+$.

Step-5: Preparation of 1H-Pyrrolo[2,3-b]pyridine-2-carbaldehyde (8)

8

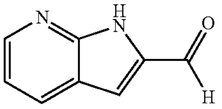

To a stirred solution N-methoxy-N-methyl-1H-pyrrolo[2,3-b]pyridine-2-carboxamide (7, 0.5 g, 2.43 mmol) in THF (10 mL), was added 1M LAH in THF (3.6 mL, 3.65 mmol) at −78° C. and the reaction mixture was stirred at same temperature for 3 h (Reaction condition e). The reaction mixture was basified using saturated $Na_2CO_3$ solution and extracted with DCM (2×25 mL). The reaction was quenched with saturated $NH_4Cl$ (10 mL) solution and the compound was extracted with EtOAc (50 mL). The organic layer was dried over anhydrous $Na_2SO_4$ and evaporated to give the crude product. Crude was purified by flash column chromatography using 25-30% EtOAc in hexane to get the compound as white solid (8) (0.3 g, 85% Yield). MS (ESI): Mass calcd. for $C_8H_6N_2O$, 146.15; m/z found, 147.1 $(M+H)^+$.

Step_6: Preparation of 1-Ethyl-1H-pyrrolo[2,3-b]pyridine-2-carbaldehyde (9)

9

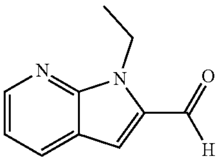

To a stirred solution 1H-pyrrolo[2,3-b]pyridine-2-carbaldehyde (8, 0.3 g, 2.19 mmol) in DMF (10 mL), was added $K_2CO_3$ (0.91 g, 6.57 mmol) followed by ethyl iodide (0.5 g, 3.28 mmol) and the reaction mixture was stirred at same temperature for 16 h (Reaction condition f). To the reaction mixture was added water (15 mL) and extracted with EtOAc (50 mL). The organic layer was dried over anhydrous $Na_2SO_4$ and evaporated to give the crude product. Crude was purified by flash column chromatography using 15-20% EtOAc in hexane to give the compound as colorless oil (9) (0.34 g, 95% Yield). MS (ESI): Mass calcd. for $C_{10}H_{11}N_2O$, 174.08; m/z found, 175.2 $(M+H)^+$.

Synthesis of 1-(cyclopropylmethyl)-1H-indole-2-carbaldehyde (Intermediate for Compound-25)

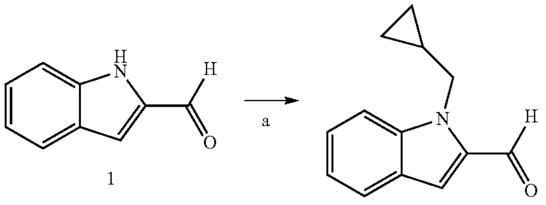

1 2

To the stirred solution of 1H-indole-2-carbaldehyde (1, 1 g, 6.89 mmol) in DMF (20 mL), were added potassium carbonate (2.8 g, 20.67 mmol) and (bromomethyl)cyclopropane (0.678 mL, 7.58 mmol) at rt. The reaction mixture was stirred at rt for 12 h (Reaction condition a). The reaction mixture was diluted with water and extracted with ethyl acetate (50 mL×2). Combined organic extracts were washed with brine, dried over sodium sulfate and evaporated to get crude product. The crude residue was purified by gradient column chromatography using 3-7% ethyl acetate in hexane to afford the 1-(cyclopropylmethyl)-1H-indole-2-carbaldehyde as yellow solid (2) (1 g, 76 Yield). $^1$HNMR (400 MHz, DMSO) δ (ppm): 9.88 (s, 1H), 7.75 (d, J=8 Hz, 1H), 7.64 (d, J=8 Hz, 1H), 7.46 (s, 1H), 7.41-7.37 (m, 1H), 7.16-7.12 (m, 1H), 4.45 (d, J=8 Hz, 2H), 1.24-1.14 (m, 1H), 0.39-0.35 (m, 4H). MS (ESI): mass calcd. for $C_{13}H_{13}NO$, 199.1; m/z found, 200.1 $(M+H)^+$.

Synthesis of 1-benzyl-1H-indole-2-carbaldehyde (Intermediate for Compound-26)

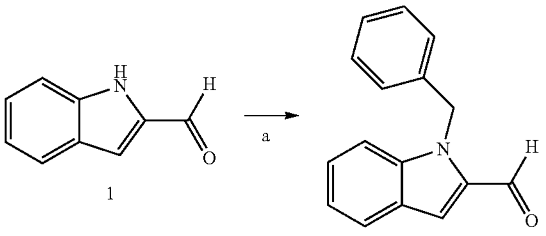

1 2

To the stirred solution of 1H-indole-2-carbaldehyde (1, 1 g, 6.89 mmol) in DMF (20 mL), were added potassium carbonate (2.8 g, 20.68 mmol) and (bromomethyl)benzene (1.2 g, 7.58 mmol) at rt (Reaction condition a). The reaction mixture was stirred at rt for 12 h. The reaction mixture was diluted with water and extracted with ethyl acetate (50 mL×2). Combined organic extracts were washed with brine, dried over sodium sulfate and evaporated to give the crude product. The crude residue was purified by gradient column chromatography using 3-7% ethyl acetate in hexane to afford the 1-benzyl-1H-indole-2-carbaldehyde as viscous liquid (2) (0.5 g, 33% Yield). $^1$HNMR (400 MHz, DMSO) δ (ppm): 9.92 (s, 1H), 7.78 (d, J=8 Hz, 1H), 7.58 (d, J=8 Hz, 1H), 7.54 (s, 1H), 7.38-7.35 (m, 1H), 7.26-7.20 (m, 2H), 7.18-7.13 (m, 2H), 7.05 (d, J=4 Hz, 2H), 5.82 (s, 2H). MS (ESI): mass calcd. for $C_{16}H_{13}NO$, 235.10; m/z found, 236.1 $(M+H)^+$.

Synthesis of 1-(pyridin-2-ylmethyl)-1H-indole-2-carbaldehyde (Intermediate for Compound-27)

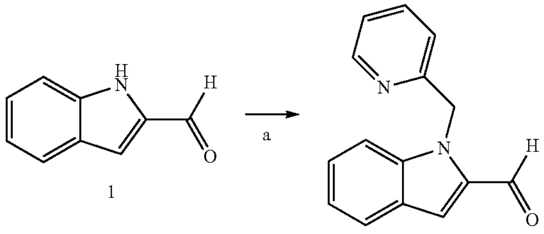

1

2

To the stirred solution of 1H-indole-2-carbaldehyde (1, 1 g, 6.89 mmol) in DMF (20 mL), were added cesium carbonate (6.7 g, 20.68 mmol) and 2-(bromomethyl)pyridine (1.1 g, 6.89 mmol) at rt (Reaction condition a). The reaction mixture was refluxed at 80° C. for 12 h. The reaction mixture was diluted with water and extracted with ethyl acetate (50 mL×2). Combined organic extracts were washed with brine, dried over sodium sulfate and evaporated to get crude product. The crude residue was purified by gradient column chromatography using 3-7% ethyl acetate in hexane to afford the 1-(pyridin-2-ylmethyl)-1H-indole-2-carbaldehyde as yellow solid (2) (0.8 g, 50% Yield). $^1$HNMR (400 MHz, DMSO) δ (ppm): 9.92 (s, 1H), 8.45 (d, J=4 Hz, 1H), 7.79 (d, J=8 Hz, 1H), 7.66 (m, 1H), 7.56 (d, J=12 Hz, 2H), 7.37-7.33 (m, 1H), 7.22-7.19 (m, 1H), 7.17-7.13 (m, 1H), 6.88 (d, J=8 Hz, 1H), 5.89 (s, 2H). MS (ESI): mass calcd. for $C_{16}H_{12}ClNO$, 269.73; m/z found, 270.1 $(M+H)^+$.

Synthesis of 1-(cyclopropylmethyl)-6-fluoro-1H-indole-2-carbaldehyde (Intermediate for Compound-28)

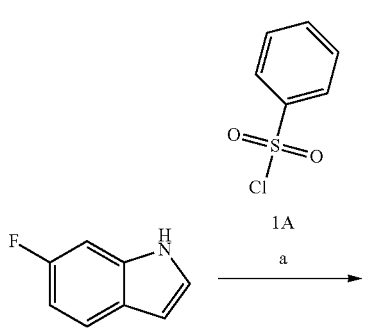

1A

1

-continued

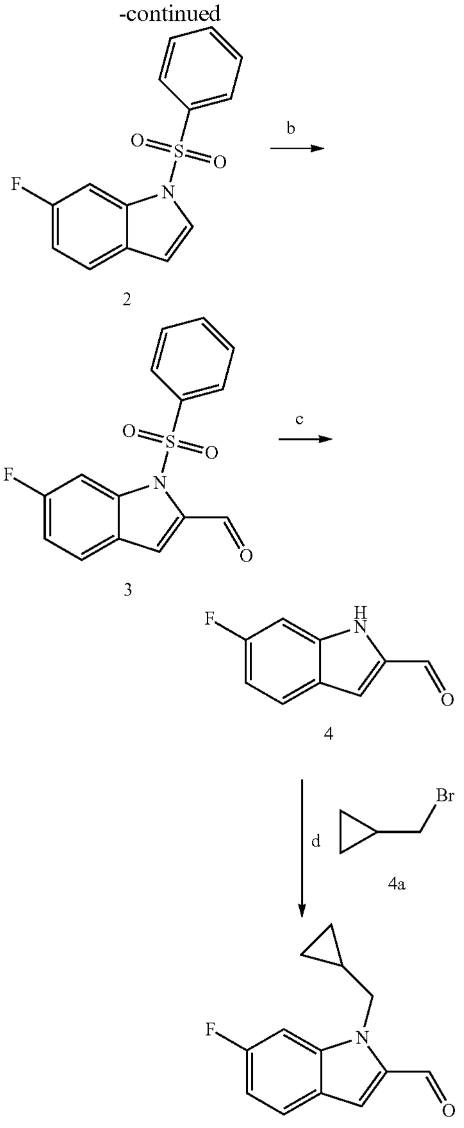

2

3

4

4a

5

Step 1: Preparation of 6-fluoro-1-(phenylsulfonyl)-1H-indole (2)

2

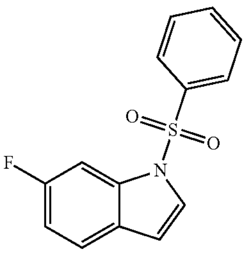

To a solution of sodium hydride (0.88 g, 22.2 mmol) in DMF (50 mL) was added solution of 6-fluoro-1H-indole (1, 3.0 g, 22.2 mmol) in DMF at 0° C., dropwise over 15 min. Benzenesulfonyl chloride in DMF (2.86 mL, 22.2 mmol)

was added at 0° C. and stirred for 2 h at rt under $N_2$ atmosphere (Reaction condition a). To the reaction mixture was added ice cold water (50 mL), then filtered off the precipitate and washed with ice cold water to obtain white solid (2) (6.0 g, 98.19%).

Step 2: preparation 6-fluoro-1-(phenylsulfonyl)-1H-indole-2-carbaldehyde (3) (Intermediate for Compound-52, 54, 68, 69, 70, 71, 72 & 73)

3

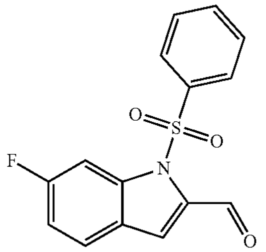

To a solution of 6-fluoro-1-(phenylsulfonyl)-1H-indole (2, 6.0 g, 22.0 mmol) in dry THF (60 mL) was added lithium diisopropylamide 2M in THF (10.9 mL g, 22.0 mmol) at −78° C. and stirred for 5-8 min, followed by addition of dry DMF (2.5 mL, 33.0 mmol) at −78° C. and stirred for 10 min at −78° C. under $N_2$ atmosphere (Reaction condition b). To the reaction mixture was added aqueous ammonium chloride (20 mL), then extracted in to EtOAc. Organic layer was washed with saturated $NH_4Cl$ solution and brine, dried over sodium sulphate, filtered and concentrated under reduced pressure to obtain yellow solid (3) (6.0 g, 90.90%). MS (ESI): m/z 304.2 $(M+H)^+$.

Step 3: Preparation of 6-fluoro-1-(phenylsulfonyl)-1H-indole-2-carbaldehyde (4)

4

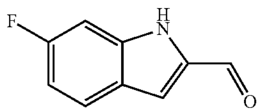

To the stirred solution of 6-Difluoro-1-(phenylsulfonyl)-1H-indole-2-carbaldehyde (3.1 g, 3.3 mmol) in THF (50 mL), was added TBAF (1M in THF) (9.15 mL, 16.5 mmol) at rt. The reaction mixture was stirred at rt for 12 h (Reaction condition c). The reaction mixture was diluted with water and extracted with ethyl acetate (50 mL×2). Combined organic extracts were washed with brine, dried over sodium sulfate and evaporated to get crude product. The crude residue was purified by gradient column chromatography using 15-25% ethyl acetate in hexane to afford 6-fluoro-1-(phenylsulfonyl)-1H-indole-2-carbaldehyde as sticky solid (4) (0.45 g, 90% Yield) MS (ESI): Mass calcd. for $C_9H_6FNO$, 163 m/z; found, 164 $(M+H)^+$.

Step 4: Preparation of 1-(cyclopropylmethyl)-6-fluoro-1H-indole-2-carbaldehyde (5)

5

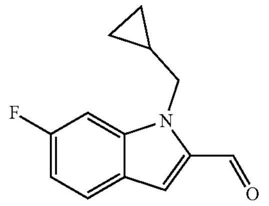

To a stirred solution 6-fluoro-1H-indole-2-carbaldehyde (4, 0.5 g, 3.44 mmol) in DMF (10 mL), was added potassium carbonate (1.42 g, 10.3 mmol) followed by (bromomethyl) cyclopropane (0.84 g, 4.13 mmol) and the reaction mixture was stirred at same temperature for 4 h (Reaction condition d). The reaction mixture was quenched with water, extracted with ethyl acetate (30 mL×2). Combined organic extracts were washed with brine, dried over sodium sulfate, filtered and evaporated to get crude product. Crude residue was purified by gradient column chromatography using 10-15% ethyl acetate in hexane to get the product as half white solid (5) (Yield: 93.4%, 0.86 g). $^1$HNMR (400 MHz, DMSO) δ (ppm): 9.81 (s, 1H), 7.69-7.66 (m, 1H), 7.25 (d, J=6.8 Hz, 1H), 7.07 (d, J=8 Hz, 1H), 6.97-6.91 (m, 1H), 4.43 (d, J=8 Hz, 2H), 1.32-1.25 (m, 1H), 0.5-0.45 (m, 2H), 0.42-0.38 (m, 2H). MS (ESI): mass calcd. for $C_{13}H_{12}FNO$, 217.09; m/z found, 218.0 $(M+H)^+$.

Synthesis of 1-(cyclopropylmethyl)-5-fluoro-1H-indole-2-carbaldehyde (Intermediate for Compound-29)

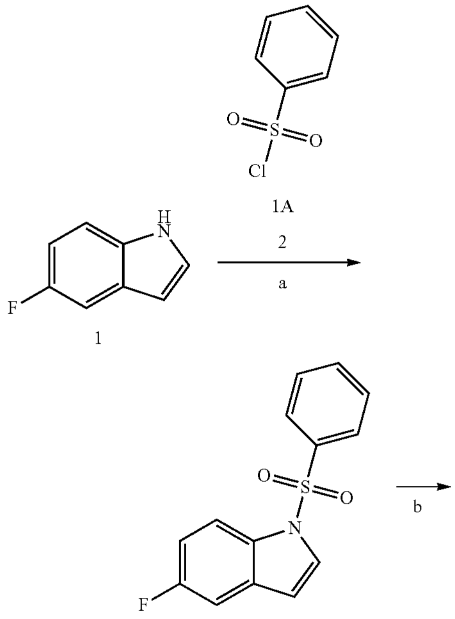

1

3

-continued

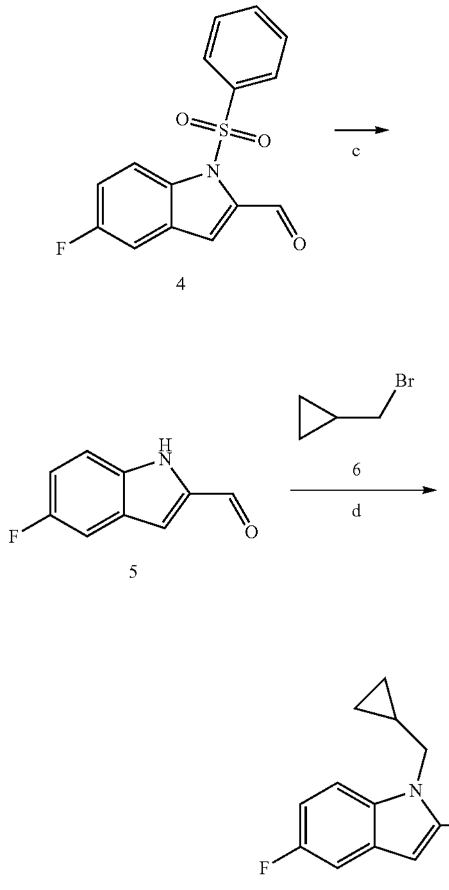

4

5

7

Step 1: Preparation of 5-fluoro-1-(phenylsulfonyl)-1H-indole (3)

3

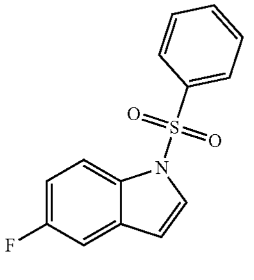

To a solution of sodium hydride (0.06 g, 15 mmol) in DMF (10 mL) was added a solution of 5-fluoro-1H-indole (1, 0.2 g, 15 mmol) in DMF at 0° C., drop wise over 15 min. followed by addition of a solution of benzenesulfonyl chloride (2, 0.26 g, 15 mmol) in DMF at 0° C. and the reaction mixture was stirred for 2 h at rt under $N_2$ atmosphere (Reaction condition a). To the reaction mixture was added ice cold water (50 mL), then the precipitate was filtered off and washed with ice cold water to obtain brown solid (3) (0.25 g, 62.50% Yield). MS (ESI) m/z 275.0 $(M+H)^+$.

Step 2: Preparation of 5-fluoro-1-(phenylsulfonyl)-1H-indole-2-carbaldehyde (4) (Intermediate for Compound-53, 74, 75, 76, & 84)

4

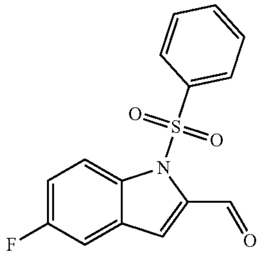

To a solution of 5-fluoro-1-(phenylsulfonyl)-1H-indole (3, 0.250 g, 1.0 mmol) in dry THF (50 mL) was added lithium diisopropylamide 1M in THF (0.5 mL g, 1.0 mmol) at −78° C., followed by addition of dry DMF (0.11 mL, 1.5 mmol) at −78° C. and stirred for 10 min at −78° C. under $N_2$ atmosphere (Reaction condition b). To the reaction mixture was added aqueous ammonium chloride (20 mL) and extracted with EtOAc. Organic layer was washed with saturated $NH_4Cl$ solution and brine, dried over sodium sulphate, filtered and concentrated under reduced pressure to obtain brown solid (4) (0.150 g, 54.54% Yield). MS (ESI) m/z 304.1 $(M+H)^+$.

Step 3: Preparation of 5-fluoro-1H-indole-2-carbaldehyde (5)

5

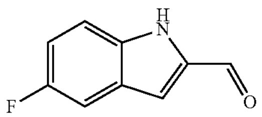

To the stirred solution of 5-fluoro-1-(phenylsulfonyl)-1H-indole-2-carbaldehyde (4, 1.85 g, 6.105 mmol) in THF (50 mL), was added TBAF (1M in THF) (9.15 mL, 9.158 mmol) at rt (Reaction condition c). The reaction mixture was stirred at rt for 12 h. The reaction mixture was diluted with water and extracted with ethyl acetate (50 mL×2). Combined organic extracts were washed with brine, dried over sodium sulfate and evaporated to get crude product. The crude residue was purified by gradient column chromatography using 15-25% ethyl acetate in hexane to afford the 5-fluoro-1H-indole-2-carbaldehyde as sticky solid (5) (0.65 g, 65% Yield) MS (ESI): Mass calcd. for $C_9H_6FNO$, 163.15; m/z found, 162.0 $[M-H]^-$.

Step 4: Preparation of 1-(cyclopropylmethyl)-5-fluoro-1H-indole-2-carbaldehyde (7)

7

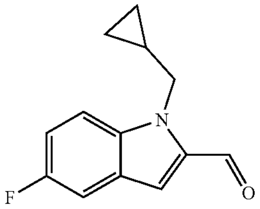

To the stirred solution of 5-fluoro-1H-indole-2-carbaldehyde (5, 0.65 g, 3.98 mmol) in DMF (50 mL), were added potassium carbonate (1.64 g, 11.94 mmol) and (bromomethyl)cyclopropane (6, 0.58 mL, 5.98 mmol) at rt. The reaction mixture was stirred at rt for 12 h (Reaction condition d). The reaction mixture was diluted with water and extracted with ethyl acetate (50 mL×2). Combined organic extracts were washed with brine, dried over sodium sulphate and evaporated to get crude product. The crude residue was purified by gradient column chromatography using 3-7% ethyl acetate in hexane to afford the 1-(cyclopropylmethyl)-5-fluoro-1H-indole-2-carbaldehyde as sticky solid (7) (0.76 g, 88% Yield). $^{1}$HNMR (400 MHz, DMSO-d6) δ (ppm): 9.90 (s, 1H), 7.73-7.69 (m, 1H), 7.55-7.52 (m, 1H), 7.44 (s, 1H), 7.29-7.24 (m, 1H), 4.50 (d, J=7.2 Hz, 2H), 1.23-1.16 (m, 1H), 0.41-0.32 (m, 4H). MS (ESI): Mass calcd. for $C_{13}H_{12}FNO$, 217.24: m/z found, 218.1 $[M+H]^+$.

Synthesis of 1-(cyclopropylmethyl)-7-methyl-1H-indole-2-carbaldehyde (Intermediate for Compound-30)

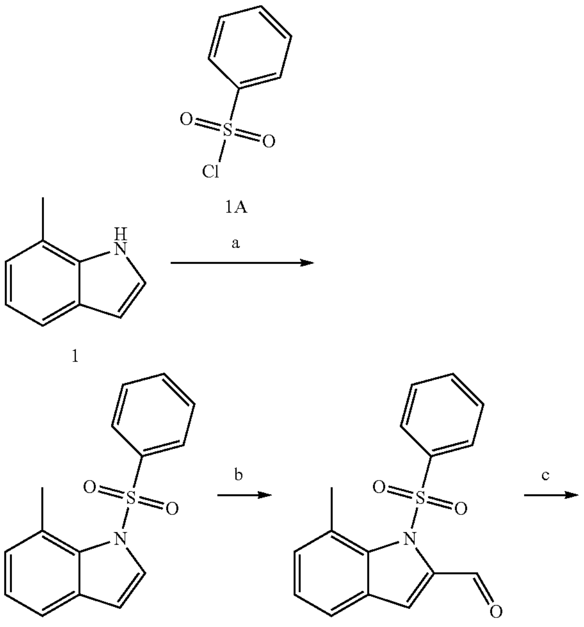

1A

1

2

3

-continued

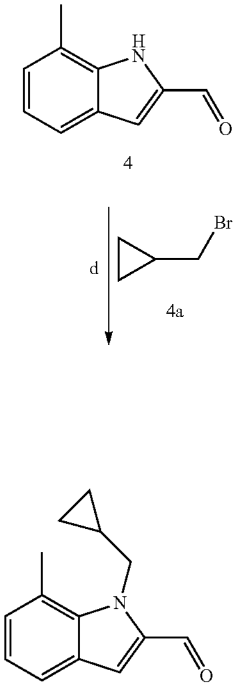

4

4a

5

Step 1: Preparation of 7-methyl-1-(phenylsulfonyl)-1H-indole (2)

2

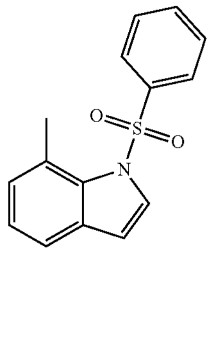

To a solution of sodium hydride (0.92 g, 23 mmol) in DMF (10 mL) was added solution of 7-methyl-1H-indole (1, 3.0 g, 23 mmol) in DMF at 0° C., dropwise over 15 min. Benzenesulfonyl chloride in DMF (2.96 mL, 23 mmol) was added at 0° C. and stirred for 2 h at rt under $N_2$ atmosphere (Reaction condition a). To the reaction mixture was added ice cold water (50 mL), then filtered off the precipitate and washed with ice cold water to obtain brown solid (2) (5.30 g, 85.50%). MS (ESI) m/z 272.1 $(M+H)^+$.

Step 2: Preparation 7-methyl-1-(phenylsulfonyl)-1H-indole-2-carbaldehyde (3)

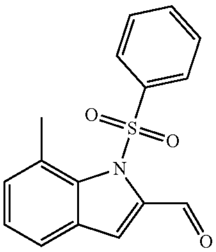

3

To a solution of 7-methyl-1-(phenylsulfonyl)-1H-indole (2, 5.3 g, 20.0 mmol) in dry THF (50 mL) was added lithium diisopropylamide 1.5M in THF (13.0 mL, 20.0 mmol) at −78° C. and stirred for 5-8 min, followed by addition of dry DMF (2.33 mL, 30.0 mmol) at −78° C. and stirred for 10 min at −78° C. under $N_2$ atmosphere (Reaction condition b). To the reaction mixture was added aqueous ammonium chloride (20 mL), then extracted in to EtOAc. Organic layer was washed with saturated $NH_4Cl$ solution and brine, dried over sodium sulphate, filtered and concentrated under reduced pressure to obtain red viscous liquid (3) (5.0 g, 85.47%). MS (ESI) m/z 300.2 $(M+H)^+$.

Step 3: Preparation of 7-methyl-1H-indole-2-carbaldehyde (4)

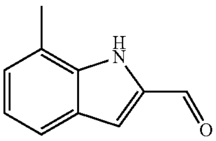

4

To the stirred solution of 7-methyl-1-(phenylsulfonyl)-1H-indole-2-carbaldehyde (3, 2 g, 6.68 mmol) in THF (20 mL), was added 1M solution of tetrabutyl ammonium fluoride in THF (10 mL, 10.2 mmol) and stirred at 80° C. for 1 h (Reaction condition c). Reaction mixture was cooled to rt, added water (20 mL) and extracted with EtOAc (100 mL). Organic layer was dried over anhydrous $Na_2SO_4$ and evaporated under vacuum. Crude was purified by column chromatography using 15-20% EtOAc in Hexane to afford the product as brown solid (4). (0.8 g, 58% Yield). MS (ESI): Mass calcd. for $C_{10}H_9NO$, 159.07; m/z found 160.1 $(M+H)^+$.

Step 4: Preparation of 1-(cyclopropylmethyl)-7-methyl-1H-indole-2-carbaldehyde (5)

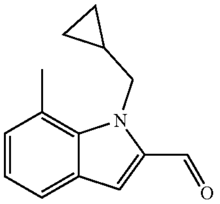

5

To the stirred solution of 7-methyl-1H-indole-2-carbaldehyde (4, 0.85 g, 5.345 mmol) in DMF (20 mL), were added potassium carbonate (2.21 g, 16.035 mmol) and (bromomethyl)cyclopropane (4a, 0.78 mL, 8.018 mmol) at rt. The reaction mixture was stirred at rt for 12 h (Reaction condition d). The reaction mixture was diluted with water and extracted with ethyl acetate (50 mL×2). Combined organic extracts were washed with brine, dried over sodium sulfate and evaporated to get crude product. The crude residue was purified by gradient column chromatography using 3-7% ethyl acetate in hexane to afford the 1-(cyclopropylmethyl)-7-methyl-1H-indole-2-carbaldehyde as sticky solid (5) (0.52 g, 45% Yield). $^1$HNMR (400 MHz, $CDCl_3$) δ (ppm): 9.82 (s, 1H), 7.58 (d, J=8.0 Hz, 1H), 7.26 (s, 1H), 7.13 (d, J=6.8 Hz, 1H), 6.26 (m, 1H), 4.83 (d, J=6.8 Hz, 2H), 2.77 (s, 3H), 1.15-1.10 (m, 1H), 0.41-0.33 (m, 4H). MS (ESI): Mass calcd. for $C_{14}H_{15}NO$, 213.28; m/z found, 214.1 $[M+H]^+$.

Synthesis of 3-(chloromethyl)thiophene (Intermediate for Compound-36)

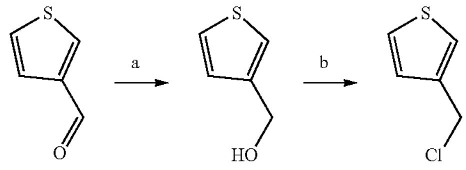

1 2 3

Step 1: Preparation of Thiophen-3-ylmethanol (2)

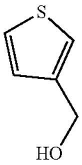

2

To the stirred solution of thiophene-3-carbaldehyde (1, 1 g, 8.92 mmol) in MeOH (10 mL), was added $NaBH_4$ (0.5 g, 13.3 mmol) portion wise at 0° C. and stirred at rt for 1 h (Reaction condition a). The reaction mixture was quenched with ice and the MeOH was evaporated. To the resulting crude added water (5 mL) and extracted with EtOAc (2×20 mL). Organic layer was washed with brine (5 mL) solution, dried over anhydrous $Na_2SO_4$ and evaporated under vacuum to give the product as brown oil (2) (0.9 g, 90%, Yield). $^1$HNMR (400 MHz, DMSO-d6) δ (ppm): 7.45-7.43 (m, 1H), 7.26 (s, 1H), 7.03 (d, J=4.4 Hz, 1H), 5.05 (t, J=6.0 Hz, 1H), 4.45 (d, J=5.6 Hz, 2H).

Step 2: Preparation of 3-(chloromethyl)thiophene (3)

3

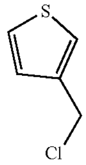

To a stirred solution thiophen-3-ylmethanol (2, 0.5 g, 4.38 mmol) in DCM (5 mL), was added $SOCl_2$ (0.6 mL, 8.77 mmol) drop wise at 0° C. and the reaction mixture was stirred at rt for 1 h (Reaction condition b). The reaction mixture was evaporated under vacuum and dried to afford the product as brown oil (3) (0.5 g, 80%, Yield). $^1$HNMR (400 MHz, DMSO-d6): δ 7.45-7.43 (m, 1H), 7.26 (s, 1H), 7.03 (d, J=4.4 Hz, 1H), 4.78 (s, 2H).

Synthesis of 3-(chloromethyl)furan (Intermediate for Compound-37)

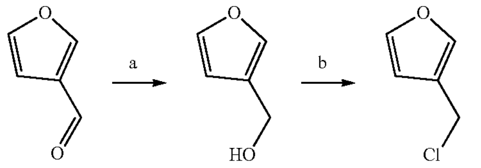

1 2 3

Step 1: Preparation of Furan-3-ylmethanol (2)

2

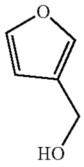

To the stirred solution of furan-3-carbaldehyde (1, 1 g, 10.4 mmol) in MeOH (10 mL), was added $NaBH_4$ (0.6 g, 15.6 mmol) portion wise at 0° C. and stirred at rt for 1 h (Reaction condition a). The reaction mixture was quenched with ice and the MeOH was evaporated. To the resulting crude added water (5 mL) and extracted with EtOAc (2×20 mL). Organic layer was washed with brine (5 mL) solution, dried over anhydrous $Na_2SO_4$ and evaporated under vacuum to give the product as brown oil (2) (0.6 g, 60%, Yield). $^1$HNMR (400 MHz, DMSO-d6) δ (ppm): 7.56-7.50 (m, 2H), 6.41 (s, 1H), 4.90 (t, J=5.2 Hz, 1H), 4.31 (d, J=6.0 Hz, 2H).

Step 2: Preparation of 3-(chloromethyl)furan (3)

3

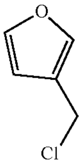

To a stirred solution furan-3-ylmethanol (2, 0.5 g, 5.10 mmol) in DCM (5 mL), was added $SOCl_2$ (0.7 mL, 10.2 mmol) drop wise at 0° C. and the reaction mixture was stirred at rt for 1 h (Reaction condition b). The reaction mixture was evaporated under vacuum and dried to afford the product as brown oil (3) (0.5 g, 84%, Yield). $^1$HNMR (400 MHz, DMSO-d6) δ (ppm): 7.75-7.65 (m, 2H), 6.53 (s, 1H), 4.68 (s, 2H).

Synthesis of 1-(1-chloroethyl)-4-fluorobenzene (Intermediate for Compound-38)

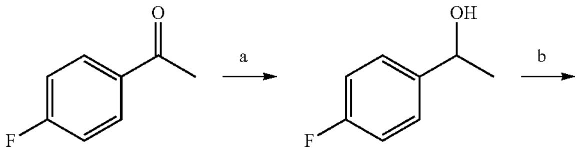

1 2

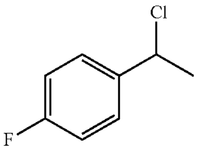

3

Step 1: Preparation of 1-(4-fluorophenyl)ethan-1-ol (2)

2

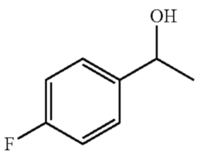

To the stirred solution of 1-(4-fluorophenyl)ethan-1-one (1, 2.0 g, 17.6 mmol) in MeOH (20 mL), was added $NaBH_4$ (1.0 g, 26.5 mmol) portion wise at 0° C. and stirred at rt for 1 h (Reaction condition a). The reaction mixture was quenched with ice and the MeOH was evaporated. To the resulting crude added water (10 mL) and extracted with EtOAc (2×25 mL). Organic layer was washed with brine (10 mL) solution, dried over anhydrous $Na_2SO_4$ and evaporated under vacuum to give the product as colourless oil (2) (1.9 g, 95%, Yield). $^1$HNMR (400 MHz, DMSO-d6) δ (ppm):

7.36-7.33 (m, 2H), 7.14-7.07 (m, 2H), 5.12 (d, J=4.0 Hz, 1H), 4.72-4.67 (m, 1H), 1.28 (d, J=6.8 Hz, 3H).

Step 2: Preparation of 1-(1-chloroethyl)-4-fluorobenzene (3)

3

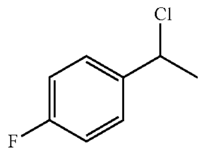

To a stirred solution 1-(4-fluorophenyl)ethan-1-ol (2, 0.5 g, 3.57 mmol) in DCM (5 mL), was added $SOCl_2$ (0.7 mL, 7.10 mmol) drop wise at 0° C. and the reaction mixture was stirred at rt for 1 h (Reaction condition b). The reaction mixture was evaporated under vacuum and dried to afford the product as brown oil (3) (0.5 g, 89%, Yield). $^1$HNMR (400 MHz, DMSO-d6) δ (ppm): 7.53-7.51 (m, 2H), 7.21-7.16 (m, 2H), 5.36-5.33 (m, 1H), 1.76 (d, J=6.8 Hz, 3H).

Synthesis of 1-ethyl-5-fluoro-1H-indole-2-carbaldehyde (Intermediate for Compound-39)

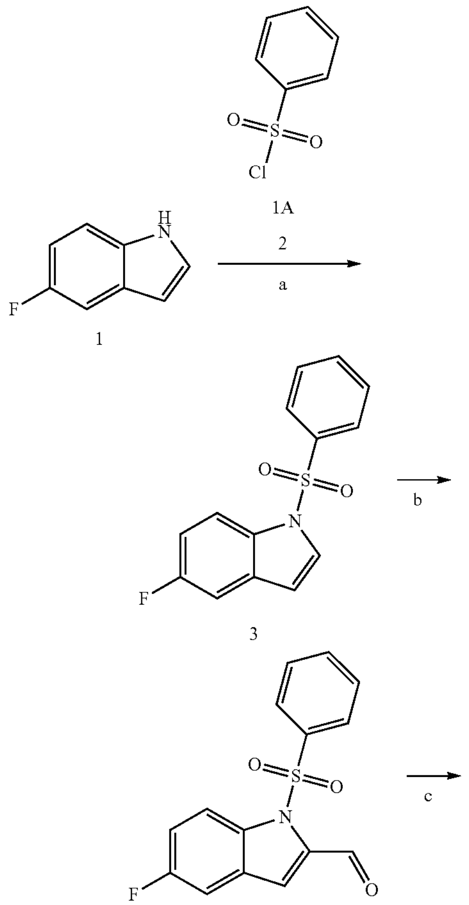

-continued

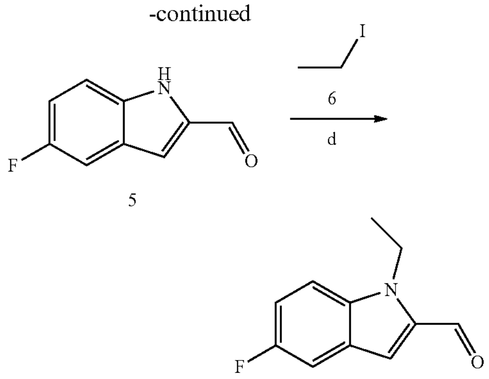

Step 1: Preparation of 5-fluoro-1-(phenylsulfonyl)-1H-indole (3)

3

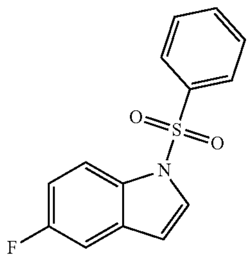

To a solution of sodium hydride (0.06 g, 15 mmol) in DMF (10 mL) was added a solution of 5-fluoro-1H-indole (1, 0.2 g, 15 mmol) in DMF at 0° C., drop wise over 15 min. followed by addition of a solution of benzenesulfonyl chloride (2, 0.26 g, 15 mmol) in DMF at 0° C. and the reaction mixture was stirred for 2 h at rt under $N_2$ atmosphere (Reaction condition a). To the reaction mixture was added ice cold water (50 mL), then the precipitate was filtered off and washed with ice cold water to obtain brown solid (3) (0.25 g, 62.50% Yield). MS (ESI) m/z 275.0 $(M+H)^+$.

Step 2: Preparation of 5-fluoro-1-(phenylsulfonyl)-1H-indole-2-carbaldehyde (4)

4

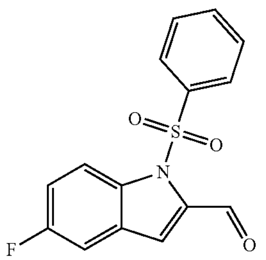

To a solution of 5-fluoro-1-(phenylsulfonyl)-1H-indole (3, 0.250 g, 1.0 mmol) in dry THF (50 mL) was added lithium diisopropylamide 1M in THF (0.5 mL g, 1.0 mmol) at −78° C., followed by addition of dry DMF (0.11 mL, 1.5 mmol) at −78° C. and stirred for 10 min at −78° C. under $N_2$ atmosphere (Reaction condition b). To the reaction mixture was added aqueous ammonium chloride (20 mL) and extracted with EtOAc. Organic layer was washed with saturated $NH_4Cl$ solution, brine, dried over sodium sulphate, filtered and concentrated under reduced pressure to obtain brown solid (4) (0.150 g, 54.54% Yield). MS (ESI) m/z 304.1 $(M+H)^+$.

Step 3: Preparation of 5-fluoro-1H-indole-2-carbaldehyde (5)

5

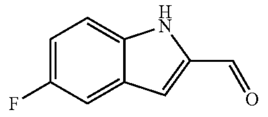

To the stirred solution of 5-fluoro-1-(phenylsulfonyl)-1H-indole-2-carbaldehyde (4, 1.85 g, 6.105 mmol) in THF (50 mL), was added TBAF (1M in THF) (9.15 mL, 9.158 mmol) at rt (Reaction condition c). The reaction mixture was stirred at rt for 12 h. The reaction mixture was diluted with water and extracted with ethyl acetate (50 mL×2). Combined organic extracts were washed with brine, dried over sodium sulfate and evaporated to get crude product. The crude residue was purified by gradient column chromatography using 15-25% ethyl acetate in hexane to afford the 5-fluoro-1H-indole-2-carbaldehyde as sticky solid (5) (0.65 g, 65% Yield) MS (ESI): Mass calcd. for $C_9H_6FNO$, 163.15; m/z found, 164.0 $(M+H)^+$.

Step 4: Preparation of 1-ethyl-5-fluoro-1H-indole-2-carbaldehyde (7)

7

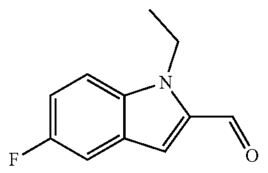

To the stirred solution of 5-fluoro-1H-indole-2-carbaldehyde (5, 0.6 g, 3.98 mmol) in DMF (50 mL), were added potassium carbonate (1.64 g, 11.94 mmol) and ethyliodide (6, 0.43 mL, 5.4 mmol) at rt (Reaction condition d). The reaction mixture was stirred at rt for 12 h. The reaction mixture was diluted with water and extracted with ethyl acetate (50 mL×2). Combined organic extracts were washed with brine, dried over sodium sulphate and evaporated to give the crude product. The crude residue was purified by gradient column chromatography using 3-7% ethyl acetate in hexane to afford the 1-(cyclopropylmethyl)-5-fluoro-1H-indole-2-carbaldehyde as sticky solid (7) (0.3 g, 43.6% Yield). MS (ESI): Mass calcd. for $C_{11}H_{10}FNO$, 191.07: m/z found, 192.1 $[M+H]^+$.

Synthesis of 1-(cyclopropylmethyl)-4-fluoro-1H-indole-2-carbaldehyde (Intermediate for Compound-40)

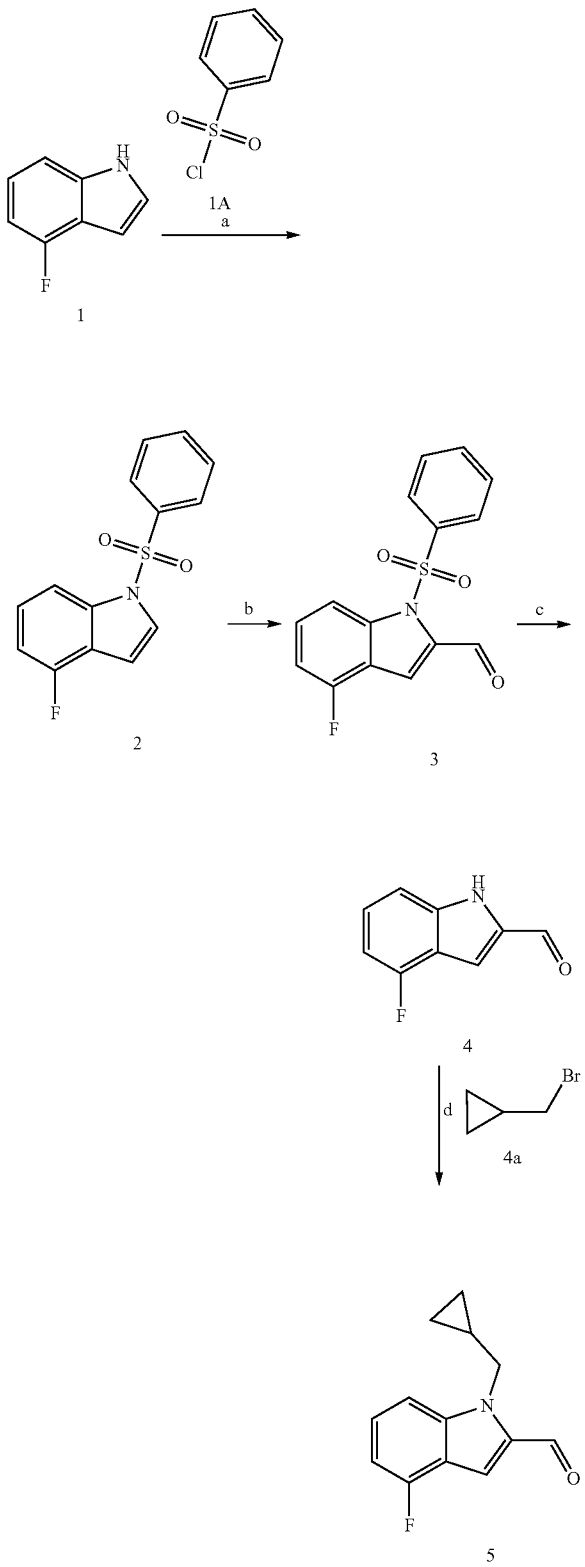

Step 1: Preparation of 4-fluoro-1-(phenylsulfonyl)-1H-indole (2)

2

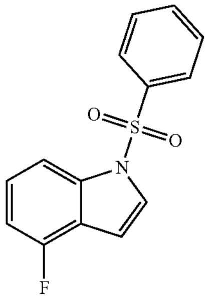

To a solution of sodium hydride (0.88 g, 22.2 mmol) in DMF (50 mL) was added solution of 4-fluoro-1H-indole (1, 3.0 g, 22.2 mmol) in DMF at 0° C., dropwise over 15 min. Benzenesulfonyl chloride in DMF (2.86 mL, 22.2 mmol) was added at 0° C. and stirred for 2 h at rt under $N_2$ atmosphere (Reaction condition a). To the reaction mixture was added ice cold water (50 mL), then filtered off the precipitate and washed with ice cold water to obtain white solid (2). (7.0 g—crude).

Step 2: Preparation of 4-fluoro-1-(phenylsulfonyl)-1H-indole-2-carbaldehyde (3)

3

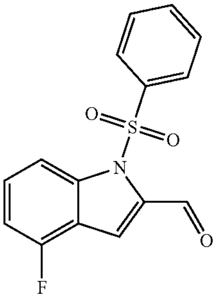

To a solution of 4-fluoro-1-(phenylsulfonyl)-1H-indole (2, 7.0 g, 22.0 mmol) in dry THF (60 mL) was added lithium diisopropylamide 2M in THF (10.9 mL, 22.0 mmol) at −78° C. and stirred for 5-8 min, followed by addition of dry DMF (2.5 mL, 33.0 mmol) at −78° C. and stirred for 10 min at −78° C. under $N_2$ atmosphere (Reaction condition b). To the reaction mixture was added aqueous ammonium chloride (20 mL), then extracted in to EtOAc. Organic layer was washed with saturated $NH_4Cl$ solution and brine, dried over sodium sulphate, filtered and concentrated under reduced pressure to obtain red liquid (3) (6.80 g, 88.31%).

Step 3: Preparation of 4-fluoro-1H-indole-2-carbaldehyde (4)

4

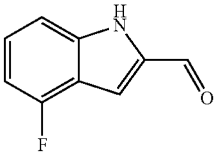

To a solution of 4-fluoro-1-(phenylsulfonyl)-1H-indole-2-carbaldehyde (4, 3.0 g, 9.9 mmol) in dry THF (20 mL) was added tetrabutyl ammonium fluoride 1M in THF (14.8 mL) and the reaction mixture was stirred for about 12 h under rt (Reaction condition c). The reaction mixture was quenched with water and, then extracted with ethyl acetate (50 mL×3). Combined organic extracts were washed with brine, dried over sodium sulfate, filtered and evaporated to get crude product. Crude residue was purified by gradient column chromatography using 5-10% ethyl acetate in hexane to get the product as yellow solid (4). (Yield: 99%, 1.6 g). MS (ESI): Mass calcd. for $C_9H_6FNO$, 163.04; m/z found 164 $(M+H)^+$.

Step-4: Preparation of 1-(cyclopropylmethyl)-4-fluoro-1H-indole-2-carbaldehyde (5)

5

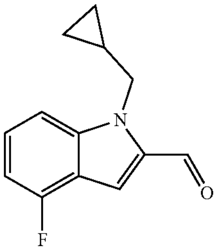

To a stirred solution of 4-fluoro-1H-indole-2-carbaldehyde (4, 1.6 g, 9.877 mmol) in DMF (10 mL), was added potassium carbonate (6.8 g, 49.38 mmol) followed by (bromomethyl)cyclopropane (6, 1.4 mL, 10.65 mmol) and the reaction mixture was stirred at rt for 12 h (Reaction condition d). The reaction mixture was quenched with water, extracted with ethyl acetate (30 mL×2). Combined organic extracts were washed with brine, dried over sodium sulfate, filtered and evaporated to get crude product. Crude residue was purified by gradient column chromatography using 5-10% ethyl acetate in hexane to get the product as brown liquid (5). (Yield: 47.6%, 1 g). $^1$HNMR (400 MHz, DMSO) δ (ppm): 9.90 (s, 1H), 7.55-7.50 (m, 2H), 7.40-7.35 (m, 1H), 6.95-6.90 (m, 1H), 4.46 (d, J=8 Hz, 2H), 1.22-1.21 (m, 1H), 0.42-0.36 (m, 4H). MS (ESI): Mass calcd. for $C_{13}H_{12}FNO$, 217.24; m/z found, 218 $[M+H]^+$.

Synthesis of 2-(chloromethyl)-4-methylthiazole (Intermediate for Compound-41)

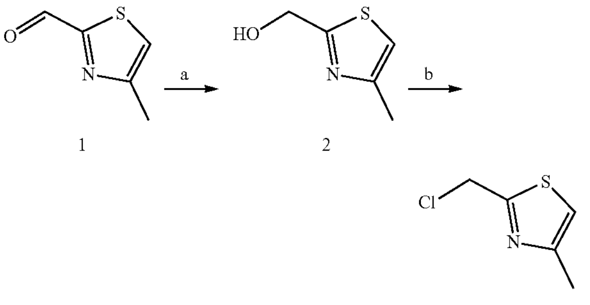

1 2 3

Step 1: Preparation of (4-methylthiazol-2-yl)methanol (2)

2

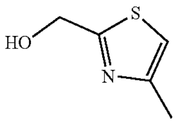

To the stirred solution of 4-methylthiazole-2-carbaldehyde (1, 1 g, 7.8 mmol) in MeOH (10 mL), was added $NaBH_4$ (0.5 g, 15.6 mmol) portion wise at 0° C. and stirred at rt for 1 h (Reaction condition a). The reaction mixture was quenched with ice and the MeOH was evaporated. To the resulting crude added water (5 mL) and extracted with EtOAc (2×20 mL). Organic layer was washed with brine (5 mL) solution, dried over anhydrous $Na_2SO_4$ and evaporated under vacuum to give the product as brown oil (2) (1 g, 79.5%, Yield). MS (ESI): mass calcd. for C5H7NOS 129.02; m/z found 130.1 $(M+H)^+$.

Step 2: Preparation of 2-(chloromethyl)-4-methylthiazole (3)

3

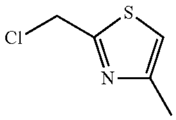

To a stirred solution (4-methylthiazol-2-yl)methanol (2, 1 g, 7.7 mmol) in DCM (20 mL), was added $SOCl_2$ (0.89 mL, 11.55 mmol) drop wise at 0° C. and the reaction mixture was stirred at rt for 1 h (Reaction condition b). The reaction mixture was evaporated under vacuum and dried to afford the product as brown oil (3) (1 g, 88.3%, Yield). $^1$HNMR (400 MHz, CDCl3) δ (ppm): 6.91 (s, 1H), 4.82 (s, 2H), 2.45 (s, 3H).

Synthesis of 5-bromo-1-(cyclopropylmethyl)-1H-indole-2-carbaldehyde (Intermediate for Compound-43)

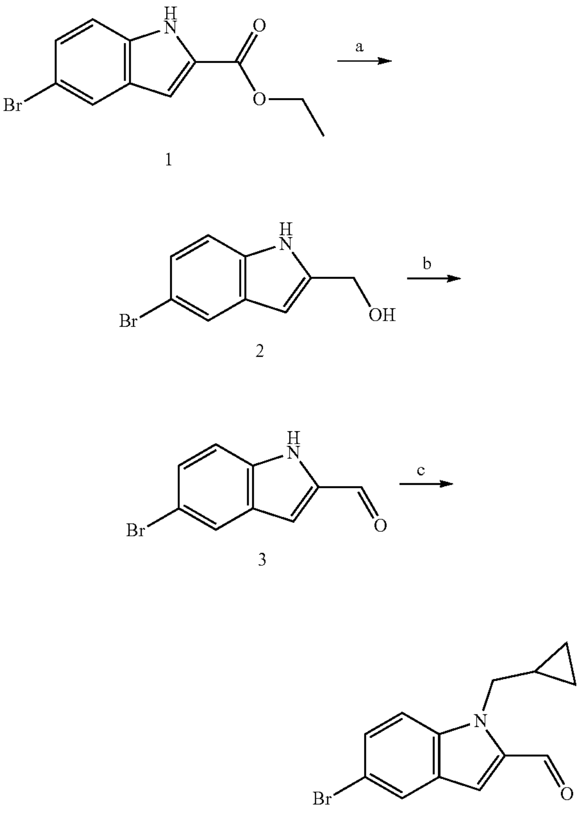

1 2 3 4

Step-1: Preparation of (5-bromo-1H-indol-2-yl)methanol (2)

2

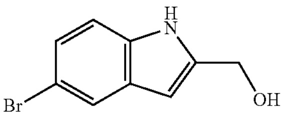

To a solution of ethyl 5-bromo-1H-indole-2-carboxylate (1, 5.0 g, 18.6 mmol) in THF (35 mL) was added solution of 1 M lithium aluminum hydride in THF (37.2 mL, 37.2 mmol) at 0° C., dropwise over 20 min. Reaction mixture was stirred for 2 h at rt under $N_2$ atmosphere (Reaction condition a). To the reaction mixture ice cold aq.$NH_4Cl$ (20 mL) was added drop wise at 0° C., diluted with water and extracted with ethyl acetate (2×200 mL). Organic layer was dried using $Na_2SO_4$ and evaporated. The crude was purified by gradient column chromatography using 20% ethyl acetate in hexane to afford pink coloured solid (2) (4.1 g, 97% yield). MS (ESI): Mass calcd. for $C_9H_8BrNO$, m/z 226.07 found 228.0$[M+H]^{2+}$.

Step-2: Preparation of 5-bromo-1H-indole-2-carbaldehyde (3)

3

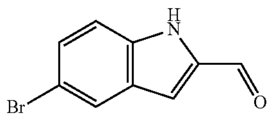

To a solution of (5-bromo-1H-indol-2-yl) methanol (3, 4.1 g, 18.1 mmol) in chloroform (50 mL) was added $MnO_2$ (15.7 g, 181 mmol) and heated at 90° C. for 2 h under $N_2$ atmosphere (Reaction condition b). Reaction mixture was filtered off and evaporated the filtrate to obtain crude. The crude was purified by gradient column chromatography using 20% ethyl acetate in hexane to afford pink coloured solid (3) (4.1 g, 97% yield). MS (ESI): Mass calcd. for $C_9H_6BrNO$, m/z 224.06 found 226.0$[M+H]^{2+}$.

Step-3: 5-bromo-1-(cyclopropylmethyl)-1H-indole-2-carbaldehyde (4)

4

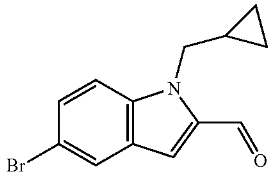

To the stirred solution of 5-bromo-1H-indole-2-carbaldehyde (3, 1.18 g, 5.22 mmol) in DMF (20 mL), were added potassium carbonate (1.4 g, 10.44 mmol) and (bromomethyl)cyclopropane (0.78 mL, 7.8 mmol) at rt. The reaction mixture was stirred at rt for 12 h (Reaction condition c). The reaction mixture was diluted with water and extracted with ethyl acetate (50 mL×2). Combined organic extracts were washed with brine, dried over sodium sulfate and evaporated to give the crude product. The crude was purified by gradient column chromatography using 20% ethyl acetate in hexane to afford the 5-bromo-1-(cyclopropylmethyl)-1H-indole-2-carbaldehyde as sticky solid (4) (0.9 g, 62% Yield). MS (ESI): Mass calcd. for $C_{13}H_{12}BrNO$, 278.15; m/z found, 280.0 $[M+H]^{2+}$.

Synthesis of 7-chloro-1-(cyclopropylmethyl)-1H-indole-2-carbaldehyde (Intermediate for Compound-44)

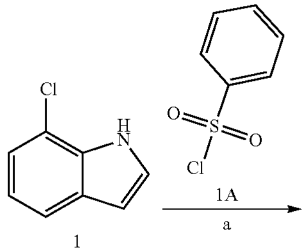

-continued

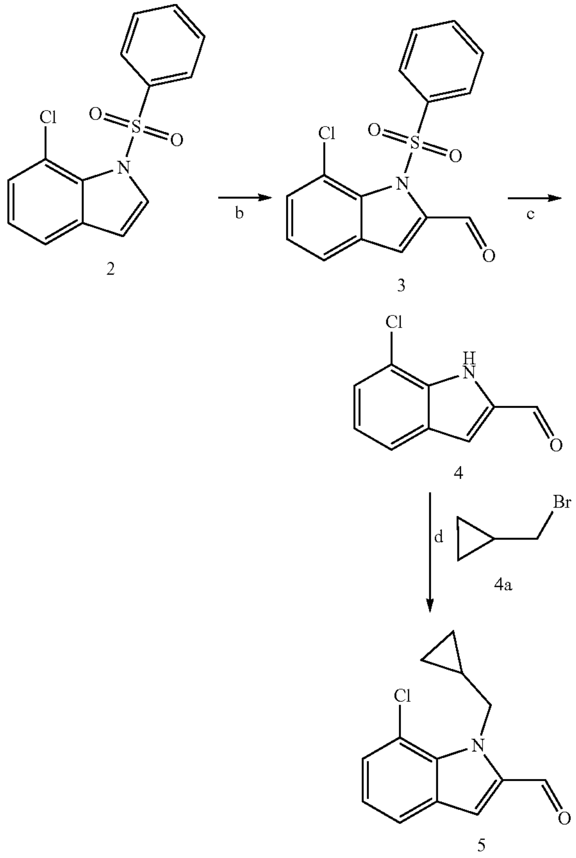

Step 1: Preparation of 7-chloro-1-(phenylsulfonyl)-1H-indole (2)

2

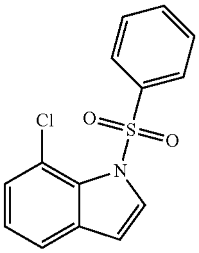

To a solution of sodium hydride (1.68 g, 42 mmol) in DMF (10 mL), was added solution of 7-chloro-1H-indole (1, 3.2 g, 21 mmol) in DMF at 0° C., dropwise over 15 min. Benzenesulfonyl chloride in DMF (2.8 mL, 23 mmol) was added at 0° C. and stirred for 2 h at rt under $N_2$ atmosphere (Reaction condition a). To the reaction mixture, ice cold water (50 mL) was added and filtered off the precipitate. The precipitate was washed with ice cold water and purified by gradient column chromatography using 30% ethyl acetate in hexane to afford title compound as pale brown solid (2) (5 g, 81.8%). MS (ESI): Mass calcd. for $C_{14}H_{10}ClNO_2S$, 219.01; m/z found, 220.1 $[M+H]^+$.

Step 2: Preparation of 7-chloro-1-(phenylsulfonyl)-1H-indole-2-carbaldehyde (3)

3

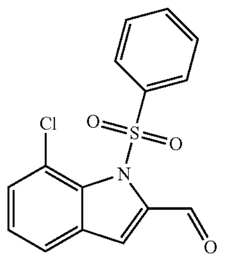

To a solution of 7-chloro-1-(phenylsulfonyl)-1H-indole (2, 5 g, 17 mmol) in dry THF (50 mL), was added lithium diisopropylamide 1.5 M in THF (17.0 mL, 34 mmol) at −78° C. and stirred for 30 min, followed by addition of dry DMF (1.65 mL, 20 mmol) at −78° C. It was stirred for 10 min at −78° C. under $N_2$ atmosphere (Reaction condition b). To the reaction mixture was added aqueous ammonium chloride (20 mL) and extracted with EtOAc. Organic layer was washed with saturated $NH_4Cl$ solution and brine, dried over sodium sulphate, filtered and concentrated under reduced pressure. The crude was purified by gradient column chromatography using 30% ethyl acetate in hexane to afford title compound as pale brown viscous liquid (3) (3.0 g, 55.3%). MS (ESI): Mass calcd. for $C_{15}H_{10}ClNO_3S$, 319.01; m/z found, 320.1 $[M+H]^+$.

Step 3: Preparation of 7-chloro-1H-indole-2-carbaldehyde (4)

4

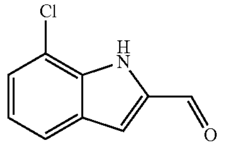

To the stirred solution of 7-chloro-1-(phenylsulfonyl)-1H-indole-2-carbaldehyde (3, 3 g, 9.40 mmol) in THF (20 mL), was added 1 M solution of tetrabutyl ammonium fluoride in THF (18.8 mL, 18.8 mmol) and stirred at 80° C. for 1 h (Reaction condition c). Reaction mixture was cooled to rt, added water (20 mL) and extracted with EtOAc (100 mL). Organic layer was dried over anhydrous $Na_2SO_4$ and evaporated under vacuum. Crude was purified by column chromatography using 15-20% EtOAc in Hexane to afford the product as brown solid (4). (1.6 g, 95% Yield). MS (ESI): Mass calcd. for $C_9H_6ClNO$, 179.01; m/z found 180.1 $(M+H)^+$.

Step 4: Preparation of 1-(cyclopropylmethyl)-7-chloro-1H-indole-2-carbaldehyde (5)

5

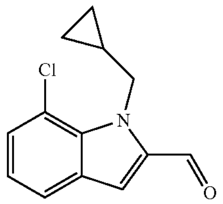

To the stirred solution of 7-chloro-1H-indole-2-carbaldehyde (4, 1 g, 5.5 mmol) in DMF (20 mL), were added cesium carbonate (3.5 g, 11 mmol) and (bromomethyl)cyclopropane (4a, 0.65 mL, 6.7 mmol) at rt (Reaction condition d). The reaction mixture was stirred at rt for 12 h. The reaction mixture was diluted with water and extracted with ethyl acetate (50 mL×2). Combined organic extracts were washed with brine, dried over sodium sulfate and evaporated to give the crude product. The crude was purified by gradient column chromatography using 20% ethyl acetate in hexane to afford the 1-(cyclopropylmethyl)-7-chloro-1H-indole-2-carbaldehyde as sticky solid (5) (0.7 g, 54% Yield). $^1$HNMR (400 MHz, $CDCl_3$) δ (ppm): 9.87 (s, 1H), 7.64 (d, J=8.0 Hz, 1H), 7.37 (d, J=7.6 Hz, 1H) 7.29 (s, 1H), 7.08 (t, J=7.6 Hz, 1H), 5.00-4.92 (m, 2H), 1.36-1.32 (m, 2H), 1.25 (m, 1H), 0.43-0.41 (m, 2H). MS (ESI): Mass calcd. for $C_{13}H_{12}ClNO$, 233.06; m/z found, 234.1 $[M+H]^+$.

Synthesis of 1-(cyclopropylmethyl)-7-methoxy-1H-indole-2-carbaldehyde (Intermediate for Compound-47)

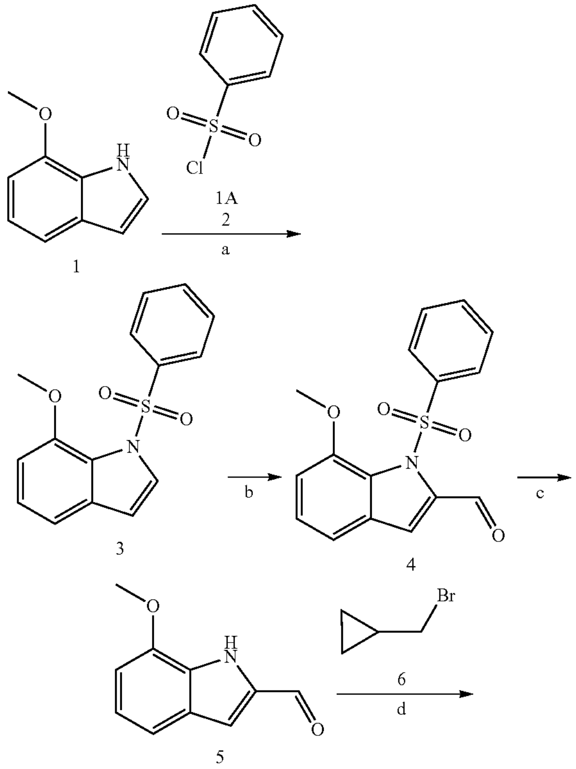

-continued

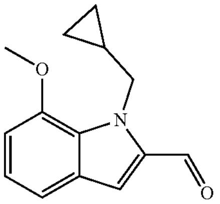

7

Step 1: Preparation of 7-methoxy-1-(phenylsulfonyl)-1H-indole

3

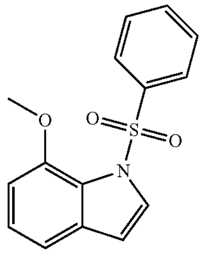

To a solution of sodium hydride (1.6 g, 40 mmol) in DMF (10 mL) was added a solution of 7-methoxy-1H-indole (1, 3 g, 20 mmol) in DMF at 0° C., drop wise over 15 min. followed by addition of a solution of benzenesulfonyl chloride (2, 2.86 mL, 22 mmol) in DMF at 0° C. and the reaction mixture was stirred for 2 h at rt under $N_2$ atmosphere. To the reaction mixture was added ice cold water (50 mL), then the precipitate was filtered off and washed with ice cold water to obtain brown solid (3) (5.6 g, 97.5% Yield). MS (ESI) m/z 288.1 $(M+H)^+$.

Step 2: Preparation of 7-methoxy-1-(phenylsulfonyl)-1H-indole-2-carbaldehyde

4

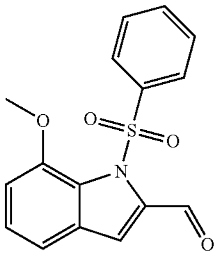

To a solution of 7-methoxy-1-(phenylsulfonyl)-1H-indole (3, 3 g, 10.4 mmol) in dry THF (50 mL) was added lithium diisopropylamide 1M in THF (5.2 mL, 20 mmol) at −78° C. and stirred for 45 min at same temperature. Dry DMF (1 mL, 12 mmol) was added at −78° C. and stirred for 10 min. To the reaction mixture was added aqueous ammonium chloride (20 mL) and extracted with EtOAc. Organic layer was washed with saturated $NH_4Cl$ solution and brine, dried over sodium sulphate, filtered and concentrated under reduced pressure to obtain brown solid (4) (1.2 g, 37.5% Yield). MS (ESI) m/z 304.1 $(M+H)^+$.

Step 3: Preparation of 7-methoxy-1H-indole-2-carbaldehyde

5

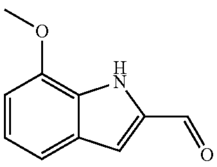

To the stirred solution of 7-methoxy-1-(phenylsulfonyl)-1H-indole-2-carbaldehyde (4, 1.1 g, 3.4 mmol) in THF (50 mL), was added TBAF (1M in THF) (6.9 mL, 6.9 mmol) at rt. The reaction mixture was stirred at rt for 12 h. The reaction mixture was diluted with water and extracted with ethyl acetate (50 mL×2). Combined organic extracts were washed with brine, dried over sodium sulfate and evaporated to get crude product. The crude residue was purified by gradient column chromatography using 15-25% ethyl acetate in hexane to afford the 5-fluoro-1H-indole-2-carbaldehyde as sticky solid (5) (0.47 g, 79.6% Yield). MS (ESI): Mass calcd. for $C_{10}H_9NO_2$, 175.06; m/z found, 176.1 $[M+H]^+$.

Step 4: Preparation of 1-(cyclopropylmethyl)-7-methoxy-1H-indole-2-carbaldehyde

6

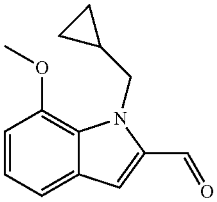

To the stirred solution of 7-methoxy-1H-indole-2-carbaldehyde (5, 0.47 g, 2.6 mmol) in DMF (50 mL), were added potassium carbonate (0.55 g, 5.2 mmol) and (bromomethyl) cyclopropane (6, 0.41 mL, 4.02 mmol) at rt. The reaction mixture was stirred at rt for 12 h. The reaction mixture was diluted with water and extracted with ethyl acetate (50 mL×2). Combined organic extracts were washed with brine, dried over sodium sulphate and evaporated to get crude product. The crude residue was purified by gradient column chromatography using 3-7% ethyl acetate in hexane to afford title compound as sticky solid (6) (0.41 g, 68% Yield). MS (ESI): Mass calcd. for $C_{14}H_{15}NO_2$, 229.1: m/z found, 230.1 $[M+H]^+$.

Synthesis of 5-(chloromethyl)-2,4-dimethylthiazole (Intermediate for Compound-48)

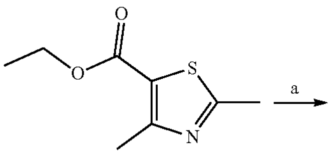

1

-continued

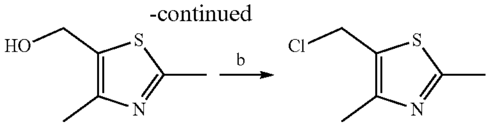

2 3

Step 1: (2,4-dimethylthiazol-5-yl)methanol

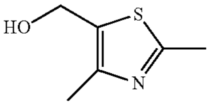

2

To the stirred solution of ethyl 2,4-dimethylthiazole-5-carboxylate (1, 0.5 g, 2.70 mmol) in THF (10 mL), was added 1M LAH in THF (4 mL, 4.05 mmol) drop wise at 0° C. and stirred at rt for 1 h. The reaction mixture was quenched with saturated $NH_4Cl$ solution, filtered through celite and extracted with EtOAc (2×25 mL). Organic layer was washed with brine (5 mL) solution, dried over anhydrous $Na_2SO_4$ and evaporate. The crude was purified by gradient column chromatography using 50-60% EtOAc in Hexane to afford the product as colourless oil. (0.3 g, 79% Yield). MS (ESI): Mass calcd. for $C_6H_9NOS$, 143.04; m/z found 144.1 $(M+H)^+$.

Step 2: 5-(chloromethyl)-2,4-dimethylthiazole

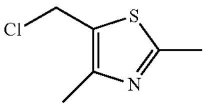

3

To a stirred solution of (2,4-dimethylthiazol-5-yl)methanol (2, 0.3 g, 2.09 mmol) in DCM (5 mL), was added $SOCl_2$ (0.3 mL, 4.19 mmol) drop wise at 0° C. and the reaction mixture was stirred at rt for 1 h. The reaction mixture was evaporated under vacuum and dried to afford the product as brown oil. (0.25 g, 75% Yield) (3). $^1$HNMR (400 MHz, DMSO-d6) δ (ppm): 4.99 (s, 2H), 2.59 (s, 3H), 2.30 (s, 3H).

Synthesis of 2-bromo-1-(3-ethylbenzo[b]thiophen-2-yl)propan-1-one (Intermediate for Compound-49)

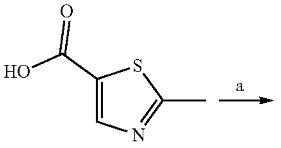

1

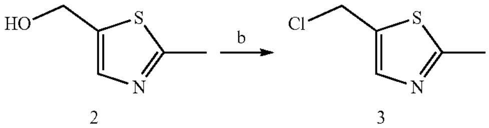

2 3

Step 1: (2-methylthiazol-5-yl)methanol

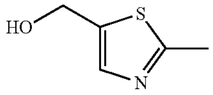

2

To the stirred solution of 2-methylthiazole-5-carboxylic acid (1, 1.0 g, 6.99 mmol) in THF (10 mL) at −10° C., was added triethylamine (1.02 mL, 7.34 mmol) followed by ethyl chloroformat (0.66 mL, 6.99 mmol) in THF (2 mL) drop wise at −10° C. and stirred at same temperature for 1 h. The reaction mixture was filtered through celite and the filtrate was cooled to −10° C. To the filtrate, suspension of $NaBH_4$ (0.68 g, 17.4 mmol) in water (2 mL) was added and allowed to attain rt and stirred for 2 h. The reaction mixture was diluted with 2N NaOH (5 mL) and extracted with EtOAc (2×25 mL). Organic layer was washed with brine (5 mL) solution, dried over anhydrous $Na_2SO_4$ and evaporated. The crude residue was purified by gradient column chromatography using 40-60% EtOAc in Hexane to afford the product as yellow oil (2) (0.2 g, 25%, Yield). MS (ESI): Mass calcd. for $C_5H_7NOS$, 129.02; m/z found 130.1 $(M+H)^+$.

Step 2: 5-(chloromethyl)-2-methylthiazole

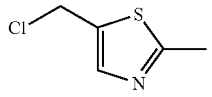

3

To a stirred solution of (2-methylthiazol-5-yl)methanol (2, 0.2 g, 1.55 mmol) in DCM (5 mL), was added $SOCl_2$ (0.23 mL, 3.10 mmol) drop wise at 0° C. and the reaction mixture was stirred at rt for 1 h. The reaction mixture was neutralized using cold $NaHCO_3$ (5 mL) solution and extracted with DCM (2×25 mL). Organic layer was washed with brine (5 mL) solution, dried over anhydrous $Na_2SO_4$ and evaporated to afford the product as yellow oil. (0.2 g, 90%, Yield). MS (ESI): Mass calcd. for $C_5H_6ClNS$, 146.99; m/z found 148.1 $(M+H)^+$.

Synthesis of ethyl 2-amino-6-methylisonicotinate (Intermediate for Compounds-25, 26 & 27)

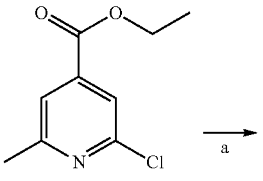

1

-continued

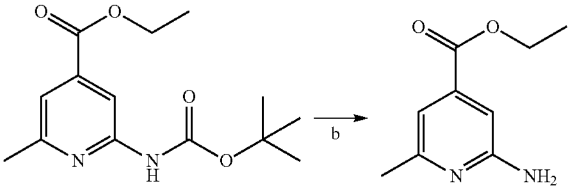

2

3

Step 1: Preparation of Ethyl 2-((tert-butoxycarbonyl)amino)-6-methylisonicotinate (2)

2

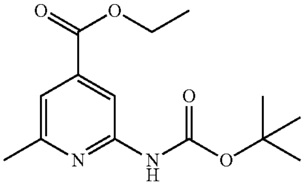

To the stirred solution of ethyl 2-chloro-6-methylisonicotinate (1, 5.2 g, 26.1 mmol) in 1,4-dioxane (50 mL), was added tert-butyl carbamate (4.6 g, 39.1 mmol), $Cs_2CO_3$ (21.3 g, 65.3 mmol), XPhos (1.24 g, 2.61 mmol) followed by Bis(dibenzylideneacetone)palladium (0) (0.75 g, 1.31 mmol) and stirred at 85° C. for 16 h (Reaction condition a). The reaction mixture was cooled to rt, filtered through celite. To this added water (100 mL) and compound was extracted with EtOAc (200 mL). Organic layer was dried over anhydrous $Na_2SO_4$ and evaporated under vacuum. Crude was purified by column chromatography using 15-20% EtOAc in Hexane to afford the product as brown gummy solid (2) (3.5 g, 58% Yield). MS (ESI): mass calcd. for $C_{14}H_{20}N_2O_4$, 280.14; m/z found 281.2 $(M+H)^+$.

Step 2: Preparation of Ethyl 2-amino-6-methylisonicotinate (3)

3

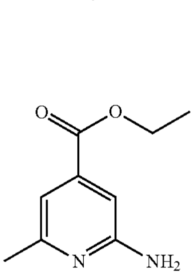

To the stirred solution of ethyl 2-((tert-butoxycarbonyl)amino)-6-methylisonicotinate (2, 3.5 g, 12.5 mmol) in DCM (30 mL), was added TFA (10 mL) and stirred at rt for 16 h (Reaction condition b). The reaction mixture was evaporated, added water (20 mL) and basified using saturated $Na_2CO_3$ solution. The precipitate formed was collected by filtration and dried to afford the product (3) as off white solid. (1.6 g, 72% Yield). MS (ESI): mass calcd. for $C_9H_{12}N_2O_2$, 180.09; m/z found 181.1 $(M+H)^+$.

Synthesis of 1-(phenylsulfonyl)-1H-indole-2-carbaldehyde (3) (Intermediate for Compound-50, 57, 58, 59, 60, 61, 62, 63, 78, 79, 81& 85)

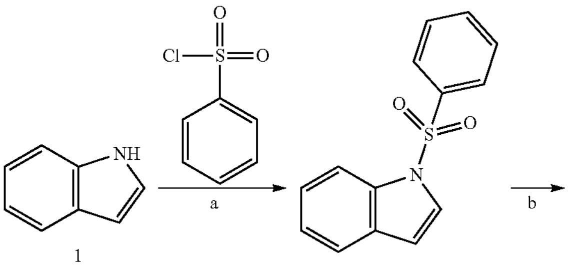

1

2

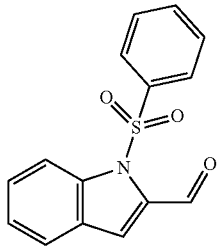

3

Step-a: Synthesis of 1-(phenylsulfonyl)-1H-indole (2)

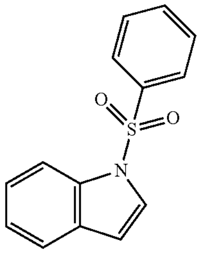 [SMILES: O=S(=O)(c1ccccc1)n1ccc2ccccc21]

To a stirred solution 1H-indole (1, 10.0 g, 85.36 mmol) in N,N-dimethylformamide (100 mL), sodium hydride (4.08 g, 170.94 mmol) was added slowly at 0° C. the reaction mixture was stirred at 0° C. for 40 min. Benzene sulphonyl chloride (22.6 g, 128.20 mmol) was added drop wise then reaction mixture was stirred at rt for 1 h. After completion of reaction, the reaction mixture was quenched with ice, solid obtained filtered and dried. The crude was purified by column chromatography (100-200 silica gel) using 20% ethyl acetate in hexane as eluent. The desired fractions were concentrated under reduced pressure to afford 1-(phenylsulfonyl)-1H-indole (2) as white solid. Yield: 16.2 g (76%). MS (ESI): 257.12; m/z found, 258.23 $[M+H]^+$.

Step-b: Synthesis of 1-(phenylsulfonyl)-1H-indole-2-carbaldehyde (3)

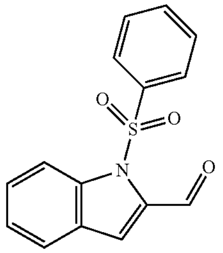 [SMILES: O=Cc1cc2ccccc2n1S(=O)(=O)c1ccccc1]

To a stirred solution 1-(phenylsulfonyl)-1H-indole (2, 16.2 g, 62.97 mmol) in tetrahydrofuran (150 mL), 2.5 M n-butyl lithium in hexane (35.5 ml, 89.07 mmol) was added drop wise at −78° C. The reaction mixture was stirred at −78° for 1 h. N,N-Dimethylformamide (6.57 ml, 83.50 mmol) was added at −78° C. and the reaction mixture was further stirred at −78° C. for 1 h. After completion of reaction, the reaction mixture was quenched with ammonium chloride, extracted with ethyl acetate (100 mL×2). Organic layer was washed with brine, dried over anhydrous sodium sulfate, filtered and evaporated to get crude product. The crude was purified by CombiFlash, using 40.0 g RediSep column and 20% ethyl acetate in hexane as eluent. The desired fractions were concentrated under reduced pressure to afford 1-(phenylsulfonyl)-1H-indole-2-carbaldehyde (3) as yellow solid. Yield: 12.6 g (73%). MS (ESI): 285.11; m/z found, 256.39 $[M+H]^+$.

Synthesis of 6-methoxy-1-(phenylsulfonyl)-1H-indole-2-carbaldehyde (3) (Intermediate for Compound-51, 67, 80, 82 & 83)

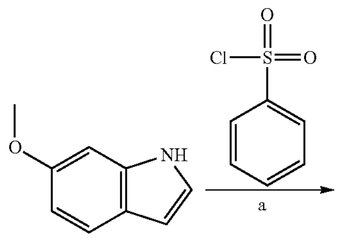

1

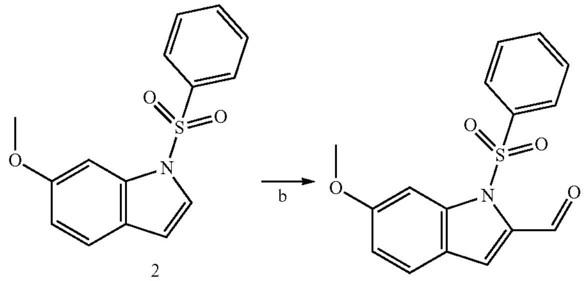

2

3

Step-a: Synthesis of 6-methoxy-1-(phenylsulfonyl)-1H-indole (2)

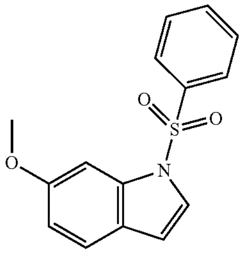 [SMILES: COc1ccc2ccn(S(=O)(=O)c3ccccc3)c2c1]

To a stirred solution 6-methoxy-1H-indole (1, 10.0 g, 68.02 mmol) in N,N-dimethylformamide (100 mL), sodium hydride (5.44 g, 136.05 mmol) was added slowly at 0° C., the reaction mixture was stirred at rt at 0° C. for 40 min. Benzene sulphonyl chloride (17.8 g, 102.03 mmol) was added drop wise then reaction mixture was stirred at rt for 1 h. After completion of reaction, the reaction mixture was quenched with ice, solid obtained filtered and dried. The crude was purified by column chromatography (100-200 silica gel) using 20% ethyl acetate in hexane as eluent. The desired fractions were concentrated under reduced pressure to afford 6-methoxy-1-(phenylsulfonyl)-1H-indole (2) as white solid. Yield: 16.5 g (84%). MS (ESI): 286.11; m/z found, 287.52 $[M+H]^+$.

Step-b: 6-methoxy-1-(phenylsulfonyl)-1H-indole-2-carbaldehyde (3)

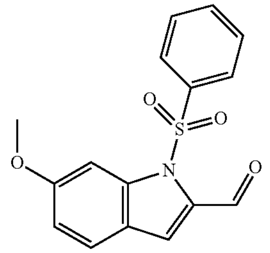 [SMILES: COc1ccc2cc(C=O)n(S(=O)(=O)c3ccccc3)c2c1]

To a stirred solution 6-methoxy-1-(phenylsulfonyl)-1H-indole (2, 6.0 g, 20.9 mmol) in tetrahydrofuran (60 mL), 2.5 M n-butyl lithium in hexane (13.37 ml, 33.44 mmol) was added drop wise at −78° C. and the reaction mixture was stirred at −78° C. for 1 h. N,N-dimethylformamide (2.3 ml, 31.3 mmol) was added at −78° C. and the reaction mixture was stirred at −78° for 1 h The reaction mixture was quenched with saturated solution of ammonium chloride, extracted with ethyl acetate (50 mL×2). Organic layer was washed with brine, dried over anhydrous sodium sulfate, filtered and evaporated to get crude product. The crude was purified by CombiFlash using 40.0 g RediSep column and 20% ethyl acetate in hexane as eluent. The desired fractions were concentrated under reduced pressure to afford 6-methoxy-1-(phenylsulfonyl)-1H-indole-2-carbaldehyde (3) as yellow solid. Yield: 5.1 g (78%). MS (ESI): 314.21; m/z found, 315.22 $[M+H]^+$.

Synthesis of 5,6-difluoro-1-(phenylsulfonyl)-1H-indole-2-carbaldehyde (Intermediate for Compound-55)

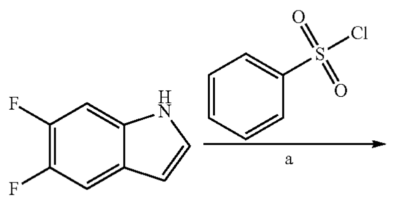

1

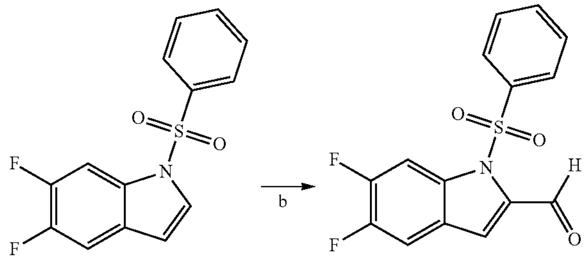

2 3

Step-1: Synthesis of 5,6-difluoro-1-(phenylsulfonyl)-1H-indole (2)

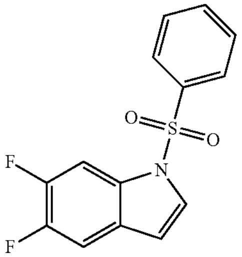 [SMILES: O=S(=O)(c1ccccc1)n1ccc2cc(F)c(F)cc21]

To a solution of 5,6-difluoro-1H-indole (1, 5.0 g, 32.67 mmol) in N,N-dimethylformamide (50 mL), sodium hydride (60%, 3.1 g, 81.61 mmol) was added portion wise over 15 min at 0° C. After 15 min benzenesulfonyl chloride (6.4 mL, 49.0 mmol) was added at 0° C. and stirred for 2 h at rt under $N_2$ atmosphere. After completion of reaction, ice cold water (150 mL) was added to reaction mixture. The solid precipitated was filtered off and washed with ice cold water. The crude was purified by CombiFlash using 40 g RediSep and 20% ethyl acetate in hexane as eluent to afford 5,6-difluoro-1-(phenylsulfonyl)-1H-indole (2) as off white solid. Yield: 8.8 g (92.63%). MS (ESI): 293; m/z found, 294.01 $[M+H]^{+1}$.

Step-2: Synthesis of 5,6-difluoro-1-(phenylsulfonyl)-1H-indole-2-carbaldehyde (3)

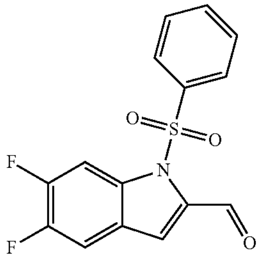 [SMILES: O=Cc1cc2cc(F)c(F)cc2n1S(=O)(=O)c1ccccc1]

To a solution of 5,6-difluoro-1-(phenylsulfonyl)-1H-indole (2, 8.8 g, 30.12 mmol) in dry tetrahydrofuran (80 mL), was added 2.5 M n-butyllithium in hexane (20.0 mL, 45.37 mmol) at −78° C. and stirred for 45 min, followed by addition of anhydrous N,N-dimethylformamide (2.5 mL, 45.37 mmol) at −78° C. The reaction mass was stirred for 30 min at −78° C. under $N_2$ atmosphere. After completion of reaction, reaction mixture was quenched with aqueous ammonium chloride (30 mL) and extracted with ethyl acetate (100 mL×2). The organic layer was washed with saturated ammonium chloride solution and brine (100 mL), dried over anhydrous sodium sulfate, filtered and concentrated under reduced pressure. The crude was purified by CombiFlash using 40 g RediSep and 30% ethyl acetate in hexane as eluent to afford 5,6-difluoro-1-(phenylsulfonyl)-1H-indole-2-carbaldehyde (3) as yellow liquid. Yield: 7.0 g, (72.9%). MS (ESI): 321.30; m/z found, 322.1 $[M+H]^+$.

Synthesis of (1-(tert-butoxycarbonyl)-6-methoxy-1H-indol-2-yl)boronic acid (Intermediate for Compound-86)

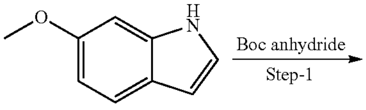

1

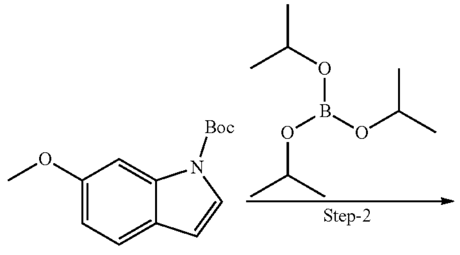

2

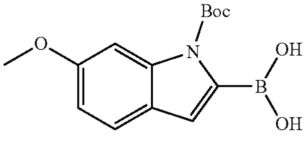

3

Step-1: Synthesis of tert-butyl-6-methoxy-1H-indole-1-carboxylate (2)

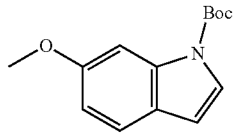 [SMILES: COc1ccc2ccn(C(=O)OC(C)(C)C)c2c1]

To a stirred solution of 6-methoxy-1H-indole (1, 2.0 g, 13.64 mmol) in dichloromethane (20 mL), was added triethylamine (5.60 ml, 40.8 mmol), N,N, dimethyl aminopyridine (0.08 g, 0.68 mmol) and boc-anhydride (3.9 mL, 16.3 mmol) at 0° C. and then the reaction mixture was stirred at room temperature for 16 h. After completion of reaction, the reaction mixture was diluted with dichloromethane (100 mL×3). The organic phase was washed with water, brine, dried over anhydrous sodium sulfate and concentrated under reduced pressure to afford the crude compound. The crude was purified by CombiFlash using 40.0 g RediSep column and 1-5% ethyl acetate in hexane as eluent to afford tert-butyl-6-methoxy-1H-indole-1-carboxylate (2) as oily liquid. Yield: 3.0 g (89%). MS (ESI): 247.12; m/z found, 246.01 $[M-H]^{-1}$.

Step-2: Synthesis of (1-(tert-butoxycarbonyl)-6-methoxy-1H-indol-2-yl)boronic Acid (3)

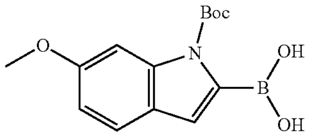 [SMILES: COc1ccc2cc(B(O)O)n(C(=O)OC(C)(C)C)c2c1]

To a stirred solution of tert-butyl-6-methoxy-1H-indole-1-carboxylate (2, 2.5 g, 10.12 mmol), triisopropyl borate (2, 2.7 mL, 20.24 mmol) in tetrahydrofuran (25 mL), was added lithium diisopropylamide 1M in tetrahydrofuran (10 mL, 20.24 mmol) drop wise at 0° C. and the reaction mixture was stirred at 0° C. for 3 h. After completion of reaction, the reaction mixture was quenched with saturated solution of ammonium chloride, extracted with ethyl acetate (50 mL×2). Organic layer was washed with brine, dried over anhydrous sodium sulfate, filtered and evaporated to get crude product. The crude was purified by CombiFlash using 40.0 g RediSep column and 10-20% ethyl acetate in hexane as eluent. The desired fractions were concentrated under reduced pressure to afford (1-(tert-butoxycarbonyl)-6-methoxy-1H-indol-2-yl)boronic acid (3) as off-white solid. Yield: 1.3 g, (44%).

$^1$HNMR (400 MHz, DMSO-d6) δ (ppm): 8.11 (s, 2H), 7.65 (s, 1H), 7.43 (d, J=8.56 Hz, 1H), 6.82 (d, J=8.56 Hz, 1H), 6.55 (s, 1H), 3.79 (s, 3H), 1.59 (s, 9H). MS (ESI): Mass calculated for $C_{14}H_{18}BNO_5$, 291.13; m/z found 191.01$[M+H-100]^{+1}$.

Example 2

General Procedure for Biological Evaluation

FP Binding Assay

Binding of compounds with PAD4 was detected by FP assay. PAD4 was diluted to 1 uM in assay buffer (100 mM HEPES, 50 mM NaCl, 1 mM DTT, 5% Glycerol and 1 mM CHAPS) and added to wells containing various concentration of compounds or DMSO vehicle (1%) in a 384 well black plate. 10 nM of fluorescein labelled probe (JPAD-00085) was added to the plate. Assay plate was incubated for 60 minutes at RT before measuring FP reading at FP module (λex 485/λem 535 nm) on Pherastar. $IC_{50}$ was calculated using XL-fit software model 205. (Lewis et. al, Nat Chem Biol. 2015, 11(3), 189-91).

Ammonia Release Biochemical Assay

Citrullination assay was detected via ammonia release. PAD4 was diluted to 120 nM in assay buffer (100 mM HEPES, 50 mM NaCl, 2 mM DDT, 0.6 mg/mL BSA, pH 7.4) added to wells containing various concentration of compound or DMSO vehicle (1% final) in black 384 well plate. Following a 60-min preincubation at RT, the reaction was initiated by the addition of substrate (1.5 mM BAEE in 200 mM HEPES, 50 mM NaCl, 350 uM CaCl2, 2 mM, pH 7.4). The reaction was stopped after 60 min by addition of stop/detection buffer containing 50 mM EDTA, 2.6 mM of o-phthaladehyde and 2.6 mM DTT. Assay was incubated at RT for 90 min before measuring fluorescence's (λex 405/λem 460 nm) on Tecan reader. $IC_{50}$ was calculated using XL-fit software model 205. (Lewis et. al Nat Chem Biol. 2015, 11(3), 189-91).

Anti-PAD4 Activity:

Table 1, below, shows the activity of selected compounds of this invention in the PAD4 assays described above. Compounds having an activity designated as "A" provided $IC_{50} \leq 1$ uM; compounds having an activity designated as "B" provided $IC_{50}$ 1-10 uM; and compounds having an activity designated as "C" provided $IC_{50} \geq 10$ uM.

TABLE 1

| | PAD4 activity | |
|---|---|---|
| Compound No. | NH3 release biochemical assay PAD4 $IC_{50}$ (uM) | FP binding assay PAD4 $IC_{50}$ (uM) |
| 1 | C | nd |
| 2 | B | nd |
| 3 | A | B |
| 4 | A | nd |
| 5 | C | nd |
| 6 | C | nd |
| 7 | C | nd |
| 8 | C | nd |
| 9 | B | nd |
| 10 | A | B |
| 11 | B | B |
| 12 | A | B |
| 13 | A | A |
| 14 | B | B |
| 15 | A | B |
| 16 | A | A |
| 17 | A | B |
| 18 | B | B |
| 19 | B | B |
| 20 | B | B |
| 21 | A | B |
| 22 | B | B |
| 23 | A | A |
| 24 | A | B |
| 25 | A | B |
| 26 | A | B |
| 27 | B | C |
| 28 | A | A |
| 29 | A | A |
| 30 | A | A |
| 31 | B | C |
| 32 | C | C |

TABLE 1-continued

| PAD4 activity | | |
|---|---|---|
| Compound No. | NH3 release biochemical assay PAD4 $IC_{50}$ (uM) | FP binding assay PAD4 $IC_{50}$ (uM) |
| 33 | B | A |
| 34 | A | B |
| 35 | A | nd |
| 36 | A | A |
| 37 | A | nd |
| 38 | B | B |
| 39 | A | A |
| 40 | B | nd |
| 41 | A | nd |
| 42 | A | nd |
| 43 | B | nd |
| 44 | A | nd |
| 45 | A | nd |
| 46 | C | nd |
| 47 | A | nd |
| 48 | B | nd |
| 49 | A | nd |
| 50 | B | nd |
| 51 | A | nd |
| 52 | A | nd |
| 53 | A | nd |
| 54 | A | nd |
| 55 | A | nd |
| 56 | B | nd |
| 57 | B | nd |
| 58 | A | nd |
| 59 | B | nd |
| 60 | A | nd |
| 61 | A | nd |
| 62 | A | nd |
| 63 | A | nd |
| 64 | A | nd |
| 65 | B | nd |
| 66 | C | nd |
| 67 | A | nd |
| 68 | A | nd |
| 69 | A | nd |
| 70 | A | nd |
| 71 | A | nd |
| 72 | A | nd |
| 73 | A | nd |
| 74 | A | nd |
| 75 | A | nd |
| 76 | A | nd |
| 77 | A | nd |
| 78 | A | nd |
| 79 | A | nd |
| 80 | A | nd |
| 81 | B | nd |
| 82 | A | nd |
| 83 | A | nd |
| 84 | B | nd |
| 85 | A | nd |
| 86 | nd | nd |

nd = not determined

Table 1 illustrates that most of the tested compounds were found to be active against the PAD4 enzyme when evaluated through both Ammonia Release Biochemical and FP Binding assays. The $IC_{50}$ values display the efficacy of the compounds in inhibiting the PAD4 enzyme activity. $IC_{50}$ value indicates how much of a particular drug or a compound is needed to inhibit a given biological process or component of a process such as an enzyme. A low value of $IC_{50}$ denotes high inhibition efficacy of the test compound (Compounds 1-48 as described herein). However, in the above Table 1, high efficacy is denoted by "A", "B", and "C", wherein "A" having least value of $IC_{50}$ and thus most effective.

The ammonia release biochemical assay showed that 55 out of 86 compounds have an $IC_{50}$ value of ≤1 μM denoted by "A". These 55 compounds were 3, 4, 10, 12, 13, 15-17, 21, 23-26, 28-30, 34-37, 39, 41, 42, 44, 45, 47, 49, 51-55, 58, 60-64, 67-80, 82, 83 & 85.

On the other hand, the FP Binding assay showed that 9 of the compounds to be actively inhibiting PAD4 enzyme activity. The individual compounds are 13, 16, 23, 28-30, 33, 36, and 39, respectively.

Therefore, it may be inferred that compounds-3, 4, 10, 12, 13, 15-17, 21, 23-26, 28-30, 34-37, 39, 41, 42, 44, 45, 47, 49, 51-55, 58, 60-64, 67-80, 82, 83 & 85 can help in treating PAD4 mediated disorders.

What is claimed is:

1. A compound of Formula (II)

Formula (II)

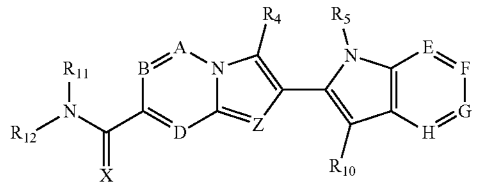

their polymorphs, stereoisomers, prodrugs, solvates, co-crystals, intermediates, pharmaceutically acceptable salts, and metabolites thereof, wherein X is selected from O or S;

Z is N;

A is $CR_1$;

B is $CR_2$;

D is $CR_3$;

E is selected from N or $CR_6$;

F is absent or is selected from N, and $CR_7$;

G is absent or is selected from N, and $CR_8$;

H is absent or is selected from N, and $CR_9$;

$R_1$, $R_2$, $R_3$, $R_4$, $R_5$, $R_6$, $R_7$, $R_8$, $R_9$ and $R_{10}$ are independently selected from hydrogen, hydroxyl, cyano, amino, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-10}$ heterocyclyl, $C_{1-10}$ heteroaryl, $C(O)C_{1-6}$ alkyl, $C(O)C_{1-6}$ haloalkyl, $C(O)NR_{15}$, $C(O)C_{1-6}$ alkylamino, $C(O)C_{5-6}$ aryl, $C(O)C_{1-6}$ heteroaryl, $SO_2C_{1-6}$ alkyl, $SO_2C_{1-6}$ haloalkyl, $SO_2C_{3-6}$ cycloalkyl, $SO_2NR_{15}$, $SO_2NC_{1-6}$ alkylamino, $SO_2C_{5-6}$ aryl, or $SO_2C_{1-6}$ heteroaryl, wherein $C_{1-6}$ alkyl, $C_{1-6}$ alkoxy, $C_{1-10}$ heteroaryl, and $C_{1-6}$ haloalkoxy, is optionally substituted with one or more of the groups selected from hydrogen, oxo, $C_{1-6}$ alkyl, $C_{1-6}$ alkoxy, $C_{1-6}$ haloalkyl, $C_{1-6}$ alkylhydroxy, $C_{3-6}$ cycloalkyl, $C_{5-9}$ aryl, $C_{1-6}$ heterocyclyl, $C_{1-6}$ heteroaryl, cyano, halogen, and hydroxyl, wherein $C_{5-9}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, $—CH_2OH$, and cyano;

$R_{11}$ and $R_{12}$ are taken together to form a 5-10 membered monocyclic or bicyclic saturated or unsaturated heterocyclic ring optionally with 1-5 heteroatoms selected from N, S or O, wherein the 5-10 membered monocyclic or bicyclic saturated or unsaturated heterocyclic ring is optionally substituted with the substituents selected from amino, $C_{1-6}$ alkylamino, $C_{1-6}$ acylamino, —NHC(NH)$CH_2$Cl, —NH(CO)CH═CH—$CH_2$—N$(CH_3)_2$, $C_{1-6}$ alkyl, halogen, $C_{1-6}$ alkoxy, or hydroxyl;

and $R_{15}$ is selected from the group consisting of hydrogen, $C_{1-6}$ alkyl, and combinations thereof.

2. The compound of Formula (II) as claimed in claim 1, their polymorphs, stereoisomers, prodrugs, solvates, co-crystals, intermediates, pharmaceutically acceptable salts, and metabolites thereof, wherein X is selected from O or S;

Z is N;

A is $CR_1$;

B is $CR_2$;

D is $CR_3$;

E is selected from N or $CR_6$;

F is absent or is selected from N, and $CR_7$;

G is absent or is selected from N, and $CR_8$;

H is absent or is selected from N, and $CR_9$;

$R_1$, $R_2$, $R_3$, $R_6$, $R_7$, $R_8$, $R_9$, and $R_{10}$ are independently selected from hydrogen, hydroxyl, halogen, $C_{1-4}$ alkyl, $C_{1-4}$ alkoxy, $C_{1-4}$ haloalkyl, $C_{1-4}$ haloalkoxy, $C_{3-5}$ cycloalkyl, or $C_{5-6}$ aryl;

$R_4$, and $R_5$ are independently selected from hydrogen, hydroxyl, cyano, amino, halogen, $C_{1-4}$ alkyl, $C_{1-4}$ alkoxy, $C_{3-6}$ cycloalkyl, $C_{1-4}$ haloalkyl, $C_{1-4}$ haloalkoxy, $C_{1-4}$ acylamino, $C_{1-4}$ alkylamino, $C_{5-9}$ aryl, $C_{1-9}$ heterocyclyl, $C_{1-9}$ heteroaryl, C(O)$C_{1-4}$ alkyl, C(O)$C_{1-4}$ haloalkyl, C(O)$NR_{15}$, C(O)$C_{1-4}$ alkylamino, C(O)$C_{5-6}$ aryl, C(O)$C_{1-6}$ heteroaryl, $SO_2C_{1-4}$ alkyl, $SO_2C_{1-4}$ haloalkyl, $SO_2C_{3-6}$ cycloalkyl, $SO_2NR_{15}$, $SO_2NC_{1-4}$ alkylamino, $SO_2C_{5-6}$ aryl, or $SO_2C_{1-6}$ heteroaryl $C_{1-4}$ alkyl, $C_{1-4}$ alkoxy, $C_{1-9}$ heteroaryl, and $C_{1-4}$ haloalkoxy, is optionally substituted with one or more of the groups selected from hydrogen, oxo, $C_{1-4}$ alkyl, $C_{1-4}$ alkoxy, $C_{1-4}$ haloalkyl, $C_{1-4}$ alkylhydroxy, $C_{3-6}$ cycloalkyl, $C_{5-6}$ aryl, $C_{1-6}$ heterocyclyl, $C_{1-6}$ heteroaryl, cyano, halogen, and hydroxyl, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2$OH, and cyano;

$R_{11}$ and $R_{12}$ are taken together to form a 5-10 membered monocyclic or bicyclic saturated or unsaturated heterocyclic ring optionally with 1-5 heteroatoms selected from N, S or O, wherein the 5-10 membered monocyclic or bicyclic saturated or unsaturated heterocyclic ring is optionally substituted with the substituents selected from amino, $C_{1-6}$ alkylamino, $C_{1-6}$ acylamino, —NHC(NH)$CH_2$Cl, —NH(CO)CH═CH—$CH_2$—N$(CH_3)_2$, $C_{1-6}$ alkyl, halogen, $C_{1-6}$ alkoxy, or hydroxyl;

and $R_{15}$ is selected from the group consisting of hydrogen, $C_{1-6}$ alkyl, and combinations thereof.

3. The compound of Formula (II) as claimed in claim 1, their polymorphs, stereoisomers, prodrugs, solvates, co-crystals, intermediates, pharmaceutically acceptable salts, and metabolites thereof, wherein X is selected from O or S;

Z is N;

A is $CR_1$;

B is $CR_2$;

D is $CR_3$;

E is selected from N or $CR_6$;

F is absent or is $CR_7$;

G is absent or is $CR_8$;

H is absent or is $CR_9$;

$R_1$, $R_2$, $R_3$, $R_6$, $R_7$, $R_8$, $R_9$, and $R_{10}$ are independently selected from hydrogen, halogen, $C_{1-2}$ alkyl, $C_{1-2}$ alkoxy, or $C_{5-6}$ aryl;

$R_4$, and $R_5$ are independently selected from hydrogen, $C_{1-4}$ alkyl, $C_{1-4}$ alkoxy, $C_{3-6}$ cycloalkyl, $C_{1-4}$ haloalkyl, $C_{1-4}$ haloalkoxy, $C_{5-9}$ aryl, $C_{1-9}$ heterocyclyl, or $C_{1-9}$ heteroaryl, wherein $C_{1-4}$ alkyl, $C_{1-4}$ alkoxy, $C_{1-9}$ heteroaryl, and $C_{1-4}$ haloalkoxy, is optionally substituted with one or more of the groups selected from hydrogen, oxo, $C_{1-4}$ alkyl, $C_{1-4}$ alkoxy, $C_{1-4}$ haloalkyl, $C_{1-4}$ alkylhydroxy, $C_{3-6}$ cycloalkyl, $C_{5-6}$ aryl, $C_{1-6}$ heterocyclyl, $C_{1-6}$ heteroaryl, cyano, halogen, and hydroxyl, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2$OH, and cyano;

$R_{11}$ and $R_{12}$ are taken together to form a 5-10 membered monocyclic or bicyclic saturated heterocyclic ring optionally with 1-5 heteroatoms selected from N, S or O, wherein the 5-10 membered monocyclic or bicyclic saturated heterocyclic ring is optionally substituted with the substituents selected from amino, $C_{1-2}$ alkylamino, or —NH(CO)CH═CH $CH_2$—N$(CH_3)_2$.

4. A compound as claimed in claim 1, of Formula (III)

Formula (III)

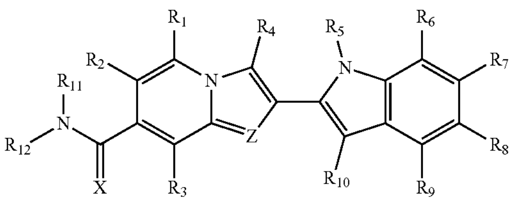

their polymorphs, stereoisomers, prodrugs, solvates, co-crystals, intermediates, pharmaceutically acceptable salts, and metabolites thereof, wherein X is selected from O or S;

Z is N;

$R_1$, $R_2$, $R_3$, $R_4$, $R_5$, $R_6$, $R_7$, $R_8$, $R_9$ and $R_{10}$ are independently selected from hydrogen, hydroxyl, cyano, amino, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-10}$ heterocyclyl, $C_{1-10}$ heteroaryl, C(O)$C_{1-6}$ alkyl, C(O)$C_{1-6}$ haloalkyl, C(O)$NR_{15}$, C(O)$C_{1-6}$ alkylamino, C(O)$C_{5-6}$ aryl, C(O)$C_{1-6}$ heteroaryl, $SO_2C_{1-6}$ alkyl, $SO_2C_{1-6}$ haloalkyl, $SO_2C_{3-6}$ cycloalkyl, $SO_2NR_{15}$, $SO_2NC_{1-6}$ alkylamino, $SO_2C_{5-6}$ aryl, or $SO_2C_{1-6}$ heteroaryl, wherein $C_{1-6}$ alkyl, $C_{1-6}$ alkoxy, $C_{1-6}$ heteroaryl, and $C_{1-6}$ haloalkoxy, is optionally substituted with one or more of the groups selected from hydrogen, oxo, $C_{1-6}$ alkyl, $C_{1-6}$ alkoxy, $C_{1-6}$ haloalkyl, $C_{1-6}$ alkylhydroxy, $C_{3-6}$ cycloalkyl, $C_{5-9}$ aryl, $C_{1-6}$ heterocyclyl, $C_{1-6}$ heteroaryl, cyano, halogen, and hydroxyl, wherein $C_{5-9}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2$OH, and cyano;

$R_{11}$ and $R_{12}$ are taken together to form a 5-10 membered monocyclic or bicyclic saturated or unsaturated heterocyclic ring optionally with 1-5 heteroatoms selected from N, S or O, wherein the 5-10 membered monocyclic or bicyclic saturated or unsaturated heterocyclic ring is optionally substituted with the substituents selected from amino, $C_{1-6}$ alkylamino, $C_{1-6}$ acylamino, —NHC(NH)$CH_2$Cl, —NH(CO)CH═CH—$CH_2$—$N(CH_3)_2$, $C_{1-6}$ alkyl, halogen, $C_{1-6}$ alkoxy, or hydroxyl;

and $R_{15}$ is selected from the group consisting of hydrogen, $C_{1-6}$ alkyl, and combinations thereof.

5. The compound of Formula (III) as claimed in claim 4, their polymorphs, stereoisomers, prodrugs, solvates, co-crystals, intermediates, pharmaceutically acceptable salts, and metabolites thereof, wherein X is selected from O or S;

Z is N;

$R_1$, $R_2$, $R_3$, $R_6$, $R_7$, $R_8$, $R_9$, and $R_{10}$ are independently selected from hydrogen, hydroxyl, halogen, $C_{1-4}$ alkyl, $C_{1-4}$ alkoxy, $C_{1-4}$ haloalkyl, $C_{1-4}$ haloalkoxy, $C_{3-5}$ cycloalkyl, or $C_{5-6}$ aryl;

$R_4$, and $R_5$ are independently selected from the hydrogen, hydroxyl, cyano, amino, halogen, $C_{1-4}$ alkyl, $C_{1-4}$ alkoxy, $C_{3-6}$ cycloalkyl, $C_{1-4}$ haloalkyl, $C_{1-4}$ haloalkoxy, $C_{1-4}$ acylamino, $C_{1-4}$ alkylamino, $C_{5-9}$ aryl, $C_{1-9}$ heterocyclyl, $C_{1-9}$ heteroaryl, C(O)$C_{1-4}$ alkyl, C(O)$C_{1-4}$ haloalkyl, C(O)$NR_{15}$, C(O)$C_{1-4}$ alkylamino, C(O)$C_{5-6}$ aryl, C(O)$C_{1-6}$ heteroaryl, $SO_2C_{1-4}$ alkyl, $SO_2C_{1-4}$ haloalkyl, $SO_2C_{3-6}$ cycloalkyl, $SO_2NR_{15}$, $SO_2NC_{1-4}$ alkylamino, $SO_2C_{5-6}$ aryl, or $SO_2C_{1-6}$ heteroaryl, wherein $C_{1-4}$ alkyl, $C_{1-4}$ alkoxy, $C_{1-9}$ heteroaryl, and $C_{1-4}$ haloalkoxy, is optionally substituted with one or more of the groups selected from hydrogen, oxo, $C_{1-4}$ alkyl, $C_{1-4}$ alkoxy, $C_{1-4}$ haloalkyl, $C_{1-4}$ alkylhydroxy, $C_{3-6}$ cycloalkyl, $C_{5-6}$ aryl, $C_{1-6}$ heterocyclyl, $C_{1-6}$ heteroaryl, cyano, halogen, and hydroxyl, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2$OH, and cyano;

$R_{11}$ and $R_{12}$ are taken together to form a 5-10 membered monocyclic or bicyclic saturated or unsaturated heterocyclic ring optionally with 1-5 heteroatoms selected from N, S or O, wherein the 5-10 membered monocyclic or bicyclic saturated or unsaturated heterocyclic ring is optionally substituted with the substituents selected from amino, $C_{1-6}$ alkylamino, $C_{1-6}$ acylamino, —NHC(NH)$CH_2$Cl, —NH(CO)CH═CH—$CH_2$—$N(CH_3)_2$, $C_{1-6}$ alkyl, halogen, $C_{1-6}$ alkoxy, or hydroxyl;

and $R_{15}$ is selected from the group consisting of hydrogen, $C_{1-6}$ alkyl, and combinations thereof.

6. The compound of Formula (III) as claimed in claim 4, their polymorphs, stereoisomers, prodrugs, solvates, co-crystals, intermediates, pharmaceutically acceptable salts, and metabolites thereof, wherein X is selected from O or S;

Z is N;

$R_1$, $R_2$, $R_3$, $R_6$, $R_7$, $R_8$, $R_9$, and $R_{10}$ are independently selected from hydrogen, halogen, $C_{1-4}$ alkyl, $C_{1-4}$ alkoxy, or $C_{5-6}$ aryl;

$R_4$, and $R_5$ are independently selected from hydrogen, $C_{1-4}$ alkyl, $C_{1-4}$ alkoxy, $C_{3-6}$ cycloalkyl, $C_{1-4}$ haloalkyl, $C_{1-4}$ haloalkoxy, $C_{5-9}$ aryl, $C_{1-9}$ heterocyclyl, or $C_{1-9}$ heteroaryl, wherein $C_{1-4}$ alkyl, $C_{1-4}$ alkoxy, $C_{1-6}$ heteroaryl, and $C_{1-4}$ haloalkoxy, is optionally substituted with one or more of the groups selected from hydrogen, oxo, $C_{1-4}$ alkyl, $C_{1-4}$ alkoxy, $C_{1-4}$ haloalkyl, $C_{1-4}$ alkylhydroxy, $C_{3-6}$ cycloalkyl, $C_{5-6}$ aryl, $C_{1-6}$ heterocyclyl, $C_{1-6}$ heteroaryl, cyano, halogen, and hydroxyl, wherein $C_{5-6}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2$OH, and cyano; and $R_{11}$ and $R_{12}$ are taken together to form a 5-10 membered monocyclic or bicyclic saturated heterocyclic ring optionally with 1-5 heteroatoms selected from N, S or O, wherein the 5-10 membered monocyclic or bicyclic saturated heterocyclic ring is optionally substituted with the substituents selected from amino, $C_{1-4}$ alkylamino, or —NH(CO)CH═CH$CH_2$—$N(CH_3)_2$.

7. The compound of Formula (II) as claimed in claim 1 or its polymorphs, stereoisomers, prodrugs, solvates, co-crystals, intermediates, pharmaceutically acceptable salts, and metabolites thereof, which is selected from a group consisting of:

(R)-(3-aminopiperidin-1-yl)(2-(3-bromo-1-(cyclopropylmethyl)-1H-indol-2-yl)-3-methylimidazo[1,2-a]pyridin-7-yl)methanone (1), (R)-(3-aminopiperidin-1-yl)(2-(1-(cyclopropylmethyl)-1H-indol-2-yl)-3-methylimidazo[1,2-a]pyridin-7-yl)methanone (2), (R)-(3-aminopiperidin-1-yl)(2-(1-benzyl-1H-indol-2-yl)-3-methylimidazo[1,2-a]pyridin-7-yl)methanone (3), (R)-(3-aminopiperidin-1-yl)(2-(1-ethyl-1H-indol-2-yl)-3-methylimidazo[1,2-a]pyridin-7-yl)methanone (4), (R)-(3-aminopiperidin-1-yl)(2-(1-ethyl-3-phenyl-1H-indol-2-yl)-3-methylimidazo[1,2-a]pyridin-7-yl)methanone (5), (R)-(3-aminopyrrolidin-1-yl)(2-(1-ethyl-3-phenyl-1H-indol-2-yl)-3-methylimidazo[1,2-a]pyridin-7-yl)methanone (6), (R)-(3-aminopyrrolidin-1-yl)(2-(1-ethyl-1H-indol-2-yl)-3-methylimidazo[1,2-a]pyridin-7-yl)methanone (7), (R)-(3-aminopyrrolidin-1-yl)(2-(1-(cyclopropylmethyl)-1H-indol-2-yl)-3-methylimidazo[1,2-a]pyridin-7-yl)methanone (8), (2-(1-(cyclopropylmethyl)-1H-indol-2-yl)-3-methylimidazo[1,2-a]pyridin-7-yl)(hexahydro-2H-pyrido[4,3-b][1,4]oxazin-6(5H)-yl)methanone (9), (R)-(3-aminopiperidin-1-yl)(3-methyl-2-(1-(pyridin-4-ylmethyl)-1H-indol-2-yl)imidazo[1,2-a]pyridin-7-yl)methanone (10), (R)-(3-aminopiperidin-1-yl)(3-methyl-2-(1-((tetrahydro-2H-pyran-4-yl)methyl)-1Hindol-2-yl)imidazo[1,2-a]pyridin-7-yl)methanone (11), (R)-(3-aminopiperidin-1-yl)(2-(1-(4-methoxybenzyl)-1H-indol-2-yl)-3-methylimidazo[1,2-a]pyridin-7-yl)methanone (12), (R)-(3-aminopiperidin-1-yl)(2-(1-(4-fluorobenzyl)-1H-indol-2-yl)-3-methylimidazo[1,2-a]pyridin-7-yl)methanone (13), (R)-4-((2-(7-(3-aminopiperidine-1-carbonyl)-3-methylimidazo[1,2-a]pyridin-2-yl)-1Hindol-1-yl)methyl)benzonitrile (14), (R)-(3-aminopiperidin-1-yl)(3-methyl-2-(1-(pyridin-3-ylmethyl)-1H-indol-2-yl)imidazo[1,2-a]pyridin-7-yl) methanone (15), (R)-(3-aminopiperidin-1-yl)(3-methyl-2-(1-(pyridin-2-ylmethyl)-1H-indol-2-yl)imidazo[1,2-a]pyridin-7-yl) methanone (16), (R)-(3-aminopiperidin-1-yl)(3-methyl-2-(1-(2,2,2-trifluoroethyl)-1H-indol-2-yl)imidazo[1,2-a]pyridin-7-yl) methanone (17), (R)-4-((2-(7-(3-aminopiperidine-1-carbonyl)-3-methylimidazo[1,2-a]pyridin-2-yl)-1Hindol-1-yl)methyl)-1-methylpyridin-2(1H)-one (18), (R)-(3-aminopiperidin-1-yl)(2-(3-ethylbenzo[b]thiophen-2-yl)-3-methylimidazo[1,2-a]pyridin-7-yl)methanone (19), (R)-(3-aminopiperidin-1-yl)(2-(1-(4-chlorobenzyl)-1H-indol-2-yl)-3-methylimidazo[1,2-a]pyridin-7-yl) methanone (20), (R)-(3-aminopiperidin-1-yl)(2-(1-(2-fluorobenzyl)-1H-indol-2-yl)-3-methylimidazo[1,2-a]pyridin-7-yl) methanone (21), (R)-(3-aminopiperidin-1-yl)(2-(1-ethyl-5-phenyl-1H-pyrrol-2-yl)-3-methylimidazo[1,2-a]pyridin-7-yl)methanone (22), (R)-(3-aminopiperidin-1-yl)(2-(1-(cyclopropylmethyl)-6-methoxy-1H-indol-2-yl)-3-methylimidazo[1,2-a]pyridin-7-yl)methanone (23), (R)-(3-aminopiperidin-1-yl)(2-(1-ethyl-1H-pyrrolo[2,3-b]pyridin-2-yl)-3-methylimidazo[1,2-a]pyridin-7-yl) methanone (24), (R)-(3-aminopiperidin-1-yl)(2-(1-(cyclopropylmethyl)-1H-indol-2-yl)-3,5-dimethylimidazo[1,2-a]pyridin-7-yl)methanone (25), (R)-(3-aminopiperidin-1-yl)(2-(l-benzyl-1H-indol-2-yl)-3,5-dimethylimidazo[1,2-a]pyridin-7-yl)methanone (26), (R)-(3-aminopiperidin-1-yl)(3,5-dimethyl-2-(1-(pyridin-2-ylmethyl)-1H-indol-2-yl)imidazo[1,2-a]pyridin-7-yl)methanone (27), (R)-(3-aminopiperidin-1-yl)(2-(l-(cyclopropylmethyl)-6-fluoro-1H-indol-2-yl)-3-methylimidazo[1,2-a]pyridin-7-yl)methanone (28), (R)-(3-aminopiperidin-1-yl)(2-(l-(cyclopropylmethyl)-5-fluoro-1H-indol-2-yl)-3-methylimidazo[1,2-a]pyridin-7-yl)methanone (29), (R)-(3-aminopiperidin-1-yl)(2-(l-(cyclopropylmethyl)-7-methyl-1H-indol-2-yl)-3-methylimidazo[1,2-a]pyridin-7-yl)methanone (30), (R)-(3-aminopiperidin-1-yl)(2-(2-ethylphenyl)-3-methylimidazo[1,2-a]pyridin-7-yl)methanone (31), (R)-(3-aminopiperidin-1-yl)(2-(l-(cyclopropylmethyl)-1H-indol-2-yl)-3-phenylimidazo[1,2-a]pyridin-7-yl) methanone (32), (R)-(3-aminopiperidin-1-yl)(3-cyclopropyl-2-(1-(cyclopropylmethyl)-1H-indol-2-yl)imidazo[1,2-a]pyridin-7-yl)methanone (33), (R)-(3-aminopiperidin-1-yl)(2-(1-(cyclopropylmethyl)-1H-indol-2-yl)-3-(methoxymethyl)imidazo[1,2-a]pyridin-7-yl)methanone (34), (R)-(3-aminopiperidin-1-yl)(2-(l-(3-fluorobenzyl)-1H-indol-2-yl)-3-methylimidazo[1,2-a]pyridin-7-yl)methanone (35), (R)-(3-aminopiperidin-1-yl)(3-methyl-2-(1-(thiophen-3-ylmethyl)-1H-indol-2-yl)imidazo[1,2-a]pyridin-7-yl) methanone (36), (R)-(3-aminopiperidin-1-yl)(2-(1-(furan-3-ylmethyl)-1H-indol-2-yl)-3-methylimidazo[1,2-a]pyridin-7-yl) methanone (37), (R)-3-aminopiperidin-1-yl)(2-(1-(1-(4-fluorophenyl) ethyl)-1H-indol-2-yl)-3-methylimidazo[1,2-a]pyridin-7-yl)methanone (38), (R)-(3-aminopiperidin-1-yl)(2-(1-ethyl-5-fluoro-1H-indol-2-yl)-3-methylimidazo[1,2-a]pyridin-7-yl)methanone (39), (R)-(3-aminopiperidin-1-yl)(2-(1-(cyclopropylmethyl)-4-fluoro-1H-indol-2-yl)-3-methylimidazo[1,2-a]pyridin-7-yl)methanone (40), (R)-(3-aminopiperidin-1-yl)(3-methyl-2-(1-((4-methylthiazol-2-yl)methyl)-1H-indol-2-yl)imidazo[1,2-a] pyridin-7-yl)methanone (41), (R)-(3-aminopiperidin-1-yl)(2-(1-(3-methoxybenzyl)-1H-indol-2-yl)-3-methylimidazo[1,2-a]pyridin-7-yl) methanone (42), (R)-(3-aminopiperidin-1-yl)(2-(5-bromo-1-(cyclopropylmethyl)-1H-indol-2-yl)-3-methylimidazo[1,2-a]pyridin-7-yl)methanone (43), (R)-(3-aminopiperidin-1-yl)(2-(7-chloro-1-(cyclopropylmethyl)-1H-indol-2-yl)-3-methylimidazo[1,2-a]pyridin-7-yl)methanone (44), (R)-(3-aminopiperidin-1-yl)(2-(1-(4-fluorobenzyl)-1H-indol-2-yl)-3-methylimidazo[1,2-a]pyridin-7-yl)methanethione (45), (R)-(3-aminopiperidin-1-yl)(3-methyl-2-(1-methyl-1H-indol-2-yl)imidazo[1,2-a]pyridin-7-yl)methanone (46), (R)-(3-aminopiperidin-1-yl)(2-(l-(cyclopropylmethyl)-7-methoxy-1H-indol-2-yl)-3-methylimidazo[1,2-a]pyridin-7-yl)methanone (47), (R)-(3-aminopiperidin-1-yl)(2-(1-((2,4-dimethylthiazol-5-yl)methyl)-1H-indol-2-yl)-3-methylimidazo[1,2-a] pyridin-7-yl)methanone (48), (R)-(3-aminopiperidin-1-yl)(3-methyl-2-(1-((2-methylthiazol-5-yl)methyl)-1H-indol-2-yl)imidazo[1,2-a] pyridin-7-yl)methanone (49), (R)-(3-aminopiperidin-1-yl)(2-(1-(3-methoxybenzyl)-1H-indol-2-yl)-3-methylimidazo[1,2-a]pyridin-7-yl) methanone trifluoroacetic acid salt (50), (R)-(3-aminopiperidin-1-yl)(2-(6-methoxy-1-(pyridin-3-ylmethyl)-1H-indol-2-yl)-3-methylimidazo[1,2-a]pyridin-7-yl)methanone (51), (R)-(3-aminopiperidin-1-yl)(2-(l-(cyclopropylmethyl)-6-fluoro-1H-indol-2-yl)-3-methylimidazo[1,2-a]pyridin-7-yl)methanone trifluoroacetic acid salt (52), (R)-(3-aminopiperidin-1-yl)(2-(5-fluoro-1-(3-methoxybenzyl)-1H-indol-2-yl)-3-methylimidazo[1,2-a]pyridin-7-yl)methanone (53), (R)-(3-aminopiperidin-1-yl)(2-(6-fluoro-1-(4-fluorobenzyl)-1H-indol-2-yl)-3-methylimidazo[1,2-a]pyridin-7-yl)methanone (54), (R)-(3-aminopiperidin-1-yl)(2-(5,6-difluoro-1-(3-methoxybenzyl)-1H-indol-2-yl)-3-methylimidazo[1,2-a]pyridin-7-yl)methanone (55), (R,E)-4-(dimethylamino)-N-(1-(2-(1-(4-fluorobenzyl)-1H-indol-2-yl)-3-methylimidazo[1,2-a]pyridine-7-carbonyl)piperidin-3-yl)but-2-enamide (56), (R)-(3-aminopiperidin-1-yl)(3-methyl-2-(l-(pyrazin-2-ylmethyl)-1H-indol-2-yl)imidazo[1,2-a]pyridin-7-yl) methanone (57), (R)-(3-aminopiperidin-1-yl)(3-methyl-2-(l-(pyrimidin-5-ylmethyl)-1H-indol-2-yl)imidazo[1,2-a]pyridin-7-yl) methanone trifluoroacetic acid salt (58), (R)-(3-aminopiperidin-1-yl)(3-methyl-2-(l-(pyridazin-3-ylmethyl)-1H-indol-2-yl)imidazo[1,2-a]pyridin-7-yl) methanone (59), (R)-(3-aminopiperidin-1-yl)(2-(l-isobutyl-1H-indol-2-yl)-3-methylimidazo[1,2-a]pyridin-7-yl)methanone (60), (R)-(3-aminopiperidin-1-yl)(2-(l-(cyclobutylmethyl)-1H-indol-2-yl)-3-methylimidazo[1,2-a]pyridin-7-yl) methanone (61), (R)-(3-aminopiperidin-1-yl)(2-(l-((3-fluoropyridin-2-yl) methyl)-1H-indol-2-yl)-3-methylimidazo[1,2-a]pyridin-7-yl)methanone (62), (R)-(3-aminopiperidin-1-yl)(2-(l-((5-methoxypyridin-2-yl)methyl)-1H-indol-2-yl)-3-methylimidazo[1,2-a] pyridin-7-yl)methanone (63), (R)-(3-aminopiperidin-1-yl)(2-(l-(2-methoxyethyl)-1H-indol-2-yl)-3-methylimidazo[1,2-a]pyridin-7-yl) methanone (64), (R)-(3-aminopiperidin-1-yl)(2-(l-(2-hydroxyethyl)-1H-indol-2-yl)-3-methylimidazo[1,2-a]pyridin-7-yl) methanone (65), (R)-(3-aminopiperidin-1-yl)(2-(6-methoxy-1-(pyridin-4-ylmethyl)-1H-indol-2-yl)-3-methylimidazo[1,2-a]pyridin-7-yl)methanone (66), (R)-(3-aminopiperidin-1-yl)(2-(l-ethyl-6-methoxy-1H-indol-2-yl)-3-methylimidazo[1,2-a]pyridin-7-yl)methanone (67), (R)-(3-aminopiperidin-1-yl)(2-(6-fluoro-1-(pyridin-4-ylmethyl)-1H-indol-2-yl)-3-methylimidazo[1,2-a]pyridin-7-yl)methanone (68), (R)-(3-aminopiperidin-1-yl)(2-(6-fluoro-1-(pyridin-3-ylmethyl)-1H-indol-2-yl)-3-methylimidazo[1,2-a]pyridin-7-yl)methanone (69), (R)-(3-aminopiperidin-1-yl)(2-(6-fluoro-1-(3-methoxybenzyl)-1H-indol-2-yl)-3-methylimidazo[1,2-a]pyridin-7-yl)methanone (70), (R)-(3-aminopiperidin-1-yl)(2-(6-fluoro-1-(4-methoxybenzyl)-1H-indol-2-yl)-3-methylimidazo[1,2-a]pyridin-7-yl)methanone (71), (R)-(3-aminopiperidin-1-yl)(2-(l-ethyl-6-fluoro-1H-indol-2-yl)-3-methylimidazo[1,2-a]pyridin-7-yl)methanone (72), (R)-(3-aminopiperidin-1-yl)(2-(6-fluoro-1-isobutyl-1H-indol-2-yl)-3-methylimidazo[1,2-a]pyridin-7-yl) methanone (73), (R)-(3-aminopiperidin-1-yl)(2-(5-fluoro-1-(pyridin-4-ylmethyl)-1H-indol-2-yl)-3-methylimidazo[1,2-a]pyridin-7-yl)methanone (74), (R)-(3-aminopiperidin-1-yl)(2-(5-fluoro-1-(4-methoxybenzyl)-1H-indol-2-yl)-3-methylimidazo[1,2-a]pyridin-7-yl)methanone (75), (R)-(3-aminopiperidin-1-yl)(2-(5-fluoro-1-(4-fluorobenzyl)-1H-indol-2-yl)-3-methylimidazo[1,2-a]pyridin-7-yl)methanone (76), (R)-(3-aminopiperidin-1-yl)(2-(7-chloro-1-(4-fluorobenzyl)-1H-indol-2-yl)-3-methylimidazo[1,2-a]pyridin-7-yl)methanone (77), (R)-(3-aminopiperidin-1-yl)(2-(l-(2,2-difluoroethyl)-1H-indol-2-yl)-3-methylimidazo[1,2-a]pyridin-7-yl) methanone trifluoroacetic acid salt (78), (R)-(3-aminopiperidin-1-yl)(2-(l-((5-fluoropyridin-2-yl) methyl)-1H-indol-2-yl)-3-methylimidazo[1,2-a]pyridin-7-yl)methanone (79), (R)-(3-aminopiperidin-1-yl)(2-(l-(4-fluorobenzyl)-6-methoxy-1H-indol-2-yl)-3-methylimidazo[1,2-a]pyridin-7-yl)methanone (80), (R)-(3-aminopiperidin-1-yl)(2-(l-(4-(hydroxymethyl) benzyl)-1H-indol-2-yl)-3-methylimidazo[1,2-a]pyridin-7-yl)methanone (81), (R)-(3-aminopiperidin-1-yl)(2-(l-isobutyl-6-methoxy-1H-indol-2-yl)-3-methylimidazo[1,2-a]pyridin-7-yl) methanone (82), (R)-(3-aminopiperidin-1-yl)(2-(l-(2,2-difluoroethyl)-6-methoxy-1H-indol-2-yl)-3-methylimidazo[1,2-a]pyridin-7-yl)methanone (83), (R)-(3-aminopiperidin-1-yl)(2-(5-fluoro-1-isobutyl-1H-indol-2-yl)-3-methylimidazo[1,2-a]pyridin-7-yl) methanone (84), and (R)-(3-aminopiperidin-1-yl)(2-(l-(4-fluoro-3-methoxybenzyl)-1H-indol-2-yl)-3-methylimidazo[1,2-a]pyridin-7-yl)methanone (85).

8. A process of preparation of compounds of Formula (II) as claimed in claim 1 or its polymorphs, stereoisomers, prodrugs, solvates, co-crystals, intermediates, pharmaceutically acceptable salts, and metabolites thereof, the process comprising reacting Formula (V) and $R_4CH_2NO_2$ with a compound selected from Formula (IVA) or Formula (IV)

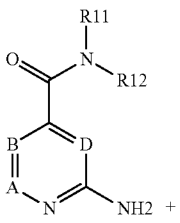

Formula (IVA)

or

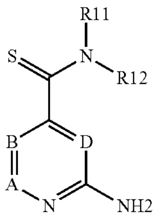

Formula (IV)

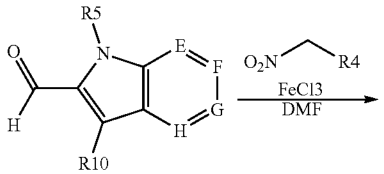

Formula (V)

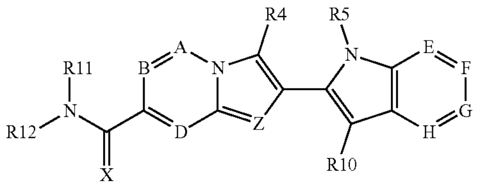

Formula (II)

wherein A of Formula (IVA) and (IV) is selected from Nor $CR_1$; B is selected from N or $CR_2$; D is selected from N or $CR_3$; $R_{11}$ and $R_{12}$ are taken together to form a $5_{-10}$ membered monocyclic or bicyclic saturated or unsaturated heterocyclic ring optionally with $1_{-5}$ heteroatoms selected from N, S or O, wherein the 5-10 membered monocyclic or bicyclic saturated or unsaturated heterocyclic ring is optionally substituted with the substituents selected from amino, $C_{1-6}$ alkylamino, $C_{1-6}$ acylamino, —NHC(NH)$CH_2$Cl, —NH(CO)CH═CH—$CH_2$—$N(CH_3)_2$, $C_{1-6}$ alkyl, halogen, $C_{1-6}$ alkoxy, or hydroxyl; $R_4$ of $R_4CH_2NO_2$ is selected from hydrogen, hydroxyl, cyano, amino, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-6}$ heterocyclyl, $C_{1-6}$ heteroaryl, C(O)$C_{1-6}$ alkyl, C(O)$C_{1-6}$ haloalkyl, C(O)$NR_{15}$, C(O)$C_{1-6}$ alkylamino, C(O)$C_{5-6}$ aryl, C(O)$C_{1-6}$ heteroaryl, $SO_2C_{1-6}$ alkyl, $SO_2C_{1-6}$ haloalkyl, $SO_2C_{3-6}$ cycloalkyl, $SO_2NR_{15}$, $SO_2NC_{1-6}$ alkylamino, $SO_2C_{5-6}$ aryl, or $SO_2C_{1-6}$ heteroaryl, wherein $C_{1-6}$ alkyl, $C_{1-6}$ alkoxy, $C_{1-6}$ heteroaryl, and $C_{1-6}$ haloalkoxy, is optionally substituted with one or more of the groups selected from hydrogen, oxo, $C_{1-6}$ alkyl, $C_{1-6}$ alkoxy, $C_{1-6}$ haloalkyl, $C_{1-6}$ alkylhydroxy, $C_{3-6}$ cycloalkyl, $C_{5-10}$ aryl, $C_{1-6}$ heterocyclyl, $C_{1-6}$ heteroaryl, cyano, halogen, and hydroxyl, wherein $C_{5-10}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2$OH, and cyano; E of Formula (V) is selected from N, $C_{5-6}$ aryl or $CR_6$; F is absent or is selected from N, and $CR_7$; G is absent or is selected from N, and $CR_8$; H is absent or is selected from N, and $CR_9$; $R_1$, $R_2$, $R_3$, $R_5$, $R_6$, $R_7$, $R_8$, $R_9$ and $R_{10}$ are independently selected from hydrogen, hydroxyl, cyano, amino, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-6}$ heterocyclyl, $C_{1-6}$ heteroaryl, C(O)$C_{1-6}$ alkyl, C(O)$C_{1-6}$ haloalkyl, C(O)$NR_{15}$, C(O)$C_{1-6}$ alkylamino, C(O)$C_{5-6}$ aryl, C(O) $C_{1-6}$ heteroaryl, $SO_2C_{1-6}$ alkyl, $SO_2C_{1-6}$ haloalkyl, $SO_2C_{3-6}$ cycloalkyl, $SO_2NR_{15}$, $SO_2NC_{1-6}$ alkylamino, $SO_2C_{5-6}$ aryl, or $SO_2C_{1-6}$ heteroaryl, wherein $C_{1-6}$ alkyl, $C_{1-6}$ alkoxy, $C_{1-6}$ heteroaryl, and $C_{1-6}$ haloalkoxy, is optionally substituted with one or more of the groups selected from hydrogen, oxo, $C_{1-6}$ alkyl, $C_{1-6}$ alkoxy, $C_{1-6}$ haloalkyl, $C_{1-6}$ alkylhydroxy, $C_{3-6}$ cycloalkyl, $C_{5-10}$ aryl, $C_{1-6}$ heterocyclyl, $C_{1-6}$ heteroaryl, cyano, halogen, and hydroxyl, wherein $C_{5-10}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2$OH, and cyano; X of Formula (II) is selected from O or S; Z is N; A is selected from Nor $CR_1$; B is selected from N or $CR_2$; D is selected from N or $CR_3$; E is selected from N or $CR_6$; F is absent or is selected from N, and $CR_7$; G is absent or is selected from N, and $CR_8$; H is absent or is selected from N, and $CR_9$; $R_1$, $R_2$, $R_3$, $R_4$, $R_5$, $R_6$, $R_7$, $R_8$, $R_9$ and $R_{10}$ are independently selected from hydrogen, hydroxyl, cyano, amino, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-6}$ heterocyclyl, $C_{1-6}$ heteroaryl, C(O)$C_{1-6}$ alkyl, C(O)$C_{1-6}$ haloalkyl, C(O) $NR_{15}$, C(O)$C_{1-6}$ alkylamino, C(O)$C_{5-6}$ aryl, $C(O)_{1-6}$ heteroaryl, $SO_2C_{1-6}$ alkyl, $SO_2C_{1-6}$ haloalkyl, $SO_2C_{3-6}$ cycloalkyl, $SO_2NR_{15}$, $SO_2NC_{1-6}$ alkylamino, $SO_2C_{5-6}$ aryl, or $SO_2C_{1-6}$ heteroaryl, wherein $C_{1-6}$ alkyl, $C_{1-6}$ alkoxy, $C_{1-6}$ heteroaryl, and $C_{1-6}$ haloalkoxy, is optionally substituted with one or more of the groups selected from hydrogen, oxo, $C_{1-6}$ alkyl, $C_{1-6}$ alkoxy, $C_{1-6}$ haloalkyl, $C_{1-6}$ alkylhydroxy, $C_{3-6}$ cycloalkyl, $C_{5-10}$ aryl, $C_{1-6}$ heterocyclyl, $C_{1-6}$ heteroaryl, cyano, halogen, and hydroxyl, wherein $C_{5-10}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2$OH, and cyano; $R_{11}$ and $R_{12}$ are taken together to form a 5-10 membered monocyclic or bicyclic saturated or unsaturated heterocyclic ring optionally with 1-5 heteroatoms selected from N, S or O, wherein the 5-10 membered monocyclic or bicyclic saturated or unsaturated heterocyclic ring is optionally substituted with the substituents selected from amino, $C_{1-6}$ alkylamino, $C_{1-6}$ acylamino, —NHC(NH)$CH_2$Cl, —NH(CO)CH═CH—$CH_2$—$N(CH_3)_2$, $C_{1-6}$ alkyl, halogen, $C_{1-6}$ alkoxy, or hydroxyl; and $R_{15}$ is selected from the group consisting of hydrogen, $C_{1-6}$ alkyl, and combinations thereof.

9. A process of preparation of compounds of Formula (III) as claimed in claim 4 or its polymorphs, stereoisomers, prodrugs, solvates, co-crystals, intermediates, pharmaceutically acceptable salts, and metabolites thereof, the process comprising reacting Formula (VII) $R_4CH_2NO_2$ with a compound selected from Formula (VIA) or Formula (VI)

wherein $R_1$, $R_2$, and $R_3$ of Formula (VIA) and Formula (VI) are independently selected from hydrogen, hydroxyl, cyano, amino, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-6}$ heterocyclyl, $C_{1-6}$ heteroaryl, C(O)$C_{1-6}$ alkyl, C(O)$C_{1-6}$ haloalkyl, C(O)$NR_{15}$, C(O)$C_{1-6}$ alkylamino, C(O)$C_{5-6}$ aryl, C(O)$C_{1-6}$ heteroaryl, $SO_2C_{1-6}$ alkyl, $SO_2C_{1-6}$ haloalkyl, $SO_2C_{3-6}$ cycloalkyl, $SO_2NR_{15}$, $SO_2NC_{1-6}$ alkylamino, $SO_2C_{5-6}$ aryl, or $SO_2C_{1-6}$ heteroaryl, wherein $C_{1-6}$ alkyl, $C_{1-6}$ alkoxy, $C_{1-6}$ heteroaryl, and $C_{1-6}$ haloalkoxy, is optionally substituted with one or more of the groups selected from hydrogen, oxo, $C_{1-6}$ alkyl, $C_{1-6}$ alkoxy, $C_{1-6}$ haloalkyl, $C_{1-6}$ alkylhydroxy, $C_{3-6}$ cycloalkyl, $C_{5-10}$ aryl, $C_{1-6}$ heterocyclyl, $C_{1-6}$ heteroaryl, cyano, halogen, and hydroxyl, wherein $C_{5-10}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2$OH, and cyano; $R_5$, $R_6$, $R_7$, $R_8$, $R_9$ and $R_{10}$ of Formula (VII) and $R_4$ of $R_4CH_2NO_2$ are independently selected from hydrogen, hydroxyl, cyano, amino, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-6}$ heterocyclyl, $C_{1-6}$ heteroaryl, C(O)$C_{1-6}$ alkyl, C(O)$C_{1-6}$ haloalkyl, C(O)$NR_{15}$, C(O)$C_{1-6}$ alkylamino, C(O)$C_{5-6}$ aryl, C(O) $C_{1-6}$ heteroaryl, $SO_2C_{1-6}$ alkyl, $SO_2C_{1-6}$ haloalkyl, $SO_2C_{3-6}$ cycloalkyl, $SO_2NR_{15}$, $SO_2NC_{1-6}$ alkylamino, $SO_2C_{5-6}$ aryl, or $SO_2C_{1-6}$ heteroaryl, wherein $C_{1-6}$ alkyl, $C_{1-6}$ alkoxy, $C_{1-6}$ heteroaryl, and $C_{1-6}$ haloalkoxy, is optionally substituted with one or more of the groups selected from hydrogen, oxo, $C_{1-6}$ alkyl, $C_{1-6}$ alkoxy, $C_{1-6}$ haloalkyl, $C_{1-6}$ alkylhydroxy, $C_{3-6}$ cycloalkyl, $C_{5-10}$ aryl, $C_{1-6}$ heterocyclyl, $C_{1-6}$ heteroaryl, cyano, halogen, and hydroxyl, wherein $C_{5-10}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2$OH, and cyano; X of Formula (III) is selected from O or S; Z is N; $R_1$, $R_2$, $R_3$, $R_4$, $R_5$, $R_6$, $R_7$, $R_8$, $R_9$ and $R_{10}$ are independently selected from hydrogen, hydroxyl, cyano, amino, halogen, $C_{1-6}$ alkyl, $C_{1-6}$ alkoxy, $C_{3-6}$ cycloalkyl, $C_{1-6}$ haloalkyl, $C_{1-6}$ haloalkoxy, $C_{1-6}$ acylamino, $C_{1-6}$ alkylamino, $C_{5-10}$ aryl, $C_{1-6}$ heterocyclyl, $C_{1-6}$ heteroaryl, C(O)$C_{1-6}$ alkyl, C(O)$C_{1-6}$ haloalkyl, C(O)$NR_{15}$, C(O)$C_{1-6}$ alkylamino, $C(O)C_{5-6}$ aryl, $C(O)C_{1-6}$ heteroaryl, $SO_2C_{1-6}$ alkyl, $SO_2C_{1-6}$ haloalkyl, $SO_2C_{3-6}$ cycloalkyl, $SO_2NR_{15}$, $SO_2NC_{1-6}$ alkylamino, $SO_2C_{5-6}$ aryl, or $SO_2C_{1-6}$ heteroaryl, wherein $C_{1-6}$ alkyl, $C_{1-6}$ alkoxy, $C_{1-6}$ heteroaryl, and $C_{1-6}$ haloalkoxy, is optionally substituted with one or more of the groups selected from hydrogen, oxo, $C_{1-6}$ alkyl, $C_{1-6}$ alkoxy, $C_{1-6}$ haloalkyl, $C_{1-6}$ alkylhydroxy, $C_{3-6}$ cycloalkyl, $C_{5-10}$ aryl, $C_{1-6}$ heterocyclyl, $C_{1-6}$ heteroaryl, cyano, halogen, and hydroxyl, wherein $C_{5-10}$ aryl, $C_{1-6}$ heteroaryl, and $C_{1-6}$ heterocyclyl, is optionally substituted with one or more of the groups selected from hydrogen, $C_{1-6}$ alkyl, $C_{1-6}$ alkoxy, oxo, halogen, hydroxyl, —$CH_2OH$, and cyano; $R_{11}$ and $R_{12}$ are taken together to form a 5-10 membered monocyclic or bicyclic saturated or unsaturated heterocyclic ring optionally with 1-5 heteroatoms selected from N, S or O, wherein the 5-10 membered monocyclic or bicyclic saturated or unsaturated heterocyclic ring is optionally substituted with the substituents selected from amino, $C_{1-6}$ alkylamino, $C_{1-6}$ acylamino, —NHC(NH)$CH_2Cl$, —NH(CO)CH═CH—$CH_2$—$N(CH_3)_2$, $C_{1-6}$ alkyl, halogen, $C_{1-6}$ alkoxy, or hydroxyl; and $R_{15}$ is selected from the group consisting of hydrogen, $C_{1-6}$ alkyl, and combinations thereof.

10. A pharmaceutical composition comprising a compound of Formula (II) or a pharmaceutically acceptable salt thereof as claimed in claim 1 together with a pharmaceutically acceptable carrier, optionally in combination with one or more other pharmaceutical compositions.

11. The pharmaceutical composition as claimed in claim 10, wherein the composition is in a form selected from a tablet, capsule, powder, syrup, solution, aerosol, and suspension.

12. A method for the treatment of rheumatoid arthritis, said method comprising administering a combination of the compounds as claimed in claim 1, with other clinically relevant agents or biological agents to a subject in need thereof.

* * * * *